US012343390B2

(12) United States Patent
Kawaoka et al.

(10) Patent No.: US 12,343,390 B2
(45) Date of Patent: Jul. 1, 2025

(54) RECOMBINANT BIOLOGICALLY CONTAINED FILOVIRUS VACCINE

(71) Applicant: Wisconsin Alumni Research Foundation (WARF), Madison, WI (US)

(72) Inventors: Yoshihiro Kawaoka, Middleton, WI (US); Peter J. Halfmann, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 314 days.

(21) Appl. No.: 17/266,049

(22) PCT Filed: Aug. 7, 2019

(86) PCT No.: PCT/US2019/045476
§ 371 (c)(1),
(2) Date: Feb. 4, 2021

(87) PCT Pub. No.: WO2020/033527
PCT Pub. Date: Feb. 13, 2020

(65) Prior Publication Data
US 2021/0290754 A1   Sep. 23, 2021

Related U.S. Application Data

(60) Provisional application No. 62/715,673, filed on Aug. 7, 2018.

(51) Int. Cl.
*A61K 39/12* (2006.01)
*C07K 7/00* (2006.01)
*C07K 16/00* (2006.01)
*C12N 7/00* (2006.01)
*A61K 39/00* (2006.01)

(52) U.S. Cl.
CPC ............ *A61K 39/12* (2013.01); *C07K 16/005* (2013.01); *C12N 7/00* (2013.01); *A61K 2039/5252* (2013.01); *A61K 2039/55572* (2013.01); *A61K 2039/55577* (2013.01); *A61K 2039/6075* (2013.01); *A61K 2039/70* (2013.01); *C12N 2760/14134* (2013.01); *C12N 2760/14152* (2013.01)

(58) Field of Classification Search
None
See application file for complete search history.

(56) References Cited

U.S. PATENT DOCUMENTS

| | | |
|---|---|---|
| 4,071,618 A | 1/1978 | Konobe et al. |
| 4,659,569 A | 4/1987 | Mitsuhashi et al. |
| 5,166,057 A | 11/1992 | Palese et al. |
| 5,578,473 A | 11/1996 | Palese et al. |
| 5,716,821 A | 2/1998 | Wertz et al. |
| 5,750,394 A | 5/1998 | Palese et al. |
| 5,786,199 A | 7/1998 | Palese |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,948,410 A | 9/1999 | Van Scharrenburg et al. |
| 5,994,526 A | 11/1999 | Meulewaeter et al. |
| 6,001,634 A | 12/1999 | Palese et al. |
| 6,033,886 A | 3/2000 | Conzelmann |
| 6,037,348 A | 3/2000 | Colacino et al. |
| 6,146,642 A | 11/2000 | Garcia-Sastre et al. |
| 6,169,175 B1 | 1/2001 | Frace et al. |
| 6,194,546 B1 | 2/2001 | Newton et al. |
| 6,270,958 B1 | 8/2001 | Olivo et al. |
| 6,271,011 B1 | 8/2001 | Lee et al. |
| 6,358,733 B1 | 3/2002 | Motwani et al. |
| 6,455,298 B1 | 9/2002 | Groner et al. |
| 6,544,785 B1 | 4/2003 | Palese et al. |
| 6,656,720 B2 | 12/2003 | Groner et al. |
| 6,825,036 B2 | 11/2004 | Makizumi et al. |
| 6,843,996 B1 | 1/2005 | Parkin et al. |
| 6,872,395 B2 | 3/2005 | Kawaoka |
| 6,890,710 B1 | 5/2005 | Palese et al. |
| 6,951,752 B2 | 10/2005 | Reiter et al. |
| 6,951,754 B2 | 10/2005 | Hoffmann |
| 6,974,695 B2 | 12/2005 | Vogels et al. |
| 7,037,707 B2 | 5/2006 | Webster et al. |
| 7,176,021 B2 | 2/2007 | Kawaoka |
| 7,211,378 B2 | 5/2007 | Kawaoka et al. |
| 7,226,774 B2 | 6/2007 | Kawaoka |
| 7,312,064 B2 | 12/2007 | Hoffmann |
| 7,335,356 B2 | 2/2008 | Hart et al. |
| 7,507,411 B2 | 3/2009 | Zhou et al. |
| 7,566,458 B2 | 7/2009 | Yang et al. |
| 7,585,657 B2 | 9/2009 | Kawaoka |
| 7,588,769 B2 | 9/2009 | Kawaoka |
| 7,601,356 B2 | 10/2009 | Jin et al. |
| 7,670,837 B2 | 3/2010 | Schwartz |
| 7,682,618 B2 | 3/2010 | Bavari et al. |
| 7,723,094 B2 | 5/2010 | Kawaoka et al. |
| 7,833,788 B2 | 11/2010 | Pau et al. |
| 7,883,844 B2 | 2/2011 | Nouchi et al. |
| 7,955,833 B2 | 6/2011 | Reiter et al. |
| 7,959,930 B2 | 6/2011 | De Wit et al. |

(Continued)

FOREIGN PATENT DOCUMENTS

| | | |
|---|---|---|
| AU | 2012204138 B2 | 5/2014 |
| AU | 2014202470 A1 | 11/2016 |

(Continued)

OTHER PUBLICATIONS

Marzi et al., Science, Apr. 2015, 348(6233):439-442. (Year: 2015).*

(Continued)

*Primary Examiner* — Stacy B Chen
(74) *Attorney, Agent, or Firm* — Schwegman Lundberg & Woessner, P.A.

(57) ABSTRACT

The invention provides a vaccine comprising a recombinant biologically contained filovirus and methods of making and using those viruses.

18 Claims, 112 Drawing Sheets

(56) References Cited

U.S. PATENT DOCUMENTS

| | | |
|---|---|---|
| 7,968,101 B2 | 6/2011 | Kawaoka et al. |
| 7,972,843 B2 | 7/2011 | Hoffmann |
| 7,993,924 B2 | 8/2011 | Billeter et al. |
| 8,012,736 B2 | 9/2011 | Hoffman et al. |
| 8,043,856 B2 | 10/2011 | Kawaoka et al. |
| 8,048,430 B2 | 11/2011 | Yang et al. |
| 8,057,806 B2 | 11/2011 | Kawaoka et al. |
| 8,093,033 B2 | 1/2012 | Kemble et al. |
| 8,114,415 B2 | 2/2012 | Hoffmann et al. |
| 8,119,337 B2 | 2/2012 | Gregersen |
| 8,119,388 B2 | 2/2012 | Schwartz et al. |
| 8,298,805 B2 | 10/2012 | Kawaoka |
| 8,309,099 B2 | 11/2012 | Hoffmann |
| 8,354,114 B2 | 1/2013 | Lu et al. |
| 8,357,376 B2 | 1/2013 | Liu et al. |
| 8,409,843 B2 | 4/2013 | Kemble et al. |
| 8,460,914 B2 | 6/2013 | Gregersen |
| 8,465,960 B2 | 6/2013 | Kawaoka et al. |
| 8,475,806 B2 | 7/2013 | Kawaoka |
| 8,507,247 B2 | 8/2013 | Kawaoka et al. |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 8,597,661 B2 | 12/2013 | Kawaoka et al. |
| 8,679,819 B2 | 3/2014 | Kawaoka |
| 8,877,209 B2 | 11/2014 | Kawaoka et al. |
| 8,900,595 B2 | 12/2014 | Kawaoka et al. |
| 9,101,653 B2 | 8/2015 | Kawaoka et al. |
| 9,109,013 B2 | 8/2015 | Kawaoka et al. |
| 9,222,118 B2 | 12/2015 | Kawaoka et al. |
| 9,254,318 B2 | 2/2016 | Kawaoka et al. |
| 9,284,533 B2 | 3/2016 | Bilsel et al. |
| 9,474,798 B2 | 10/2016 | Watanabe et al. |
| 9,757,446 B2 | 9/2017 | LeFebvre et al. |
| 9,890,363 B2 | 2/2018 | Kawaoka |
| 9,926,535 B2 | 3/2018 | Kawaoka et al. |
| 9,950,057 B2 | 4/2018 | Kawaoka et al. |
| 10,053,671 B2 | 8/2018 | Kawaoka et al. |
| 10,059,925 B2 | 8/2018 | Kawaoka et al. |
| 10,119,124 B2 | 11/2018 | Watanabe et al. |
| 10,130,697 B2 | 11/2018 | Watanabe |
| 10,172,934 B2 | 1/2019 | Kawaoka et al. |
| 10,246,686 B2 | 4/2019 | Kawaoka et al. |
| 10,358,630 B2 | 7/2019 | Kawaoka et al. |
| 10,494,613 B2 | 12/2019 | Kawaoka et al. |
| 10,513,692 B2 | 12/2019 | Kawaoka et al. |
| 10,633,422 B2 | 4/2020 | Kawaoka et al. |
| 10,808,229 B2 | 10/2020 | Kawaoka et al. |
| 11,007,262 B2 | 5/2021 | Watanabe et al. |
| 11,046,934 B2 | 6/2021 | Kawaoka et al. |
| 11,180,737 B2 | 11/2021 | Kawaoka et al. |
| 11,197,925 B2 | 12/2021 | Kawaoka et al. |
| 11,197,926 B2 | 12/2021 | Kawaoka et al. |
| 11,241,492 B2 | 2/2022 | Kawaoka et al. |
| 11,384,339 B2 | 7/2022 | Kawaoka et al. |
| 11,389,523 B2 | 7/2022 | Kawaoka et al. |
| 11,390,649 B2 | 7/2022 | Kawaoka et al. |
| 11,739,303 B2 | 8/2023 | Kawaoka et al. |
| 11,807,872 B2 | 11/2023 | Kawaoka et al. |
| 11,851,648 B2 | 12/2023 | Kawaoka et al. |
| 2002/0010143 A1 | 1/2002 | Barbosa et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2003/0194694 A1 | 10/2003 | Kawaoka |
| 2003/0215794 A1 | 11/2003 | Kawaoka et al. |
| 2004/0002061 A1 | 1/2004 | Kawaoka |
| 2004/0029251 A1 | 2/2004 | Hoffman et al. |
| 2004/0057967 A1 | 3/2004 | Bavari et al. |
| 2004/0063141 A1 | 4/2004 | Lok |
| 2004/0077086 A1 | 4/2004 | Reiter et al. |
| 2004/0132164 A1 | 7/2004 | Doyle et al. |
| 2004/0142322 A1 | 7/2004 | Malcolm et al. |
| 2004/0219170 A1 | 11/2004 | Kawaoka |
| 2004/0241139 A1 | 12/2004 | Hobom et al. |
| 2004/0242518 A1 | 12/2004 | Chen et al. |
| 2005/0003349 A1 | 1/2005 | Kawaoka |
| 2005/0037487 A1 | 2/2005 | Kawaoka et al. |
| 2005/0095583 A1 | 5/2005 | Pekosz et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266023 A1 | 12/2005 | Bavari et al. |
| 2005/0266026 A1 | 12/2005 | Hoffmann et al. |
| 2006/0057116 A1 | 3/2006 | Kawaoka et al. |
| 2006/0088909 A1 | 4/2006 | Compans |
| 2006/0099609 A1 | 5/2006 | Bavari et al. |
| 2006/0134138 A1 | 6/2006 | Kawaoka et al. |
| 2006/0166321 A1 | 7/2006 | Kawaoka et al. |
| 2006/0188977 A1 | 8/2006 | Schwartz et al. |
| 2006/0216702 A1 | 9/2006 | Compans et al. |
| 2006/0240515 A1 | 10/2006 | Dimitrov et al. |
| 2006/0246092 A1 | 11/2006 | Neirynck et al. |
| 2007/0141699 A1 | 6/2007 | Kawaoka |
| 2007/0231348 A1 | 10/2007 | Kawaoka et al. |
| 2008/0009031 A1 | 1/2008 | Kawaoka |
| 2008/0187557 A1 | 8/2008 | Sambhara |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0292658 A1 | 11/2008 | De Wit et al. |
| 2008/0293040 A1 | 11/2008 | Kawaoka et al. |
| 2008/0311148 A1 | 12/2008 | Hoffmann |
| 2008/0311149 A1 | 12/2008 | Hoffmann |
| 2009/0017444 A1 | 1/2009 | Kawaoka et al. |
| 2009/0047728 A1 | 2/2009 | Kawaoka et al. |
| 2009/0074812 A1 | 3/2009 | Watanabe et al. |
| 2009/0081252 A1 | 3/2009 | Gregersen |
| 2009/0181446 A1 | 7/2009 | Nouchi et al. |
| 2009/0311669 A1 | 12/2009 | Kawaoka |
| 2009/0324640 A1 | 12/2009 | Kawaoka et al. |
| 2010/0080825 A1 | 4/2010 | Kawaoka et al. |
| 2010/0112000 A1 | 5/2010 | Schwartz |
| 2010/0183671 A1 | 7/2010 | Gregersen et al. |
| 2010/0247572 A1 | 9/2010 | Kawaoka |
| 2010/0267116 A1 | 10/2010 | Kawaoka et al. |
| 2011/0020374 A1 | 1/2011 | Frazer |
| 2011/0027314 A1 | 2/2011 | Broeker |
| 2011/0045022 A1 | 2/2011 | Tsai |
| 2011/0081373 A1 | 4/2011 | Kawaoka et al. |
| 2011/0110978 A1 | 5/2011 | Kawaoka et al. |
| 2011/0159031 A1 | 6/2011 | Falkner et al. |
| 2011/0236417 A1 | 9/2011 | Watanabe et al. |
| 2011/0263554 A1 | 10/2011 | Kawaoka et al. |
| 2011/0300604 A1 | 12/2011 | Kawaoka et al. |
| 2012/0020997 A1 | 1/2012 | Hoffman et al. |
| 2012/0034600 A1 | 2/2012 | Gregersen |
| 2012/0058124 A1 | 3/2012 | Kurosawa et al. |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2012/0251568 A1 | 10/2012 | Garcia-sastre et al. |
| 2013/0095135 A1 | 4/2013 | Collignon et al. |
| 2013/0183741 A1 | 7/2013 | Park et al. |
| 2013/0230552 A1 | 9/2013 | Kawaoka et al. |
| 2013/0243744 A1 | 9/2013 | Betenbaugh |
| 2013/0316434 A1 | 11/2013 | Reiter et al. |
| 2014/0227310 A1 | 8/2014 | Li et al. |
| 2015/0017205 A1 | 1/2015 | Kawaoka et al. |
| 2015/0166967 A1 | 6/2015 | Kawaoka et al. |
| 2015/0307851 A1 | 10/2015 | Kawaoka et al. |
| 2015/0368621 A1 | 12/2015 | Kawaoka et al. |
| 2016/0024193 A1 | 1/2016 | Ayalon et al. |
| 2016/0024479 A1 | 1/2016 | Kawaoka et al. |
| 2016/0115518 A1 | 4/2016 | Kawaoka et al. |
| 2016/0208223 A1 | 7/2016 | Kawaoka et al. |

(56) References Cited

U.S. PATENT DOCUMENTS

| | | | |
|---|---|---|---|
| 2016/0215040 A1 | 7/2016 | Kyratsous et al. |
| 2016/0355790 A1 | 12/2016 | Kawaoka et al. |
| 2017/0058265 A1 | 3/2017 | Kawaoka et al. |
| 2017/0067029 A1 | 3/2017 | Kawaoka et al. |
| 2017/0096645 A1 | 4/2017 | Watanabe et al. |
| 2017/0097334 A1 | 4/2017 | Kawaoka et al. |
| 2017/0121391 A1 | 5/2017 | Kawaoka et al. |
| 2017/0258888 A1 | 9/2017 | Kawaoka |
| 2017/0298120 A1 | 10/2017 | Sasisekharan |
| 2017/0354730 A1 | 12/2017 | Kawaoka et al. |
| 2018/0245054 A1 | 8/2018 | Kawaoka et al. |
| 2018/0273588 A1 | 9/2018 | Kawaoka et al. |
| 2018/0340152 A1 | 11/2018 | Kawaoka et al. |
| 2019/0032023 A1 | 1/2019 | Kawaoka et al. |
| 2019/0048324 A1 | 2/2019 | Kawaoka et al. |
| 2019/0117759 A1 | 4/2019 | Wantanabe et al. |
| 2019/0167781 A1 | 6/2019 | Kawaoka et al. |
| 2020/0188506 A1 | 6/2020 | Kawaoka et al. |
| 2020/0237899 A1 | 7/2020 | Kawaoka et al. |
| 2020/0263142 A1 | 8/2020 | Kawaoka et al. |
| 2020/0263143 A1 | 8/2020 | Kawaoka et al. |
| 2020/0291384 A1 | 9/2020 | Kawaoka et al. |
| 2021/0061862 A1 | 3/2021 | Kawaoka et al. |
| 2021/0102178 A1 | 4/2021 | Kawaoka et al. |
| 2021/0228708 A1 | 7/2021 | Smith et al. |
| 2021/0246432 A1 | 8/2021 | Kawaoka et al. |
| 2021/0252130 A1 | 8/2021 | Watanabe et al. |
| 2021/0299249 A1 | 9/2021 | Kawaoka et al. |
| 2022/0025339 A1 | 1/2022 | Kawaoka et al. |
| 2022/0202926 A1 | 6/2022 | Kawaoka et al. |
| 2022/0202927 A1 | 6/2022 | Kawaoka et al. |
| 2022/0241396 A1 | 8/2022 | Kawaoka et al. |
| 2023/0321217 A1 | 10/2023 | Kawaoka et al. |
| 2023/0346911 A1 | 11/2023 | Kawaoka et al. |
| 2024/0010995 A1 | 1/2024 | Kawaoka et al. |
| 2024/0076632 A1 | 3/2024 | Kawaoka et al. |
| 2024/0238403 A1 | 7/2024 | Kawaoka et al. |
| 2024/0318167 A1 | 9/2024 | Kawaoka et al. |

FOREIGN PATENT DOCUMENTS

| | | |
|---|---|---|
| AU | 2014290203 B2 | 12/2020 |
| AU | 2017221444 B2 | 11/2021 |
| BR | PI0410702 B1 | 4/2022 |
| CA | 2379012 A1 | 1/2001 |
| CA | 2816242 C | 1/2019 |
| CN | 1826407 A | 8/2006 |
| CN | 101472941 A | 7/2009 |
| CN | 1826407 B | 9/2013 |
| CN | 103540614 B | 2/2018 |
| CN | 109477074 A | 3/2019 |
| CN | 113874496 A | 12/2021 |
| CN | 114929269 A | 8/2022 |
| EP | 0702085 A1 | 3/1996 |
| EP | 0704533 A1 | 4/1996 |
| EP | 1201760 A1 | 5/2002 |
| EP | 2010557 B1 | 2/2014 |
| EP | 1572910 B1 | 12/2015 |
| EP | 1631663 B1 | 8/2016 |
| EP | 2747778 B1 | 12/2017 |
| EP | 3009507 B1 | 6/2020 |
| EP | 2493912 B1 | 7/2020 |
| EP | 3022296 B1 | 12/2022 |
| IL | 171831 A | 5/2015 |
| JP | 07-203958 | 8/1995 |
| JP | H08510749 A | 11/1996 |
| JP | H10500113 A | 1/1998 |
| JP | 2002536992 | 11/2002 |
| JP | 2003528570 A | 9/2003 |
| JP | 2004500842 A | 1/2004 |
| JP | 2004531232 A | 10/2004 |
| JP | 2005523698 A | 8/2005 |
| JP | 2005245302 A | 9/2005 |
| JP | 2005535288 A | 11/2005 |
| JP | 2006525815 A | 11/2006 |
| JP | 2007518395 A | 7/2007 |
| JP | 2007525175 A | 9/2007 |
| JP | 2007529997 A | 11/2007 |
| JP | 2008520248 A | 6/2008 |
| JP | 2009511084 A | 3/2009 |
| JP | 2009514850 A | 4/2009 |
| JP | 2009523252 A | 6/2009 |
| JP | 2009532352 A | 9/2009 |
| JP | 2009539965 A | 11/2009 |
| JP | 2010530248 A | 9/2010 |
| JP | 2011530295 A | 12/2011 |
| JP | 101113432 B1 | 2/2012 |
| JP | 4927290 | 5/2012 |
| JP | 4927290 B2 | 5/2012 |
| JP | 2013507990 A | 3/2013 |
| JP | 2013511280 A | 4/2013 |
| JP | 2014039551 A | 3/2014 |
| JP | 2014131516 A | 7/2014 |
| JP | 2016500007 A | 1/2016 |
| JP | 2016521553 A | 7/2016 |
| JP | 2016144463 A | 8/2016 |
| JP | 2016524915 A | 8/2016 |
| JP | 2016169225 A | 9/2016 |
| JP | 2017527557 | 9/2017 |
| JP | 2017197555 A | 11/2017 |
| JP | 2018064493 A | 4/2018 |
| JP | 6352974 B2 | 6/2018 |
| JP | 6375329 B2 | 7/2018 |
| JP | 2019510481 A | 4/2019 |
| JP | 2020010711 A | 1/2020 |
| JP | 2020114250 A | 7/2020 |
| JP | 2021500891 A | 1/2021 |
| JP | 2021036878 A | 3/2021 |
| JP | 2021184761 A | 12/2021 |
| JP | 2021536228 A | 12/2021 |
| JP | 2022066209 A | 4/2022 |
| JP | 2022522112 A | 4/2022 |
| JP | 2022527235 A | 6/2022 |
| JP | 2022172369 A | 11/2022 |
| JP | 2022551805 A | 12/2022 |
| JP | 2023109845 A | 8/2023 |
| MX | 285206 | 3/2011 |
| NO | 341506 | 11/2017 |
| WO | WO-9610631 A1 | 4/1996 |
| WO | WO-9610632 A1 | 4/1996 |
| WO | WO-9640955 A1 | 12/1996 |
| WO | WO-9737000 A1 | 10/1997 |
| WO | WO-9802530 A1 | 1/1998 |
| WO | WO-9848834 A1 | 11/1998 |
| WO | WO-9853078 A1 | 11/1998 |
| WO | WO-9928445 A1 | 6/1999 |
| WO | WO-0053786 A1 | 9/2000 |
| WO | WO-0060050 A2 | 10/2000 |
| WO | WO-2000060050 A2 | 10/2000 |
| WO | WO-0060050 A3 | 1/2001 |
| WO | WO-2001004333 A1 | 1/2001 |
| WO | WO-2001025462 A1 | 4/2001 |
| WO | WO-0179273 A2 | 10/2001 |
| WO | WO-2001079273 A2 | 10/2001 |
| WO | WO-0183794 A2 | 11/2001 |
| WO | WO-2001083794 A2 | 11/2001 |
| WO | WO-0210143 A1 | 1/2002 |
| WO | WO-02064757 A2 | 8/2002 |
| WO | WO-02074795 A2 | 9/2002 |
| WO | WO-03068923 A2 | 8/2003 |
| WO | WO-2003068923 A2 | 8/2003 |
| WO | WO-03076462 A1 | 9/2003 |
| WO | WO-2003080846 A1 | 10/2003 |
| WO | WO-03091401 A2 | 11/2003 |
| WO | WO-2003091401 A2 | 11/2003 |
| WO | WO-2004142322 A1 | 7/2004 |
| WO | WO-2004094466 A2 | 11/2004 |
| WO | WO-04112831 A2 | 12/2004 |
| WO | WO-2004112831 A2 | 12/2004 |
| WO | WO-2004112831 A3 | 12/2004 |
| WO | WO-05028658 A2 | 3/2005 |
| WO | WO-05028658 A3 | 3/2005 |
| WO | WO-2005028658 A2 | 3/2005 |
| WO | WO-2005062820 A2 | 7/2005 |

(56) References Cited

FOREIGN PATENT DOCUMENTS

| | | |
|---|---|---|
| WO | WO-2006051069 A2 | 5/2006 |
| WO | WO-2007044024 A2 | 4/2007 |
| WO | WO-2007044024 A3 | 4/2007 |
| WO | WO-2007126810 A2 | 11/2007 |
| WO | WO-2007126810 A3 | 11/2007 |
| WO | WO-2007146057 A2 | 12/2007 |
| WO | WO-2007146057 A3 | 12/2007 |
| WO | WO-08156681 A3 | 12/2008 |
| WO | WO-2008147496 A2 | 12/2008 |
| WO | WO-2008147496 A3 | 12/2008 |
| WO | WO-2008156681 A2 | 12/2008 |
| WO | WO-2008156778 A2 | 12/2008 |
| WO | WO-2008156778 A3 | 12/2008 |
| WO | WO-2008157583 A1 | 12/2008 |
| WO | WO-09008921 A3 | 1/2009 |
| WO | WO-09008921 A9 | 1/2009 |
| WO | WO-2009007244 A2 | 1/2009 |
| WO | WO-2009008921 A2 | 1/2009 |
| WO | WO-2009014919 A2 | 1/2009 |
| WO | WO-2008156778 A9 | 2/2009 |
| WO | WO-09128867 A2 | 10/2009 |
| WO | WO-2009152181 A1 | 12/2009 |
| WO | WO-2009128867 A3 | 3/2010 |
| WO | WO-2010053573 A2 | 5/2010 |
| WO | WO-2010053573 A3 | 7/2010 |
| WO | WO-2011014645 A1 | 2/2011 |
| WO | WO-2011056591 A1 | 5/2011 |
| WO | WO-2011087839 A1 | 7/2011 |
| WO | WO 2011/130627 A2 * | 10/2011 |
| WO | WO-2011126370 A1 | 10/2011 |
| WO | WO-2012045882 A2 | 4/2012 |
| WO | WO-2012177924 A2 | 12/2012 |
| WO | WO-2013032942 A1 | 3/2013 |
| WO | WO-2013032942 A9 | 3/2013 |
| WO | WO-2013034069 A1 | 3/2013 |
| WO | WO-2013087945 A2 | 6/2013 |
| WO | WO-2013148302 A1 | 10/2013 |
| WO | WO-2014195920 A2 | 12/2014 |
| WO | WO-2015009743 A1 | 1/2015 |
| WO | WO-2015134488 A1 | 9/2015 |
| WO | WO-2015142671 A2 | 9/2015 |
| WO | WO-2015196150 A2 | 12/2015 |
| WO | WO-2015196150 A3 | 12/2015 |
| WO | WO-2016207853 A2 | 12/2016 |
| WO | WO-2017007839 A1 | 1/2017 |
| WO | WO-2017040203 A1 | 3/2017 |
| WO | WO-2017136575 A1 | 8/2017 |
| WO | WO-2017143236 A1 | 8/2017 |
| WO | WO-2019084310 A1 | 5/2019 |
| WO | WO-2020033527 A2 | 2/2020 |
| WO | WO-2020041311 A1 | 2/2020 |
| WO | WO-2020/033527 A3 | 3/2020 |
| WO | WO-2020061443 A2 | 3/2020 |
| WO | WO-2020163804 A1 | 8/2020 |
| WO | WO-2020167432 A2 | 8/2020 |
| WO | WO-2020223699 A1 | 11/2020 |
| WO | WO-2020167432 A3 | 12/2020 |
| WO | WO-2020264141 A1 | 12/2020 |
| WO | WO-2021041624 A2 | 3/2021 |
| WO | WO-2021041624 A3 | 5/2021 |
| WO | WO-2021150874 A1 | 7/2021 |
| WO | WO-2021195410 A1 | 9/2021 |
| WO | WO-2021242597 A1 | 12/2021 |
| WO | WO-2022245888 A1 | 11/2022 |
| WO | WO-2023125889 A1 | 7/2023 |
| WO | WO-2023164556 A2 | 8/2023 |
| WO | WO-2023164556 A3 | 10/2023 |
| WO | WO-2024015510 A1 | 1/2024 |
| WO | WO-2024197167 A1 | 9/2024 |

OTHER PUBLICATIONS

Wolff and Reichl, Expert Rev. Vaccines, 2011, 10(10):1451-1475. (Year: 2011).*

"Japanese Application Serial No. 2021-506434, Response filed Feb. 18, 2022 to Office Action mailed Dec. 21, 2021", Claims not amended in response filed.
"Japanese Application Serial No. 2021-506434, Notification of Reasons for Refusal mailed May 10, 2022", w English translation, 10 pgs.
"Japanese Application Serial No. 2021-506434, Response filed Nov. 7, 2022 to Notification of Reasons for Refusal mailed May 10, 2022", w English Claims, 13 pgs.
"International Application Serial No. PCT/US2019/045476, International Search Report mailed Feb. 11, 2020", 8 pgs.
"International Application Serial No. PCT/US2019/045476, Invitation to Pay Additional Fees mailed Dec. 17, 2019", 14 pgs.
"International Application Serial No. PCT/US2019/045476, Written Opinion mailed Feb. 11, 2020", 13 pgs.
Halfmann, P., et al., "Replication-deficient ebolavirus as a vaccine candidate", Journal of Virology, vol. 83, No. 8, XP002563468; ISSN: 1098-5514; the whole document, (Apr. 2009).
U.S. Appl. No. 16/785,449, filed Feb. 7, 2020, Humanized Cell Line.
U.S. Appl. No. 17/004,583, filed Aug. 27, 2020, Recombinant Influenza Viruses With Stabilized HA for Replication in Eggs.
U.S. Appl. No. 17/155,625, filed Jan. 22, 2021, Recombinant Influenza Viruses With Stabilized HA.
U.S. Appl. No. 17/212,836, filed Mar. 25, 2021, Recombinant Multivalent Influenza Viruses.
U.S. Appl. No. 18/173,535, filed Feb. 23, 2023, Broadly Protective Influenza B Virus Vaccines.
U.S. Appl. No. 17/936,194, filed Sep. 28, 2022, Compositions Comprising Complexes Displaying Antigens and Methods of Using the Compositions.
Result 17, NCBI Blast nucleotide search of Seq ID No. 2, database "nr", (Jul. 18, 2006), 3 pgs.
Result 1, NCBI Blast nucleotide search of Seq ID No. 3, database "nr"; Result 4, NCBI Blast nucleotide search of Seq ID No. 4, database "nr", (Jul. 22, 2006), 11 pgs.
Result 2, NCBI Blast nucleotide search of Seq ID No. 5, database "nr"; Result 4, NCBI Blast nucleotide search of Seq ID No. 6, database "nr", (Jul. 22, 2006), 6 pgs.
Results 1, NCBI Blast nucleotide search of Seq ID No. 7, database "nr"; Result 1, NCBI Blast nucleotide search of Seq ID No. 8, database "nr", (Jul. 23, 2006), 8 pgs.
Result 7, NCBI Blast nucleotide search of Seq ID: 1, database "nr", (Jul. 18, 2006), 3 pgs.
Flumisttm Package Insert Template, [Online]. Retrieved from the Internet: http://www.fda.gov/downloads/BiologicsBioodVaccines!Vaccines/ApprovedProducts/UCM294307.pdf, (Mar. 1, 2012), 26 pgs.
"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.
"U.S. Appl. No. 10/855,975 Response filed Aug. 28, 2007 to Final Office Action mailed Jun. 28, 2007", 16 pgs.
"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.
"Final O.A Jun. 28, 2007", 5 pgs.
"Application Serial No. 04809419.7, Office Action Mailed Sep. 9, 2009", 3 pgs.
"U.S. Appl. No. 09/834,095, Advisory Action mailed Jan. 8, 2004", 3 pgs.
"U.S. Appl. No. 09/834,095, Final Office Action mailed Aug. 26, 2003", 12 pgs.
"U.S. Appl. No. 09/834,095, Non-Final Office Action mailed Nov. 4, 2002", 12 pgs.
"U.S. Appl. No. 09/834,095, Notice of Allowance mailed Sep. 27, 2004", 13 pgs.

(56) References Cited

OTHER PUBLICATIONS

"U.S. Appl. No. 09/834,095, Office Action mailed Apr. 20, 2004", 11 pgs.
"U.S. Appl. No. 09/834,095, Response filed Feb. 4, 2003 to Office Action mailed Nov. 4, 2002", 14 pgs.
"U.S. Appl. No. 09/834,095, Response filed Jun. 12, 2003 to Restriction Requirement mailed Apr. 22, 2003", 2 pgs.
"U.S. Appl. No. 09/834,095, Response filed Jun. 18, 2004 to Office Action mailed Apr. 20, 2004", 11 pgs.
"U.S. Appl. No. 09/834,095, Response filed Aug. 1, 2002 to Restriction Requirement nailed Jul. 1, 2002", 3 pgs.
"U.S. Appl. No. 09/834,095, Response filed Nov. 26, 2003 to Final Office Action mailed Aug. 26, 2003", 10 pgs.
"U.S. Appl. No. 09/834,095, Restriction Requirement mailed Apr. 22, 2003", 5 pgs.
"U.S. Appl. No. 09/834,095, Restriction Requirement mailed Jul. 1, 2002", 9 pgs.
"U.S. Appl. No. 09/834,095, Supplemental Amendment filed Aug. 4, 2004", 7 pgs.
"U.S. Appl. No. 10/081,170, Advisory Action mailed Sep. 27, 2004", 3 pgs.
"U.S. Appl. No. 10/081,170, Final Office Action mailed Apr. 12, 2006", 7 pgs.
"U.S. Appl. No. 10/081,170, Final Office Action mailed Jul. 13, 2004", 8 pgs.
"U.S. Appl. No. 10/081,170, Non Final Office Action mailed Jan. 15, 2004", 9 pgs.
"U.S. Appl. No. 10/081,170, Non Final Office Action mailed Feb. 8, 2005", 9 pgs.
"U.S. Appl. No. 10/081,170, Non Final Office Action mailed Aug. 24, 2005", 9 pgs.
"U.S. Appl. No. 10/081,170, Notice of Allowance mailed Sep. 18, 2006", 8 Pgs.
"U.S. Appl. No. 10/081,170, Preliminary Amendment filed May 20, 2003", 2 pgs.
"U.S. Appl. No. 10/081,170, Preliminary Amendment filed Jun. 6, 2002", 1 pg.
"U.S. Appl. No. 10/081,170, Response filed Jan. 24, 2006 to Non Final Office Action mailed Aug. 24, 2005", 11 pgs.
"U.S. Appl. No. 10/081,170, Response filed Apr. 12, 2004 to Non Final Office Action mailed Jan. 15, 2004", 12 pgs.
"U.S. Appl. No. 10/081,170, Response filed Jun. 8, 2005 to Non Final Office Action mailed Feb. 8, 2005", 11 pgs.
"U.S. Appl. No. 10/081,170, Response filed Aug. 17, 2006 to Final Office Action mailed Apr. 12, 2006", 9 pgs.
"U.S. Appl. No. 10/081,170, Response filed Sep. 13, 2004 to Final Office Action mailed Jul. 13, 2004", 10 pgs.
"U.S. Appl. No. 10/081,170, Response filed Oct. 10, 2003 to Restriction Requirement mailed Sep. 10, 2003", 3 pgs.
"U.S. Appl. No. 10/081,170, Restriction Requirement mailed Sep. 10, 2003", 4 pgs.
"U.S. Appl. No. 10/353,856, Final Office Action mailed Jun. 1, 2006", 10 pgs.
"U.S. Appl. No. 10/353,856, Non-Final Office Action mailed Sep. 30, 2005", 9 pgs.
"U.S. Appl. No. 10/353,856, Non-Final Office Action mailed Dec. 16, 2004", 11 pgs.
"U.S. Appl. No. 10/353,856, Notice of Allowance mailed Oct. 18, 2006", 9 pgs.
"U.S. Appl. No. 10/353,856, Preliminary Amendment filed May 20, 2003", 2 pgs.
"U.S. Appl. No. 10/353,856, PTO Response to 312 Amendment mailed Mar. 8, 2007", 2 pgs.
"U.S. Appl. No. 10/353,856, Response filed Feb. 28, 2006 to Non-Final Office Action mailed Sep. 30, 2005", 10 pgs.
"U.S. Appl. No. 10/353,856, Response filed Apr. 7, 2005 to Non-Final Office Action mailed Dec. 16, 2004", 10 pgs.
"U.S. Appl. No. 10/353,856, Response filed Aug. 17, 2006 to Final Office Action mailed Jun. 1, 2006", 11 pgs.

"U.S. Appl. No. 10/353,856, Response filed Oct. 8, 2004 to Restriction Requirement mailed Sep. 10, 2004", 2 pgs.
"U.S. Appl. No. 10/353,856, Restriction Requirement mailed Sep. 10, 2004", 5 pgs.
"U.S. Appl. No. 10/353,856, Supplemental Amendment filed Jan. 9, 2007", 4 pgs.
"U.S. Appl. No. 10/353,856, Supplemental Preliminary Amendment filed Jun. 23, 2003", 4 pgs.
"U.S. Appl. No. 10/827,995, Final Office Action mailed Nov. 15, 2006", 10 pgs.
"U.S. Appl. No. 10/827,995, Non-Final Office Action mailed Jun. 2, 2006", 15 pgs.
"U.S. Appl. No. 10/827,995, Non-Final Office Action mailed Oct. 25, 2007", 7 pgs.
"U.S. Appl. No. 10/827,995, Notice of Allowance mailed Feb. 17, 2009", 9 pgs.
"U.S. Appl. No. 10/827,995, Notice of Allowance mailed Jul. 2, 2008", 9 pgs.
"U.S. Appl. No. 10/827,995, Notice of Allowance mailed Oct. 17, 2008", 7 pgs.
"U.S. Appl. No. 10/827,995, Notice of Non-Compliant Amendment Jul. 25, 2007", 4 pgs.
"U.S. Appl. No. 10/827,995, Proposed Examiner's Amendment mailed Jun. 5, 2008", 6 pgs.
"U.S. Appl. No. 10/827,995, Response filed Mar. 3, 2008 to Office Action mailed Oct. 25, 2007", 10 pgs.
"U.S. Appl. No. 10/827,995, Response filed May 14, 2007 Final Office Action mailed Nov. 15, 2006", 16 pgs.
"U.S. Appl. No. 10/827,995, Response filed Aug. 13, 2007 to Notice of Non-Compliant Amendment Jul. 25, 2007", 16 pgs.
"U.S. Appl. No. 10/827,995, Response filed Aug. 17, 2006 Non-Final Office Action mailed Jun. 2, 2006", 15 pgs.
"U.S. Appl. No. 10/855,875 , Response filed May 17, 2012 to Non Final Office Action mailed Mar. 15, 2012", 15 pgs.
"U.S. Appl. No. 10/855,875, Final Office Action mailed Mar. 11, 2008", FOAR, 20 Pgs.
"U.S. Appl. No. 10/855,875, Final Office Action mailed Aug. 2, 2006", 34 pgs.
"U.S. Appl. No. 10/855,875, Final Office Action mailed Dec. 10, 2010", 15 pgs.
"U.S. Appl. No. 10/855,875, Non Final Office Action mailed Mar. 15, 2012", 15 pgs.
"U.S. Appl. No. 10/855,875, Non-Final Office Action mailed Feb. 19, 2010", 7 pgs.
"U.S. Appl. No. 10/855,875, Non-Final Office Action mailed May 3, 2007", 13 pgs.
"U.S. Appl. No. 10/855,875, Non-Final Office Action mailed Aug. 7, 2009", 32 pgs.
"U.S. Appl. No. 10/855,875, Non-Final Office Action mailed Nov. 6, 2008", 12 pgs.
"U.S. Appl. No. 10/855,875, Non-Final Office Action mailed Nov. 30, 2005", 13 pgs.
"U.S. Appl. No. 10/855,875, Notice of Allowance mailed Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action mailed Aug. 2, 2007", 14 pgs.
"U.S. Appl. No. 10/855,875, Response filed Mar. 18, 2011 to Final Office Action mailed Dec. 10, 2010", 15 pgs.
"U.S. Appl. No. 10/855,875, Response filed Aug. 17, 2010 to Non Final Office Action mailed Feb. 19, 2010", 20 pgs.
"U.S. Appl. No. 10/855,875, Response filed Dec. 7, 2009 to Non Final Office Action mailed Aug. 7, 2009", 15 pgs.
"U.S. Appl. No. 10/855,875, Response filed Mar. 31, 2009 to Non Final Office Action mailed Nov. 6, 2008", 14 pgs.
"U.S. Appl. No. 10/855,875, Response filed May 1, 2006 Non-Final Office Action mailed Nov. 30, 2005", 13 pgs.
"U.S. Appl. No. 10/855,875, Response filed Aug. 18, 2008 to final Office Action mailed Mar. 11, 2008", 15 pgs.
"U.S. Appl. No. 10/855,875, Response filed Sep. 20, 2005 to Restriction Requirement mailed Jul. 26, 2005", 4 pgs.

(56) References Cited

OTHER PUBLICATIONS

"U.S. Appl. No. 10/855,875, Restriction Requirement mailed Dec. 23, 2011", 9 pgs.
"U.S. Appl. No. 10/855,875, Restriction Requirement mailed Jul. 26, 2005", 9 pgs.
"U.S. Appl. No. 10/855,975, Advisory Action mailed Sep. 6, 2006", 3 pgs.
"U.S. Appl. No. 10/855,975, Advisory Action mailed Sep. 13, 2007", 3 pgs.
"U.S. Appl. No. 10/855,975, Advisory Action mailed Dec. 24, 2008", 4 pgs.
"U.S. Appl. No. 10/855,975, Final Office Action mailed May 17, 2006", 7 pgs.
"U.S. Appl. No. 10/855,975, Final Office Action mailed Jun. 28, 2007", 7 pgs.
"U.S. Appl. No. 10/855,975, Final Office Action mailed Aug. 7, 2008", 5 pgs.
"U.S. Appl. No. 10/855,975, Non-Final Office Action mailed Jan. 4, 2008", 10 pgs.
"U.S. Appl. No. 10/855,975, Non-Final Office Action mailed Jan. 19, 2007", 7 pgs.
"U.S. Appl. No. 10/855,975, Non-Final Office Action mailed May 29, 2009", 5 pgs.
"U.S. Appl. No. 10/855,975, Non-Final Office Action mailed Nov. 30, 2005", 11 pgs.
"U.S. Appl. No. 10/855,975, Notice of Allowance mailed Dec. 16, 2009", 19 pgs.
"U.S. Appl. No. 10/855,975, Response filed Jan. 29, 2009 to Advisory Action mailed Dec. 24, 2008", 15 pgs.
"U.S. Appl. No. 10/855,975, Response filed Feb. 28, 2006 to Non-Final Office Action mailed Nov. 30, 2005", 15 pgs.
"U.S. Appl. No. 10/855,975, Response filed Apr. 3, 2008 to Non Final Office Action mailed Jan. 4, 2008", 16 pgs.
"U.S. Appl. No. 10/855,975, Response filed Apr. 19, 2007 to Non-Final Office Action mailed Jan. 19, 2007", 16 pgs.
"U.S. Appl. No. 10/855,975, Response filed Aug. 13, 2009 to Non Final Office Action mailed May 29, 2009", 19 pgs.
"U.S. Appl. No. 10/855,975, Response filed Aug. 17, 2006 to Final Office Action mailed May 17, 2006", 13 pgs.
"U.S. Appl. No. 10/855,975, Response filed Aug. 28, 2007 to Final Office Action mailed Jun. 28, 2007", 15 pgs.
"U.S. Appl. No. 10/855,975, Response filed Sep. 28, 2005 to Restriction Requirement mailed Jul. 12, 2005", 3 pgs.
"U.S. Appl. No. 10/855,975, Response filed Dec. 11, 2008 to Final Office Action mailed Aug. 7, 2008", 14 pgs.
"U.S. Appl. No. 10/855,975, Restriction Requirement mailed Jul. 12, 2005", 8 pgs.
"U.S. Appl. No. 10/855,875, Response filed Nov. 2, 2007 to Office Action mailed May 3, 2007", 16 pgs.
"U.S. Appl. No. 11/043,768 Non-Final Office Action mailed Sep. 27, 2010", 8 pgs.
"U.S. Appl. No. 11/043,768, Final Office Action mailed Jun. 27, 2008", 8 pgs.
"U.S. Appl. No. 11/043,768, Non-Final Office Action mailed Feb. 23, 2010", 6 pgs.
"U.S. Appl. No. 11/043,768, Non-Final Office Action mailed Feb. 23, 2009", 7 pgs.
"U.S. Appl. No. 11/043,768, Non-Final Office Action mailed Nov. 28, 2007", 9 pgs.
"U.S. Appl. No. 11/043,768, Notice of Allowance mailed Jun. 29, 2011", 12 pgs.
"U.S. Appl. No. 11/043,768, Response filed May 2, 2011 to Final Office Action mailed Feb. 3, 2011", 11 pgs.
"U.S. Appl. No. 11/043,768, Response filed Jun. 15, 2010 to Non Final Office Action mailed Feb. 23, 2010", 9 pgs.
"U.S. Appl. No. 11/043,768, Response filed Jun. 23, 2009 to Non-Final Office Action mailed Feb. 23, 2009", 9 pgs.
"U.S. Appl. No. 11/043,768, Response filed Sep. 13, 2007 to Restriction Requirement mailed Mar. 13, 2007", 10 pgs.

"U.S. Appl. No. 11/043,768, Response filed Oct. 26, 2010 to Non Final Office Action mailed Sep. 27, 2010", 11 pgs.
"U.S. Appl. No. 11/043,768, Response filed Dec. 12, 2008 to Final Office Action mailed Jun. 27, 2008", 9 pgs.
"U.S. Appl. No. 11/043,768, Response filed Mar. 10, 2008 to Office Action mailed Nov. 28, 2007", 12 pgs.
"U.S. Appl. No. 11/043,768, Restriction Requirement mailed Mar. 13, 2007", 9 pgs.
"U.S. Appl. No. 11/043,786, Final Office Action mailed Feb. 3, 2011", 10 pgs.
"U.S. Appl. No. 11/283,498, Non Final Office Action mailed Sep. 3, 2009", 5 pgs.
"U.S. Appl. No. 11/283,498, Non Final Office Action mailed Jul. 9, 2007", 7 pgs.
"U.S. Appl. No. 11/283,498, Non-Final Office Action mailed Jan. 23, 2008", 20 pgs.
"U.S. Appl. No. 11/283,498, Non-Final Office Action mailed Apr. 29, 2010", 10 pgs.
"U.S. Appl. No. 11/283,498, Notice of Allowance mailed Feb. 23, 2011", 9 pgs.
"U.S. Appl. No. 11/283,498, Response filed Jan. 4, 2010 to Non Final Office Action mailed Sep. 3, 2009", 12 pgs.
"U.S. Appl. No. 11/283,498, Response filed Oct. 28, 2010 to Non Final Office Action mailed Apr. 29, 2010", 13 pgs.
"U.S. Appl. No. 11/283,498, Response filed Nov. 7, 2007 to Office Action mailed Jul. 9, 2007", 17 pgs.
"U.S. Appl. No. 11/283,498, Response filed Apr. 16, 2007 to Restriction Requirement mailed Oct. 16, 2006", 17 pgs.
"U.S. Appl. No. 11/283,498, Response filed Jul. 22, 2008 to Non Final Office Action mailed Jan. 23, 2008", 12 pgs.
"U.S. Appl. No. 11/283,498, Restriction Requirement mailed Oct. 16, 2006", 6 pgs.
"U.S. Appl. No. 11/283,498, Supplemental Amendment Response to Non Final Office Action mailed Oct. 28, 2010", 11 pgs.
"U.S. Appl. No. 11/509,249, Final Office Action mailed Jun. 12, 2008", 5 pgs.
"U.S. Appl. No. 11/509,249, Non Final Office Action with Restriction Requirement mailed Aug. 24, 2007", 8 pgs.
"U.S. Appl. No. 11/509,249, Notice of Allowance mailed Apr. 9, 2009", 7 pgs.
"U.S. Appl. No. 11/509,249, Notice of Allowance mailed Nov. 17, 2008", 4 pgs.
"U.S. Appl. No. 11/509,249, Response filed Feb. 20, 2008 to Non Final Office Action mailed Aug. 24, 2007", 11 pgs.
"U.S. Appl. No. 11/509,249, Response filed Oct. 6, 2008 to Office Action mailed Jun. 12, 2008", 11 pgs.
"U.S. Appl. No. 11/644,179 , Response filed Oct. 21, 2013 to Final Office Action mailed May 21, 2013", 8 pgs.
"U.S. Appl. No. 11/644,179, Final Office Action mailed May 21, 2013", 11 pgs.
"U.S. Appl. No. 11/644,179, Final Office Action mailed Jul. 2, 2010", 8 pgs.
"U.S. Appl. No. 11/644,179, Non Final Office Action mailed Nov. 29, 2012", 19 pgs.
"U.S. Appl. No. 11/644,179, Non Final Office Action mailed Dec. 8, 2009", 7 pgs.
"U.S. Appl. No. 11/644,179, Notice of Allowance mailed Nov. 1, 2013", 11 pgs.
"U.S. Appl. No. 11/644,179, Preliminary Amendment filed Dec. 22, 2006", 5 pgs.
"U.S. Appl. No. 11/644,179, Response filed Jan. 30, 2008 to Restriction Requirement mailed Oct. 30, 2007", 5 pgs.
"U.S. Appl. No. 11/644,179, Response filed Apr. 8, 2010 to Non Final Office Action mailed Dec. 8, 2009", 8 pgs.
"U.S. Appl. No. 11/644,179, Response filed Aug. 17, 2010 to Final Office Action mailed Jul. 2, 2010", 8 pgs.
"U.S. Appl. No. 11/644,179, Restriction Requirement mailed Oct. 30, 2007", 7 pgs.
"U.S. Appl. No. 11/644,179, Supplemental Preliminary Amendment filed Feb. 6, 2008", 6 pgs.
"U.S. Appl. No. 11/644,179, Response filed Feb. 20, 2013 to Non Final Office Action mailed Nov. 29, 2012", 10 pgs.

(56) References Cited

OTHER PUBLICATIONS

"U.S. Appl. No. 11/654,863 Final Office Action mailed Jul. 17, 2017", 11 pgs.
"U.S. Appl. No. 11/654,863 Restriction Requirement mailed Sep. 3, 2010", 5 pgs.
"U.S. Appl. No. 11/654,863, Appeal Brief filed Apr. 30, 2014", 22 pgs.
"U.S. Appl. No. 11/654,863, Appeal Decision mailed Aug. 3, 2016", 11 pgs.
"U.S. Appl. No. 11/654,863, Decision on Pre-Appeal Brief Request mailed Dec. 5, 2013", 2 pgs.
"U.S. Appl. No. 11/654,863, Declaration of Dr. Heinz Feldmann dated Jan. 9, 2018", 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief mailed Jun. 18, 2014", 10 pgs.
"U.S. Appl. No. 11/654,863, Final Office Action mailed Jul. 11, 2013", 9 pgs.
"U.S. Appl. No. 11/654,863, Final Office Action mailed Sep. 12, 2018", 12 pgs.
"U.S. Appl. No. 11/654,863, Final Office Action mailed Oct. 25, 2011", 9 pgs.
"U.S. Appl. No. 11/654,863, Non Final Office Action mailed Feb. 11, 2013", 10 pgs.
"U.S. Appl. No. 11/654,863, Non Final Office Action mailed Mar. 29, 2018", 12 pgs.
"U.S. Appl. No. 11/654,863, Non Final Office Action mailed Jun. 27, 2011", 9 pgs.
"U.S. Appl. No. 11/654,863, Non Final Office Action mailed Dec. 2, 2010", 8 pgs.
"U.S. Appl. No. 11/654,863, Non Final Office Action mailed Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action mailed Jul. 17, 2017", 9 pgs.
"U.S. Appl. No. 11/654,863, Response filed Apr. 18, 2012 to Final Office Action mailed Oct. 25, 2011", 8 pgs.
"U.S. Appl. No. 11/654,863, Response filed Jun. 2, 2011 to Non Final Office Action mailed Dec. 2, 2010", 6 pgs.
"U.S. Appl. No. 11/654,863, Response filed Jun. 7, 2013 to Non Final Office Action mailed Feb. 11, 2013", 10 pgs.
"U.S. Appl. No. 11/654,863, Response filed Jun. 21, 2017 to Non Final Office Action mailed Dec. 21, 2016", 11 pgs.
"U.S. Appl. No. 11/654,863, Response filed Jul. 9, 2018 to Non Final Office Action mailed Mar. 29, 2018", 10 pgs.
"U.S. Appl. No. 11/654,863, Response filed Sep. 28, 2010 to Restriction Requirement mailed Sep. 3, 2010", 6 pgs.
"U.S. Appl. No. 11/654,863, Response filed Oct. 6, 2011 to Non Final Office Action mailed Jun. 27, 2011", 9 pgs.
"U.S. Appl. No. 11/729,557, Advisory Action mailed May 9, 2011", 3 pgs.
"U.S. Appl. No. 11/729,557, Advisory Action mailed Dec. 24, 2014", 3 pgs.
"U.S. Appl. No. 11/729,557, Final Office Action mailed Feb. 2, 2011", 14 pgs.
"U.S. Appl. No. 11/729,557, Final Office Action mailed Aug. 20, 2009", 13 Pgs.
"U.S. Appl. No. 11/729,557, Final Office Action mailed Sep. 12, 2014", 14 pgs.
"U.S. Appl. No. 11/729,557, Non Final Office Action mailed Feb. 18, 2015", 13 pgs.
"U.S. Appl. No. 11/729,557, Non Final Office Action mailed Feb. 26, 2014", 16 pgs.
"U.S. Appl. No. 11/729,557, Non-Final Office Action mailed Jan. 30, 2009", 20 pgs.
"U.S. Appl. No. 11/729,557, Non-Final Office Action mailed Feb. 22, 2010", 16 pgs.
"U.S. Appl. No. 11/729,557, Non-Final Office Action mailed Aug. 23, 2010", 15 pgs.
"U.S. Appl. No. 11/729,557, Notice of Allowance mailed Sep. 30, 2015", 11 pgs.
"U.S. Appl. No. 11/729,557, Respons filed Jun. 22, 2010 to Non Final Office Action mailed Feb. 22, 2010", 33 pgs.
"U.S. Appl. No. 11/729,557, Response filed Apr. 27, 2011 to Final Office Action mailed Feb. 2, 2011", 14 pgs.
"U.S. Appl. No. 11/729,557, Response filed Apr. 30, 2009 to Non Final Office Action mailed Jan. 30, 2009", 18 pgs.
"U.S. Appl. No. 11/729,557, Response filed May 22, 2014 to Non Final Office Action mailed Feb. 26, 2014", 13 pgs.
"U.S. Appl. No. 11/729,557, Response filed May 28, 2008 to Restriction Requirement mailed Nov. 28, 2007", 13 pgs.
"U.S. Appl. No. 11/729,557, Response filed Jun. 22, 2010 to Non Final Office Action mailed Feb. 22, 2010", 16 pgs.
"U.S. Appl. No. 11/729,557, Response filed Jun. 22, 2015 to non Final Office Action mailed Feb. 18, 2015", 13 pgs.
"U.S. Appl. No. 11/729,557, Respnse filed Oct. 28, 2010 to Non Final Office Action mailed Aug. 23, 2010", 13 pgs.
"U.S. Appl. No. 11/729,557, Response filed Dec. 1, 2009 to Final Office Action mailed Aug. 26, 2009", 16 pgs.
"U.S. Appl. No. 11/729,557, Response filed Dec. 11, 2014 to Final Office Action mailed Sep. 12, 2014", 15 pgs.
"U.S. Appl. No. 11/729,557, Restriction Requirement mailed Nov. 28, 2007", 9 pgs.
"U.S. Appl. No. 11/810,956, Final Office Action mailed Mar. 22, 2010", 8 pgs.
"U.S. Appl. No. 11/810,956, Non-Final Office Action mailed Aug. 11, 2009", 9 pgs.
"U.S. Appl. No. 11/810,956, Response filed Jan. 11, 2010 to Non Final Office Action mailed Aug. 11, 2009", 8 pgs.
"U.S. Appl. No. 11/810,956, Response filed Apr. 23, 2009 to Restriction Requirement mailed Mar. 23, 2009", 6 pgs.
"U.S. Appl. No. 11/810,956, Restriction Requirement mailed Mar. 23, 2009", 6 pgs.
"U.S. Appl. No. 12/058,389, Advisory Action mailed Jan. 2, 2013", 2 pgs.
"U.S. Appl. No. 12/058,389, Final Office Action mailed Jan. 22, 2010", 8 pgs.
"U.S. Appl. No. 12/058,389, Final Office Action mailed Nov. 14, 2012", 7 pgs.
"U.S. Appl. No. 12/058,389, Non Final Office Action mailed Aug. 10, 2012", 5 pgs.
"U.S. Appl. No. 12/058,389, Non Final Office Action mailed Dec. 8, 2011", 8 pgs.
"U.S. Appl. No. 12/058,389, Non-Final Office Action mailed Apr. 13, 2009", 12 pgs.
"U.S. Appl. No. 12/058,389, Notice of Allowability mailed Mar. 22, 2013", 8 pgs.
"U.S. Appl. No. 12/058,389, Notice of Allowance mailed Feb. 20, 2013", 9 pgs.
"U.S. Appl. No. 12/058,389, Preliminary Amendment filed Jun. 23, 2008", 7 pgs.
"U.S. Appl. No. 12/058,389, Respnse filed Nov. 6, 2012 to Non Final Office Action mailed Aug. 10, 2012", 7 pgs.
"U.S. Appl. No. 12/058,389, Response filed Feb. 6, 2009 to Restriction Requirement mailed Dec. 3, 2008", 7 pgs.
"U.S. Appl. No. 12/058,389, Response filed Apr. 10, 2012 to Non Final Office Action mailed Dec. 8, 2011", 7 pgs.
"U.S. Appl. No. 12/058,389, Response filed Jun. 16, 2010 to Final Office Action mailed Jan. 22, 2010", 6 pgs.
"U.S. Appl. No. 12/058,389, Response filed Oct. 13, 2009 to Non Final Office Action mailed Apr. 13, 2009", 9 pgs.
"U.S. Appl. No. 12/058,389, Response filed Dec. 18, 2012 to Non Final Office Action mailed Nov. 14, 2012", 7 pgs.
"U.S. Appl. No. 12/058,389, Restriction Requirement mailed Dec. 3, 2008", 7 pgs.

(56) References Cited

OTHER PUBLICATIONS

"U.S. Appl. No. 12/113,690, Final Office Action mailed Apr. 15, 2011", 10 pgs.
"U.S. Appl. No. 12/113,690, Non-Final Office Action mailed Nov. 10, 2010", 11 pgs.
"U.S. Appl. No. 12/113,690, Notice of Allowability mailed Aug. 19, 2013", 9 pgs.
"U.S. Appl. No. 12/113,690, Notice of Allowance mailed Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action mailed Apr. 15, 2011", 17 pgs.
"U.S. Appl. No. 12/113,690, Response filed Aug. 5, 2010 to Restriction Requirement mailed Apr. 6, 2010", 14 pgs.
"U.S. Appl. No. 12/113,690, Response filed Dec. 22, 2010 to Non Final Office Action mailed Nov. 10, 2010", 19 pgs.
"U.S. Appl. No. 12/113,690, Restriction Requirement mailed Apr. 6, 2010", 10 pgs.
"U.S. Appl. No. 12/139,183, Non Final Office Action mailed Jan. 6, 2011", 12 pgs.
"U.S. Appl. No. 12/139,183, Non-Final Office Action mailed Jan. 4, 2010", 6 pgs.
"U.S. Appl. No. 12/139,183, Non-Final Office Action mailed Jul. 13, 2010", 15 pgs.
"U.S. Appl. No. 12/139,183, Notice of Allowance mailed Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action mailed Jan. 6, 2011", 21 pgs.
"U.S. Appl. No. 12/139,183, Response filed Apr. 12, 2010 to Non Final Office Action mailed Jan. 4, 2010", 17 pgs.
"U.S. Appl. No. 12/139,183, Response filed Aug. 18, 2009 to Restriction Requirement mailed Jul. 24, 2009", 16 pgs.
"U.S. Appl. No. 12/139,183, Response filed Sep. 21, 2010 to Non Final Office Action mailed Jul. 13, 2010", 21 pgs.
"U.S. Appl. No. 12/139,183, Restriction Requirement mailed Jul. 24, 2009", 12 pgs.
"U.S. Appl. No. 12/214,414, Advisory Action mailed Feb. 2, 2016", 5 pgs.
"U.S. Appl. No. 12/214,414, Advisory Action mailed Apr. 15, 2015", 6 pgs.
"U.S. Appl. No. 12/214,414, Advisory Action mailed Oct. 21, 2011", 5 pgs.
"U.S. Appl. No. 12/214,414, Examiner Interview Summary mailed Dec. 11, 2015", 3 pgs.
"U.S. Appl. No. 12/214,414, Final Office Action mailed Jan. 20, 2015", 28 pgs.
"U.S. Appl. No. 12/214,414, Final Office Action mailed Aug. 2, 2011", 7 pgs.
"U.S. Appl. No. 12/214,414, Final Office Action mailed Nov. 18, 2015", 17 pgs.
"U.S. Appl. No. 12/214,414, Non Final Office Action mailed Jun. 12, 2014", 28 pgs.
"U.S. Appl. No. 12/214,414, Non Final Office Action mailed Dec. 10, 2010", 6 pgs.
"U.S. Appl. No. 12/214,414, Non-Final Office Action mailed Mar. 2, 2010", 9 pgs.
"U.S. Appl. No. 12/214,414, Notice of Allowance mailed Jun. 7, 2016", 18 pgs.
"U.S. Appl. No. 12/214,414, Response filed Jan. 19, 2016 to Final Office Action mailed Nov. 18, 2015", 14 pgs.
"U.S. Appl. No. 12/214,414, Response filed Feb. 18, 2016 to Final Office Action mailed Nov. 18, 2015", 14 pgs.
"U.S. Appl. No. 12/214,414, Response filed Mar. 26, 2015 to Final Office Action mailed Jan. 20, 2015", 13 pgs.
"U.S. Appl. No. 12/214,414, Response filed May 3, 2011 to Non Final Office Action mailed Dec. 10, 2010", 12 pgs.
"U.S. Appl. No. 12/214,414, Response filed Jul. 20, 2015 to Advisory Action mailed Apr. 15, 2015", 14 pgs.
"U.S. Appl. No. 12/214,414, Response filed Aug. 31, 2010 to Non Final Office Action mailed Mar. 2, 2010", 11 pgs.
"U.S. Appl. No. 12/214,414, Response filed Oct. 3, 2011 to Non Final Office Action mailed Aug. 2, 2011", 9 pgs.
"U.S. Appl. No. 12/214,414, Response filed Oct. 14, 2014 to Non Final Office Action mailed Jun. 12, 2014", 16 pgs.
"U.S. Appl. No. 12/214,414, Response filed Dec. 21, 2011 to Advisory Action mailed Oct. 21, 2011", 10 pgs.
"U.S. Appl. No. 12/245,296, Final Office Action mailed Jul. 11, 2013", 15 pgs.
"U.S. Appl. No. 12/245,296, Final Office Action mailed Dec. 17, 2010", 16 pgs.
"U.S. Appl. No. 12/245,296, Non Final Office Action mailed Mar. 25, 2013", 14 pgs.
"U.S. Appl. No. 12/245,296, Non-Final Office Action mailed Jun. 1, 2010", 13 pgs.
"U.S. Appl. No. 12/245,296, Notice of Allowance mailed Aug. 1, 2014", 10 pgs.
"U.S. Appl. No. 12/245,296, Preliminary Amendment mailed Jan. 28, 2009", 14 pgs.
"U.S. Appl. No. 12/245,296, Response filed Jan. 8, 2013 to Final Office Action mailed Jul. 11, 2013", 10 pgs.
"U.S. Appl. No. 12/245,296, Response filed Apr. 8, 2010 to Restriction Requirement mailed Mar. 9, 2010", 6 pgs.
"U.S. Appl. No. 12/245,296, Response filed May 17, 2011 to Final Office Action mailed Dec. 17, 2010", 10 pgs.
"U.S. Appl. No. 12/245,296, Response filed Jun. 7, 2013 to Non Final Office Action mailed Mar. 25, 2013", 9 pgs.
"U.S. Appl. No. 12/245,296, Response filed Oct. 1, 2010 to Non Final Office Action mailed Jun. 1, 2010", 12 pgs.
"U.S. Appl. No. 12/245,296, Restriction Requirement mailed Mar. 9, 2010", 6 pgs.
"U.S. Appl. No. 12/467,492, Restriction Requirement mailed Nov. 22, 2010", 6 pgs.
"U.S. Appl. No. 12/470,287, Response filed Jan. 23, 2012 to Non Final Office Action mailed Jul. 22, 2011", 13 pgs.
"U.S. Appl. No. 12/470,287, Response filed May 31, 2012 to Final Office Action mailed Apr. 3, 2012", 14 pgs.
"U.S. Appl. No. 12/470,287, Corrected Notice of Allowability mailed Sep. 11, 2012", 2 pgs.
"U.S. Appl. No. 12/470,287, Final Office Action mailed Apr. 3, 2012", 7 pgs.
"U.S. Appl. No. 12/470,287, Non Final Office Action mailed Jul. 22, 2011", 9 pgs.
"U.S. Appl. No. 12/470,287, Notice of Allowance mailed Jun. 19, 2012", 5 pgs.
"U.S. Appl. No. 12/470,287, Response filed Apr. 28, 2011 to Restriction Requirement mailed Dec. 29, 2010", 8 pgs.
"U.S. Appl. No. 12/470,287, Restriction Requirement mailed Dec. 29, 2010", 6 pgs.
"U.S. Appl. No. 12/854,578, Response filed Oct. 1, 2012 to Non Final Office Action mailed Jun. 29, 2012", 10 pgs.
"U.S. Appl. No. 12/854,578, Final Office Action mailed Nov. 29, 2012", 8 pgs.
"U.S. Appl. No. 12/854,578, Non Final Office Action mailed Jun. 29, 2012", 8 pgs.
"U.S. Appl. No. 12/854,578, Notice of Allowance mailed Apr. 10, 2013", 6 pgs.
"U.S. Appl. No. 12/854,578, PTO Response to 312 Amendment mailed Jul. 18, 2013", 2 pgs.
"U.S. Appl. No. 12/854,578, Response filed Feb. 28, 2013 to Final Office Action mailed Nov. 29, 2012", 8 pgs.
"U.S. Appl. No. 12/854,578, Restriction Requirement mailed Apr. 6, 2012", 6 pgs.
"U.S. Appl. No. 12/912,411, Advisory Action mailed Feb. 5, 2014", 3 pgs.
"U.S. Appl. No. 12/912,411, Examiner Interview Summary mailed Feb. 11, 2014", 2 pgs.
"U.S. Appl. No. 12/912,411, Final Office Action mailed Jan. 14, 2015", 10 pgs.

(56) References Cited

OTHER PUBLICATIONS

"U.S. Appl. No. 12/912,411, Final Office Action mailed Oct. 25, 2013", 11 pgs.
"U.S. Appl. No. 12/912,411, Non Final Office Action mailed Jun. 7, 2013", 8 pgs.
"U.S. Appl. No. 12/912,411, Non Final Office Action mailed Sep. 24, 2014", 11 pgs.
"U.S. Appl. No. 12/912,411, Notice of Allowability mailed May 20, 2015", 7 pgs.
"U.S. Appl. No. 12/912,411, Notice of Allowance mailed Apr. 8, 2015", 11 pgs.
"U.S. Appl. No. 12/912,411, Response filed Jan. 27, 2014 to Final Office Action mailed Oct. 25, 2013", 11 pgs.
"U.S. Appl. No. 12/912,411, Response filed Feb. 18, 2013 to Restriction Requirement mailed Oct. 17, 2012", 9 pgs.
"U.S. Appl. No. 12/912,411, Response filed Feb. 25, 2014 to Final Office Action mailed Oct. 25, 2013", 11 pgs.
"U.S. Appl. No. 12/912,411, Response filed Mar. 16, 2015 to Final Office Action mailed Jan. 14, 2015", 9 pgs.
"U.S. Appl. No. 12/912,411, Response filed Oct. 7, 2013 to Non Final Office Action mailed Jun. 7, 2013", 10 pgs.
"U.S. Appl. No. 12/912,411, Response filed Dec. 31, 2014 to Non Final Office Action mailed Sep. 24, 2014", 12 pgs.
"U.S. Appl. No. 12/912,411, Restriction Requirement mailed Oct. 17, 2012", 9 pgs.
"U.S. Appl. No. 13/070,110 Response filed Feb. 14, 2017 to Final Office Action mailed Sep. 14, 2016", 8 pgs.
"U.S. Appl. No. 13/070,110, Advisory Action mailed Mar. 3, 2017", 5 pgs.
"U.S. Appl. No. 13/070,110, Examiner Interview Summary mailed Jan. 16, 2018", 3 pgs.
"U.S. Appl. No. 13/070,110, Final Office Action mailed Apr. 3, 2015", 18 pgs.
"U.S. Appl. No. 13/070,110, Final Office Action mailed Jun. 12, 2013", 7 pgs.
"U.S. Appl. No. 13/070,110, Final Office Action mailed Sep. 14, 2016", 12 pgs.
"U.S. Appl. No. 13/070,110, Non Final Office Action mailed Jul. 21, 2017", 14 pgs.
"U.S. Appl. No. 13/070,110, Non Final Office Action mailed Oct. 2, 2014", 24 pgs.
"U.S. Appl. No. 13/070,110, Non Final Office Action mailed Dec. 11, 2015", 19 pgs.
"U.S. Appl. No. 13/070,110, Non Final Office Action mailed Dec. 21, 2012", 7 pgs.
"U.S. Appl. No. 13/070,110, Notice of Allowance mailed Mar. 26, 2018", 6 pgs.
"U.S. Appl. No. 13/070,110, Notice of Allowance mailed Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication mailed Aug. 15, 2018", 2 pgs.
"U.S. Appl. No. 13/070,110, Response filed Jan. 22, 2018 to Non Final Office Action mailed Jul. 21, 2017", 10 pgs.
"U.S. Appl. No. 13/070,110, Response filed Mar. 22, 2013 to Non Final Office Action mailed Dec. 21, 2012", 8 pgs.
"U.S. Appl. No. 13/070,110, Response filed May 27, 2016 to Non Final Office Action mailed Dec. 11, 2015", 13 pgs.
"U.S. Appl. No. 13/070,110, Response filed Jun. 20, 2017 to Advisory Action mailed Mar. 3, 2017", 13 pgs.
"U.S. Appl. No. 13/070,110, Response filed Sep. 3, 2014 to Restriction Requirement mailed Jul. 8, 2014", 7 pgs.
"U.S. Appl. No. 13/070,110, Response filed Oct. 2, 2015 to Final Office Action mailed Apr. 3, 2015", 11 pgs.
"U.S. Appl. No. 13/070,110, Response filed Nov. 12, 2013 to Final Office Action mailed Jun. 12, 2013", 9 pgs.
"U.S. Appl. No. 13/070,110, Response filed Dec. 30, 2014 to Non Final Office Action mailed Oct. 2, 2014", 13 pgs.
"U.S. Appl. No. 13/070,110, Restriction Requirement mailed Jul. 8, 2014", 7 pgs.
"U.S. Appl. No. 13/113,244, Final Office Action mailed Feb. 27, 2014", 8 pgs.
"U.S. Appl. No. 13/113,244, Non Final Office Action mailed Jul. 5, 2013", 6 pgs.
"U.S. Appl. No. 13/113,244, Non Final Office Action mailed Oct. 1, 2012", 7 pgs.
"U.S. Appl. No. 13/113,244, Notice of Allowance mailed Jun. 30, 2014", 9 pgs.
"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement mailed Oct. 31, 2011", 10 pgs.
"U.S. Appl. No. 13/113,244, Response filed Feb. 20, 2013 to Non Final Office Action mailed Oct. 1, 2012", 12 pgs.
"U.S. Appl. No. 13/113,244, Response filed Jun. 13, 2014 to Final Office Action mailed Feb. 27, 2014", 6 pgs.
"U.S. Appl. No. 13/113,244, Response filed Oct. 31, 2013 to Non Final Office Action mailed Jul. 5, 2013", 12 pgs.
"U.S. Appl. No. 13/113,244, Restriction Requirement mailed Oct. 31, 2011", 8 pgs.
"U.S. Appl. No. 13/127,951, Advisory Action mailed Jul. 16, 2014", 3 pgs.
"U.S. Appl. No. 13/127,951, Final Office Action mailed Apr. 9, 2014", 23 pgs.
"U.S. Appl. No. 13/127,951, Non Final Office Action mailed Sep. 26, 2013", 18 pgs.
"U.S. Appl. No. 13/127,951, Notice of Allowance mailed Jul. 20, 2015", 7 pgs.
"U.S. Appl. No. 13/127,951, Preliminary Amendment filed May 5, 2011", 7 pgs.
"U.S. Appl. No. 13/127,951, PTO Response to Rule 312 Communication mailed Oct. 23, 2015", 2 pgs.
"U.S. Appl. No. 13/127,951, Response filed Mar. 18, 2014 to Non Final Office Action nailed Sep. 26, 2013", 14 pgs.
"U.S. Appl. No. 13/127,951, Response filed Jul. 7, 2014 to Final Office Action mailed Apr. 9, 2014", 10 pgs.
"U.S. Appl. No. 13/127,951, Response filed Aug. 30, 2013 to Restriction Requirement mailed Apr. 30, 2013", Aug. 30, 13.
"U.S. Appl. No. 13/127,951, Response filed Oct. 9, 2014 to Advisory Action mailed Jul. 16, 2014", 10 pgs.
"U.S. Appl. No. 13/127,951, Restriction Requirement mailed Apr. 30, 2013", 15 pgs.
"U.S. Appl. No. 13/594,611, Final Office Action mailed Aug. 15, 2014", 7 pgs.
"U.S. Appl. No. 13/594,611, Non Final Office Action mailed Apr. 24, 2014", 9 pgs.
"U.S. Appl. No. 13/594,611, Notice of Allowance mailed Jan. 13, 2015", 7 pgs.
"U.S. Appl. No. 13/594,611, PTO Response to Rule 312 Communication mailed Apr. 16, 2015", 2 pgs.
"U.S. Appl. No. 13/594,611, Response filed Feb. 25, 2014 to Restriction Requirement mailed Jan. 27, 2014", 8 pgs.
"U.S. Appl. No. 13/594,611, Response filed Jul. 7, 2014 to Non Final Office Action mailed Apr. 24, 2014", 9 pgs.
"U.S. Appl. No. 13/594,611, Response filed Dec. 15, 2014 to Final Office Action mailed Aug. 15, 2014", 10 pgs.
"U.S. Appl. No. 13/594,611, Restriction Requirement mailed Jan. 27, 2014", 8 pgs.
"U.S. Appl. No. 14/332,121, Non Final Office Action mailed May 16, 2016", 9 pgs.
"U.S. Appl. No. 14/332,121, Notice of Allowance mailed Feb. 15, 2017", 10 pgs.
"U.S. Appl. No. 14/332,121, Notice of Allowance mailed Jun. 15, 2017", 8 pgs.
"U.S. Appl. No. 14/332,121, Notice of Allowance mailed Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement mailed Jul. 30, 2015", 9 pgs.

(56) References Cited

OTHER PUBLICATIONS

"U.S. Appl. No. 14/332,121, Response filed Sep. 7, 2017 to Notice of Allowability mailed Jun. 15, 2017", 8 pgs.
"U.S. Appl. No. 14/332,121, Response filed Oct. 11, 2016 to Non Final Office Action mailed May 16, 2016", 9 pgs.
"U.S. Appl. No. 14/332,121, Restriction Requirement mailed Jul. 30, 2015", 9 pgs.
"U.S. Appl. No. 14/332,121, Supplemental Amendment filed Jan. 23, 2017", 10 pgs.
"U.S. Appl. No. 14/528,997, Advisory Action mailed Aug. 9, 2017", 3 pgs.
"U.S. Appl. No. 14/528,997, Final Office Action mailed Feb. 10, 2017", 9 pgs.
"U.S. Appl. No. 14/528,997, Non Final Office Action mailed Jun. 16, 2016", 12 pgs.
"U.S. Appl. No. 14/528,997, Non Final Office Action mailed Jun. 29, 2018", 7 pgs.
"U.S. Appl. No. 14/528,997, Notice of Allowance mailed Mar. 8, 2019", 7 pgs.
"U.S. Appl. No. 14/528,997, PTO Response to Rule 312 Communication mailed Jun. 19, 2019", 2 pgs.
"U.S. Appl. No. 14/528,997, Response filed Mar. 16, 2016 to Restriction Requirement mailed Sep. 16, 2015", 11 pgs.
"U.S. Appl. No. 14/528,997, Response filed Jul. 27, 2017 to Final Office Action mailed Feb. 10, 2017", 11 pgs.
"U.S. Appl. No. 14/528,997, Response filed Oct. 10, 2016 to Non Final Office Action mailed Jun. 16, 2016", 12 pgs.
"U.S. Appl. No. 14/528,997, Response filed Nov. 16, 2018 to Non Final Office Action mailed Jun. 29, 2018", 11 pgs.
"U.S. Appl. No. 14/528,997, Restriction Requirement mailed Sep. 16, 2015", 8 pgs.
"U.S. Appl. No. 14/699,213, Advisory Action mailed Mar. 7, 2018", 3 pgs.
"U.S. Appl. No. 14/699,213, Final Office Action mailed Dec. 1, 2017", 11 pgs.
"U.S. Appl. No. 14/699,213, Non Final Office Action mailed Jun. 2, 2017", 12 pgs.
"U.S. Appl. No. 14/699,213, Non-Final Office Action mailed Jan. 11, 2019", 10 pgs.
"U.S. Appl. No. 14/699,213, Notice of Allowance mailed Jul. 30, 2019", 8 pgs.
"U.S. Appl. No. 14/699,213, Preliminary Amendment filed Apr. 30, 2015", 8 pgs.
"U.S. Appl. No. 14/699,213, PTO Response to Rule 312 Communication mailed Nov. 19, 2019", 2 pgs.
"U.S. Appl. No. 14/699,213, Response filed Feb. 15, 2017 to Restriction Requirement mailed Aug. 15, 2016", 9 pgs.
"U.S. Appl. No. 14/699,213, Response filed Feb. 27, 2018 to Final Office Action mailed Dec. 1, 2017", 34 pgs.
"U.S. Appl. No. 14/699,213, Response filed Aug. 22, 2017 to Non Final Office Action mailed Jun. 2, 2017", 12 pgs.
"U.S. Appl. No. 14/699,213, Response filed Apr. 11, 2019 to Non-Final Office Action mailed Jan. 11, 2019", 13 pgs.
"U.S. Appl. No. 14/699,213, Restriction Requirement mailed Aug. 15, 2016", 10 pgs.
"U.S. Appl. No. 14/745,236, Advisory Action mailed Nov. 15, 2017", 2 pgs.
"U.S. Appl. No. 14/745,236, Final Office Action mailed Aug. 25, 2017", 16 pgs.
"U.S. Appl. No. 14/745,236, Non Final Office Action mailed Feb. 2, 2017", 14 pgs.
"U.S. Appl. No. 14/745,236, Notice of Allowability mailed Jul. 5, 2018", 4 pgs.
"U.S. Appl. No. 14/745,236, Notice of Allowance mailed Feb. 5, 2018", 9 pgs.
"U.S. Appl. No. 14/745,236, PTO Response to Rule 312 Communication mailed Jul. 10, 2018", 2 pgs.
"U.S. Appl. No. 14/745,236, Response filed May 2, 2017 to Non Final Office Action mailed Feb. 2, 2017", 10 pgs.
"U.S. Appl. No. 14/745,236, Response filed Nov. 6, 2017 to Final Office Action mailed Aug. 25, 2017", 12 pgs.
"U.S. Appl. No. 14/745,236, Response filed Dec. 14, 2017 to Final Office Action mailed Aug. 25, 2017", 12 pgs.
"U.S. Appl. No. 14/745,236, Response filed Dec. 23, 2016 to Restriction Requirement mailed Sep. 23, 2016", 8 pgs.
"U.S. Appl. No. 14/745,236, Restriction Requirement mailed Sep. 23, 2016", 8 pgs.
"U.S. Appl. No. 14/816,807, Non Final Office Action mailed Oct. 3, 2017", 7 pgs.
"U.S. Appl. No. 14/816,807, Notice of Allowance mailed Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication mailed Jul. 6, 2018", 2 pgs.
"U.S. Appl. No. 14/816,807, Response filed Jan. 3, 2018 to Non Final Office Action mailed Oct. 3, 2017", 8 pgs.
"U.S. Appl. No. 14/816,807, Response filed May 1, 2017 to Restriction Requirement mailed Nov. 1, 2016", 9 pgs.
"U.S. Appl. No. 14/816,807, Restriction Requirement mailed Nov. 1, 2016", 8 pgs.
"U.S. Appl. No. 14/919,431, Preliminary Amendment filed Jan. 4, 2016", 8 pgs.
"U.S. Appl. No. 15/000,851, Non Final Office Action mailed Jan. 26, 2017", 15 pgs.
"U.S. Appl. No. 15/000,851, Notice of Allowance mailed Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action mailed Jan. 26, 2017", 16 pgs.
"U.S. Appl. No. 15/000,851, Response filed Oct. 12, 2016 to Restriction Requirement mailed May 12, 2016", 11 pgs.
"U.S. Appl. No. 15/000,851, Restriction Requirement mailed May 12, 2016", 6 pgs.
"U.S. Appl. No. 15/000,851, Supplemental Amendment filed Apr. 4, 2016", 10 pgs.
"U.S. Appl. No. 15/170,556, Final Office Action mailed Jul. 30, 2019", 6 pgs.
"U.S. Appl. No. 15/170,556, Non Final Office Action mailed Feb. 8, 2019", 11 pgs.
"U.S. Appl. No. 15/170,556, Non Final Office Action mailed Jul. 27, 2018", 10 pgs.
"U.S. Appl. No. 15/170,556, Notice of Allowability mailed Jan. 29, 2020", 4 pgs.
"U.S. Appl. No. 15/170,556, Notice of Allowance mailed Nov. 27, 2019", 8 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement mailed Feb. 16, 2018", 8 pgs.
"U.S. Appl. No. 15/170,556, Response filed Oct. 29, 2018 to Non Final Office Action mailed Jul. 27, 2018", 9 pgs.
"U.S. Appl. No. 15/170,556, Response filed Nov. 18, 2019 to Final Office Action mailed Jul. 30, 2019", 8 pgs.
"U.S. Appl. No. 15/170,556, Response filed Apr. 15, 2019 to Non Final Office Action mailed Feb. 8, 2019", 9 pgs.
"U.S. Appl. No. 15/170,556, Restriction Requirement mailed Feb. 16, 2018", 7 pgs.
"U.S. Appl. No. 15/170,556, PTO Response to Rule 312 Communication mailed Apr. 3, 2020", 2 pgs.
"U.S. Appl. No. 15/203,581, Examiners Interview Summary mailed Sep. 11, 2017", 1 pg.
"U.S. Appl. No. 15/203,581, Notice of Allowance mailed Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication mailed Dec. 27, 2017", 2 pgs.
"U.S. Appl. No. 15/203,581, Response filed Aug. 15, 2017 to Restriction Requirement mailed Jun. 16, 2017", 8 pgs.

(56) References Cited

OTHER PUBLICATIONS

"U.S. Appl. No. 15/203,581, Restriction Requirement mailed Jun. 16, 2017", 8 pgs.
"U.S. Appl. No. 15/204,381, Advisory Action mailed Feb. 7, 2019", 3 pgs.
"U.S. Appl. No. 15/204,381, Advisory Action mailed Aug. 25, 2020", 3 pgs.
"U.S. Appl. No. 15/204,381, Final Office Action mailed Feb. 27, 2020", 21 pgs.
"U.S. Appl. No. 15/204,381, Final Office Action mailed Jul. 9, 2021", 14 pgs.
"U.S. Appl. No. 15/204,381, Final Office Action mailed Sep. 21, 2018", 10 pgs.
"U.S. Appl. No. 15/204,381, Non Final Office Action mailed Feb. 23, 2018", 10 pgs.
"U.S. Appl. No. 15/204,381, Non Final Office Action mailed Jun. 13, 2019", 23 pgs.
"U.S. Appl. No. 15/204,381, Non Final Office Action mailed Oct. 6, 2020", 15 pgs.
"U.S. Appl. No. 15/204,381, Preliminary Amendment filed Oct. 25, 2016", 74 pgs.
"U.S. Appl. No. 15/204,381, Response filed Jan. 2, 2019 to Final Office Action mailed Sep. 21, 2018", 6 pgs.
"U.S. Appl. No. 15/204,381, Response filed Jan. 19, 2018 to Restriction Requirement mailed Oct. 13, 2017", 6 pgs.
"U.S. Appl. No. 15/204,381, Response filed Apr. 6, 2021 to Non Final Office Action mailed Oct. 6, 2020", 12 pgs.
"U.S. Appl. No. 15/204,381, Response filed May 30, 2018 to Non Final Office Action mailed Feb. 23, 2018", 9 pgs.
"U.S. Appl. No. 15/204,381, Response filed Jul. 27, 2020 to Final Office Action mailed Feb. 27, 2020", 11 pgs.
"U.S. Appl. No. 15/204,381, Response filed Aug. 27, 2020 to Advisory Action mailed Aug. 25, 2020", 2 pgs.
"U.S. Appl. No. 15/204,381, Response Filed Nov. 14, 2019 to Non Final Office Action mailed Jun. 13, 2019", 9 pgs.
"U.S. Appl. No. 15/204,381, Response Filed Mar. 21, 2019 to Advisory Action mailed Feb. 7, 2019", 7 pgs.
"U.S. Appl. No. 15/204,381, Restriction Requirement mailed Oct. 13, 2017", 10 pgs.
"U.S. Appl. No. 15/227,147, Preliminary Amendment filed Oct. 10, 2016", 7 pgs.
"U.S. Appl. No. 15/227,147, Restriction Requirement mailed Jan. 19, 2017", 14 pgs.
"U.S. Appl. No. 15/247,006 Response filed Jun. 4, 2019 to Final Office Action mailed Feb. 4, 2019", 7 pgs.
"U.S. Appl. No. 15/247,006, Examiner Interview Summary mailed Nov. 27, 2017", 4 pgs.
"U.S. Appl. No. 15/247,006, Final Office Action mailed Feb. 4, 2019", 8 pgs.
"U.S. Appl. No. 15/247,006, Non Final Office Action mailed Apr. 20, 2018", 7 pgs.
"U.S. Appl. No. 15/247,006, Non Final Office Action mailed Sep. 8, 2017", 8 pgs.
"U.S. Appl. No. 15/247,006, Notice of Allowance mailed Jun. 24, 2019", 7 pgs.
"U.S. Appl. No. 15/247,006, Notice of Allowance mailed Oct. 8, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement mailed Mar. 17, 2017", 12 pgs.
"U.S. Appl. No. 15/247,006, Response filed Oct. 22, 2018 to Non Final Office Action mailed Apr. 20, 2018", 14 pgs.
"U.S. Appl. No. 15/247,006, Response filed Dec. 7, 2017 to Non Final Office Action mailed Sep. 8, 2017", 13 pgs.
"U.S. Appl. No. 15/247,006, Restriction Requirement mailed Mar. 17, 2017", 9 pgs.
"U.S. Appl. No. 15/292,595, Non Final Office Action mailed Sep. 25, 2017", 13 pgs.
"U.S. Appl. No. 15/292,595, Notice of Allowance mailed Feb. 28, 2018", 9 pgs.
"U.S. Appl. No. 15/292,595, Notice of Allowance mailed Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action mailed Sep. 25, 2017", 9 pgs.
"U.S. Appl. No. 15/436,245, Corrected Notice of Allowability mailed Nov. 10, 2021", 2 pgs.
"U.S. Appl. No. 15/436,245, Final Office Action mailed Mar. 24, 2021", 9 pgs.
"U.S. Appl. No. 15/436,245, Final Office Action mailed Nov. 18, 2019", 9 pgs.
"U.S. Appl. No. 15/436,245, Non Final Office Action mailed Apr. 19, 2019", 9 pgs.
"U.S. Appl. No. 15/436,245, Non Final Office Action mailed Sep. 4, 2020", 9 pgs.
"U.S. Appl. No. 15/436,245, Notice of Allowance mailed Aug. 3, 2021", 9 pgs.
"U.S. Appl. No. 15/436,245, Preliminary Amendment filed May 5, 2017", 3 pgs.
"U.S. Appl. No. 15/436,245, PTO Response to Rule 312 Communication mailed Oct. 27, 2021", 2 pgs.
"U.S. Appl. No. 15/436,245, Response filed Apr. 27, 2020 to Final Office Action mailed Nov. 18, 2019", 10 pgs.
"U.S. Appl. No. 15/436,245, Response filed Jun. 24, 2021 to Final Office Action mailed Mar. 24, 2021", 11 pgs.
"U.S. Appl. No. 15/436,245, Response filed Dec. 4, 2020 to Non Final Office Action mailed Sep. 4, 2020", 12 pgs.
"U.S. Appl. No. 15/436,245, Response filed Jul. 29, 2019 to Non-Final Office Action mailed Apr. 19, 2019", 11 pgs.
"U.S. Appl. No. 15/436,245, Restriction Requirement mailed Oct. 11, 2018", 9 pgs.
"U.S. Appl. No. 15/436,245, Supplemental Amendment filed Jul. 19, 2021", 10 pgs.
"U.S. Appl. No. 15/593,039, Non Final Office Action mailed Feb. 6, 2018", 8 pgs.
"U.S. Appl. No. 15/593,039, Notice of Allowance mailed Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication mailed Oct. 9, 2018", 2 pgs.
"U.S. Appl. No. 15/593,039, Response filed Apr. 30, 2018 to Non Final Office Action mailed Feb. 4, 2018", 8 pgs.
"U.S. Appl. No. 15/593,039, Response filed Dec. 18, 2017 to Restriction Requirement mailed Oct. 18, 2017", 8 pgs.
"U.S. Appl. No. 15/593,039, Restriction Requirement mailed Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Notice of Allowance mailed Nov. 15, 2018", 7 pgs.
"U.S. Appl. No. 15/865,364, Preliminary Amendment filed Apr. 10, 2018", 10 pgs.
"U.S. Appl. No. 15/905,454, Preliminary Amendment filed Nov. 2, 2018", 5 pgs.
"U.S. Appl. No. 15/905,454, Restriction Requirement mailed Jan. 3, 2019", 6 pgs.
"U.S. Appl. No. 15/915,486 Supplemental Preliminary Amendment Filed Mar. 12, 2019", 5 pgs.
"U.S. Appl. No. 15/915,486, Advisory Action mailed Jun. 28, 2021", 7 pgs.
"U.S. Appl. No. 15/915,486, Advisory Action mailed Jul. 13, 2020", 3 pgs.
"U.S. Appl. No. 15/915,486, Final Office Action mailed Jan. 11, 2022", 9 pgs.
"U.S. Appl. No. 15/915,486, Final Office Action mailed Jan. 27, 2020", 8 pgs.
"U.S. Appl. No. 15/915,486, Final Office Action mailed Feb. 1, 2021", 8 pgs.

(56) References Cited

OTHER PUBLICATIONS

"U.S. Appl. No. 15/915,486, Non Final Office Action mailed Sep. 2, 2021", 8 pgs.
"U.S. Appl. No. 15/915,486, Non Final Office Action mailed Sep. 15, 2020", 10 pgs.
"U.S. Appl. No. 15/915,486, Non Final Office Action mailed Oct. 24, 2019", 10 pgs.
"U.S. Appl. No. 15/915,486, Response filed Jan. 3, 2020 to Non Final Office Action mailed Oct. 24, 2019", 8 pgs.
"U.S. Appl. No. 15/915,486, Response filed Jun. 1, 2021 to Final Office Action mailed Feb. 1, 2021", 10 pgs.
"U.S. Appl. No. 15/915,486, Response filed Jun. 23, 2020 to Final Office Action mailed Jan. 27, 2020", 7 pgs.
"U.S. Appl. No. 15/915,486, Response filed Jul. 27, 2021 to Advisory Action mailed Jun. 28, 2021", 10 pgs.
"U.S. Appl. No. 15/915,486, Response filed Nov. 30, 2021 to Non Final Office Action mailed Sep. 2, 2021", 6 pgs.
"U.S. Appl. No. 15/915,486, Response filed Dec. 21, 2020 to Non Final Office Action mailed Sep. 15, 2020", 7 pgs.
"U.S. Appl. No. 15/915,486, Restriction Requirement mailed Aug. 5, 2019", 9 pgs.
"U.S. Appl. No. 15/966,092, Interview Summary mailed Mar. 2, 2021", 2 pgs.
"U.S. Appl. No. 15/966,092, Non Final Office Action mailed Jun. 26, 2020", 22 pgs.
"U.S. Appl. No. 15/966,092, Notice of Allowance mailed Feb. 11, 2021", 5 pgs.
"U.S. Appl. No. 15/966,092, Response filed Oct. 26, 2020 to Non Final Office Action mailed Jun. 26, 2020", 9 pgs.
"U.S. Appl. No. 16/046,250, Non Final Office Action mailed Mar. 6, 2020", 10 pgs.
"U.S. Appl. No. 16/046,250, Notice of Allowance mailed Jun. 15, 2020", 9 pgs.
"U.S. Appl. No. 16/046,250, Response filed Jun. 3, 2020 to Non Final Office Action mailed Mar. 6, 2020", 10 pgs.
"U.S. Appl. No. 16/046,250, Response filed Oct. 25, 2019 to Restriction Requirement mailed Jul. 25, 2019", 9 pgs.
"U.S. Appl. No. 16/046,250, Restriction Requirement mailed Jul. 25, 2019", 7 pgs.
"U.S. Appl. No. 16/170,321, Advisory Action mailed Feb. 23, 2021", 3 pgs.
"U.S. Appl. No. 16/170,321, Corrected Notice of Allowability mailed Sep. 29, 2021", 2 pgs.
"U.S. Appl. No. 16/170,321, Final Office Action mailed Dec. 14, 2020", 13 pgs.
"U.S. Appl. No. 16/170,321, Non Final Office Action mailed Apr. 13, 2020", 13 pgs.
"U.S. Appl. No. 16/170,321, Notice of Allowance mailed Aug. 4, 2021", 10 pgs.
"U.S. Appl. No. 16/170,321, PTO Response to Rule 312 Communication mailed Sep. 1, 2021", 2 pgs.
"U.S. Appl. No. 16/170,321, Response filed Jan. 24, 2020 to Restriction Requirement mailed Nov. 27, 2019", 9 pgs.
"U.S. Appl. No. 16/170,321, Response filed Jan. 26, 2021 to Final Office Action mailed Dec. 14, 2020", 9 pgs.
"U.S. Appl. No. 16/170,321, Response filed Mar. 9, 2021 to Advisory Action mailed Feb. 23, 2021", 9 pgs.
"U.S. Appl. No. 16/170,321, Response filed Sep. 11, 2020 to Non Final Office Action mailed Apr. 13, 2020", 9 pgs.
"U.S. Appl. No. 16/170,321, Restriction Requirement mailed Nov. 27, 2019", 10 pgs.
"U.S. Appl. No. 16/173,605 Preliminary Amendment Filed Nov. 18, 2019", 5 pgs.
"U.S. Appl. No. 16/173,605, Final Office Action mailed Jul. 27, 2020", 7 pgs.
"U.S. Appl. No. 16/173,605, Non Final Office Action mailed Mar. 13, 2020", 10 pgs.
"U.S. Appl. No. 16/173,605, Notice of Allowance mailed Jan. 13, 2021", 6 pgs.
"U.S. Appl. No. 16/173,605, Response filed Jul. 13, 2020 to Non Final Office Action mailed Mar. 13, 2020", 13 pgs.
"U.S. Appl. No. 16/173,605, Response filed Dec. 21, 2020 to Final Office Action mailed Jul. 27, 2020", 7 pgs.
"U.S. Appl. No. 16/545,761, Final Office Action mailed Oct. 20, 2021", 10 pgs.
"U.S. Appl. No. 16/545,761, Non Final Office Action mailed Feb. 11, 2021", 12 pgs.
"U.S. Appl. No. 16/545,761, Notice of Allowance mailed Mar. 9, 2022", 6 pgs.
"U.S. Appl. No. 16/545,761, Preliminary Amendment filed Feb. 7, 2020", 9 pgs.
"U.S. Appl. No. 16/545,761, PTO Response to Rule 312 Communication mailed May 13, 2022", 2 pgs.
"U.S. Appl. No. 16/545,761, Response filed Feb. 16, 2022 to Final Office Action mailed Oct. 20, 2021", 10 pgs.
"U.S. Appl. No. 16/545,761, Response filed Jun. 30, 2021 to Non Final Office Action mailed Feb. 11, 2021", 13 pgs.
"U.S. Appl. No. 16/547,262, Non Final Office Action mailed Mar. 31, 2021", 13 pgs.
"U.S. Appl. No. 16/547,262, Notice of Allowance mailed Jul. 22, 2021", 7 pgs.
"U.S. Appl. No. 16/547,262, Response filed Jun. 30, 2021 to Non Final Office Action mailed Mar. 31, 2021", 12 pgs.
"U.S. Appl. No. 16/547,262, Response filed Dec. 17, 2020 to Restriction Requirement mailed Jul. 17, 2020", 12 pgs.
"U.S. Appl. No. 16/547,262, Restriction Requirement mailed Jul. 17, 2020", 6 pgs.
"U.S. Appl. No. 16/694,748, Non Final Office Action mailed Nov. 9, 2021", 6 pgs.
"U.S. Appl. No. 16/694,748, Notice of Allowance mailed Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 2022 to Non Final Office Action mailed Nov. 9, 2021", 7 pgs.
"U.S. Appl. No. 16/694,748, Response filed Jul. 27, 2021 to Restriction Requirement mailed Jan. 27, 2021", 8 pgs.
"U.S. Appl. No. 16/694,748, Restriction Requirement mailed Jan. 27, 2021", 9 pgs.
"U.S. Appl. No. 16/749,910, Notice of Allowance mailed Sep. 22, 2021", 10 pgs.
"U.S. Appl. No. 16/749,910, Response filed Jun. 17, 2021 to Restriction Requirement mailed Apr. 19, 2021", 11 pgs.
"U.S. Appl. No. 16/749,910, Restriction Requirement mailed Apr. 19, 2021", 9 pgs.
"U.S. Appl. No. 16/785,449, Advisory Action mailed Jun. 7, 2023", 17 pgs.
"U.S. Appl. No. 16/785,449, Final Office Action mailed Mar. 18, 2022", 12 pgs.
"U.S. Appl. No. 16/785,449, Non Final Office Action mailed Jul. 21, 2021", 9 pgs.
"U.S. Appl. No. 16/785,449, Non Final Office Action mailed Sep. 22, 2022", 13 pgs.
"U.S. Appl. No. 16/785,449, Response filed Jan. 20, 2023 to Non Final Office Action mailed Sep. 22, 2022", 8 pgs.
"U.S. Appl. No. 16/785,449, Response filed May 22, 2023 to Final Office Action mailed Mar. 22, 2023", 9 pgs.
"U.S. Appl. No. 16/785,449, Response filed Jun. 27, 2022 to Final Office Action mailed Mar. 18, 2022", 7 pgs.
"U.S. Appl. No. 16/785,449, Response filed Jul. 2, 2021 to Restriction Requirement mailed Jun. 21, 2021", 6 pgs.
"U.S. Appl. No. 16/785,449, Response filed Dec. 17, 2021 to Non Final Office Action mailed Jul. 21, 2021", 8 pgs.
"U.S. Appl. No. 16/785,449, Restriction Requirement mailed Jun. 21, 2021", 8 pgs.
"U.S. Appl. No. 16/785,449, Final Office Action mailed Mar. 22, 2023", 16 pgs.
"U.S. Appl. No. 16/865,194, Notice of Allowance mailed Mar. 3, 2022", 9 pgs.
"U.S. Appl. No. 16/865,194, Response filed Dec. 20, 2021 to Restriction Requirement mailed Oct. 20, 2021", 11 pgs.

(56) References Cited

OTHER PUBLICATIONS

"U.S. Appl. No. 16/865,194, Restriction Requirement mailed Oct. 20, 2021", 7 pgs.
"U.S. Appl. No. 17/004,583, 312 Amendment filed Mar. 16, 2023", 7 pgs.
"U.S. Appl. No. 17/004,583, Advisory Action mailed Aug. 30, 2022", 2 pgs.
"U.S. Appl. No. 17/004,583, Final Office Action mailed Jun. 9, 2022", 6 pgs.
"U.S. Appl. No. 17/004,583, Non Final Office Action mailed Feb. 24, 2022", 5 pgs.
"U.S. Appl. No. 17/004,583, Non Final Office Action mailed Sep. 29, 2022", 8 pgs.
"U.S. Appl. No. 17/004,583, Notice of Allowability mailed Feb. 10, 2023", 4 pgs.
"U.S. Appl. No. 17/004,583, Notice of Allowance mailed Feb. 1, 2023", 10 pgs.
"U.S. Appl. No. 17/004,583, Notice of Allowance mailed May 15, 2023", 7 pgs.
"U.S. Appl. No. 17/004,583, Preliminary Amendment filed Dec. 21, 2020", 6 pgs.
"U.S. Appl. No. 17/004,583, PTO Response to Rule 312 Communication mailed Feb. 23, 2023", 4 pgs.
"U.S. Appl. No. 17/004,583, PTO Response to Rule 312 Communication mailed Apr. 6, 2023", 3 pgs.
"U.S. Appl. No. 17/004,583, Response filed Jan. 31, 2022 to Restriction Requirement mailed Nov. 24, 2021", 7 pgs.
"U.S. Appl. No. 17/004,583, Response filed May 24, 2022 to Non Final Office Action mailed Feb. 24, 2022", 9 pgs.
"U.S. Appl. No. 17/004,583, Response filed Aug. 9, 2022 to Final Office Action mailed Jun. 9, 2022", 9 pgs.
"U.S. Appl. No. 17/004,583, Response filed Sep. 8, 2022 to Advisory Action mailed Aug. 30, 2022", 15 pgs.
"U.S. Appl. No. 17/004,583, Response filed Dec. 29, 2022 to Non Final Office Action mailed Sep. 29, 2022", 8 pgs.
"U.S. Appl. No. 17/004,583, Restriction Requirement mailed Nov. 24, 2021", 10 pgs.
"U.S. Appl. No. 17/004,583, Supplemental Amendment filed Mar. 28, 2023", 6 pgs.
"U.S. Appl. No. 17/155,625, Advisory Action mailed Jan. 20, 2023", 3 pgs.
"U.S. Appl. No. 17/155,625, Final Office Action mailed Sep. 28, 2022", 18 pgs.
"U.S. Appl. No. 17/155,625, Non Final Office Action mailed May 26, 2022", 10 pgs.
"U.S. Appl. No. 17/155,625, Notice of Allowance mailed Apr. 12, 2023", 11 pgs.
"U.S. Appl. No. 17/155,625, Response filed Feb. 28, 2023 to Advisory Action mailed Jan. 20, 2023", 8 pgs.
"U.S. Appl. No. 17/155,625, Response filed May 2, 2022 to Restriction Requirement mailed Mar. 3, 2022", 7 pgs.
"U.S. Appl. No. 17/155,625, Response filed Aug. 29, 2022 to Non Final Office Action mailed May 26, 2022", 8 pgs.
"U.S. Appl. No. 17/155,625, Response filed Dec. 28, 2022 to Final Office Action mailed Sep. 28, 2022", 8 pgs.
"U.S. Appl. No. 17/155,625, Restriction Requirement mailed Mar. 3, 2022", 9 pgs.
"U.S. Appl. No. 17/212,836, Non Final Office Action mailed Feb. 16, 2023", 12 pgs.
"U.S. Appl. No. 17/212,836, Response filed May 16, 2023 to Non Final Office Action mailed Feb. 16, 2023", 7 pgs.
"U.S. Appl. No. 17/212,836, Response filed Oct. 19, 2022 to Restriction Requirement mailed Aug. 19, 2022", 6 pgs.
"U.S. Appl. No. 17/212,836, Restriction Requirement mailed Aug. 19, 2022", 7 pgs.
"U.S. Appl. No. 17/229,001, Preliminary Amendment filed Apr. 26, 2021", 7 pgs.
"U.S. Appl. No. 17/352,845, Non Final Office Action mailed Dec. 16, 2022", 15 pgs.
"U.S. Appl. No. 17/578,939, Preliminary Amendment filed Apr. 14, 2022", 9 pgs.
"U.S. Appl. No. 17/813,178, Preliminary Amendment filed Jan. 18, 2023", 7 pgs.
"U.S. Appl. No. 14/528,997, Preliminary Amendment filed Dec. 8, 2014", 3 pgs.
"U.S. Appl. No. 14/919,431, Restriction Requirement mailed Feb. 3, 2016", 18 pgs.
"Australian Application Serial No. 2001255336, Examiner's First Report mailed Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2003219745, Examiner's First Report mailed Feb. 14, 2007", 2 pgs.
"Australian Application Serial No. 2003219745, Response filed Mar. 14, 2008 to Examiner's First Report mailed Feb. 14, 2007", 24 pgs.
"Australian Application Serial No. 2004249133, First Examiner's Report mailed May 5, 2008", 4 pgs.
"Australian Application Serial No. 2004249133, Response filed Mar. 30, 2009 to First Examiner's Report mailed May 5, 2008", 30 pgs.
"Australian Application Serial No. 2004274860, Office Action mailed May 21, 2008", 2 pgs.
"Australian Application Serial No. 2007245192, Office Action mailed Aug. 25, 2011", 2 pgs.
"Australian Application Serial No. 2007245192, Response filed Feb. 28, 2012 to Office Action mailed Aug. 25, 2011", 22 pgs.
"Australian Application Serial No. 2008203186, First Examiner Report mailed Jan. 28, 2011", 2 pgs.
"Australian Application Serial No. 2008203186, Office Action Received mailed Sep. 16, 2010", 1 page.
"Australian Application Serial No. 2008203186, Response filed Mar. 28, 2011 to First Examiner Report mailed Jan. 28, 2011", 53 pgs.
"Australian Application Serial No. 2008203186, Response filed Aug. 29, 2011 to Official Action dated Apr. 13, 2011", 20 pgs.
"Australian Application Serial No. 2012204138, First Examiner Report mailed Jul. 16, 2013", 4 pgs.
"Australian Application Serial No. 2012204138, Response filed Dec. 24, 2013 to First Examiner Report mailed Jul. 16, 2013", 21 pgs.
"Australian Application Serial No. 2014202470, First Examiner Report mailed Jul. 20, 2015", 2 pgs.
"Australian Application Serial No. 2014202470, Response filed Jul. 4, 2016 to Subsequent Examiners Report mailed Feb. 1, 2016", 3 pgs.
"Australian Application Serial No. 2014202470, Response filed Jul. 20, 2016 to Subsequent Examiners Report mailed Jul. 19, 2016", 15 pgs.
"Australian Application Serial No. 2014202470, Response filed Dec. 1, 2015 to First Examiner Report mailed Jul. 20, 2015", 22 pgs.
"Australian Application Serial No. 2014202470, Subsequent Examiners Report mailed Feb 1, 2016", 2 pgs.
"Australian Application Serial No. 2014202470, Subsequent Examiners Report mailed Jul. 19, 2016", 3 pgs.
"Australian Application Serial No. 2014290203, First Examination Report mailed Oct. 10, 2019", 4 pgs.
"Australian Application Serial No. 2014290203, Response filed Mar. 13, 2020 to First Examination Report mailed Oct. 10, 2019", 16 pgs.
"Australian Application Serial No. 2014290203, Response filed Jun. 24, 2020 to Subsequent Examiners Report mailed Mar. 23, 2020", 16 pgs.
"Australian Application Serial No. 2014290203, Response filed Sep. 29, 2020 to Subsequent Examiners Report mailed Jul. 21, 2020", 25 pgs.
"Australian Application Serial No. 2014290203, Response filed Dec. 9, 2020 to Subsequent Examiners Report mailed Oct. 6, 2020", 14 pgs.
"Australian Application Serial No. 2014290203, Subsequent Examiners Report mailed Mar. 23, 2020", 6 pgs.

(56) References Cited

OTHER PUBLICATIONS

"Australian Application Serial No. 2014290203, Subsequent Examiners Report mailed Jul. 21, 2020", 5 pgs.
"Australian Application Serial No. 2014290203, Subsequent Examiners Report mailed Oct. 6, 2020", 4 pgs.
"Australian Application Serial No. 2017221444, First Examination Report mailed Jul. 8, 2020", 6 pgs.
"Australian Application Serial No. 2017221444, Fourth Examiners Report mailed Jun. 29, 2021", 3 pgs.
"Australian Application Serial No. 2017221444, Response filed Jan. 25, 2021 to Subsequent Examiners Report mailed Nov. 27, 2020", 18 pgs.
"Australian Application Serial No. 2017221444, Response filed Jun. 2, 2021 to Subsequent Examiners Report mailed Feb. 24, 2021", 20 pgs.
"Australian Application Serial No. 2017221444, Response filed Jul. 6, 2021 to Fourth Examiners Report mailed Jun. 29, 2021", 7 pgs.
"Australian Application Serial No. 2017221444, Response filed Nov. 13, 2020 to First Examination Report mailed Jul. 8, 2020", 13 pgs.
"Australian Application Serial No. 2017221444, Subsequent Examiners Report mailed Feb. 24, 2021", 4 pgs.
"Australian Application Serial No. 2017221444, Subsequent Examiners Report mailed Nov. 27, 2020", 4 pgs.
"Australian Application Serial No. 2021201844, First Examination Report filed Sep. 29, 2022", 3 pgs.
"Australian Application Serial No. 2021201844, Voluntary Amendment filed Dec. 6, 2021", 17 pgs.
"Australian Application Serial No. 2008203186, Subsequent Examiner Report mailed Apr. 13, 2011", 2 pgs.
"Avian Inluenza", Queensland Government—Department of Primary Industries, (Observed Feb. 22, 2003), 2 pgs.
"Brazil Application Serial No. PI 0410702-0, Office Action mailed Oct. 6, 2020", (w/ English Translation), 9 pgs.
"Brazil Application Serial No. PI 0410702-0, Response filed Dec. 14, 2020 to Office Action mailed Oct. 6, 2020", (w/ English Translation of Claims), 42 pgs.
"Brazil Application Serial No. PI0307679-2, Office Action malled May 16, 2017", 2 pgs.
"Brazil Application Serial No. PI0307679-2, Response filed Jul. 13, 2017 to Office Action mailed May 16, 2017", 9 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI 0410702-0, Office Action mailed Nov. 1, 2019", (w/ English Translation), 6 pgs.
"Brazilian Application Serial No. PI 0410702-0, Response filed Feb. 6, 2020 to Office Action mailed Nov. 1, 2019", (w/ English Translation of Claims), 92 pgs.
"Brazilian Application Serial No. PI0307679-2, Final Office Action mailed Jul. 7, 2020", w/o English Translation, 6 pgs.
"Brazilian Application Serial No. PI0307679-2, Office Action mailed May 13, 2019", (w/ English Translation), 17 pgs.
"Brazilian Application Serial No. PI0307679-2, Office Action mailed Oct. 3, 2019", (w/ English Translation), 6 pgs.
"Brazilian Application Serial No. PI0307679-2, Office Action mailed Dec. 20, 2016", 2 pgs.
"Brazilian Application Serial No. PI0307679-2, Response filed Feb. 1, 2017 to Office Action mailed Dec. 20, 2016", 6 pgs.
"Brazilian Application Serial No. PI0307679-2, Response filed Aug. 16, 2019 to Office Action mailed May 13, 2019", (w/ English Translation of Claims), 29 pgs.
"Brazilian Application Serial No. PI0307679-2, Response filed Dec. 11, 2019 to Office Action mailed Oct. 3, 2019", w/ English Claims, 59 pgs.
"Brazilian Application Serial No. PI0410702-0, Office Action mailed Feb. 23, 2012", w/ English Translation, 4 pgs.
"Brazilian Application Serial No. PI0410702-0, Office Action mailed Apr. 1, 2020", (w/ English Summary), 6 pgs.
"Brazilian Application Serial No. PI0410702-0, Response filed May 7, 2012 to Office Action mailed Feb. 23, 2012", w/ English Claims, 11 pgs.
"Brazilian Application Serial No. PI0410702-0, Response filed Aug. 28, 2020 to Office Action mailed Apr. 1, 2020", (w/ English Translation of Claims), 86 pgs.
"Canadian Application Serial No. 11/509,249, Response filed May 16, 2011 to Office Acttion mailed Nov. 18, 2010", 15 pgs.
"Canadian Application Serial No. 2,406,180, Office Action mailed Sep. 9, 2008", 5 pgs.
"Canadian Application Serial No. 2,406,180, Office Action mailed Nov. 10, 2011", 3 pgs.
"Canadian Application Serial No. 2,406,180, Office Action mailed Nov. 23, 2009", 3 pgs.
"Canadian Application Serial No. 2,406,180, Office Action mailed Dec. 10, 2010", 2 Pgs.
"Canadian Application Serial No. 2,406,180, Response filed Jan. 26, 2009 to Official Action mailed Sep. 9, 2008", 22 pgs.
"Canadian Application Serial No. 2,406,180, Response filed May 7, 2012 to Office Action mailed Nov. 10, 2011", 11 pgs.
"Canadian Application Serial No. 2,406,180, Response filed May 21, 2010 to Office action mailed Nov. 23, 2009", 13 pgs.
"Canadian Application Serial No. 2,406,180, Response filed Jun. 14, 2011 to Office Action mailed Dec. 10, 2010", 10 pgs.
"Canadian Application Serial No. 2,406,180, Response mailed Jun. 10, 2011 to Office Action mailed Dec. 10, 2010", 10 pgs.
"Canadian Application Serial No. 2,492,097, Office Action mailed Jan. 10, 2012", 4 pgs.
"Canadian Application Serial No. 2,492,097, Office Action mailed Apr. 24, 2008", 3 pgs.
"Canadian Application Serial No. 2,492,097, Office Action mailed Jul. 31, 2009", 3 pgs.
"Canadian Application Serial No. 2,492,097, Response filed Jan. 29, 2010 to Office Action mailed Jul. 31, 2009", 13 pgs.
"Canadian Application Serial No. 2,492,097, Response filed May 2, 2012 to Office Action mailed Jan. 10, 2012", 12 pgs.
"Canadian Application Serial No. 2,492,097, Response filed Oct. 23, 2008 to Office Action mailed Apr. 24, 2008", 14 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action mailed Jun. 6, 2011", 2 pgs.
"Canadian Application Serial No. 2,522,081, Office Action mailed Aug. 30, 2010", 2 pgs.
"Canadian Application Serial No. 2,522,081, Office Action mailed Oct. 8, 2009", 6 pgs.
"Canadian Application Serial No. 2,522,081, Response filed Feb. 28, 2011 to Office Action mailed Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action mailed Jun. 6, 2011", 11 pgs.
"Canadian Application Serial No. 2,525,953, Amendment and Response filed Feb. 1, 2017 to Office Action mailed Aug. 1, 2016", 28 pgs.
"Canadian Application Serial No. 2,525,953, Non Final Office Action mailed Mar. 30, 2022", 4 pgs.
"Canadian Application Serial No. 2,525,953, Office Action mailed Jan. 21, 2016", 6 pgs.
"Canadian Application Serial No. 2,525,953, Office Action mailed Jan. 29, 2020", 4 pgs.
"Canadian Application Serial No. 2,525,953, Office Action mailed Apr. 28, 2021", 7 pgs.
"Canadian Application Serial No. 2,525,953, Office Action mailed Jul. 31, 2012", 4 pgs.
"Canadian Application Serial No. 2,525,953, Office Action mailed Aug. 1, 2016", 6 pgs.
"Canadian Application Serial No. 2,525,953, Office Action mailed Aug. 16, 2013", 3 pgs.
"Canadian Application Serial No. 2,525,953, Office Action mailed Oct. 3, 2017", 4 pgs.

(56) References Cited

OTHER PUBLICATIONS

"Canadian Application Serial No. 2,525,953, Office Action mailed Nov. 2, 2018", 6 pgs.
"Canadian Application Serial No. 2,525,953, Office Action mailed Nov. 6, 2014", 3 pgs.
"Canadian Application Serial No. 2,525,953, Office Action mailed Jun. 22, 2011", 4 pgs.
"Canadian Application Serial No. 2,525,953, Office Action received Jun. 22, 2011", 4 pgs.
"Canadian Application Serial No. 2,525,953, Response filed Jan. 31, 2013 to Office Action mailed Jul. 31, 2012", 11 pgs.
"Canadian Application Serial No. 2,525,953, Response filed Feb. 1, 2017 to Office Action mailed Aug. 1, 2016", 28 pgs.
"Canadian Application Serial No. 2,525,953, Response filed Feb. 14, 2014 to Office Action mailed Aug. 16, 2013", 16 pgs.
"Canadian Application Serial No. 2,525,953, Response filed Apr. 3, 2018 to Office Action mailed Oct. 3, 2017", 46 pgs.
"Canadian Application Serial No. 2,525,953, Response filed May 1, 2015 to Office Action mailed Nov. 6, 2014", 23 pgs.
"Canadian Application Serial No. 2,525,953, Response filed May 2, 2019 to Office Action mailed Nov. 2, 2018", 31 pgs.
"Canadian Application Serial No. 2,525,953, Response filed May 25, 2020 to Office Action mailed Jan. 29, 2020", 35 pgs.
"Canadian Application Serial No. 2,525,953, Response filed Jul. 11, 2016 to Office Action mailed Jan. 21, 2016", 21 pgs.
"Canadian Application Serial No. 2,525,953, Response filed Aug. 26, 2021 to Office Action mailed Apr. 28, 2021", 16 pgs.
"Canadian Application Serial No. 2,525,953, Response filed Dec. 22, 2011 to Office Action mailed Jun. 22, 2011", 17 pgs.
"Canadian Application Serial No. 2,647,985 , Response filed Sep. 30, 2013 to Office Action mailed May 15, 2013", 20 pgs.
"Canadian Application Serial No. 2,647,985, Office Action mailed May 15, 2013", 3 pgs.
"Canadian Application Serial No. 2,816,242, Office Action mailed Jun. 16, 2014", 3 pgs.
"Canadian Application Serial No. 2,816,242, Office Action mailed Jul. 12, 2017", 4 pgs.
"Canadian Application Serial No. 2,816,242, Office Action mailed Sep. 16, 2016", 4 pgs.
"Canadian Application Serial No. 2,816,242, Office Action mailed Oct. 5, 2015", 6 pgs.
"Canadian Application Serial No. 2,816,242, Response filed Jan. 3, 2018 to Office Action mailed Jul. 12, 2017", 13 pgs.
"Canadian Application Serial No. 2,816,242, Response filed Mar. 10, 2017 to Office Action mailed Sep. 16, 2016", 18 pgs.
"Canadian Application Serial No. 2,816,242, Response filed Apr. 5, 2016 to Office Action mailed Oct. 5, 2015", 13 pgs.
"Canadian Application Serial No. 2,816,242, Response filed Dec. 16, 2014 to Office Action mailed Jun. 16, 2014", 9 pgs.
"Canadian Application Serial No. 2492097, Office Action mailed Nov. 18, 2010", 4 pgs.
"Canadian Application Serial No. 3,014,435, Office Action mailed Oct. 26, 2021", 4 pgs.
"Canadian Application Serial No. 3,014,435, Office Action mailed Nov. 6, 2020", 5 pgs.
"Canadian Application Serial No. 3,014,435, Office Action mailed Nov. 13, 2019", 4 pgs.
"Canadian Application Serial No. 3,014,435, Response filed Feb. 25, 2022 to Office Action mailed Oct. 26, 2021", 15 pgs.
"Canadian Application Serial No. 3,014,435, Response filed Mar. 5, 2021 to Office Action mailed Nov. 6, 2020", 20 pgs.
"Canadian Application Serial No. 3,014,435, Response filed Mar. 13, 2020 to Office Action mailed Nov. 13, 2019", 18 pgs.
"Chinese Application Serial No. 202080048487.4, Voluntary Amendment filed Dec. 5, 2022", w/ English Claims, 33 pgs.
"Chinese Application Serial No. 03808356.6, Office Action mailed Sep. 5, 2008", (English Translation), 6 pgs.
"Chinese Application Serial No. 03808356.6, Office Action received Jul. 1, 2011", (w/ English Translation of Office Action), 8 pgs.
"Chinese Application Serial No. 03808356.6, Reexamination Notice mailed Nov. 26, 2012", (w/ English Translation), 9 pgs.
"Chinese Application Serial No. 03808356.6, Response filed Mar. 11, 2013 to Office Action mailed Nov. 26, 2012", (w/ English Translation of Amended Claims), 9 pgs.
"Chinese Application Serial No. 03808356.6, Response filed Mar. 16, 2009 to Office Action mailed Sep. 5, 2008", (w/ English Translation of Claims), 8 pgs.
"Chinese Application Serial No. 03808356.6, Response filed Oct. 14, 2011 to Office Action mailed Jul. 1, 2011", (w/ English Translation of Amended Claims), 25 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action mailed Mar. 1, 2010", (w/ English Translation of Claims), 16 pgs.
"Chinese Application Serial No. 200480017037.X, Response filed Aug. 4, 2009 to Second Office Action mailed Mar. 20, 2009", (w/ English Translation of Amended Claims), 15 pgs.
"Chinese Application Serial No. 200480017037.X, Second Office Action mailed Mar. 20, 2009", (English Translation), 7 pgs.
"Chinese Application Serial No. 200480017037.X, Third Office Action mailed Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton mailed May 6, 2010", (w/ English Translation of Claims), 26 pgs.
"Chinese Application Serial No. 200480021259.9, First Office Action issued on Aug. 24, 2007", (w/ English Translation), 9 pgs.
"Chinese Application Serial No. 200480021259.9, Notice of Reexamination mailed Jul. 3, 2012", (w/ English Translation), 10 pgs.
"Chinese Application Serial No. 200480021259.9, Office Action mailed Jan. 11, 2011", (w/ English Translation), 15 pgs.
"Chinese Application Serial No. 200480021259.9, Office Action mailed May 6, 2010", (w/ English Translation), 12 pgs.
"Chinese Application Serial No. 200480021259.9, Office Action mailed Jul. 3, 2012", (w/ English Translation), 10 pgs.
"Chinese Application Serial No. 200480021259.9, Reexamination Decision mailed Mar. 25, 2013", (w/ English Translation), 17 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Office Action issued on Aug. 24, 2007", (w/ English Translation of Claims), 13 pgs.
"Chinese Application Serial No. 200480021259.9, Response filed Oct. 16, 2012 to Office Action mailed Jul. 3, 2012", (w/ English Translation of Claims), 13 pgs.
"Chinese Application Serial No. 200480022014, First Office Action mailed Aug. 24, 2007", w/English Translation, 6 pgs.
"Chinese Application Serial No. 200580046922.5, Office Action mailed Jul. 24, 2009", 12 pgs.
"Chinese Application Serial No. 200780020095.1, Decision on Rejection mailed Jul. 22, 2013", (w/ English Translation), 11 pgs.
"Chinese Application Serial No. 200780020095.1, First Office Action mailed Jun. 24, 2011", (w/ English Translation), 13 pgs.
"Chinese Application Serial No. 200780020095.1, Office Action mailed Jan. 29, 2013", (w/ English Translation), 10 pgs.
"Chinese Application Serial No. 200780020095.1, Office Action mailed Mar. 5, 2015", (w/ English Translation), 12 pgs.
"Chinese Application Serial No. 200780020095.1, Office Action mailed Apr. 26, 2016", (w/ English Summary), 4 pgs.
"Chinese Application Serial No. 200780020095.1, Office Action mailed May 3, 2012", (w/ English Translation), 10 pgs.
"Chinese Application Serial No. 200780020095.1, Office Action mailed Nov. 2, 2016", (w/ English Translation), 11 pgs.
"Chinese Application Serial No. 200780020095.1, Response filed Jan. 6, 2017 to Office Action mailed Nov. 2, 2016", (w/ English Translation of Claims), 15 pgs.

(56) References Cited

OTHER PUBLICATIONS

"Chinese Application Serial No. 200780020095.1, Response filed Jun. 9, 2013 to Office Action mailed Jan. 29, 2013", (w/ English Translation of Claims), 10 pgs.

"Chinese Application Serial No. 200780020095.1, Response filed Jun. 23, 2015 to Office Action mailed Mar. 5, 2015", (w/ English Translation of Claims), 16 pgs.

"Chinese Application Serial No. 200780020095.1, Response filed Jun. 30, 2016 to Office Action mailed Apr. 26, 2016", (w/ English Translation of Claims), 22 pgs.

"Chinese Application Serial No. 200780020095.1, Response filed Sep. 17, 2012 to Office Action mailed May 3, 2012", (w/ English Translation of Claims), 17 pgs.

"Chinese Application Serial No. 200780020095.1, Response filed Nov. 5, 2013 to to Decision on Rejection mailed Jul. 22, 2013", (w/ English Translation of Claims), 12 pgs.

"Chinese Application Serial No. 200780020095.1, Response filed Nov. 8, 2011 to Office Action mailed Jun. 24, 2011", (w/ English Translation of Amended Claims), 20 pgs.

"Chinese Application Serial No. 201310400039.8, Notice of Reexamination mailed Aug. 26, 2016", (w/ English Translation), 7 pgs.

"Chinese Application Serial No. 201310400039.8, Office Action mailed Feb. 12, 2015", (w/ English Translation), 10 pgs.

"Chinese Application Serial No. 201310400039.8, Office Action mailed Feb. 15, 2016", (w/ English Translation), 12 pgs.

"Chinese Application Serial No. 201310400039.8, Office Action mailed Apr. 1, 2017", (English Translation), 10 pgs.

"Chinese Application Serial No. 201310400039.8, Office Action mailed Aug. 7, 2015", (w/ English Translation), 10 pgs.

"Chinese Application Serial No. 201310400039.8, Office Action mailed Aug. 21, 2014", (w/ English Translation), 13 pgs.

"Chinese Application Serial No. 201310400039.8, Office Action Response mailed Jun. 16, 2017", W / English Claims, 8 pgs.

"Chinese Application Serial No. 201310400039.8, Response filed Jan. 4, 2015 to Office Action mailed Aug. 21, 2014", (w/ English Translation of Claims), 10 pgs.

"Chinese Application Serial No. 201310400039.8, Response filed Apr. 27, 2015 to Office Action mailed Feb. 12, 2015", (w/ English Translation of Claims), 16 pgs.

"Chinese Application Serial No. 201310400039.8, Response filed Jun. 1, 2016 to Office Action mailed Feb. 15, 2016", (w/ English Translation of Claims), 9 pgs.

"Chinese Application Serial No. 201310400039.8, Response filed Oct. 10, 2016 to Notice of Reexamination mailed Aug. 26, 2016", (w/ English Translation of Claims), 12 pgs.

"Chinese Application Serial No. 201310400039.8, Response filed Oct. 20, 2015 to Office Action mailed Aug. 7, 2015", (w/ English Translation of Claims), 11 pgs.

"Chinese Application Serial No. 201310400039.8, Response filed Aug. 14, 2017 to Office Action Response mailed Jun. 16, 2017", W/ English Claims, 11 pgs.

"Chinese Application Serial No. 201310400039.8, Response filed Aug. 7, 2017 to Office Action Response mailed Jun. 16, 2017", W/ English Claims, 10 pgs.

"Chinese Application Serial No. 201780024821.0, Office Action mailed Jun. 15, 2022", (w/ English Translation), 6 pgs.

"Chinese Application Serial No. 201780024821.0, Office Action mailed Nov. 30, 2021", (w/ English Translation), 21 pgs.

"Chinese Application Serial No. 201780024821.0, Response filed Apr. 12, 2022 to Office Action mailed Nov. 30, 2021", (w/ English Translation of Claims). 17 pgs.

"Chinese Application Serial No. 201780024821.0, Response filed Aug. 30, 2022 to Office Action mailed Jun. 15, 2022", w/ English Claims, 18 pgs.

"Chinese Application Serial No. 201780024821.0, Response to Examiner Telephone Interview filed Sep. 26, 2022", w/ English Claims, 10 pgs.

"Chinese Application Serial No. 202080048487.4, Notification to Make Rectification mailed Jan. 18, 2022", w/o English Translation, 1 pg.

"Chinese Application Serial No. 202080048487.4, Notification to Make Rectification mailed May 26, 2022", w/o English translation, 1 pg.

"Chinese Application Serial No. 200480021259.9, Office Action mailed May 8, 2009", (w/ English Translation), 6 pgs.

"Confirmed Cases of Avian Influenza A(H5N1)", World Health Organization, (Jan. 28, 2004), 1 pg.

"Declaration of Anne Koch Ballard dated Oct. 6, 2011", 1 pg.

"Eurasian Application No. 200501890, Notice of Allowance mailed Jun. 23, 2009", 1 pg.

"Eurasian Application Serial No. 200501890, Office Action mailed Mar. 23, 2007", (w English Translation), 2 pgs.

"Eurasian Application Serial No. 200501890, Office Action mailed Sep. 4, 2008", (English Translation), 1 pg.

"Eurasian Application Serial No. 200501890, Office Action mailed Dec. 17, 2007", (w/ English Translation), 6 pgs.

"Eurasian Application Serial No. 200501890, Response filed Mar. 26, 2008 to Office Action mailed Dec. 17, 2007", (w/ English Translation of Claims), 15 pgs.

"Eurasian Application Serial No. 200501890, Response filed Jun. 14, 2007 to Office Action mailed Mar. 23, 2007", (w/ English Translation of Claims), 11 pgs.

"Eurasian Application Serial No. 200501890, Response filed Dec. 17, 2008 to Office Action mailed Sep. 4, 2008", (w/ English Translation of Claims), 14 pgs.

"Eurasian Application Serial No. 200701097, Office Action mailed Sep. 4, 2008", OAR-MISC, 2 pgs.

"Eurasion Application Serial No. 200701097, Office Action mailed Jun. 16, 2009", 3 pgs.

"European Application 04750333.9, Communication dated Oct. 12, 2006", 6 pgs.

"European Application 04750333.9, Communication dated Dec. 8, 2006", 4 pgs.

"European Application 04750333.9, Communication dated Apr. 11, 2008", 6 pgs.

"European Application 04750333.9, Response filed Oct. 4, 2007 to Communication dated Dec. 8, 2006", 42 pgs.

"European Application 04750333.9, Response filed Nov. 21, 2006 to Communication Oct. 12, 2006", 4 pgs.

"European Application Serial 17709236.8 , Response filed Apr. 26, 2019 to Communication Pursuant to Rules 161(1) and 162 EPC mailed Oct. 19, 2018", 9 pgs.

"European Application Serial No. 03716017.3, Office Action mailed Aug. 23, 2012", 4 pgs.

"European Application Serial No. 01928486.8 Office Action mailed Oct. 1, 2009", 2 pgs.

"European Application Serial No. 01928486.8, Communication dated Aug. 10, 2007", 3 pgs.

"European Application Serial No. 01928486.8, Communication dated Sep. 20, 2005", 4 pgs.

"European Application Serial No. 01928486.8, Office Action mailed Feb. 19, 2009", 3 pgs.

"European Application Serial No. 01928486.8, Response filed Jan. 30, 2006 to Communication dated Sep. 20, 2005", 9 pgs.

"European Application Serial No. 01928486.8, Response filed Aug. 28, 2009 to Communication mailed Feb. 19, 2009", 5 pgs.

"European Application Serial No. 01928486.8, Response filed Jan. 21, 2008 to Communication dated Aug. 10, 2007", 11 pgs.

"European Application Serial No. 01928486.8, Response filed Dec. 9, 2009 to Office Action mailed Oct. 1, 2009", 11 pgs.

"European Application Serial No. 02724994.5, Office Action mailed Mar. 27, 2009", 2 pgs.

"European Application Serial No. 03716017.3, Communication and Supplementary European Search Report mailed Jan. 2, 2008", 8 pgs.

"European Application Serial No. 03716017.3, Communication mailed May 23, 2006", 3 pgs.

"European Application Serial No. 03716017.3, Communication mailed Jul. 26, 2006", 2 pgs.

"European Application Serial No. 03716017.3, Communication mailed Oct. 20, 2008", 7 pgs.

"European Application Serial No. 03716017.3, Further Written Submissions filed Mar. 19, 2015", 45 pgs.

(56) References Cited

OTHER PUBLICATIONS

"European Application Serial No. 03716017.3, Office Action mailed Jul. 27, 2010", 4 pgs.
"European Application Serial No. 03716017.3, Response filed Feb. 4, 2011 to Office Action mailed Jul. 27, 2010", 12 pgs.
"European Application Serial No. 03716017.3, Response filed Feb. 27, 2015 to Summons mailed Nov. 3, 2014", 29 pgs.
"European Application Serial No. 03716017.3, Response filed Mar. 4, 2013 to Examination Notification Art. 94(3) mailed Aug. 23, 2012", 19 pgs.
"European Application Serial No. 03716017.3, Response filed Mar. 24, 2015 to Office Action mailed Nov. 3, 2014", 38 pgs.
"European Application Serial No. 03716017.3, Response filed Jul. 28, 2006 to Communication mailed May 23, 2006", 5 pgs.
"European Application Serial No. 03716017.3, Response filed Aug. 19, 2009 to Communication mailed Oct. 20, 2008", 17 pgs.
"European Application Serial No. 03716017.3, Response filed Sep. 28, 2015", 13 pgs.
"European Application Serial No. 03716017.3, Result of Consultation mailed Mar. 17, 2015", 5 pgs.
"European Application Serial No. 03716017.3, Summons to Attend Oral proceedings mailed Nov. 3, 2014", 5 pgs.
"European Application Serial No. 04750333.9, Office Action mailed Jan. 22, 2009", 5 pgs.
"European Application Serial No. 04750333.9, Response filed Oct. 21, 2008 to Communication mailed Apr. 11, 2008", 15 pgs.
"European Application Serial No. 04750333.9, Response filed Nov. 17, 2009 to Communication mailed Jan. 22, 2009", 17 pgs.
"European Application Serial No. 04750333.9, Summons To Attend Oral Proceedings mailed Aug. 3, 2011", 13 pgs.
"European Application Serial No. 04776133.3, Communication mailed Mar. 30, 2006", 3 pgs.
"European Application Serial No. 04776133.3, Examination Notification Art. 94(3) mailed Jul. 28, 2015", 4 pgs.
"European Application Serial No. 04776133.3, Examination Notification Art. 94(3) mailed Nov. 25, 2013", 5 pgs.
"European Application Serial No. 04776133.3, Office Action mailed Jan. 5, 2010", 4 pgs.
"European Application Serial No. 04776133.3, Response filed Jan. 25, 2007 to Communication mailed Mar. 30, 2006", 20 pgs.
"European Application Serial No. 04776133.3, Response filed Apr. 30, 2014 to Examination Notification Art. 94(3) mailed Nov. 25, 2013", 12 pgs.
"European Application Serial No. 04776133.3, Response filed Jul. 15, 2010 to Office Action mailed Jan. 5, 2010", 9 pgs.
"European Application Serial No. 04776133.3, Response filed Sep. 18, 2015 to Examination Notification Art. 94(3) mailed Jul. 28, 2015", 47 pgs.
"European Application Serial No. 04809419.7, Communication mailed Apr. 3, 2007", 3 pgs.
"European Application Serial No. 04809419.7, Response filed Oct. 19, 2007 to Communication mailed Apr. 3, 2007", 20 pgs.
"European Application Serial No. 07754132.4, Office Action mailed Apr. 28, 2009", 4 pgs.
"European Application Serial No. 07754132.4, Office Action mailed Sep. 5, 2011", 5 pgs.
"European Application Serial No. 07754132.4, Office Action mailed Nov. 2, 2012", 4 pgs.
"European Application Serial No. 07754132.4, Response filed Feb. 5, 2010 to Office Action mailed Apr. 28, 2009", 15 pgs.
"European Application Serial No. 07754132.4, Response filed Mar. 15, 2012 to Office Action mailed Sep. 5, 2011", 21 pgs.
"European Application Serial No. 07754132.4, Response filed May 10, 2013 to Office Action mailed Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC mailed Apr. 4, 2018", 7 pgs.
"European Application Serial No. 10777154.5, Communication Pursuant to Article 94(3) EPC mailed Jun. 11, 2019", 3 pgs.
"European Application Serial No. 10777154.5, Communication Pursuant to Article 94(3) EPC mailed Oct. 12, 2017", 7 pgs.
"European Application Serial No. 10777154.5, Examination Notification Art. 94(3) mailed Oct. 6, 2014", 7 pgs.
"European Application Serial No. 10777154.5, Office Action mailed May 2, 2016", 6 pgs.
"European Application Serial No. 10777154.5, Office Action mailed Jul. 4, 2012", 2 pgs.
"European Application Serial No. 10777154.5, Response field May 13, 2019 to Summons to Attend Oral Proceedings mailed Jan. 7, 2019", 35 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Jan. 14, 2013 to Office Action mailed Jul. 4, 2012", 12 pgs.
"European Application Serial No. 10777154.5, Response filed Feb. 21, 2018 to Communication Pursuant to Article 94(3) EPC mailed Oct. 12, 2017", 12 pgs.
"European Application Serial No. 10777154.5, Response filed Jul. 29, 2019 to Communication Pursuant to Article 94(3) EPC mailed Jun. 11, 2019", 57 pgs.
"European Application Serial No. 10777154.5, Response filed Sep. 7, 2018 to Communication Pursuant to Article 94(3) EPC mailed Apr. 4, 2018", 18 pgs.
"European Application Serial No. 10777154.5, Response filed Sep. 8, 2016 to Office Action mailed May 2, 2016", 69 pgs.
"European Application Serial No. 10777154.5, Summons to Attend Oral Proceedings mailed Jan. 7, 2019", 5 pgs.
"European Application Serial No. 12761841.1, Communication pursuant to Article 94(3) EPC mailed Dec. 23, 2016", 6 pgs.
"European Application Serial No. 12761841.1, Response filed Feb. 23, 2017 to Communication pursuant to Article 94(3) EPC mailed Dec. 23, 2016", 9 pgs.
"European Application Serial No. 12761841.1, Voluntary Amendment filed Dec. 1, 2014", 5 pgs.
"European Application Serial No. 14745060.5, Communication Pursuant to Article 94(3) EPC mailed Feb. 6, 2018", 5 pgs.
"European Application Serial No. 14745060.5, Communication Pursuant to Article 94(3) EPC mailed Mar. 12, 2020", 4 pgs.
"European Application Serial No. 14745060.5, Communication Pursuant to Article 94(3) EPC mailed Jul. 18, 2019", 5 pgs.
"European Application Serial No. 14745060.5, Communication Pursuant to Article 94(3) EPC mailed Sep. 15, 2021", 4 pgs.
"European Application Serial No. 14745060.5, Communication Pursuant to Article 94(3) EPC mailed Sep. 18, 2018", 4 pgs.
"European Application Serial No. 14745060.5, Communication Pursuant to Article 94(3) EPC mailed Nov. 9, 2020", 4 pgs.
"European Application Serial No. 14745060.5, Office Action mailed Feb. 23, 2016", 2 pgs.
"European Application Serial No. 14745060.5, Response filed Jan. 5, 2022 to Communication Pursuant to Article 94(3) EPC mailed Sep. 15, 2021", 78 pgs.
"European Application Serial No. 14745060.5, Response filed Jan. 28, 2020 to Communication Pursuant to Article 94(3) EPC mailed Jul. 18, 2019", 9 pgs.
"European Application Serial No. 14745060.5, Response filed Mar. 27, 2019 to Communication Pursuant to Article 94(3) EPC mailed Sep. 18, 2018", 13 pgs.
"European Application Serial No. 14745060.5, Response filed May 12, 2021 to Communication Pursuant to Article 94(3) EPC mailed Nov. 9, 2020", 12 pgs.
"European Application Serial No. 14745060.5, Response filed Jun. 15, 2018 to Communication Pursuant to Article 94(3) EPC mailed Feb. 6, 2018", 14 pgs.
"European Application Serial No. 14745060.5, Response filed Jul. 17, 2020 to Communication Pursuant to Article 94(3) EPC mailed Mar. 12, 2020", 52 pgs.
"European Application Serial No. 14745060.5, Response filed Dec. 22, 2016 to Communication pursuant to Rules 161(1) and 162 EPC mailed Feb. 23, 2016", 6 pgs.
"European Application Serial No. 15197386.4, Communication Pursuant to Article 94(3) EPC mailed Feb. 21, 2018", 5 pgs.

(56) References Cited

OTHER PUBLICATIONS

"European Application Serial No. 15197386.4, Communication Pursuant to Article 94(3) EPC mailed Apr. 21, 2017", 5 pgs.
"European Application Serial No. 15197386.4, Communication Pursuant to Article 94(3) EPC mailed Jun. 19, 2019", 4 pgs.
"European Application Serial No. 15197386.4, extended European Search Report mailed Feb. 26, 2016", 11 pgs.
"European Application Serial No. 15197386.4, Response filed Jul. 3, 2018 to Communication Pursuant to Article 94(3) EPC mailed Feb. 21, 2018", 7 pgs.
"European Application Serial No. 15197386.4, Response filed Aug. 27, 2019 to Communication Pursuant to Article 94(3) EPC mailed Jun. 19, 2019", 61 pgs.
"European Application Serial No. 15197386.4, Response filed Oct. 20, 2016 to Extended European Search Report mailed Feb. 26, 2016", 4 pgs.
"European Application Serial No. 15197386.4, Response filed Oct. 31, 2017 to Communication Pursuant to Article 94(3) EPC mailed Apr. 21, 2017", 5 pgs.
"European Application Serial No. 16778485.9, Communication Pursuant to Article 94(3) EPC mailed Feb. 18, 2022", 4 pgs.
"European Application Serial No. 16778485.9, Communication Pursuant to Article 94(3) EPC mailed May 25, 2020", 5 pgs.
"European Application Serial No. 16778485.9, Communication Pursuant to Article 94(3) EPC mailed Aug. 22, 2019", 5 pgs.
"European Application Serial No. 16778485.9, Office Action mailed Apr. 30, 2018", 3 pgs.
"European Application Serial No. 16778485.9, Response filed Aug. 9, 2022 to Communication Pursuant to Article 94(3) EPC mailed Feb. 18, 2022", 14 pgs.
"European Application Serial No. 16778485.9, Response filed Oct. 5, 2020 to Communication Pursuant to Article 94(3) EPC mailed May 25, 2020", 14 pgs.
"European Application Serial No. 16778485.9, Response filed Nov. 8, 2018 to Office Action mailed Apr. 30, 2018", 18 pgs.
"European Application Serial No. 16778485.9, Response filed Dec. 19, 2019 to Communication Pursuant to Article 94(3) EPC mailed Aug. 22, 2019", 20 pgs.
"European Application Serial No. 17709236.8, Communication Pursuant to Article 94(3) EPC mailed Jun. 8, 2022", 6 pgs.
"European Application Serial No. 17709236.8, Communication Pursuant to Article 94(3) EPC mailed Jul. 6, 2021", 10 pgs.
"European Application Serial No. 17709236.8, Response filed Jan. 17, 2022 to Communication Pursuant to Article 94(3) EPC mailed Jul. 6, 2021", 13 pgs.
"European Application Serial No. 17709236.8, Response filed Oct. 11, 2022 to Communication Pursuant to Article 94(3) EPC mailed Jun. 8, 2022", 65 pgs.
"European Application Serial No. 18800815.5, Response to Communication pursuant to Rules 161 (1) and 162 EPC filed Dec. 15, 2020", 14 pgs.
"European Application Serial No. 19778696.5, Response to Communication persuant to Rules 161 and 162 filed Oct. 15, 2021", 39 pgs.
"European Application Serial No. 20714015.3, Response to Communication persuant to Rules 161 and 162 filed Apr. 7, 2022", 10 pgs.
"European Application Serial No. 20731609.2, Response to Communication persuant to Rules 161 and 162 filed Mar. 16, 2022", 17 pgs.
"European Application Serial No. 20768781.5, Response to Communication persuant to Rules 161 and 162 filed Oct. 17, 2022", 17 pgs.
"Evaluation of Medicines for human Use", EMEA/CPMP/BWP/2289/01, London The European Agency for the Evaluation of Medicinal Products, Committee for Proprietary Medicinal Products (CPMP), (Feb. 20, 2003), 14.
"Fluzone Influenza Virus Vaccine", Sanofi Aventis Pasteur, Swiftwater, (Jul. 2005), 12 pgs.
"Gen Bank Accession AFP82914", matrix protein 1 [Influenza A virus (A/reassortant/IVR-148(Brisbane/59/2007 x Texas/1/1977) (H1N1))], (2012), 2 pgs.
"Gen Bank Accession JX414012", Influenza A virus (A/reassortant/IVR-148(Brisbane/59/2007 x Texas/1/1977)(H1 N1)) segment 7 matrix protein 2 (M2) and matrix protein 1 (M1) genes, complete cds, (2012), 2 pgs.
"Gen Bank Accessions QHU79173", surface glycoprotein [Severe acute respiratory syndrome coronavirus 2], (Mar. 17, 2020), 3 pgs.
"Genbank", CY002484.1, (2005), 2 pgs.
"Genbank Accession # AAA43733, Neuraminidase Protein of Influenza B/Beijing/1/87 virus,", (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"GFP antibody (ab6556) datasheet", (r) abcam. [online]. [retrieved on Dec. 5, 2004]. Retrieved from the Internet: <URL: http://www.abcam.com/index.html?datasheet=6556>, (2004), 5 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, 2006), 1 pg.
"https://www.abcam.com/gfp-antibody-ab6556", [online]. [accessed on Dec. 5, 2004]. Retrieved from the Internet: http://www.abcam.com/index.html?datasheet=6556, (Dec. 5, 2004), 5 pgs.
"Indian Application Serial No. 02082/KOLNP/2005, Examination Report mailed Mar. 17, 2008", 1 pg.
"Indian Application Serial No. 02082/KOLNP/2005, Examination Report mailed Dec. 28, 2007", 1 pg.
"Indian Application Serial No. 02082/KOLNP/2005, First Examination Report mailed Jan. 25, 2007", 9 pgs.
"Indian Application Serial No. 02082/KOLNP/2005, Response filed Jan. 22, 2008 to Examination Report mailed Dec. 28, 2007", 13 pgs.
"Indian Application Serial No. 02082/KOLNP/2005, Response filed Jun. 10, 2008 to Examination Report mailed Mar. 17, 2008", 3 pgs.
"Indian Application Serial No. 02082/KOLNP/2005, Response filed Nov. 19, 2007 to First Examination Report mailed Jan. 25, 2007", 26 pgs.
"Indian Application Serial No. 1026/KOLNP/2009, First Examiner Report mailed Mar. 13, 2014", 2 pgs.
"Indian Application Serial No. 2272/KOLNP/2005, First Examination Report mailed Mar. 17, 2008", 10 pgs.
"Indian Application Serial No. 2272/KOLNP/2005, Response filed Mar. 16, 2009 to Subsequent Examination Report mailed Mar. 6, 2009", 12 pgs.
"Indian Application Serial No. 2272/KOLNP/2005, Response filed Oct. 11, 2008 to First Examination Report mailed Mar. 17, 2008", 27 pgs.
"Indian Application Serial No. 2272/KOLNP/2005, Subsequent Examination Report mailed Mar. 6, 2009", 1 pg.
"Indian Application Serial No. 2388/KOLNP/2005, First Examination Report mailed Mar. 28, 2007", 10 pgs.
"Influenza B/Ann Arbor/1/66 (cold-adapted) nonstructural protein (seg 8) RNA, complete cds", GenBank Accession M20224, (Aug. 2, 1993), 2 pgs.
"Influenza B/lee/40, neuraminidase & nb (seg 6) ma", Database EM_VI E.B.I. Hinxton U.K., (Jun. 13, 1985), 10 pgs.
"Influenza virus A/CHR/ 157/83 genomic RNA for haemagglutinin", (2012), 2 pgs.
"International Application No. PCT/US2004/016680, International Search Report", (Feb. 2, 2005), 7 pgs.
"International Application Serial No. PCT/US2021/033365, International Search Report mailed Sep. 24, 2021", 6 pgs.
"International Application Serial No. PCT/US2021/033365, Written Opinion mailed Sep. 24, 2021", 6 pgs.
"International Application Serial No. PCT/US01/11963, Amendment filed Sep. 9, 2002 to Written Opinion dated Aug. 7, 2002", 12 pgs.

(56) References Cited

OTHER PUBLICATIONS

"International Application Serial No. PCT/US01/11963, International Preliminary Examination Report mailed Oct. 15, 2002", 13 pgs.
"International Application Serial No. PCT/US01/11963, International Search Report mailed May 7, 2002", 5 pgs.
"International Application Serial No. PCT/US01/11963, Written Opinion mailed Jun. 14, 2002", 2 pgs.
"International Application Serial No. PCT/US01/11963, Written Opinion mailed Aug. 7, 2002", 6 pgs.
"International Application Serial No. PCT/US02/05455, International Preliminary Examination Report dated Aug. 17, 2004", 4 pgs.
"International Application Serial No. PCT/US02/05455, International Search Report mailed Mar. 25, 2003", 3 pgs.
"International Application Serial No. PCT/US03/04233, International Search Report mailed Dec. 16, 2005", 7 pgs.
"International Application Serial No. PCT/US2004/012050, International Search Report mailed Feb. 2, 2005", 8 pgs.
"International Application Serial No. PCT/US2004/012050, Written Opinion mailed Feb 2, 2005", 12 pgs.
"International Application Serial No. PCT/US2004/016649, International Preliminary Report on Patentability mailed Dec. 15, 2005", 7 pgs.
"International Application Serial No. PCT/US2004/016649, International Search Report mailed Apr. 18, 2005", 6 pgs.
"International Application Serial No. PCT/US2004/016680, International Preliminary Report on Patentability mailed Dec. 15, 2005", 11 pgs.
"International Application Serial No. PCT/US2005/041991, International Search Report mailed Jun. 4, 2007", 5 pgs.
"International Application Serial No. PCT/US2005/041991, Written Opinion mailed Jun. 4, 2007", 6 pgs.
"International Application Serial No. PCT/US2007/007562, International Preliminary Report on Patentability mailed Oct. 9, 2008", 5 pgs.
"International Application Serial No. PCT/US2007/007562, International Search Report mailed Jan. 14, 2008", 8 pgs.
"International Application Serial No. PCT/US2007/007562, Written Opinion mailed Jan. 14, 2008", 9 pgs.
"International Application Serial No. PCT/US2007/013407, International Search Report mailed Oct. 24, 2008", 10 pgs.
"International Application Serial No. PCT/US2007/013407, Written Opinion mailed Oct. 24, 2008", 14 pgs.
"International Application Serial No. PCT/US2008/004125, International Search Report mailed Feb. 20, 2009", 6 pgs.
"International Application Serial No. PCT/US2008/004125, Written Opinion mailed Feb. 20, 2009", 8 pgs.
"International Application Serial No. PCT/US2008/005641, International Preliminary Report on Patentability dated Nov. 10, 2009", 9 pgs.
"International Application Serial No. PCT/US2008/005641, International Search Report mailed Feb. 4, 2009", 6 pgs.
"International Application Serial No. PCT/US2008/005641, Written Opinion mailed Feb. 4, 2009", 8 pgs.
"International Application Serial No. PCT/US2008/007417, International Search Report mailed Jan. 30, 2009", 20 pgs.
"International Application Serial No. PCT/US2008/007417, Written Opinion mailed Jan. 30, 2009", 10 pgs.
"International Application Serial No. PCT/US2008/007582, International Preliminary Report on Patentability mailed Jan. 7, 2010", 9 pgs.
"International Application Serial No. PCT/US2008/007582, International Search Report and Written Opinion mailed Feb. 18, 2009", 16 pgs.
"International Application Serial No. PCT/US2009/000056, International Search Report mailed Feb. 9, 2010", 3 pgs.
"International Application Serial No. PCT/US2009/000056, Written Opinion mailed Feb. 9, 2010", 5 pgs.
"International Application Serial No. PCT/US2009/006019, International Preliminary Report on Patentability mailed May 19, 2011", 8 pgs.
"International Application Serial No. PCT/US2009/006019, Invitation to Pay Additional Fee mailed Apr. 6, 2010", 8 pgs.
"International Application Serial No. PCT/US2009/006019, Search Report mailed Jun. 10, 2010", 7 Pgs.
"International Application Serial No. PCT/US2009/006019, Written Opinion mailed Jun. 10, 2010", 6 pgs.
"International Application Serial No. PCT/US2010/054128, Preliminary Report on Patentability mailed May 10, 2012", 10 pgs.
"International Application Serial No. PCT/US2010/054128, Search Report mailed Feb. 23, 2011", 6 pgs.
"International Application Serial No. PCT/US2010/054128, Written Opinion mailed Feb. 23, 2011", 8 pgs.
"International Application Serial No. PCT/US2012/052368, International Preliminary Report on Patentability mailed Mar. 13, 2014", 8 pgs.
"International Application Serial No. PCT/US2012/052368, International Search Report mailed Dec. 3, 2012", 4 pgs.
"International Application Serial No. PCT/US2012/052368, Written Opinion mailed Dec. 3, 2012", 6 pgs.
"International Application Serial No. PCT/US2014/046731, International Preliminary Report on Patentability mailed Jan. 28, 2016", 12 pgs.
"International Application Serial No. PCT/US2014/046731, International Search Report mailed Nov. 25, 2014", 9 pgs.
"International Application Serial No. PCT/US2014/046731, Written Opinion mailed Nov. 25, 2014", 10 pgs.
"International Application Serial No. PCT/US2015/036803, International Preliminary Report on Patentability mailed Dec. 29, 2016", 10 pgs.
"International Application Serial No. PCT/US2015/036803, International Search Report mailed Dec. 11, 2015", 8 pgs.
"International Application Serial No. PCT/US2015/036803, Invitation to Pay Add'l Fees and Partial Search Rpt mailed Oct. 2, 2015", 8 pgs.
"International Application Serial No. PCT/US2015/036803, Written Opinion mailed Dec. 11, 2015", 8 pgs.
"International Application Serial No. PCT/US2016/041172, International Preliminary Report on Patentability mailed Jan. 18, 2018", 10 pgs.
"International Application Serial No. PCT/US2016/041172, International Search Report mailed Oct. 27, 2016", 6 pgs.
"International Application Serial No. PCT/US2016/041172, Written Opinion mailed Oct. 27, 2016", 8 pgs.
"International Application Serial No. PCT/US2016/048691, International Preliminary Report on Patentability mailed Mar. 15, 2018", 7 pgs.
"International Application Serial No. PCT/US2016/048691, International Search Report mailed Nov. 22, 2016", 7 pgs.
"International Application Serial No. PCT/US2016/048691, Written Opinion mailed Nov. 22, 2016", 6 pgs.
"International Application Serial No. PCT/US2017/018443, International Preliminary Report on Patentability mailed Aug. 30, 2018", 11 pgs.
"International Application Serial No. PCT/US2017/018443, International Search Report mailed May 22, 2017", 9 pgs.
"International Application Serial No. PCT/US2017/018443, Written Opinion mailed May 22, 2017", 9 pgs.
"International Application Serial No. PCT/US2018/057576, International Preliminary Report on Patentability mailed May 7, 2020", 12 pgs.
"International Application Serial No. PCT/US2018/057576, International Search Report mailed Mar. 25, 2019", 7 pgs.
"International Application Serial No. PCT/US2018/057576, Invitation to Pay Additional Fees and Partial Search Report mailed Jan. 31, 2019", 16 pgs.
"International Application Serial No. PCT/US2018/057576, Written Opinion mailed Mar. 25, 2019", 10 pgs.
"International Application Serial No. PCT/US2019/047263, International Preliminary Report on Patentability mailed Mar. 4, 2021", 8 pgs.
"International Application Serial No. PCT/US2019/047263, International Search Report mailed Dec. 20, 2019", 5 pgs.
"International Application Serial No. PCT/US2019/047263, Written Opinion mailed Dec. 20, 2019", 6 pgs.

(56) References Cited

OTHER PUBLICATIONS

"International Application Serial No. PCT/US2020/014659, International Preliminary Report on Patentability mailed Aug. 5, 2021", 12 pgs.
"International Application Serial No. PCT/US2020/014659, International Search Report mailed Nov. 6, 2020", 7 pgs.
"International Application Serial No. PCT/US2020/014659, Invitation to Pay Additional Fees mailed Sep. 16, 2020", 11 pgs.
"International Application Serial No. PCT/US2020/014659, Written Opinion mailed Nov. 6, 2020", 10 pgs.
"International Application Serial No. PCT/US2020/017342, International Preliminary Report on Patentability mailed Aug. 19, 2021", 8 pgs.
"International Application Serial No. PCT/US2020/017342, International Search Report mailed Jun. 26, 2020", 6 pgs.
"International Application Serial No. PCT/US2020/017342, Written Opinion mailed Jun. 26, 2020", 6 pgs.
"International Application Serial No. PCT/US2020/031176, International Preliminary Report on Patentability mailed Nov. 11, 2021", 9 pgs.
"International Application Serial No. PCT/US2020/031176, International Search Report mailed Jul. 22, 2020", 6 pgs.
"International Application Serial No. PCT/US2020/031176, Written Opinion mailed Jul. 22, 2020", 7 pgs.
"International Application Serial No. PCT/US2020/048130, International Preliminary Report on Patentability mailed Mar. 10, 2022", 11 pgs.
"International Application Serial No. PCT/US2020/048130, International Search Report mailed Apr. 20, 2021", 9 pgs.
"International Application Serial No. PCT/US2020/048130, Invitation to Pay Additional Fees mailed Jan. 13, 2021", 7 pgs.
"International Application Serial No. PCT/US2020/048130, Written Opinion mailed Apr. 20, 2021", 9 pgs.
"International Application Serial No. PCT/US2021/014586, International Preliminary Report on Patentability mailed Aug. 4, 2022", 10 pgs.
"International Application Serial No. PCT/US2021/014586, International Search Report mailed May 20, 2021", 7 pgs.
"International Application Serial No. PCT/US2021/014586, Written Opinion mailed May 20, 2021", 8 pgs.
"International Application Serial No. PCT/US2021/024200, International Preliminary Report jon Patentability mailed Oct. 6, 2022", 8 pgs.
"International Application Serial No. PCT/US2021/024200, International Search Report mailed Jul. 16, 2021", 6 pgs.
"International Application Serial No. PCT/US2021/024200, Written Opinion mailed Jul. 16, 2021", 6 pgs.
"International Application Serial No. PCT/US2021/033365, International Preliminary Report on Patentability mailed Dec. 8, 2022", 8 pgs.
"Israel Application Serial No. 163,546, Office Action mailed Nov. 12, 2009", w/English Translation, 1 pg.
"Israel Application Serial No. 163,546, Office Action mailed Dec. 26, 2007", w/English Translation, 1 pg.
"Israel Application Serial No. 163,546, Response filed May 9, 2008 to Office Action mailed Dec. 26, 2007", w/English Translation, 2 pgs.
"Israel Application Serial No. 163,546, Response filed Jun. 8, 2010 to Office Action mailed Nov. 12, 2009", w/English Claims, 3 pgs.
"Israel Application Serial No. 163,546, Response filed Aug. 16, 2009 to Substantive Examination Report mailed Feb. 23, 2009", w/English Claims, 4 pgs.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report mailed Jul. 28, 2008", w/English Claims, 13 pgs.
"Israel Application Serial No. 163546, Office Action mailed Jun. 8, 2010", w/English Translation, 2 pgs.
"Israel Application Serial No. 183026, Office Action mailed Feb. 9, 2009", w/English Translation, 2 pgs.
"Israel Application Serial No. 238584, Office Action mailed Jul. 24, 2017", w/English Translation, 2 pgs.
"Israel Application Serial No. 238584, Response filed Nov. 21, 2017 to Office Action mailed Jul. 24, 2017", W/English Translation, 2 pgs.
"Israeli Application Serial No. 171831, Notification of Defects mailed Nov. 10, 2008", w/English Translation, 10 pgs.
"Israeli Application Serial No. 163,546, First Examination Report mailed Jul. 28, 2008", (English Translation), 2 pgs.
"Israeli Application Serial No. 163,546, Substantive Examination Report mailed Feb. 23, 2009", w/English Translation, 3 pgs.
"Israeli Application Serial No. 171372, Office Action mailed Feb. 21, 2010", w/English Translation, 2 pgs.
"Israeli Application Serial No. 171372, Office Action mailed Nov. 6, 2008", (Translation), 12 pgs.
"Israeli Application Serial No. 171372, Response filed Nov. 18, 2010 to Office Action mailed Feb. 21, 2010", w/English Translation, 19 pgs.
"Israeli Application Serial No. 171831, Office Action mailed Feb. 21, 2010", w/English Translation, 2 pgs.
"Israeli Application Serial No. 171831, Office Action mailed Apr. 18, 2012", (English Translation), 2 pgs.
"Israeli Application Serial No. 171831, Response filed Jan. 20, 2011 to Office Action mailed Feb. 21, 2010", w/English Translation, 18 pgs.
"Israeli Application Serial No. 171831, Response filed Jun. 24, 2009 to Notification of Defects mailed Nov. 10, 2008", w/English Claims, 10 pgs.
"Israeli Application Serial No. 171831, Response filed Nov. 6, 2012 to Office Action mailed Apr. 18, 2012", w/English Claims, 54 pgs.
"Israeli Application Serial No. 211324, Office Action mailed Sep. 18, 2014", w/English Translation, 5 pgs.
"Israeli Application Serial No. 211324, Office Action mailed Oct. 18, 2015", w/English Translation, 4 pgs.
"Israeli Application Serial No. 211324, Response filed Feb. 16, 2016 to Office Action mailed Oct. 18, 2015", w/English Claims, 4 pgs.
"Israeli Application Serial No. 211324, Response filed Mar. 31, 2015 to Office Action mailed Sep. 8, 2014", w/English Translation, 21 pgs.
"Israeli Application Serial No. 238584, Notification of Defects in Patent Application mailed Jul. 21, 2019", (w/ English Translation), 5 pgs.
"Israeli Application Serial No. 238584, Office Action mailed Apr. 14, 2016", (English Translation), 3 pgs.
"Israeli Application Serial No. 238584, Office Action mailed Aug. 23, 2018", (w/ English Translation), 6 pgs.
"Israeli Application Serial No. 238584, Response filed Aug. 3, 2016 to Office Action mailed Apr. 14, 2016", (English Translation of Claims), 19 pgs.
"Israeli Application Serial No. 238584, Response filed Nov. 21, 2017 to Office Action mailed Jul. 24, 2017", (Translation), 2 pgs.
"Israeli Application Serial No. 238584, Response filed Nov. 21, 2019 to Notification of Defects in Patent Application mailed Jul. 21, 2019", (w/ English Translation of Claims), 6 pgs.
"Israeli Application Serial No. 238584, Response Filed Dec. 10, 2018 to Office Action mailed Aug. 23, 2018", (w/ English Translation of Claims), 10 pgs.
"Israeli Application Serial No. 171372,Office Action mailed Feb. 20, 2011", (Translation), 2 pgs.
"Japanese Application No. 2001-576868, Office Action mailed May 31, 2011", (w/ English Translation), 5 pgs.
"Japanese Application No. 2001-576868, Response filed Apr. 26, 2011 to Office Action mailed Nov. 2, 2010", (w/ Translation of Amended Claims), 14 pgs.
"Japanese Application Serial No. 2022-144599, Voluntary Amendment filed Nov. 9, 2022", w/ English Claims, 14 pgs.
"Japanese Application Serial No. 2022-544779, Voluntary Amendment filed Sep. 9, 2022", w/ English Claims, 8 pgs.
"Japanese Application Serial No. 2001-576868, Office Action mailed Nov. 2, 2010", w/ English Translation), 10 pgs.

(56) References Cited

OTHER PUBLICATIONS

"Japanese Application Serial No. 2001-576868, Response filed Dec. 1, 2011 to Office Action mailed May 3, 2011", (w/ English Translation of Amended Claims), 37 pgs.
"Japanese Application Serial No. 2003-315106, Amended Claims filed Oct. 15, 2009 in Response to Office Action mailed Jun. 24, 2009", (English Translation), 6 pgs.
"Japanese Application Serial No. 2003-315106, Notice of Allowance mailed Jan. 5, 2010", (w/ English Translation), 5 pgs.
"Japanese Application Serial No. 2003-315106, Office Action mailed Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Notice of Allowance mailed Nov. 30, 2009", w/out English Translation, 3 pgs.
"Japanese Application Serial No. 2003-568038, Office Action mailed May 15, 2009", (w/ English Translation), 7 pgs.
"Japanese Application Serial No. 2003-568038, Office Action mailed Jul. 10, 2008", (w/ English Translation), 11 pgs.
"Japanese Application Serial No. 2003-568038, Office Action mailed Jul. 21, 2005", w/out English Translation, 3 pgs.
"Japanese Application Serial No. 2003-568038, Request for Examination filed Aug. 19, 2005 in Response to Official Action mailed Jul. 21, 2005", (w/ Partial English Translation of Specification), 8 pgs.
"Japanese Application Serial No. 2003-568038, Response filed Sep. 14, 2009 to Office Action mailed May 15, 2009", (w/ English Translation of Amended Claims), 10 pgs.
"Japanese Application Serial No. 2003-568038, Response filed Dec. 10, 2008 to Office Action mailed Jul. 10, 2008", (w/ English Translation of Amended Claims), 15 pgs.
"Japanese Application Serial No. 2006-513125, Office Action mailed Mar. 9, 2010", (English Translation), 11 pgs.
"Japanese Application Serial No. 2006-513125, Response filed Aug. 30, 2010 to Office Action mailed Mar. 9, 2010", (w/ English Translation of Amended Claims), 60 pgs.
"Japanese Application Serial No. 2006-533439, Decision of Final Rejection mailed Aug. 14, 2012", (w/ English Translation), 5 pgs.
"Japanese Application Serial No. 2006-533439, Office Action mailed Mar. 9, 2010", (w/ English Translations), 20 pgs.
"Japanese Application Serial No. 2006-533439, Office Action mailed Mar. 27, 2012", w/ English Translation, 8 pgs.
"Japanese Application Serial No. 2006-533439, Response filed May 21, 2012 to Office Action mailed Mar. 27, 2012", (w/ English Translation of Amended Claims), 19 pgs.
"Japanese Application Serial No. 2006-533439, Response filed Aug. 3, 2011 to Office Action mailed Feb. 15, 2011", (w/ English Translation of Amended Claims), 18 pgs.
"Japanese Application Serial No. 2006-533439,Office Action mailed Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2008-315106, Office Action mailed Jun. 24, 2009", (w/ English Translation), 10 pgs.
"Japanese Application Serial No. 2008-315106, Response filed Oct. 15, 2009 to Office Action mailed Jun. 24, 2009", w/English Translation, 103 pgs.
"Japanese Application Serial No. 2008-315106, Response filed Oct. 15, 2009 to Office Action mailed Jun. 24, 2009", (w/ English Translation of Amended Claims), 103 pgs.
"Japanese Application Serial No. 2008-315106, Response filed Dec. 3, 2009 to Office Action mailed Jun. 24, 2009", (w/ English Translation of Claims), 9 pgs.
"Japanese Application Serial No. 2009-238781, Office Action mailed Oct. 11, 2011", (w/ English (Translation), 3 pgs.
"Japanese Application Serial No. 2009-502945, Examiners Decision of Final Refusal mailed Nov. 12, 2013", (w/ English Translation), 8 pgs.
"Japanese Application Serial No. 2009-502945, Office Action mailed Oct. 23, 2012", (w/ English Translation), 16 pgs.
"Japanese Application Serial No. 2009-502945, Response filed Apr. 10, 2013 to Office Action mailed Oct. 23, 2012", (w/ English Translation of Claims), 18 pgs.
"Japanese Application Serial No. 2011-111048, Office Action mailed Jun. 25, 2013", (w/ English Translation), 7 pgs.
"Japanese Application Serial No. 2011-111048, Office Action mailed Sep. 18, 2012", (w/ English Translation), 10 pga.
"Japanese Application Serial No. 2011-111048, Response filed Sep. 25, 2012 to Office Action mailed Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action mailed Jun. 10, 2014", (w/ English Translation), 7 pgs.
"Japanese Application Serial No. 2012-273898, Response filed Sep. 4, 2014 to Office Action mailed Jun. 10, 2014", W/ English Claims, 9 pgs.
"Japanese Application Serial No. 2012-536963, Amendment and Argument filed Jun. 26, 2015 to Office Action mailed Jan. 6, 2015", (w/ English Translation of Amended Claims), 12 pgs.
"Japanese Application Serial No. 2012-536963, Examiners Decision of Final Refusal mailed Nov. 17, 2015", (w/ English Translation), 8 pgs.
"Japanese Application Serial No. 2012-536963, Office Action mailed Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action mailed Jan. 6, 2015", (w/ English Translation), 9 pgs.
"Japanese Application Serial No. 2014-049025 Response filed Sep. 4, 2015 to Office Action mailed Jun. 16, 2015", (w/ Amended Claims), 12 pgs.
"Japanese Application Serial No. 2014-049025, Examiners Decision of Final Refusal mailed Feb. 2, 2016", W/ English Translation, 5 pgs.
"Japanese Application Serial No. 2014-049025, Office Action mailed Jun. 16, 2015", (w/ English Translation), 6 pgs.
"Japanese Application Serial No. 2014-527339, Examiners Decision of Final Refusal mailed Feb. 7, 2017", (w/ English Translation), 5 pgs.
"Japanese Application Serial No. 2014-527339, Office Action mailed May 31, 2016", (w/ English Translation), 10 pgs.
"Japanese Application Serial No. 2014-527339, Response filed Sep. 16, 2016 to Office Action mailed May 31, 2016", (w/ English Translation of Amended Claims), 33 pgs.
"Japanese Application Serial No. 2016-053990, Office Action mailed Jun. 6, 2017", (w/ English (Translation), 4 pgs.
"Japanese Application Serial No. 2016-053990, Response filed Dec. 6, 2017 to Office Action mailed Jun. 6, 2017", (w/ English Translation of Amended Claims), 14 pgs.
"Japanese Application Serial No. 2016-110879, Office Action mailed May 30, 2017", (w/ English Translation), 7 pgs.
"Japanese Application Serial No. 2016-110879, Response filed Nov. 30, 2017 to Office Action mailed May 30, 2017", (w/ English Translation of Claims), 25 pgs.
"Japanese Application Serial No. 2016-527046, Examiners Decision of Final Refusal mailed May 21, 2019", (w/ English Translation), 20 pgs.
"Japanese Application Serial No. 2016-527046, Reasons For Rejection mailed Aug. 14, 2018", (w/ English Translation), 14 pgs.
"Japanese Application Serial No. 2016-527046, Response Filed Dec. 4, 2018 to Reasons For Rejection mailed Aug. 14, 2018", (w/ English Translation of Amended Claims), 18 pgs.
"Japanese Application Serial No. 2017-111526, Office Action mailed May 14, 2019", (w/ English Translation), 6 pgs.
"Japanese Application Serial No. 2017-111526, Office Action mailed Jun. 26, 2018", (w/ English Translation), 5 pgs.
"Japanese Application Serial No. 2017-111526, Response Filed Dec. 21, 2018 to Office Action mailed Jun. 26, 2018", (w/ English Translation of Amended Claims), 7 pgs.

(56) References Cited

OTHER PUBLICATIONS

"Japanese Application Serial No. 2018-510751, Examiners Decision of Final Refusal mailed Dec. 17, 2019", w/ English Translation, 10 pgs.
"Japanese Application Serial No. 2018-510751, Notification of Reasons for Refusal mailed Mar. 13, 2019", (w/ English Translation), 14 pgs.
"Japanese Application Serial No. 2018-510751, Response filed Apr. 17, 2020 to Examiners Decision of Final Refusal mailed Dec. 17, 2019", w/ English Claims, 7 pgs.
"Japanese Application Serial No. 2018-510751, Response filed Aug. 9, 2019 to Notification of Reasons for Refusal mailed Mar. 13, 2019", (w/ English Translation of Claims), 24 pgs.
"Japanese Application Serial No. 2018-543688, Notification of Reasons for Rejection mailed Oct. 29, 2019", w/ English Translation, 14 pgs.
"Japanese Application Serial No. 2018-543688, Office Action mailed Jun. 30, 2020", w/ English translation, 11 pgs.
"Japanese Application Serial No. 2018-543688, Response filed Apr. 28, 2020 to Notification of Reasons for Rejection mailed Oct. 29, 2019", w/ English Claims, 12 pgs.
"Japanese Application Serial No. 2019-171818, Examiners Decision of Final Refusal mailed Oct. 5, 2021", (w/ English Translation), 15 pgs.
"Japanese Application Serial No. 2019-171818, Notification of Reasons for Rejection mailed Nov. 10, 2020", (w/ English Translation), 11 pgs.
"Japanese Application Serial No. 2019-171818, Preliminary Examination Report mailed May 10, 2022", (w/ English Translation), 2 pgs.
"Japanese Application Serial No. 2019-171818, Response filed Feb. 4, 2022 to Examiners Decision of Final Refusal mailed Oct. 5, 2021", (w/ English Translation of Claims), 21 pgs.
"Japanese Application Serial No. 2019-171818, Response filed May 10, 2021 to Notification of Reasons for Rejection mailed Nov. 10, 2020", (w/ English Translation of Claims), 12 pgs.
"Japanese Application Serial No. 2019-171818, Response filed Dec. 2, 2022 to Preliminary Examination Report mailed May 10, 2022", w/ English Claims, 44 pgs.
"Japanese Application Serial No. 2019-171818, Trial Brief filed Mar. 30, 2022", (w/ English Translation), 14 pgs.
"Japanese Application Serial No. 2020-073952, Examiners Decision of Final Refusal mailed Aug. 4, 2022", w/ English translation, 3 pgs.
"Japanese Application Serial No. 2020-073952, Final Notification of Reasons for Refusal mailed Jan. 25, 2022", w/ English Translation, 11 pgs.
"Japanese Application Serial No. 2020-073952, Notification of Reasons for Refusal mailed May 20, 2021", w/o English Translation, 2 pgs.
"Japanese Application Serial No. 2020-073952, Response filed Apr. 20, 2022 to Final Notification of Reasons for Refusal mailed Jan. 25, 2022", w/ English Claims, 40 pgs.
"Japanese Application Serial No. 2020-073952, Response filed Sep. 9, 2021 to Notification of Reasons for Refusal mailed May 20, 2021", w/ English Claims, 27 pgs.
"Japanese Application Serial No. 2020-073952, Response filed Dec. 2, 2022 to Examiners Decision of Final Refusal mailed Aug. 4, 2022", w/ English Claims, 36 pgs.
"Japanese Application Serial No. 2020-182549, Examiners Decision of Final Refusal mailed Jun. 7, 2022", (w/ English Translation), 11 pgs.
"Japanese Application Serial No. 2020-182549, Notification of Reasons for Refusal mailed Nov. 30, 2021", (w/ English Translation), 10 pgs.
"Japanese Application Serial No. 2020-182549, Response filed Feb. 28, 2022 to Notification of Reasons for Refusal mailed Nov. 30, 2021", (w/ English Translation of Claims), 52 pgs.
"Japanese Application Serial No. 2020-182549, Response filed Oct. 6, 2022 to Examiners Decision of Final Refusal mailed Jun. 7, 2022", w/ English Claims, 21 pgs.
"Japanese Application Serial No. 2020-523276, Examiners Decision of Final Refusal mailed May 10, 2022", w/ English Translation, 13 pgs.
"Japanese Application Serial No. 2020-523276, Notification of Reasons for Refusal mailed Jul. 27, 2021", w/ English Translation, 12 pgs.
"Japanese Application Serial No. 2020-523276, Response filed Jan. 12, 2022 to Notification of Reasons for Refusal mailed Jul. 27, 2021", w/ English Claims, 27 pgs.
"Japanese Application Serial No. 2021-146743, Notification of Reasons for Rejection mailed Aug. 17, 2022", w/ English Translation, 3 pgs.
"Japanese Application Serial No. 2021-506434, Examiners Decision of Final Refusal mailed Jan. 10, 2023", w/ English Translation, 10 pgs.
"Japanese Application Serial No. 2021-509824, Voluntary Amendment filed Aug. 18, 2022", w/ English Claims, 39 pgs.
"Japanese Application Serial No. 2021-542525, Notification of Reasons for Refusal mailed Dec. 13, 2022", w/ English Translation, 14 pgs.
"Japanese Application Serial No. 2006-513125,Final Office Action mailed Jan. 18, 2011", (English Translation), 4 pgs.
"Korean Application Serial No. 10-2005-7020077, Response filed Apr. 28, 2008 to Examination Report mailed Dec. 28, 2007", (w/ English Translation of Revised Claims), 41 pgs.
"Korean Application Serial No. 10-2004-7012647, Office Action mailed Feb. 26, 2010", (w/ English Translation), 7 pgs.
"Korean Application Serial No. 10-2004-7012647, Response filed Jun. 10, 2010 to Office Action mailed Feb. 26, 2010", (w/ English Translation of Claims), 17 pgs.
"Korean Application Serial No. 10-2005-7020077, Examination Report mailed Dec. 28, 2007", (w/ English Translation), 8 pgs.
"Korean Application Serial No. 10-2005-7020077, Notice of Preliminary Rejection mailed Jun. 28, 2007", (w/ English Translation), 9 pgs.
"Korean Application Serial No. 10-2005-7020077, Response filed Aug. 28, 2007 to Notice of Preliminary Rejection mailed Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action malled Aug. 6, 2008", W/ English Translation, 4 pgs.
"Korean Application Serial No. 10-2005-7022564, Response and Amendment filed Dec. 29, 2008 to Office Action mailed Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action mailed Aug. 6, 2008", (w/ English Translation of Claims), 16 pgs.
"Korean Application Serial No. 10-2010-7011520, Office Action mailed Jul. 20, 2010", (w/ English Translation), 6 pgs.
"Korean Application Serial No. 10-2010-7011520, Response filed Oct. 20, 2010 to Office Actiion mailed Jul. 20, 2010", (w/ English Translation of Amended Claims), 30 pgs.
"Korean Application Serial No. 10-2010-7011520, Amended Claims filed May 24, 2011 in Response to Office Action mailed Feb. 24, 2011", (English Translation of Amended Claims), 22 pgs.
"Korean Application Serial No. 10-2010-7011520, Office Action mailed Feb. 24, 2011", (w/ English Translation), 5 pgs.
"Mexican Application No. PA/a/2005/012712 Office Action mailed Jul. 21, 2009", (w/ English Translation), 9 pgs.
"Mexican Application Serial No. MX/a/2009/006341, Office Action mailed Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.

(56) References Cited

OTHER PUBLICATIONS

"Mexican Application Serial No. MX/a/2012/009249 Response filed Sep. 10, 2015 to Office Action mailed May 19, 2015", (w/ English Translation of Claims), 21 pgs.
"Mexican Application Serial No. MX/a/2012/009249, Office Action mailed Feb. 5, 2016", W/ English Claims, 2 pgs.
"Mexican Application Serial No. MX/a/2012/009249, Office Action mailed May 19, 2015", (English Translation), 1 pg.
"Mexican Application Serial No. MX/a/2012/009249, Response filed Mar. 29, 2016 to Office Action mailed Feb. 5, 2016", (English Translation of Claims), 18 pgs.
"Mexican Application Serial No. PA/a/2004/007914, Office Action mailed Feb. 14, 2008", (w/ English Translation), 3 pgs.
"Mexican Application Serial No. PA/a/2004/007914, Office Action mailed Feb. 22, 2008", (English Translation), 3 pgs.
"Mexican Application Serial No. PA/a/2004/007914, Response filed Jun. 11, 2008 to Office Action mailed Feb. 22, 2008", (w/ English Translation of Claims), 68 pgs.
"Mexican Application Serial No. PA/a/2005/011250, Office Action mailed Aug. 23, 2010", W/ English Translation, 4 pgs.
"Mexican Application Serial No. PA/a/2005/011250, Response Filed Dec. 20, 2010 to Office Action mailed Aug. 23, 2010", (w/ English Translation of Claims), 14 pgs.
"Mexican Application Serial No. PA/a/2005/012712 , Office Action Mailed Aug. 11, 2009", (English Translation), 5 pgs.
"Mexican Application Serial No. PA/a/2005/012712 , Response filed Sep. 28, 2009 to Office Action Mailed Jul. 21, 2009", (w/ English Translation of Claims), 24 pgs.
"Mexican Application Serial No. PA/a/2005/012712, Office Action mailed May 12, 2010", (w/ English Translation), 19 pgs.
"Mexican Application Serial No. PA/a/2005/012712, Office Action mailed Jun. 9, 2010", (w/ English Translation), 11 pgs.
"Mexican Application Serial No. PA/a/2005/012712, Office Action mailed Nov. 30, 2009", (w/ English Translation), 14 pgs.
"Mexican Application Serial No. PA/a/2005/012712, Official Action mailed Mar. 5, 2009", (English Translation), 2 pgs.
"Mexican Application Serial No. PA/a/2005/012712, Response filed Feb. 3, 2010 to Office Action mailed Nov. 30, 2009", (w/ English Translation of Amended Claims), 22 pgs.
"Mexican Application Serial No. PA/a/2005/012712, Response filed Sep. 27, 2010 to Office Action mailed May 12, 2010", (w/ English Translation of Claims), 19 pgs.
"Mexico Application Serial No. PA/a/2005/012712, Response filed Jun. 12, 2009 to Official Action mailed Mar. 5, 2009", (w/ English Translation of Claims), 11 pgs.
"Neuraminidase [Influenza A virus (A/Aichi/2/1968 (H3N2))]", GenBank: BAD16642.1, NCBI, [online]. Retrieved from the Internet: <URL: http://www.ncbi.nlm.nih.gov/protein/46401580>, (2008), 3 pgs.
"Neuraminidase [Influenza B virus]", GenBank: CAB71147.1, NCBI, [online]. Retrieved from the Internet: <URL: http://www.ncbi.nlm.nih.gov/protein/6851026>, (2005), 3 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report mailed Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report mailed Feb. 29, 2008", 2 pgs.
"New Zealand Application Serial No. 543446, Examination Report mailed May 12, 2008", 1 pg.
"New Zealand Application Serial No. 543446, Response mailed Mar. 20, 2008 to Examination Report mailed Feb. 29, 2008", 2 pgs.
"New Zealand Application Serial No. 543587, Examination Report mailed Mar. 1, 2007", 1 pg.
"New Zealand Application Serial No. 543587, Examination Report mailed Jul. 7, 2006", 2 pgs.
"New Zealand Application Serial No. 543587, Response filed Aug. 7, 2007 to Examination Reports mailed Jul. 7, 2006 and Mar. 1, 2007", 24 pgs.
"New Zealand Application Serial No. 543587, Second Examination Report mailed Feb. 25, 2008", 2 pgs.
"New Zealand Application Serial No. 555245, First Examination Report mailed Aug. 26, 2008", 2 pgs.
"New Zealand Application Serial No. 555245, Subsequent Examiner Report mailed Jul. 3, 2009", pg.
"Nonstructural protein 1 [influenza B virus (B/Hong Kong/330/2001)]", GenBank AAT69443.1, (2006), 1 pg.
"Norway Application Serial No. 20056074, Office Action mailed Jan. 17, 2017", (English Translation), 5 pgs.
"Norway Application Serial No. 20056074, Office Action mailed Apr. 25, 2017", (w English Translation), 3 pgs.
"Norway Application Serial No. 20056074, Office Action Response mailed 04-1817", W/ English Claims, 27 Pgs.
"Norway Application Serial No. 20056074, Response filed Jul. 25, 2017 to Office Action mailed Apr. 25, 2017", (w/ English Translation of Amended Claims), 111 pgs.
"Norweigan Application Serial No. 20056074, Office Action mailed Apr. 25, 2017", (Translation), 3 pgs.
"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structure of Small Viral RNA Segment", Database UniProt EBI / Accession No. NC_002023, (Jul. 10, 2008), 15 pgs.
"PCT Application Serial No. PCT/US2005/041991, International Preliminary Report on Patentability / Written Opinion mailed Jul. 19, 2007", 8 pgs.
"Polymerase acidic [influenza A virus (A/swine/Shizuoka/120/97(H3N2))]", GenBank AAO15329.1, (2003), 1 pg.
"Polymerase PA [Influenza A virus (A/swine/Yangzhou/1/2008(H9N2))]", GenBank: ADK98493.1, [Online]. Retrieved from the Internet: <URL: https://www.ncbi.nlm.nih.gov/protein/ADK98493.1/>, 2 pgs.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Non-structural protein 1; Short=NS1; AltName: Full=NS1 B", GenPept Accesion P08013, NS1 of Influenza B strain B/Yamagata/1/73, (Dec. 9, 2015), 2 pgs.
"RNA World", http://faculty.uca.edu/~benw/biol4415/lecture10a/tsld003.htm, (Observed Feb. 25, 2003), 1 pg.
"Russian Federation Application No. 2005136233, Office Action mailed Dec. 25, 2007", 2 pgs.
"Russian Federation Application No. 2005136233, Response filed May 29, 2008 to Office Action mailed Dec. 25, 2007", (w/ Partial English Translation), 7 pgs.
"Russian Federation Application Serial No. 2005136233, First Office Action mailed Feb. 27, 2007", (w/ English Translation), 5 pgs.
"Russian Federation Application Serial No. 2005136233, Response filed Jun. 14, 2007 to First Office Action mailed Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200507467-9, Invitation to Respond to Written Opinion mailed Jun. 19, 2007", 5 pgs.
"Singaporean Application Serial No. 200506858-0, Examination Report mailed Feb. 9, 2007", 4 pgs.

(56) References Cited

OTHER PUBLICATIONS

"Singaporean Application Serial No. 200506858-0, Response filed Dec. 22, 2006 to Written Opinion mailed Jul. 26, 2006", 18 pgs.
"Singaporean Application Serial No. 200506858-0, Written Opinion mailed Jul. 26, 2006", 8 pgs.
"Singaporean Application Serial No. 200507468-7, Examination Report mailed Mar. 19, 2008", 5 pgs.
"Singaporean Application Serial No. 200507468-7, Invitation to Respond to Written Opinion mailed Jun. 12, 2007", 6 pgs.
"Singaporean Application Serial No. 200507468-7, Response filed Nov. 7, 2007 to Invitation to Respond to Written Opinion mailed Jun. 12, 2007", 9 pgs.
"ST3GAL6 Gene ID: 478535", ncbi, nlm, [Online]. Retrieved from the Internet: <URL: https://www.ncbi.nlm.nih.gov/gene/47853> Sep. 14, 2022, (Aug. 17, 2022), 14 pgs.
"The Influenza Virus: Structure and Replication", Rapid Reference to Influenza. Elsevier Ltd, [Online]. Retrieved from the Internet: http://www.rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action mailed Jun. 17, 2009", W/ English Claims, 14 pgs.
"Ukrainian Application Serial No. 200512619, Office Action mailed Feb. 27, 2009", (w/ English Translation), 21 pgs.
"Ukrainian Application Serial No. 200512619, Office Action mailed Jun. 17, 2009", (w/ English Translation), 4 pgs.
"Ukrainian Application Serial No. 200512619, Response filed Apr. 8, 2009 to Office Action mailed Feb. 27, 2009", (w/ English Translation of Claims), 9 pgs.
Abram, M. E, et al., "Nature, position, and frequency of mutations made in a single cycle of HIV-1 replication", J Virol., 84(19), (Oct. 2010), 9864-78.
Air, Gillian M., et al., "Antigenic, Sequence, and Crystal Variation in Influenza B Neuraminidase", Virology, 177(2), (1990), 578-587.
Air, Gillian M., et al., "Antigenic, Sequence, and Crystal Variation in Influenza B Neuraminidase", Virology vol. 177, (1990), 578-587.
Akarsu, H., et al., "Crystal structure of the M1 protein-binding domain of the influenza A virus nuclear export protein (NEP/NS2).", EMBO J., 22(18), (Sep. 15, 2003), 4646-55.
Albo, C., et al., "The 5' Ends of Thogoto Virus (Orthomyxoviridae) mRNAS Are Homogeneous in both Length and Sequence", Journal of Virology, 70(12), (1996), 9013-9017.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem cell transplant recipients", Bone Marrow Transplant 411-415, (2005), 5 pgs.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008), 1-12.

Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Bedford, M. T, et al., "FBP WW domains and the Abl SH3 domain bind to a specific class of proline-rich ligands", EMBO J., 16(9), (May 1, 1997), 2376-83.
Betakova, T., et al., "The NB protein is an integral component of the membrane of influenza B virus.", J Gen Virol., 77 ( Pt 11), (Nov. 1996), 2689-94.
Biere, Barbara, et al., "Differentiation of Influenza B Virus Lineages Yamagata and Victoria by Real-Time PCR", Journal of Clinical Microbiology, vol. 48, No. 4 1425-1427, (2010), 3 pgs.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza A Virus", Journal of General Virology (2003) 84,, (2003), 517-527.
Bowie, et al., "Deciphering the Message in Protein Sequences: Tolerance to Amino Acid Substitutions", Science, 247, (Mar. 1990), 1306-1310.
Bowie, J. U., et al., "Deciphering the Message in Protein Sequences: Tolerance to Amino Acid Substitutions", Science, 247(4948) 1306-1310, (1990), 5 pgs.
Boyer, J. C., et al., "Infectious transcripts and cDNA clones of RNA viruses", Virology, 198(2), (Feb. 1994), 415-426.
Bradfute, S. B., "The Early Clinical Development of Ebola Virus Treatments", Exp. Opin. Invest. Drugs 26(1):, (2017), 5 pgs.
Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Brands, R., et al., "Influvac: A Safe Madin Darby Canine Kidney (MDCK) Cell Culture-Based Influenza Vaccine", Dev. Biol. Stand., 98, (1999), 93-100.
Brassard, D.L., et al., "Influenza B virus NB glycoprotein is a component of the virion", Virol., 220(2), No Document, (1996), 350-360.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.
Broecker, Felix, et al., "Extending the Stalk Enhances Inmunogenicity of the Influenza Virus Neuraminidase", Journal of Virology, 93(18), e00840-19, (Sep. 1, 2019), 1-12.
Broecker, Felix, et al., "Immunodominance of Antigenic Site B in the Hemagglutinin of the Current H3N2 In?uenza Virus in Humans and Mice", Journal of Virology, 92(20): e01100-18, (Oct. 2018), 1-13.
Brooke, C B, "Biological activities of 'noninfectious' influenza A virus particles", Future Virol 9(1) 41-51, (Jan. 2014), 16 pgs.

(56) References Cited

OTHER PUBLICATIONS

Brown, E. G., et al., "Genetic analysis of mouse-adapted influenza A virus identifies roles for the NA, PB1, and PB2 genes in virulence", Virus Research, 61(1), (May 1999), 63-76.
Brown, TA, "Studying DNA", Genomes—NCBI Bookshelf, Brown TA. Genomes. 2nd edition. Oxford: Wiley-Liss; 2002, (2002), 26 pgs.
Bruhl, P., et al., "Humoral and Cell-Mediated Immunity to Vero Cell-Derived Influenza Vaccine", Vaccine, 19, (2001), 1149-1158.
Buchholz, U. J., et al., "Generation of Bovine Respiratory Syncytial Virus (BRSV) From cDNA: BRSV NS2 is Not Essential for Virus Replication in Tissue Culture, and the Human RSV Leader Region Acts as a Functional BRSV Genome Promoter", Journal of Virology, 73(1), (1999), 251-259.
Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.
Bukreyev, A., et al., "Recovery of infectious respiratory syncytial virus expressing an additional, foreign gene", Journal of Virology, 70(10), (Oct. 1996), 6634-6641.
Bullido, R., et al., "Influenza A Virus NEP (NS2 protein) Downregulates RNA Synthesis of Model Template RNAs", Journal of Virology, 75(10), (May 2001), 4912-4917.
Bullido, R., et al., "Influenza A virus NEP(NS2 protein) downregulates RNA synthesis of model template RNAs", Journal of Virology, vol. 75 4912-4917, (May 2001), 6 pgs.
Burmeister, W. P., et al., "The 2.2 A resolution crystal structure of influenza B neuraminidase and its complex with sialic acid", The EMBO Journal, 11(1), (1992), 49-56.
Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.
Cao, S., et al., "Characterization of the Nucleocytoplasmic Shuttle of the Matrix Protein of Influenza B Virus", Journal of Virology., 88(13), (Jul. 2014), 7464-7473.
Cardona, C. J., "Avian Influenza", http://www.vetmed.ucdavis.edu/vetex/INF-PO_AvianinfluenzaFS.html, ((Observed Feb. 22, 2003), 3 pgs.
Castrucci, M. R, et al., "Attenuation of Influenza A Virus by Insertion of a Foreign Epitope into the Neuraminidase", Journal of Virology, 66(8), (1992), 4647-4653.
Castrucci, M. R., et al., "Biologic Importance of Neuraminidase Stalk Length in Influenza A Virus", Journal of Virology, 67(2), (1993), 759-764.
Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Catchpole, A P, et al., "Alternative base pairs attenuate influenza A virus when introduced into the duplex region of the conserved viral RNA promoter of either the NS or the PA gene", Journal of General Virology, 84, (2003), 507-515.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Chang, M. W., et al., "Analysis of HIV Wild-Type and Mutant Structures via in Silico Docking against Diverse Ligand Libraries", J. Chem. Inf. Model., 47(3), (2007), 1258-1262.
Chen, H, et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
Chiba, Shiho, et al., "Multivalent nanoparticle-based vaccines protect hamsters against SARS-CoV-2 after a single immunization", Communications Biology, 4: 597, (2021), 1-9.
Cho, Alice, et al., "Implications of Broadly Neutralizing Antibodies in the Development of a Universal Influenza Vaccine", Current Opinion In Virology, vol. 17 110-115, (Apr. 1, 2016), 6 pgs.
Chothia, Cyrus, et al., "Canonical Structures for the Hypervariable Regions of Immunoglobulins.", J Mol Biol., 196(4), (1987), 901-917.
Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.
Chung, C, et al., "Glycoengineering of Chinese Hamster Ovary Cells for Improving Biotherapeutics Efficacies", A dissertation submitted to Johns Hopkins University in conformity with the requirements for the degree of Doctor of Philosophy, Retrieved from the Internet: <https://jscholarship.library.jhu.edu/handle/177>, (2016), 137 pgs.
Claas, E C. J., et al., "Human Influenza A H5N1 Virus Related to a Highly Pathogenic Avian Influenza Virus", The Lancet, 351, (1998), 472-477.
Clarke, D. K., et al., "Rescue of Mumps Virus From cDNA", Journal of Virology, 74(10), (2000), 4831-4838.
Cohen, Alexander A., et al., "Mosaic nanoparticles elicit cross-reactive immune responses to zoonotic coronaviruses in mice", Science, 371(6530), and Supplementary Materials, (2021), 735-741 (30 pgs).
Coleman, P. M., et al., "Sequence and Structure Alignment of Paramyxovirus Hemagglutinin-Neuraminidase with Influenza Virus Neuraminidase", Journal of Virology, 67(6), (1993), 2972-2980.
Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77 (Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.
Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.

(56) References Cited

OTHER PUBLICATIONS

Cunningham, Brian C, et al., "High-Resolution Epitope Mapping of hGH-Receptor Interactions by Alanine-Scanning Mutagenesis", Science 244:4908, (1989), 6 pgs.
Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.
Daddario-Dicaprio, K. M, et al., "Cross-protection against Marburg virus strains by using a live, attenuated recombinant vaccine", J Virol., 80(19), (Oct. 2006), 9659-66.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Del Guidice, G., et al., "What are the limits of adjuvanticity?", (Abstract), Vaccine, 20(Suppl 1), S38-S41, (2001), 1 pg.
Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.
Desselberger, Ulrich, et al., "The 3' and 5'-terminal sequences of influenza A, B and C virus RNA segments are highly conserved and show partial inverted complementarity", Gene, 8 (3), (Feb. 1980), 315-328.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dollenmaier, G., et al., "Membrane-Associated Respiratory Syncytial Virus F Protein Expressed From A Human Rhinovirus Type 14 Vector Is Immunogenic", Virology, 281(2), (Mar. 15, 2001), 216-230.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Du, Q., "Ribozyme Enzymology", http://academic.brooklyn.cuny.edu/chem/zhuang/QD/toppage1.htm, (Observed Feb. 25, 2003), 8 pgs.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Duhaut, S., et al., "Approximately 150 Nucleotides from the 5' End of an Influenza a segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", Virology, 248(2), Academic Press, Orlando, US, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Dumoulin, Mireille, et al., "Single-domain antibody fragments with high conformational stability", Protein Science, 11, (2002), 500-515.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P, et al., "Human Parainfluenza Virus Type 3 (PIV3) Expressing The Hemagglutinin Protein Of Measles Virus Provides A Potential Method For Immunization Against Measles Virus and PIV3 In Early Infancy", Journal of Virology, 74(15), (Aug. 2000), 6821-6831.
Durbin, A. P., et al., "Recovery of infectious human parainfluenza virus type 3 from cDNA", Virology, 235(2), (Sep. 1, 1997), 323-332.
Dyall, J., et al., ""Identification of inhibitors of Ebola virus with a subgenomic replication system"", Antiviral Research,70(1), 19th International Conference on Antiviral Research, San Juan, PR (May 7-11, 20006), (May 2006), p. A39.
Elhefnawi, M, et al., "Identification of novel conserved functional motifs across most Influenza A viral strains", Virology Journal, 8:44, (2011), 10 pages.
Elliott, R. M., "Emerging Viruses: The Bunyaviridae", Molecular Medicine, 3(9), (1997), 572-577.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, K., et al., "Influenza virus NS1 protein stimulates translation of the M1 protein", Journal of Virology, 68 1432-1437, (1994), 6 pgs.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.
Enterlein, S., et al., "Untersuchungen zur Replikation und Transkription von Marburgund Ebolavirus", [Online]. 2005, Philipps-Universitat Marburg, XP002563470, Retrieved from the Internet:

(56) References Cited

OTHER PUBLICATIONS

<URL:http://deposit.ddb.de/cgi-bin/dokserv?>idn=977005607&dok_var=d1&dok_ext=pdf&filename=977005607.pdf> [retrieved on Jan. 15, 2010], (2005), p. 70—p. 84.
Essere, Boris, et al., "Critical role of segment-specific packaging signals in genetic reassortment of influenza A viruses", Proc. Natl. Acad. Sci. USA, 110(40), (2013), E3840-E3848.
Fahey, J. L., et al., "Status of Immune-Based Therapies in HIV Infection and Aids", Clinincal and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fields, S., et al., "Nucleotides Sequences of Influenza Virus Segments 1 and 3 Reveal Mosaic Structure of Small Viral RNA Segment", Cell, 28, (1982), 303-313.
Fischer, W. B, et al., "Viral ion channels: structure and function.", Biochim Biophys Acta., 1561(1), (Mar. 19, 2002), 27-45.
Flandorfer, A., et al., "Chimeric Influenza A Viruses with a Functional Influenza B Virus Neuraminidase or Hemagglutinin", Journal of Virology, 77(17), (2003), 9116-9123.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.
Friers, et al., "Soluble recombinant influenza vaccines", Phil. Trans. R. Soc. Lond. B (2001). vol. 356 1961-1963, (2001), 4 pgs.
Fuji, Y., et al., "Selective incorporation of influenza virus RNA segments into virions", Proc. Natl. Acad. Sci. USA, 100(4) 2002-2007, (2003), 6 pgs.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Fujii, Y, et al., "The packaging of influenza viral genome", Virus, 52 (1), Uirusu (Japanese Journal Name), (Jun. 2002), 203-206.
Gao, Qinshan, et al., "A Nine-Segment In?uenza A Virus Carrying Subtype H1 and H3 Hemagglutinins", Journal of Virology, 84(16), (Aug. 2010), 8062-8071.
Gao, Qinshan, et al., "A Seven-Segmented Influenza A Virus Expressing the Influenza C Virus Glycoprotein HEF", Journal of Virology, 82(13), (Jul. 2008), 6419-6426.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of Influenza A Virus", Dev. Biol. Stand. vol. 82, (1994), 237-246.
Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "The cytoplasmic tail of the neuraminidase protein of influenza A virus does not play an important role in the packaging of this protein into viral envelopes", Virus Research, 37(1), (1995), 37-47.
Garcia-Sastre, A., et al., "Use of a mammalian internal ribosomal entry site element for expression of a foreign protein by a transfectant influenza virus.", Journal of Virology, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", Newsday. com, (Feb. 20, 2003), 3 pgs.
Genbank, ABD36884.1, (2007), 2 pgs.
Gerdil, C., "The Annual Production Cycle for Influenza Vaccine", Vaccine, 21 1776-1779, (2003), 4 pgs.
Ghate, Anita A, et al., "Influenza Type B Neuraminidase Can Replace the Function of Type A Neuraminidase", Virology, 264 (2), (Nov. 1999), 265-277.
Giddings, A M, et al., "The matrix protein of HIV-1 is not sufficient for assembly and release of virus-like particles", Virology, 248(1), (1998), 108-16.
Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011), 283 pgs.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein Is The Major Driving Force in Virus Budding", Journal of Virology, 74 11538-11547, (Dec. 1, 2000), 10 pgs.
Gorman, O T, et al., "Evolution of influenza A virus PB2 genes: implications for evolution of the ribonucleoprotein complex and origin of human influenza A virus", J. Virol., 64(10), (Oct. 1990), 4893-4902.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Goto, Hideo, et al., "The Genome-Packaging Signal of the Influenza A Virus Genome Comprises a Genome Incorporation Signal and a Genome-Bundling Signal", Journal of Virology; vol. 87 No. 21, (Nov. 2013), 11316-11322.
Govorkova, E A, et al., "Replication of Influenza A Viruses in a Green Monkey Kidney Continuous Cell Line (Vero)", J. Infect. Dis. 172(1), (1995), 250-253.
Grambas, S., et al., "Influence of amantadine resistance mutations on the pH regulatory function of the M2 protein of influenza A viruses", Virology, 191(2), (Dec. 1992), 541-549.
Green, R. F., et al., "Glycosylation Does Not Determine Segregation of Viral Envelope Proteins in the Plasma Membrane of Epithelial Cells", J. Cell Biol., 89(2), (1981), 230-239.
Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.
Groseth, A., et al., "RNA Polymerase I-Driven Minigenome System for Ebola Viruses", Journal of Virology, 79(7), (2005), 4425-4433.

(56) References Cited

OTHER PUBLICATIONS

Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Gubareva, "Molecular mechanisms of influenza virus resistance to neuraminidase inhibitors", Virus Research, vol. 103, (2004), pp. 199-203.
Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000 ISSN: 0166-3542, (Sep. 1, 2004), 209-215.
Hagen, M., et al., "Recombinant Influenza Virus Polymerase: Requirement of both 5' and 3' Viral Ends for Endonuclease Activity", Journal of Virology, 68(3), (1994), 1509-1515.
Hai, Rong, et al., "Influenza B Virus NS1-Truncated Mutants: Live-Attenuated Vaccine Approach", Journal of Virology, 82(21), (2008), 10580-10590.
Halfmann, P., et al., "Generation of biologically contained Ebola viruses", Proceedings of the National Academy of Sciences of the United States of America 1129-1133, vol. 105, No. 4, XP002563467 ISSN: 1091-6490 the whole document, (Jan. 29, 2008), 6 pgs.
Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.
Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.
Halstead, Scott B,. et al., "Dengue Antibody-Dependent Enhancement: Knowns and Unknowns", Microbiology Spectrum, 2(6), (2014), 1-18.
Harding, Alfred T, et al., "Rationally Designed Influenza Virus Vaccines That Are Antigenically Stable during Growth in Egg", MBIO, vol. 8, No. 3, eO0669-17, (Jul. 5, 2017), 1-16.
Harmsen, M. M., et al., "Properties, production, and applications of camelid single-domain antibody fragments", Appl Microbiol Biotechnol,77, (2007), 13-22.
Harty, R. N, et al., "A PPxY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Harvey, K. F, et al., "All three WW domains of murine Nedd4 are involved in the regulation of epithelial sodium channels by intracellular Na+.", J Biol Chem., 274(18), (Apr. 30, 1999), 12525-30.
Hatada, E., et al., "Binding of Influenza A Virus NS1 Protein to dsRNA in vitro", Journal of General Virology, 73, (1992), 3325-3329.
Hatakeyama, S., et al., "Dissection and identification of regions required to form pseudoparticles by the interaction between the nucleocapsid (N) and membrane (M) proteins of SARS coronavirus", Virology, 380(1), (2008), 99-108.
Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.
Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.
Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.

Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
He, X., et al., "Generation of SARS-CoV-2 reporter replicon for high-throughput antiviral screening and testing", Proc. Natl. Acad. Sci. USA, 118(15): e2025866118, (2021), 8 pgs.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hickman, Danielle, et al., "An avian live attenuated master backbone for potential use in epidemic and pandemic influenza vaccines", Journal of General Virology, 89(Part 11), (2008), 2682-2690.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs.).
Hiti, A. L., et al., "P03470—Neuraminidase", Entrez Protein Database, http://www.ncbi.nlm.nih.gov/entrez/viewer.fcgi?db=protein&val=84028231, (1982), 730-734.
Ho, Y., et al., "Assembly of human severe acute respiratory syndrome coronavirus-like particles", Biochem Biophys Res Commun, 318(4), (2004), 833-838.
Hoenen, T., et al., "11. Reverse Genetics Systems for Filoviruses", In: Perez, Daniel (Ed.), Reverse Genetics of RNA Viruses: Methods and Protocols, Methods in Molecular Biology, vol. 1602, (2017), 159-170.
Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.
Hoffman, E., et al., "Ambisense Approach for the Generation of Influenza A Virus: vRNA and mRNA Synthesis from One Template", Virology 267(2) 310-317, (Feb. 15, 2006), 8 pgs.
Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.
Hoffman, M. A., et al., "An Infectious Clone of Human Parainfluenza Virus Type 3", Journal of Virology, 71(6), (1997), 4272-4277.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Hoffmann, Erich, et al., "A DNA transfection system for generation of influenza A virus from eight plasmids", Proceedings of the National Academy of Sciences, vol. 97, No. 11, (2000), 6108-6113.
Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.
Holsinger, L. J., et al., "Influenza A Virus M2 Ion Channel Protein: a Structure-Function Analysis", Journal of Virology, 68 (3), (1994), pp. 1551-1563.
Honda, A., et al., "RNA Polymerase of Influenza Virus: Role of NP in RNA Chain Elongation", The Journal of Biochemistry, 104(6), (1988), 1021-1026.

(56) References Cited

OTHER PUBLICATIONS

Honda, Ayae, et al., "Differential Roles of Viral RNA and cRNA in Functional Modulation of the Influenza Virus RNA Polymerase", The Journal of Biological Chemistry, 276(33), (2001), 31179-31185.

Horimoto, "Designing Vaccines for Pandemic Influenza", Current Topics Microbiol Immunol 333, (2009), 165-176.

Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14) 8031-8038, (2003), 11 pgs.
Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.
Horimoto, T., et al., "The Development and Characterization of H5 Influenza Virus Vaccines Derived from a 2003 Human Isolate", Vaccine, 24(17) 3669-3676, (2006), 8 pgs.
Hossain, M. J., et al., "Establishment and Characterization of a Madin-Darby Canine Kidney Reporter Cell Line for Influenza A Virus Assays", J Clin Microbiol, 48(7), (2010), 2515-2523.
Hsieh, P.-K., et al., "Assembly of Severe Acute Respiratory Syndrome Coronavirus RNA Packaging Signal into Virus-Like Particles Is Nucleocapsid Dependent", J Virol., 79(22), (2005), 13848-13855.
Huang, T. S, et al., "Determinaton of Influenza Virus Proteins Required for Genome Replication", Jounal of Virology, vol. 64 5669-5673, (1990), 5 pgs.
Huang, T.-S., et al., "Determination of Influenza Virus Proteins Required for Genome Replication", Journal of Virology, 64(11), (1990), 5669-5673.
Huang, Y., et al., "Generation of Synthetic Severe Acute Respiratory Syndrome Coronavirus Pseudoparticles: Implications for Assembly and Vaccine Production", J. Virol,, 78(22), (Nov. 2004), 12557-12565.
Huddleston, J. A., et al., "The Sequence of the Nucleoprotein Gene of Human Influenza A Virus, Strain A/NT/60/68", Nucleic Acids Research, 10(3), (1982), 1029-1038.
Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR .(Suppl 1), XP002574255 ISSN: 0022-1899 'abstract, (Feb. 1999), 240-247.
Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.
Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.
Hughes, M. T, et al., "Influenza A Viruses Lacking Sialidase Activity Can Undergo Multiple Cycles of Replication in Cell Culture, Eggs, or Mice", Journal of Virology, 74(11) 5206-212, (2000), 7 pgs.
Huisman, W., et al., "Vaccine-induced enhancement of viral infections", Vaccine, 27(4), (2009), 505-512.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Hurt, A. C, et al., "Identification of a human influenza type B strain with reduced sensitivity to neuraminidase inhibitor drugs", Virus Research, vol. (103), (2004), 205-211.
Hutchinson, Edward C., et al., "Genome packaging in influenza A virus", Journal of General Virology, 91 (Pt 2), (2010), 313-328.
Hwang, Jung-Shan, et al., "Expression of Functional Influenza Virus RNA Polymerase in the Methylotrophic Yeast *Pichia pastoris*", Journal of Virology, 74(9), (2000), 4074-4084.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.
Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, et al., "Characterization of recombinant influenza B viruses with key neuraminidase inhibitor resistance mutations,", Journal of Antimicrobial Chemotherapy, vol. (55), (2005), 162-169.
Jackson, D., et al., "A reverse genetics approach for recovery of recombinant influenza B viruses entirely from cDNA.", J Virol., 76(22), (Nov. 2002), 11744-7.
Jahrling, P. B., et al., "Ebola Hemorrhagic Fever: Evaluation of Passive Immunotherapy in Nonhuman Primates", J. Infect. Dis. 196, (2007), 4 pgs.
Jang, S.-W., et al., "Deoxygedunin, a Natural Product with Potent Neurotrophic Activity in Mice", PLoS ONE 5(7): e11528, (2010), 1-15.
Jasenosky, Luke D, et al., "Ebola Virus VP40-Induced Particle Formation and Association with the Lipid Bilayer", Journal of Virology, 75 (110, (Jun. 2001), 5205-5214.
Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.
Jiang, H, et al., "Influenza virus genome C4 promoter/origin attenuates its transcription and replication activity by the low polymerase recognition activity", Virology, 408(2), (2010), 190-196.
Jiang, Y., et al., "Genome wide analysis of protein protein interactions and involvement of viral proteins in SARS CoV 2 replication", Cell Biosci, 11:140, 2021, 16 pgs., (2021), 16 pgs.
Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.
Jin, H., et al., "Influenza virus hemagglutinin and neuraminidase cytoplasmic tails control particle shape", The EMBO Journal, 16(6), (1997), 1236-1247.
Jin, H., et al., "The influenza virus hemagglutinin cytoplasmic tail is not essential for virus assembly or infectivity", The EMBOL Journal, 13(22), (1994), 5504-5515.
Johnson, David A, et al., "TLR4 Agonists as Vaccine Adjuvants", Vaccine Adjuvants and Delivery Systems, (2007), 131-156.
Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.
Ju, X., et al., "A novel cell culture system modeling the SARS-CoV-2 life cycle", PloS Pathogens, 17(3): e1009439, (2021), 23 pgs.
Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.
Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.
Kawaoka, Y, et al., "Sequence requirements for cleavage activation of influenza virus hemagglutinin expressed in mammalian cells", Proc Natl Acad Sci., 85(2), (1988), 324-328.

(56) References Cited

OTHER PUBLICATIONS

Kawaoka, Y., "Identification by siRNA of host proteins involved in Ebolavirus replication", Great Lakes Regional Center of Excellence for Biodefense and Emerging Infectious Diseases Research, [Online]; Retrieved from the Internet: URL:http://www.rcebiodefense.org/glrce/docs/2007/Kawaoka.pdf> [retrieved on Jan. 13, 2010] p. 10, under item C, -& Anonymous: "Index of GLRCE: documents from 2007" Great Lakes Regional Center of Excellence Index, [Online] 2007, XP002563469 Retrieved from the Internet: URL:http://www.rcebiodefense.org/glrce/docs/2007/> [retrieved on Jan. 14, 2010] -& Kawaoka Y.:, (2007), pp. 1-19.

Kawaoka, Y., "Mutant Cells With Altered Sialic Acid", U.S. Appl. No. 11/644,179, filed Dec. 22, 2006, 51 pgs.

Kawaoka, Y., "Prevention and Control of Ebola Virus Infection (Ongoing Research)", Great Lakes Regional Center of Excellence (GLRCE) Annual Meeting Schedule, (Abstract), [online] [retrieved on Jan. 14, 2010]. Retrieved from the Internet: <URL:http://www.rcebiodefense.org/girce/annualmeeting/2007Agenda.pdf>, (Nov. 29, 2007), 4 pgs.

Keitel, W. A., et al., "Chapter 28—Live Cold-Adapted, Reassortant Influenza Vaccines (USA)", In: Textbook of Influenza, Nicoholson, K. G., et al., Editors, Blackwell Science Ltd., (1998), 373-390.

Kijima, H., et al., "Therapeutic Application of Ribozymes", Pharmac. Ther., 68(2), (1995), 247-267.

Kilbourne, E. D, et al., "Related studies of a recombinant influenza-virus vaccine. I. Derivation and characterization of virus and vaccine", J Infect Dis., 124(5), (Nov. 1971), 449-62.

Kim, H., et al., "Cold adaptation generates mutations associated with the growth of influenza B vaccine viruses", Vaccine, 33(43), (2015), 5786-5793.

Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.

Kimura, N., et al., "An In Vivo Study of the Replication Origin in the Influenza Virus Complementary RNA", The Journal of Biochemistry, 113(1), (1993), 88-92.

Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.

Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.

Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.

Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.

Kistner, O., et al., "Development of a mammalian cell (Vero) derived candidate influenza virus vaccine", Vaccine, 16(9-10), (May-Jun. 1998), 960-8.

Kistner, O., et al., "Development of a Vero Cell-Derived Influenza Whole Virus Vaccine", Dev. Biol. Stand., 98, (1999), 101-110.

Kistner, Otfried, et al., "Cell culture (Vero) derived whole virus (H5N1) vaccine based on wild-type virus strain induces cross-protective immune responses", Vaccine, 25(32), (2007), 6028-6036.

Kittel, Christian, et al., "Generation of an Influenza A Virus Vector Expressing Biologically Active Human Interleukin-2 from the NS Gene Segment", Journal of Virology, 79(16), (Aug. 2005), 10672-10677.

Kobayashi, H., et al., "A replication-incompetent influenza virus bearing the HN glycoprotein of human parainfluenza virus as a bivalent vaccine", Vaccine, 31(52), (2013), 6239-6246.

Kobayashi, M., et al., "Reconstitution of Influenza Virus RNA Polymerase From Three Subunits Expressed Using Recombinant Baculovirus System", Virus Research, 22, (1992), 235-245.

Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.

Kon, Theone C, et al., "Influenza Vaccine Manufacturing: Effect of Inactivation, Splitting and Site of Manufacturing. Comparison of Influenza Vaccine Production Processes", PLoS ONE, 11(3), e0150700, (Mar. 9, 2016), 19 pgs.

Konarska, M. M., et al., "Structure of RNAs Replicated by the DNA-Dependent T7 RNA Polymerase", Cell, 63(2), (1990), 609-618.

Konduru, K., et al., "Ebola virus glycoprotein Fc fusion protein confers protection against lethal challenge in vaccinated mice", Vaccine, 29(16), (Apr. 5, 2011), 2968-77.

Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.

Kopecky, S. A, et al., "Matrix protein and another viral component contribute to induction of apoptosis in cells infected with vesicular stomatitis virus", J Virol., 75(24), (Dec. 2001), Abstract Only.

Kovacova, A., et al., "Sequence similarities and evolutionary relationships of influenza virus A hemagglutinins.", Virus Genes, 24(1), (2002), 57-63.

Kovacova, Andrea, et al., "Sequence Similarities and Evolutionary Relationships of Influenza Vrus A Hemagglutinins", Virus Genes, 24(1), (2002), 57-63.

Kovesdi, et al., "Adenoviral vectors for gene transfer", Current Opinion in Biotechnology, vol. 8, (1997), 583-589.

Kovesdi, I., et al., "Adenoviral Vectors for Gene Transfer", Current Opinion in Biotechnology, 8(5), (Oct. 1997), 583-589.

Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.

Krystal, M., "Influenza B/Lee/40, hemagglutinin (seg 4), complete segment.", Database EM_VI E.B.I. Hinxton U.K., (Apr. 25, 1990), 9 pgs.

Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.

Kumar, P. K. R., et al., "Artificial Evolution and Natural Ribozymes", The FASEB Journal, 9, (1995), 1183-1195.

Kunik, Vered, et al., "Paratome: an online tool for systematic identification of antigen-binding regions in antibodies based on sequence or structure", Nucleic Acids Research, vol. 40, Issue W1, (2012), W521-W524.

Kunkel, T. A., "Rapid and Efficient Site-Specific Mutagenesis Without Phenotypic Selection", Proc. Natl. Acad. Sci. USA, 82, (1985), 488-492.

Kuwahara, Tomoko, et al., "Characterization of cell-derived and egg-passaged influenza A/Saitama/103/2014 (H3N2) strain", The 65th Annual Meeting of the Japanese Society of Virology, (2017), 1 pg.

Kuwahara, Tomoko, et al., "Isolation of an Egg-Adapted Influenza A(H3N2) Virus without Amino Acid Substitutions at the Antigenic Sites of Its Hemagglutinin", Japanese Journal of Infectious Diseases, 71(3), (2018), 234-238.

Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.

Latham, T, et al., "Formation of Wild-Type and Chimeric Influenza Virus-Like Particles following Simultaneous Expression of Only Four Structural Proteins", Journal of Virology 75 (13), (2001), 6154-6165.

Lawson, N. D., "Recombinant Vesicular Stomatitis Viruses From DNA", Proc. Natl. Acad. Sci. USA, 92(10), (1995), 4477-4481.

Laxman, B., "Noninvasive Real-Time Imaging of Apoptosis", PNAS, 99(26), (2002), 16551-16555.

(56) References Cited

OTHER PUBLICATIONS

Lazarovits, Janette, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.

Le, T., "CaSpeR5, a family of *Drosophila* transgenesis and shuttle vectors with improved multiple cloning sites", Biotechniques, 42(2), (Feb. 2007), 164-166.

Leahy, M. B., et al., "An Endonuclease Switching Mechanism in the Virion RNA and cRNA Promoters of Thogoto Orthomyxovirus", Journal of Virology, 72(3), (1998), 2305-2309.

Leahy, M. B., et al., "In Vitro Polymerase Activity of Thogoto Virus: Evidence for a Unique Cap-Snatching Mechanism in a Tick-Borne Orthomyxovirus", Journal of Virology, 71(11), (1997), 8347-8351.

Leahy, M. B., et al., "Striking Conformational Similarities between the Transcription Promoters of Thogoto and Influenza A Viruses: Evidence for Intrastrand Base Pairing in the 5' Promoter Arm", Journal of Virology, 71(11), (1997), 8352-8356.

Leal, et al., "New challenges in therapeutic vaccines against HIV infection", Expert Review of Vaccines, vol. 16, No. 6, (2017), 587-600.

Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.

Lee, D.-H., et al., "H9N2 avian influenza virus-like particle vaccine provides protective immunity and a strategy for the differentiation of infected from vaccinated animals", Vaccine, vol. 29, (2011), 4003-4007.

Lee, Dong-Hun, et al., "Progress and hurdles in development of influenza virus-like particle vaccines for veterinary use", Korean Vaccine Society, (2014), 133-139.

Lee, Jeffrey E., et al., "Complex of a Protective Antibody with Its Ebola Virus GP Peptide Epitope: Unusual Features of a V?x Light Chain", J. Mol. Biol., 375, (2007), 202-216.

Lee, Jong-Soo, et al., "The Highly Conserved HA2 Protein of the Influenza A Virus Induces a Cross Protective Immune Response", Journal of Virological Methods, 194(1-2), (2013), 280-288.

Lee, M. S, et al., "Genetic and pathogenic characterization of H6NI avian influenza viruses isolated in Taiwan between 1972 and 2005", Avian Diseases, 50(4), (Dec. 2006), 561-571.

Lefranc, Marie-Paule, et al., "IMGT unique numbering for immunoglobulin and T cell receptor variable domains and Ig superfamily V-like domains", Developmental & Comparative Immunology, 27, (2003), 55-77.

Lembo, A, et al., "Administration of a synthetic TLR4 agonist protects mice from pneumonic tularemia.", J Immunol., 180(11), 7574-81.

Levis, R., et al., "Deletion Mapping of Sindbis Virus DI RNAs Derived From cDNAs Defines the Sequences Essential for Replication and Packaging", Cell, 44, (1986), 137-145.

Li, et al., "Selection of antigenically advanced variants of seasonal influenza viruses", Nature Microbiology, 1 (6), (2016), 1-10.

Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.

Li, Junwei, et al., "Engineering Influenza Viral Vectors", Bioengineered, vol. 4, No. 1, (Jan. 1, 2013), 9-14.

Li, K. S., et al., "Genesis of a highly pathogenic and potentially pandemic H5N1 influenza virus in eastern Asia", Nature, vol. 430, (2004), 209-213 pgs.

Li, K. S, et al., "Genesis of a highly pathogenic and potentially pandemic H5NI influenza virus in eastern Asia", Nature, 430(6996), (Jul. 8, 2004), 209-213.

Li, Qi, et al., "Screening of the high yield influenza B virus on MDCK cell and cloning of its whole genome", (English Abstract), Chinese Journal of Virology, 3, (Sep. 30, 2004), 1 pg.

Li, Qi, et al., "Screening of the high yield influenza B virus on MDCK cell and cloning of its whole genome", International Congress Series 1263, (2004), 610-614.

Li, S., et al., "Electroporation of Influenza Virus Ribonucleoprotein Complexes for Rescue of the Nucleoprotein and Matrix Genes", Virus Research, 37(2), (1995), 153-161.

Li, S., et al., "Influenza A Virus Transfectants with Chimeric Hemagglutinins Containing Epitopes from Different Subtypes", Journal of Virology, 66(1), (1992), 399-404.

Li, S., et al., "Recombinant Influenza A Virus Vaccines for the Pathogenic Human A/Hong Kong/97 (H5N1) Viruses", J Infect Dis., 179(5), (1999), 1132-1138.

Li, Shengqiang, et al., "Influenza A Virus Transfectants with Chimeric Hemagglutinins containing Epitopes from different subtypes", Journal of Virology 399-404, (1992), 6 pgs.

Li, Y, et al., "The I binding specificity of human VH4-34 (VH4-21) encoded antibodies is determined by both VH framework region 1 and complementarity determining region 3", J. Mol. Biol. 256 577-589, (1996), 13 pgs.

Li, Y, et al., "Viral liposomes released from insect cells infected with recombinant baculovirus expressing the matrix protein of vesicular stomatitis virus", Journal of Virology, 67 (7), (1993), 4415-4420.

Lin, Y P, et al., "Adaptation of egg-grown and transfectant influenza viruses for growth in mammalian cells: selection of hemagglutinin mutants with elevated pH of membrane fusion", Virology, 233(2), (1997), 402-410.

Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, vol. 233, Issue 2, (1997), 402-410.

Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.

Liu, C., et al., "Influenza type A virus neuraminidase does not play a role in viral entry, replication, assembly, or budding.", Journal of Virology, 69(2), (1995), 1099-1106.

Liu, C., et al., "Selection and Characterization of a Neuraminidase-Minus Mutant of Influenza Virus and its Rescue by Cloned Neuraminidase Genes", Virology, 194(1), (1993), 403-407.

Liu, Y., et al., "A live-attenuated SARS-CoV-2 vaccine candidate with accessory protein deletions", bioRxiv [online]. [retrieved Jun. 10, 2022]. Retrieved from the Internet: <URL: https://www.biorxiv.org/content/10.1101/2022.02.14.480460v1.full.pdf>, (2022), 44 pgs.

Liu, Z, et al., "Fine mapping of the antigen-antibody interaction of scFv215 A recombinant antibody inhibiting RNA polymerase II from *Drosophila melanogaster*", J. Mol. Recog. 12:103-111, (1999), 9 pgs.

Lobo, Ingrid A., "Predicting Vaccine Effectiveness Using Systems Biology", Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.

Longnecker, R., et al., "WW- and SH3-domain interactions with Epstein-Barr virus LMP2A", Exp Cell Res., 257(2), (Jun. 15, 2000), Abstract Only.

Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.

Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.

Lugovtsev, V. Y., et al., "Genetic Composition and Mutational Pattern of Influenza B Viruses Adapted to Replication in Embryonated Eggs", GenBank: AAT69446.1, (2005), 1 pg.

Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.

Luytjes, W., "Amplification, Expression, and Packaging of a Foreign Gene by Influenza Virus", Cell, 59(6), (1989), 1107-1113.

(56) References Cited

OTHER PUBLICATIONS

Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.
Manicassamy, Balaji, et al., "Analysis of in vivo dynamics of influenza virus infection in mice using a GFP reporter virus", Proc Natl Acad Sci. USA, 107(25), (2010), 11531-11536.
Mansky, L. M, "Retrovirus mutation rates and their role in genetic variation", J Gen Virol., 79 (Pt 6), (Jun. 1998), 1337-45.
Manz, Benjamin, et al., "Disruption of the Viral Polymerase Complex Assembly as a Novel Approach to Attenuate Influenza A Virus", The Journal of Biological Chemistry, 286(10), (2011), 8414-8424.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
Marsh, Glenn A., et al., "Specific Residues of the Influenza A Virus Hemagglutinin Viral RNA Are Important for Efficient Packaging into Budding Virions", Journal of Virology, 81(18), (Sep. 2007), 9727-9736.
Martin, J., et al., "Studies of the Binding Properties of Influenza Hemagglutinin Receptor-Site Mutants", Virology, 241(1), (Feb. 1, 1998), 101-111.
Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.
Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.
Matrosovich, M, et al., "Overexpression of the [alpha]-2,6-sialyltransferase in MDCK cells increases influenza virus sensitivity to neuraminidase inhibitors", Journal of Virology, The American Society for Microbiology, US, vol. 77, No. 15, (Aug. 1, 2003), 8418-8425.
Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.
Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21) 12364-12373, (2014), 10 pgs.
Matta, M, et al., "Cell-surface sialoglycoconjugate structures in wild-type and mutant Crithidia fasciculata", Parasitol. Res., 85(4), (1999), 293-299.
Mccown, M F, et al., "The influenza A virus M2 cytoplasmic tail is required for infectious virus production and efficient genome packaging.", J Virol., 79(6), (Mar. 2005), 3595-605.
Mccown, M. F, et al., "Distinct domains of the influenza a virus M2 protein cytoplasmic tail mediate binding to the M1 protein and facilitate infectious virus production.", J Virol., 80(16), (Aug. 2006), 8178-89.
Mccullers, et al., "Multiple Genotypes of Influenza B Virus Circulated between 1979 and 2003,", Journal of Virology, vol. (78), No. (23) 12817-12828, (2004), 13 pgs.
Mccullers, Jonathan A., et al., "A single amino acid change in the C-terminal domain of the matrix protein M1 of influenza B virus confers mouse adaption and virulence", Virology, 336(2) 318-326, (Jun. 5, 2005), 9 pgs.
Mckee, Dwight L, et al., "Candidate drugs against SARS-CoV-2 and COVID-19", Pharmacological Research, Academic Press, London, GB, vol. 157, (Apr. 29, 2020), 9 pgs.
Mckimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.
Mcsharry, J. J, et al., "Phenotypic Drug Susceptibility Assay for Influenza Virus Neuraminidase Inhibitors", Cinical and Diagnostic Laboratory Immunology vol. (11), No. (2),, (2004), 10 pgs.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of biologically active influenza virus core proteins using a vaccinia virus-T7 RNA polymerase expression system", Journal of General Virology, 75 2109-2114, (1994), 6 pgs.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mishin, V. P, et al., "Protection afforded by intranasal immunization with the neuraminidase-lacking mutant of influenza A virus in a ferret model", Vaccine, 23(22), (Apr. 22, 2005), 2922-7.
Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Mitnaul, L. J., et al., "Balanced Hemagglutinin and Neuraminidase Activities are Critical for Efficient Replication of Influenza A Virus", Journal of Virology, 74 (13), (2000), 6015-6020.
Mittler, E., et al., "Role of the transmembrane domain of marburg virus surface protein GP in assembly of the viral envelope.", J Virol., 81(8), (Apr. 2007), 3942-8.
Miyoshi, H., et al., "Development of Self-Inactivating Lentivirus Vector", Journal of Virology, 72(10), (1998), 8150-8157.
Monto, A. S, et al., "Detection of influenza viruses resistant to neuraminidase inhibitors in global surveillance during the first 3 years of their use", Antimicrobal Agents and Chemotherapy, 50(7) 2395-2402, (2006), 8 pgs.
Monto, Arnold S, et al., "Comparative efficacy of inactivated and live attenuated influenza vaccines.", N Engl J Med., 361(13) 1260-7, (Sep. 24, 2009), 8 pgs.
Morita, S., et al., "Plat-E: an efficient and stable system for transient packaging of retroviruses", Gene Therapy, 7(12), (2000), 1063-1066.
Moss, B., et al., "New Mammalian Expression Vectors", Nature, 348, (1990), 91-92.
Moyer, S. A., et al., "Assembly and Transcription of Synthetic Vesicular Stomatitis Virus Nucleocapsids", Journal of Virology, 65(5), (1991), 2170-2178.
Muhlberger, E., et al., "Comparision orf the Transcription and Replication Strategies of Marburg Virus and Ebola Virus by Using Artificial Replication Systems", Journal of Virology, 73(3) 2333-2342, (1999), 10 pgs.
Muhlberger, E., et al., "Three of the four nucleocapsid proteins of Marburg virus,NP, VP35, and L, are sufficient to mediate replication and transcription of Marburg virus-specific monocistronic minigenomes", Journal of Virology, 72(11) 8756-8764, (1998), 11 pgs.
Muhlberger, Elke, "Filovirus replication and transcription", Future Virol., 2:205, (2007), 16 pgs.
Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Muramoto, Y., et al., "Hierarchy among Viral RNA (vRNA) Segments in Their Role in vRNA Incorporation into Influenza A Virions", J. Virol., 80(5), (2006), 2318-2325.
Muramoto, Yukiko, "Hierarchy among Viral RNA (vRNA) Segments in Their Role in vRNA Incorporation into Influenza A Virions", Journal of Virology, 80(5), (2006), 2318-2325.

(56) References Cited

OTHER PUBLICATIONS

Murphy, B. R, et al., "An influenza A live attenuated reassortant virus possessing three temperature-sensitive mutations in the PB2 polymerase gene rapidly loses temperature sensitivity following replication in hamsters", Vaccine, 15(12-13) 1372-8, (1997), 7 pgs.
Murphy, Brian R, et al., "Virulence of Avian Influenza A Viruses for Squirrel Monkeys", Infection and Immunity 37 (3), (Sep. 1982), 1119-1126.
Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.
Muyldermans, S, "Nanobodies: Natural single-domain antibodies", Ann. Rev. Biochem. 82, (2013), 1 pg.
Naim, H. Y., et al., "Basis for Selective Incorporation of Glycoproteins into the Influenza Virus Envelope", Journal of Virology, 67(8), (1993), 4831-4841.
Naito, S., et al., "Function and Structure of RNA Polymerase From Vesicular Stomatitis Virus", The Journal of Biological Chemistry, 251(14), (1976), 4307-4314.
Nara, et al., "How Can Vaccines Against Influenza and Other Viral Diseases Be Made More Effective?", PLoS Biology, 8 (12), (2010), e1000571.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "A Decade After the Generation of a Negative-Sense RNA Virus From Cloned cDNA-What Have We Learned?", Journal of General Virology, 83(11), (Nov. 2002), 2635-2662.
Neumann, G., et al., "An Improved Reverse Genetics System for Influenza A Virus Generation and Its Implications for Vaccine Production", Proc. Natl. Acad. Scl. USA, 102(46) 16825-16829, (2005), 5 pgs.
Neumann, G., et al., "An improved reverse genetics system for influenza A virus generation and its implications for vaccine production", Proc. Natl. Acad. Sci. USA. 102(46), (2005), 16825-16829.
Neumann, G., et al., "Emergence and pandemic potential of swine-origin HlN1 influenza virus", Nature (London), 459(7249), (Jun. 2009), 931-939.
Neumann, G., et al., "Generation of influenza A virus from cloned cDNAs—historical perspective and outlook for the new millenium.", Rev Med Virol., 12(1), XP002314285, (Jan.-Feb. 2002), 13-30.
Neumann, G., et al., "Generation of influenza A viruses entirely from cloned cDNAs", Proc. Natl. Acad. Sci. USA., 96(16), (1999), 9345-9350.
Neumann, G., et al., "Genetic Engineering of Influenza and Other Negative-Strand RNA Viruses Containing Segmented Genomes", Advances in Virus Research, 53, (1999), 265-300.
Neumann, G., et al., "Influenza A virus NS2 protein mediates vRNP nuclear export through NES-independent interaction with hCRM1", The EMBO Journal, 19 (24), (2000), 6751-6758.
Neumann, G., et al., "Mutational analysis of influenza virus promoter elements in vivo", Journal of General Virology, 76 1709-1717, (1995), 9 pgs.
Neumann, G., et al., "Nuclear Import and Export of Influenza Virus Nucleoprotein", Journal of Virology, 71(12), (1997), 9690-9700.
Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.
Neumann, G., et al., "Reverse genetics of influenza virus.", Virology, 287(2), (Sep. 1, 2001), 243-50.

Neumann, G., et al., "Reverse Genetics of Influenza Viruses—Applications in Research and Vaccine Design", Monographs in Virology, 27, (2008), 118-133.
Neumann, G., et al., "RNA Polymerase I-Mediated Expression of Influenza Viral RNA Molecules", Virology, 202(1), (1994), 477-479.
Neumann, G., et al., "Synthesis of Influenza Virus: New impetus from an old enzyme, RNA polymerase 1", Virus Research 82(1-2), (Jan. 30, 2002), 153-158.
Neumann, Gabriele, "Minireview Reverse Genetics of Influenza Virus", Virology, vol. 287, (2001), 243-250.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.
Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.
Niwa, H., et al., "Efficient Selection for High-Expression Transfectants With a Novel Eukaryotic Factor", Gene, 108(2), (1991), 193-199.
Noda, Takeshi, et al., "Three-dimensional analysis of ribonucleoprotein complexes in influenza A virus", Nature Communications, 3, (2012), 1-6.
Odagiri, T., et al., "Nucleotide Sequence of the PA Gene of Influenza A/WSN/33 (H1N1)", Nucleic Acids Research, 18 (3), Department of Virology, (Jan. 9, 1990), 1 pg.
Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3), (1997), 2138-2145.
Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.
Onishi, M., et al., "Applications of retrovirus-mediated expression cloning", Experimental Hematology, 24(2), (1996), 324-329.
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Ozaki, "Generation of High-Yielding Influenza A Viruses in African Green Monkey Kidney (Vero) Cells by Reverse Genetics", J Virol 78(4), (2004), 1851-1857.
Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.
Ozawa, M., et al., "An adenovirus vector-mediated reverse genetics system for Influenza A virus generation", Journal of Virology, The American society For Microbiology, US vol. 81 (17), XP002471230, ISSN: 0022-538X, (Jun. 27, 2007), 9556-9559.
Ozawa, M., et al., "Replication-incompetent influenza A viruses that stably express a foreign gene", Journal of General Virology, 92(Part 12)., (2011), 2879-2888.
Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.
Palese, P., et al., "47. Orthomyxoviridae: The Viruses and Their Replication", In: Fields Virology (5th Edition), (2007), 90 pgs.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.

(56) References Cited

OTHER PUBLICATIONS

Pattnaik, A. K., et al., "The Termini of VSV DI Particle RNAs are Sufficient to Signal RNA Encapsidation, Replication, and Budding to Generate Infectious Particles", Virology, 206, (1995), 760-764.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Peiris, J. S. M., et al., "Re-Emergence of Fatal Human Influenza A Subtype H5N1 Disease", The Lancet, 363 617-619, (2004), 3 pgs.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.
Pelet, T., et al., "High throughput screening assay for negative single stranded RNA virus polymerase inhibitors", Journal of Virological Methods, 128 29-36, (2005), 8 pgs.
Percy, N., et al., "Expression of a Foreign Protein by Influenza A Virus", Journal of Virology, 68(7), (1994), 4486-4492.
Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.
Perez, D. R., et al., "The Matrix 1 Protein of Influenza A Virus Inhibits the Transcriptase Activity of a Model Influenza Reporter Genome in Vivo", Virology, 249(1), (1998), 52-61.
Perez, Jasmine T., et al., "Unit 15G.4—Insertion of a GFP Reporter Gene in Influenza Virus", Curr Protoc Microbiol., (2013), 20 pgs.
Peterson, B. C., et al., "Homologous sequences other than insertion elements can serve as recombination sites in plasmid drug resistance gene amplification", Journal of Bacteriology, Oct. 1983. 156(1) 177-185, (1983), 5 pgs.
Piatti, G., "Identification of immunodominant epitopes In the filamentous Hemagglutinin of Bordetella pertusis", FEMS Immunology and Medical Microbiology, 23(3), (1999), 235-241.
Piller, S C., et al., "Vpr protein of human immunodeficiency virus type 1 forms cation-selective channels in planar lipid bilayers", PNAS, 93, (1996), 111-1115.
Ping, J., et al., "Development of high-yield influenza B virus vaccine viruses", Proc. Natl. Acad. Sci. USA, 113(51), (Dec. 5, 2016), E8296-E8305.
Ping, Jihui, et al., "Development of high-yield influenza A virus vaccine viruses", Nature Communications, [online]. Retrieved from the Internet: <http://www.nature.com/article-assets/npg/ncomms/2015/150902/ncomms9148/extref/ncomms9148-sl.pdf>, (Sep. 2, 2015), 50 pgs.
Pinto, L. H., et al., "Influenza Virus M2 Protein Has Ion Channel Activity", Cell, 69, (May 1992), pp. 517-528.
Plant, E P, et al., "Mutations to A/PuertoRico/8/34 PB1 gene improves seasonal reassortant influenza A virus growth kinetics", Vaccine, 31(1), (Dec. 1, 2012), 207-212.
Pleschka, S., et al., "A Plasmid-Based Reverse Genetics System for Influenza A Virus", Journal of Virology, 70(6), (1996), 4188-4192.
Pley, H. W., et al., "Three-Dimensional Structure of a Hammerhead Ribozyme", Nature, 372, (1994), 68-74.
Popova, Lyubov, et al., "Immunodominance of Antigenic Site B over Site of Hemagglutinin of Recent H3N2 Influenza Viruses", PLOS ONE, vol. 7 No. 7, (Jul. 25, 2012), e41895.
Portela, A., et al., "Replication of orthomyxoviruses", Advances in Virus Research, 54, (1999), 319-348.
Potter, C. W., "Chapter 1—Chronicle of Influenza Pandemics", In: Textbook of Influenza, Nicholson, K. G., et al., Editors, (Blackwell Scientific Publication), (1998), 3-18.
Preston, Andrew, "Choosing a Cloning Vector", Methods in Molecular Biology, vol. 235, E. coli Plasmid Vectors 19-27, Edited by: N. Casali and A. Preston, (2003), 9 pgs.
Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.
Puzelli, S., et al., "Changes in the Hemagglutinins and Neuraminidase of Human Influenza B Viruses Isolated in Italy During the 2001-02, 2002-03, and 2003-04 Seasons", Journal of Medical Virology, 74(4) 629-640, (2004), 12 pgs.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981), 4 pgs.
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Ramanunninair, Manojkumar, et al., "Molecular Signature of High Yield (Growth) Influenza A Virus Reassortants Prepared as Candidate Vaccine Seeds", PLoS ONE, 8(6): e65955, (2013), 1-16.
Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.
Rayner, J., et al., "Alphavirus vectors and vaccination", Reviews in Medical Virology, 12, (2002), 279-296.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Restifo, N. P., et al., "Transfectant Influenza A Viruses are Effective Recombinant Immunogens in the Treatment of Experimental Cancer", Virology, 249(1), (1998), 89-97.
Ricardo-Lax, I., et al., "Replication and single-cycle delivery of SARS-CoV-2 replicons", Science, 374(6571), (2021), 1099-1106 (9 pgs).
Rimmelzwaan, G. F., et al., "Use of GFP-expressing influenza viruses for the detection of influenza virus A/H5N1 neutralizing antibodies", Vaccine, 29(18), (2011), 3424-3430.
Roberts, A., et al., "Minireview—Recovery of Negative-Strand RNA Viruses From Plasmid DNAs: A Positive Approach Revitalizes a Negative Field", Virology, 247(1), (1998), 1-6.
Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.
Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 (Pt 4) 799-802, (Apr. 1984), 4 pgs.
Ruigrok, R W, et al., "Structural Characterization and Membrane Binding Properties of the Matrix Protein VP40 of Ebola Virus", Journal of Molecular Biology, 300(1), (2000), 103-112.
Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.
Sansom, M. S., et al., "Influenza virus M2 Protein: a molecular modelling study of the ion channel", Protein Engineering, 6 (1), (1993), pp. 65-74.
Saphire, E. O., et al., "Feverish Quest for Ebola Immunotherapy: Straight or Cocktail", Trends Microbial, 24(9), (Sep. 2016), 684-686.

(56) References Cited

OTHER PUBLICATIONS

Satterlee, B., "Production of H5N1 avian influenza virus vaccine by plasmid-based reverse genetics technology", Basic Biotechnology eJournal, vol. 4, pp. 93-98, (2008), 93-98 Pgs.
Saunders, Kevin O., et al., "Neutralizing antibody vaccine for pandemic and pre-emergent coronaviruses", Nature, 594, (2021), 553-559 (27 pgs.).
Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schmidt, Kristina Maria, et al., "Marburg Virus Reverse Genetics Systems", Viruses 2016, 8, 178; doi: 10.3390 / v8060178, www.mdpi.com/journal/viruses, (2016), 17 pgs.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17(5), (1998), 1289-1296.
Schotsaert, M, et al., "Universal M2 ectodomain-based influenza A vaccines: preclinical and clinical developments", Expert Rev Vaccines. Apr. 2009;8(4):, 499-508.
Schultz-Cherry, S., et al., "Influenza Virus NS1 Protein Induces Apoptosis in Cultured Cells", Journal of Virology, 75(17), (2001), 7875-7881.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.
Sheridan, Cormac, et al., "Innovators target vaccines for variants and shortages in global South", Nature Biotechnology, 39(4), (Apr. 2021), 393-396.
Shi, Pei-Yong, "Infectious cDNA Clone of the Epidemic West Nile Virus from New York City", Journal of Virology 5847-5856, (Jun. 2002), 10 pgs.
Shimojima, M., et al., "Tyro3 family-mediated cell entry of Ebola and Marburg viruses", J Virol., 80(20), (Oct. 2006), 10109-16.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Shortridge, K. F., et al., "Characterization of Avian H5N1 Influenza Viruses From Poultry in Hong Kong", Virology, 252 331-342, (1998), 12 pgs.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Silvas, J. A., et al., "Contribution of SARS-CoV-2 Accessory Proteins to Viral Pathogenicity in K18 Human ACE2 Transgenic Mice", J Virol, 95(17): e00402-21, (Sep. 2021), 1-14.
Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22), (2008), 11318-11330.
Skehel, J. J., et al., "On the Mechanism of Inhibition of Influenza Virus Replication by Amantadine Hydrochloride", The Journal of General Virology, 38 (1), (1977), pp. 97-110.
Smatti, Maria K., et al., "Viral-Induced Enhanced Disease Illness", Front Microbiol, vol. 9: Article 2991, (Dec. 2018), 1-19.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Smura, T, "Surface glycoprotein [Severe acute respiratory syndrome coronavirus 2]", Gen Bank Accessions QH062107, (Feb. 11, 2020), 2 pgs.
Stray, S. J., et al., "Influenza virus infection of desialylated cells", Glycobiology, 10(7), (2000), 649-658.
Strobel, I., et al., "Efficient Expression Of The Tumor-Associated Antigen MAGE-3 In Human Dendritic Cells, Using An Avian Influenza Virus Vector", Human Gene Therapy, 11(16), (2000), 2207-2218.
Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Characterization of an Avian Influenza A (H5N1) Virus Isolated From a Child With a Fatal Respiratory Illness", Science, 279, (1998), 393-396.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugawara, K., et al., "Development of Vero Cell-Derived Inactivated Japanese Encephalities Vaccine", Biologicals, 30 303-314, (2002), 12 pgs.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sun, Weina, et al., "Development of Influenza B Universal Vaccine Candidates Usingthe "Mosaic" Hemagglutinin Approach", American Society For Microbiology, Journal of Virology, Vaccines and Antiviral Agents, vol. 93, Issue 12, (Jun. 2019), 17 pgs.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.
Takada, A., et al., "Downregulation of beta1 integrins by Ebola virus glycoprotein: implication for virus entry", Virology, 278(1), (Dec. 2000), Abstract Only.
Takada, Ayato, et al., "A system for functional analysis of Ebola? virus?glycoprotein", Proc. Natl. Acad. Sci. USA, 94(26), (1997), 14764-14769.
Takada, Ayato, et al., "Antibody-dependent enhancement of viral infection: molecular mechanisms and in vivo implications", Rev Med Virol, 13(6), (2003), 387-398.
Takada, Ayato, et al., "Epitopes Required for Antibody-Dependent Enhancement of Ebola Virus Infection", J Infect Dis, 196 (Suppl 2), (2007), S347-S356.
Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.
Takada, Ayato, et al., "Infectivity-Enhancing Antibodies to Ebola Virus Glycoprotein", Journal of Virology, 75(5), (2001), 2324-2330.
Takada, Ayato, et al., "Protective efficacy of neutralizing antibodies against Ebola virus infection", Vaccine, 25(6), (2007), 993-999.
Takada, Ayato, et al., "The pathogenesis of Ebola hemorrhagic fever", Trends in Microbiology, 9(10), (2001), 506-511.

(56) References Cited

OTHER PUBLICATIONS

Takada, Kosuke, et al., "A Humanized MDCK Cell Line for the Efficient Isolation and Propagation of Human Influenza Viruses", Nature Microbiology, Nature Publishing Group UK, London, vol. 4, No. 8, (Apr. 29, 2019), 1268-1273.
Takeda, M., et al., "Influenza a virus M2 ion channel activity is essential for efficient replication in tissue culture.", J Virol., 76(3), (Feb. 2002), 1391-9.
Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tan, Tiong Kit, et al., "A COVID-19 vaccine candidate using SpyCatcher multimerization of the SARS-CoV-2 spike protein receptor-binding domain induces potent neutralising antibody responses", Nature Communications, 12: 542, (2021), 1-16.
Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Terry, G., et al., "The Contruction of Defective Interfering Rubella Virus Particles", Archives of Virology, 145(3), (2000), 625-633.
Tetsutani, K., et al., "Adjuvants in Influenza Vaccines", Vaccine 2012, vol. 30, (2012), 4 pgs.
Thao, Tran Thi Nhu, et al., "Rapid reconstruction of SARS-CoV-2 using a synthetic genomics platform", Nature, vol. 582 561-565, (2020), 24 pgs.
Theriault, S., "The role of reverse genetics systems in determining filovirus pathogenicity", Archives of Virology, Supplementum. 157-177, (2005), 22 pgs.
Thompson, Christine M, et al., "Critical assessment of influenza VLP production in Sf9 and HEK293 expression systems", BMC Biotechnology, 15(1), (May 16, 2015), 12 pgs.
Thompson, W. W., et al., "Mortality Associated With Influenza and Respiratory Syncytial Virus in the United States", JAMA, 289(2) 179-186, (2003), 8 pgs.
Tobler, K, et al., "Effect of cytoplasmic tail truncations on the activity of the M(2) ion channel of influenza A virus", J Virol., 73(12), (Dec. 1999), 9695-9701.
Towner, J S, et al., "Generation of eGFP express ing recombinant Zaire ebolavirus for analysis of early pathogenesis events and high-throughput antiviral drug screening", Virology, Academic Press ,Orlando, US , vol. 332, No. 1 20-27, XP004715289 ISSN: 0042-6822 the whole document, (Feb. 5, 2005), 8 pgs.
Treanor, J. J, et al., "The B allele of the NS gene of avian influenza viruses, but not the A allele, attenuates a human influenza a virus for squirrel monkeys", Virology, 171(1), (1989), 1-9.
Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Vanessa, Monteil, et al., "Inhibition of SARS-CoV-2 Infections in Engineered Human Tissues Using Clinical-Grade Soluble Human ACE2", Cell, vol. 181 905-913, Retrieved from the Internet: <URL:https://www.ncbi.nlm.nih.gov/pmc/articles/PMC7181998/pdf/main.pdf>, (Apr. 24, 2020), 17 pgs.
Varner, Chad, "Developing Synthetic Multivalent Cellular Effectors", Thesis, School of Chemical and Biomolecular Engineering, Georgia Institute of Technology, (Aug. 2017), 88 pgs.
Verma, I. M, et al., "Gene Therapy—Promises, Problems and Prospects", Nature, 389, (1997), 239-242.
Via, L. E, et al., "Isolation of restriction fragments from large plasmids recovered from bacteria with multiple plasmids", Biotechniques, 11(4), (Oct. 1991), Abstract Only.
Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org:, Downloaded from http://jvi.asm.org/ on Aug. 20, 2012 by Univ. of Wisonsin—Mad, (Feb. 1, 2012), 7.
Victor, Sylvia, et al., "A Replication-Incompetent PB2-Knockout Influenza A Virus Vaccine Vector", Journal of Virology, vol. 86, No. 8, (Apr. 2012), 4123-4128.
Vincke, C, et al., "Introduction to heavy chain antibodies and derived nanobodies", Meth. Mol. Biol. 911, (2012), 13 pgs.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Walker, W. S, et al., "HEL-Flu: an influenza virus containing the hen egg lysozyme epitope recognized by CD4+ T cells from mice transgenic for an alphabeta TCR", J. Immunol., 159(6), (Sep. 1997), 2563-2566.
Wan, Yushun, et al., "Molecular mechanism for Antibody-Dependent Enhancement of Coronavirus EntrM", Journal of Virology, 94(5): e02015-19, (2019), 1-15.
Wang, et al., "Glycoengineering of CHO Cells to Improve Product Quality", Methods in Molecular Biology book series (MIMB, vol. 1603) 25-44, (May 11, 2017), 256 pgs.
Wang, B., et al., "Construction of Non-infectious SARS-CoV-2 Replicons and Their Application in Drug Evaluation", Virologica Sinica, 36, (2021), 890-900.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Sheng-Fan, et al., "Antibody-dependent SARS coronavirus infection is mediated by antibodies against spike proteins", Biochem Biophys Res Commun, 451 208-214, (2014), 8 pgs.
Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.
Wang, Wenlig, et al., "Robust Immunity and Heterologous Protection against Influenza in Mice Elicited by a Novel Recombinant NP-M2e Fusion Protein Expressed in E. coli", PLoS ONE 7(12): e52488, (Dec. 2012), 1-13.
Wanitchang, Asawin, et al., "Characterization of influenza A virus pseudotyped with the spike protein of porcine epidemic diarrhea virus", Archives of Virology, 163(12), (2018), 3255-3264.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Warfield, et al., PNAS, vol. 100(26), (2003), pp. 5889-15894.

(56) References Cited

OTHER PUBLICATIONS

Watanabe, S., et al., "Ebola virus (EBOV) VP24 inhibits transcription and replication of the EBOV genome", J Infect Dis., 196(Suppl 2), (Nov. 15, 2007), S284-90.
Watanabe, S., et al., "Influenza A Virus Lacking M2 Protein as a Live Attenuated Vaccine", Journal of Virology, 83(11), (2009), 5947-5950.
Watanabe, S., et al., "Production of Novel Ebola Virus-Like Particles from cDNAs: an Alternative to Ebola Virus Generation by Reverse Genetics", Journal of Virology, 78(2), (Jan. 2004), 999-1005.
Watanabe, T., et al., "Influenza A virus can undergo mulitple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals To Generate a Novel In?uenza Virus-Based Vector Stably Expressing Two Foreign Genes", Journal of Virology, 77(19), (Oct. 2003), 10575-10583.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Weber, F., et al., "Conserved vRNA end sequences of Thogoto-orthomyxovirus suggest a new panhandle structure", Archives of Virology, 142(5), (1997), 1029-1033.
Weber, F., et al., "Nucleoprotein Viral RNA and mRNA of Thogoto Virus: a Novel "Cap-Stealing" Mechanism in Tick-Borne Othomyxoviruses?", Journal of Virology, 70(12), (1996), 8361-8367.
Webster, R G, et al., "Evolution and molecular epidemiology of H9N2 influenza A viruses from quail in southern China", XP002744257, retrieved from EBI accession No. UNIPROT:A3R6C9 Database accession No. A3R6C9 the whole document, (Apr. 3, 2007), 1 pg.
Wei, Hung-Ju, et al., "Fabrication of influenza virus-like particles using M2 fusion proteins for imaging single viruses and designing vaccines", Vaccine, 29, (2011), 7163-7172.
Wei, Kai, et al., "Influenza A Virus Acquires Enhanced Pathogenicity and Transmissibility after Serial Passages in Swine", Journal of Virology, 88(20), (Oct. 2014), 11981-11994.
Wentworth, D E, et al., "The NIAID Influenza Genome Sequencing Project", XP002744258, retrieved from EBI accession No. UNIPROT:U3S198 Database accession No. U3S198 the whole document, (Dec. 11, 2013), 1 pg.
Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Wiedmer, T., et al., "Identification of three new members of the phospholipid scramblase gene family", Biochim Biophys Acta, 1467(1), (Jul. 31, 2000), Abstract Only.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wills, J. W., et al., "An Assembly Domain of the Rous Sarcoma Virus Gag Protein Required Late in Budding", Journal of Virology, 68(10), (1994), 6605-6618.
Wilson, et al., "Vaccine Potential of Ebola Virus VP24, VP30, VP35 and VP40 Proteins", Virology 286, (2001), 384-90.
Wilson, Julie A, et al., "Epitopes Involved in Antibody-Mediated Protection from Ebola Virus", Science, 287(5458), (Mar. 2000), 1664-1666.

Winkler, K, et al., "Changing the antigen binding specificity by single point mutations of an anti-p24 (HIV-1) antibody", J. Immunol. 165 4505-4514, (2000), 11 pgs.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wood, J. M., et al., "From Lethal Virus to Life-Saving Vaccine: Developing Inactivated Vaccines for Pandemic Influenza", Nature Reviews Microbiology, 2(10), (2004), 842-847.
Wu, Rui, et al., "A live bivalent influenza vaccine based on a H9N2 virus strain", Vaccine, 28, (2010), 673-680.
Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.
Xiang, J., et al., "Modification in framework region I results in a decreased affinity of chimeric anti-Tag72 antibody", Mol. Immunol. 28(1/2), (1991), 141-148.
Xu, Jiayu, et al., "The Cold-Adapted, Temperature-Sensitive SARS-Co V-2 Strain TS11 Is Attenuated in Syrian Hamsters and a Candidate Attenuated Vaccine", Viruses 2023, 15, 95. https://doi.org/10.3390/v15010095, (2023), 23.
Xu, Ruodan, et al., "Construction of SARS-CoV-2 Virus-Like Particles by Mammalian Expression System", Frontiers in Bioengineering and Technology, 8:862, (2020), 1-6.
Xu, X., et al., "Reassortment and evolution of current human influenza A and B viruses", Virus Research, 103, (2004), 55-60.
Yagi, Y., et al., "In silico panning for a non-competitive peptide inhibitor", BMC Bioinformatics, 8(11), (2007), 11 pgs.
Yamamoto, K., et al., "Orientation Dependence in Homologous Recombination", Genetics May 1996; 143(1): 27-36, (1996), 27-36.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yang, P., et al., "Hemagglutinin Specificity and Neuraminidase Coding Capacity of Meuraminidase-Deficient Influenza Viruses", Virology, 229(1), (1997), 155-165.
Yang, Z. Y, et al., "Identification of the Ebola virus glycoprotein as the main viral determinant of vascular cell cytotoxicity and injury", Nat Med., 6(8), (Aug. 2000), Abstract Only.
Yannarell, Dean A., et al., "Factors affecting the yield of cold-adapted influenza virus vaccine", Journal of Virological Methods, vol. 64, 161-169, (1997), 1 pg.
Yasuda, J., "Growth Control of Influenza A Virus by M1 Protein: Analysis of Transfectant Viruses Carrying the Chimeric M Gene", Journal of Virology, 68(12), (1994), 8141-8146.
Yen, H L, et al., "Neuraminidase Inhibitor-Resistant Recombinant A/Vietnam/1203/04 (K5N1) Influenza Viruses Retain Their Replication Efficiency and Pathogenicity In Vitro and In Vivo", Journal Of Virology., vol. 81, No. 22, (Nov. 15, 2007), 12418-12426.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yip, Ming S., et al., "Antibody-dependent infection of human macrophages by severe acute respiratory syndrome coronavirus", Virology Journal, 11: 82, (2014), 11 pgs.
Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.

(56) References Cited

OTHER PUBLICATIONS

Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.

Zanin, M., et al., "An Amino Acid in the Stalk Domain of N1 Neuraminidase Is Critical for Enzymatic Activity", Journal of Virology, 2017, Vo. 91, No. 2, (Jan. 2017), 12 pgs.

Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.

Zeitlin, L., et al., "Antibody Therapeutics for Ebola Virus Disease", Curr. Opin. Viral. 17:, (2016), 11 pgs.

Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.

Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.

Zhang, Q.-Y., et al., "SARS-CoV-2 replicon for high-throughput antiviral screening", J Gen Virol., 102(5), (2021), 1-4.

Zhang, V. Q, et al., "Easy two-step method for randomizing and cloning gene fragments", Methods Mol Biol., 634, (2010), Abstract Only.

Zhang, Xuming, et al., "Expression of Interferon-y by a Coronavirus Defective-Interfering RNA Vector and its Effect on Viral Replication, Spread, and Pathogenicity", Medical Institute, University of Southern California School of Medicine, (May 1997), 327-338.

Zhang, Y., et al., "A bacterial artificial chromosome (BAC)-vectored noninfectious replicon of SARS-CoV-2", Antiviral Research, vol. 185, 104974, (Jan. 2021), 1-9.

Zhao, Lili, et al., "New Insights into the Nonconserved Noncoding Region of the Subtype-Determinant Hemagglutinin and Neuraminidase Segments of Influenza A Viruses", Journal of Virology, 88(19) 11493-11503, (Oct. 2014), 11 pgs.

Zhou, Yan, "Membrane-Anchored Incorporation of a Foreign Protein in Recombinant Influenza Virions", Virology 246(1), (1998), 83-94.

Zobel, A., et al., "RNA Polymerase I Catalysed Transcription of Insert Viral cDNA", Nucleic Acids Research, 21(16), (1993), 3607-3614.

"U.S. Appl. No. 16/785,449, Corrected Notice of Allowability mailed Sep. 11, 2023", 10 pgs.

"U.S. Appl. No. 16/785,449, Corrected Notice of Allowability mailed Nov. 8, 2023", 10 pgs.

"U.S. Appl. No. 16/785,449, Corrected Notice of Allowability mailed Nov. 17, 2023", 10 pgs.

"U.S. Appl. No. 16/785,449, Notice of Allowance mailed Aug. 7, 2023", 14 pgs.

"U.S. Appl. No. 16/785,449, Response filed Jul. 13, 2023 to Advisory Action mailed Jun. 7, 2023", 12 pgs.

"U.S. Appl. No. 17/004,583, Notice of Allowability mailed Aug. 1, 2023", 2 pgs.

"U.S. Appl. No. 17/212,836, Advisory Action mailed Aug. 29, 2023", 3 pgs.

"U.S. Appl. No. 17/212,836, Final Office Action mailed Jun. 22, 2023", 15 pgs.

"U.S. Appl. No. 17/212,836, Response filed Aug. 22, 2023 to Final Office Action mailed Jun. 22, 2023", 7 pgs.

"U.S. Appl. No. 18/173,535, Preliminary Amendment filed Jun. 26, 2023", 16 pgs.

"U.S. Appl. No. 18/365,082, Preliminary Amendment filed Aug. 3, 2023", 4 pgs.

"International Application Serial No. PCT/US2023/027622, International Search Report mailed Nov. 7, 2023", 5 pgs.

"International Application Serial No. PCT/US2023/027622, Written Opinion mailed Nov. 7, 2023", 6 pgs.

"International Application Serial No. PCT/US2023/063136, International Search Report mailed Sep. 8, 2023", 6 pgs.

"International Application Serial No. PCT/US2023/063136, Written Opinion mailed Sep. 8, 2023", 7 pgs.

Abdoli, Mohsen, et al., "Intranasal administration of cold-adapted live-attenuated SARS-CoV-2 candidate vaccine confers protection against SARS-CoV-2", Virus Research 319 198857, (2022), 10 pgs.

Faizuloev, Evgeny, et al., "Cold-adapted SARS-CoV-2 variants with different sensitivity exhibit an attenuated phenotype and confer protective immunity", Science Direct Vaccine 41 892-902, (2023), 12 pgs.

Liu, Shufeng, et al., "Stable Cell Clones Harboring Self-Replicating SARS-CoV-2 RNAs for Drug Screen", Journal of Virology, vol. 96, No. 6, [Online] Retrieved from the internet: <https://www.ncbi.nlm.nih.gov/pmc/articles/PMC8941906/pdf/jvi.02216-21.pdf>, (Mar. 23, 2022), 13 pgs.

Lu, Shan, et al., "The SARS-CoV-2 nucleocapsid phosphoprotein forms mutually exclusive condensates with RNA and the membrane-associated M protein", nature communications 12:502, (2021), 15 pgs.

Netland, Jason, et al., "Immunization with an attenuated severe acute respiratory syndrome coronavirus deleted in E protein protects against lethal respiratory disease", Virolog, vol. 399, No. 1, (Jan. 27, 2010), 9 pgs.

Plescia, Caroline B, et al., "SARS-CoV-2 viral budding and entry can be modeled using BSL-2 level virus-like particles", JBC Research Article, (Nov. 19, 2020), 10 pgs.

Seo, Sang Heui, et al., "Cold-Adapted Live Attenuated SARS-COV-2 Vaccine Completely Protects Human ACE2 Transgenic Mice from SARS-Cov-2 Infection", Vaccines 2020 8, 584, (Oct. 3, 2020), 17 pgs.

Swann, Heather, et al., "Minimal system for assembly of SARS CoV 2 virus like particles", Scientific Reports 10:21877 nature portfolio, (2020), 1-5.

Zhang, Xianwen, et al., "A trans-complementation system for SARS-CoV-2 recapitulates authentic viral replication without virulence", Cell, Elsevier, Amsterdam NL, vol. 184, No. 8, (Feb. 23, 2021), 24 pgs.

Zhang, Zhikuan, "Structure of SARS-CoV-2 membrane protein essential for virus assembly", nature communications 13:4399, (Aug. 5, 2022), 12 pgs.

"U.S. Appl. No. 17/212,836, Non Final Office Action mailed Jun. 13, 2024", 14 pgs.

"U.S. Appl. No. 18/525,460, Preliminary Amendment filed Jun. 7, 2024", 6 pgs.

"Comparison of four adjuvants revealed the strongest protection against lethal pneumococcal challenge following immunization with PsaA-PspA fusion protein and AS02 as adjuvant", https://pubmed.ncbi.nlm.nih.gov/30707297/, 1.

"International Application Serial No. PCT/US2023/063136, International Preliminary Report on Patentability mailed Sep. 6, 2024", 9 pgs.

"International Application Serial No. PCT/US2024/020952, International Search Report mailed Jul. 30, 2024", 3 pgs.

"International Application Serial No. PCT/US2024/020952, Written Opinion mailed Jul. 30, 2024", 5 pgs.

Aria, Yasuha, et al., "PB2 mutations arising during H9N2 influenza evolution in the Middle East confer enhanced replication and growth in mammals", PLOS Pathogens 15(7): e1007919. https://doi.org/10.1371/journal.ppat.1007919, (Jul. 2, 2019), 25 pages.

Chang, Chi-Chieh, et al., "Subunit vaccines with a saponin-based adjuvant boost humoral and cellular immunity to MERS coronavirus", Vaccine 41 (2023) 3337-3346, journal homepage: www.elsevier.com/locate/vaccine, (2023), 11.

Fan, Haitian, et al., "Structures of influenza A virus RNA polymerase offer insight into viral genome replication", Nature 573, 287-290 (2019). https://doi.org/10.1038/s41586-019-1530-7, (Sep. 4, 2019), 35 pages.

(56) References Cited

OTHER PUBLICATIONS

Ho, Nataschja I, et al., "Saponin-based adjuvants enhance antigen cross-presentation in human CD11c+ CD1c+ CD5− CD163+ conventional type 2 dendritic cells", J Immunother Cancer 2023, (2023), 17.

Kamiki, Haruhiko, et al., "Novel Biological System with Terminal Sialic Acid Knockout Cells", J Virol 96:e00416-22. https://doi.org/10.1128/jvi.00416-22, (Jul. 18, 2022), 15 pages.

Klimov, A.I., et al., "Correlation of amino acid residues in the M1 and M2 proteins of influenza virus with high yielding properties", Virus Research, vol. 19, Issue 1, 1991, pp. 105-114, ISSN 0168-1702, https://doi.org/10.1016/0168-1702(91)90098-G. (https://www.sciencedirect.com/science/article/pii/016817029190098G), (Mar. 1991), 10 pages.

Ma, Wenjun, et al., "The NS Segment of an H5N1 Highly Pathogenic Avian Influenza Virus (HPAIV) Is Sufficient To Alter Replication Efficiency, Cell Tropism, and Host Range of an H7N1 HPAIV", J Virol. Feb. 2010;84(4):2122-33. doi: 10.1128/JVI.01668-09. Epub Dec. 9, 2009. PMID: 20007264; PMCID: PMC2812369., (Feb. 2010), 12 pages.

Mahesutihan, Madina, et al., "CypA Regulates AIP4-Mediated M1 Ubiquitination of Influenza A Virus", Virologica Sinica 33 (2018): 440-448., (Oct. 16, 2018), 9 pages.

Webby, Richard, et al., "Are we ready for pandemic influenza?", Science 302.5650 (2003): 1519-1522., (Nov. 28, 2003).

Zhao, Tingmei, et al., "Vaccine adjuvants: mechanisms and platforms", Signal Transduction and Targeted Therapy, www.nature.com/sigtrans, (Jul. 19, 2023), 24.

"U.S. Appl. No. 18/525,460, Notice of Allowance mailed Oct. 23, 2024", 11 pgs.

"U.S. Appl. No. 18/365,082, Restriction Requirement mailed Oct. 24, 2024", 12 pgs.

"U.S. Appl. No. 18/461,321, Non Final Office Action mailed Nov. 14, 2024", 6 pgs.

"U.S. Appl. No. 17/212,836, Response filed Nov. 26, 2024 to Non Final Office Action mailed Jun. 13, 2024", 9 pgs.

"U.S. Appl. No. 17/212,836, Notice of Allowance mailed Jan. 2, 2025", 8 pgs.

"U.S. Appl. No. 18/461,321, Response filed Jan. 7, 2025 to Non Final Office Action mailed Nov. 14, 2024", 6 pgs.

* cited by examiner

```
   1 cggacacaca aaaagaaaga aaagtttttt atacttttg tgtgcgaata actatgagga
  61 agattaatca ttttcctcaa actcaaacta atattaacat tgagattgat ctcatcattt
 121 accaattgga gacaatttaa ctagtcaatc ccccattgg gggcattcct aaagtgttgc
 181 aaaggtatgt gggtcgtatt gctttgcctt ttcctaacct ggctcctcct acaattctaa
 241 cctgcttgat aagtgtgatt acctgagtaa tagactaatt tcgtcctggt aattagcatt
 301 ttctagtaaa accaatacta tctcaagtcc taagagaagg tgagaagagg gtcccgaggt
 361 atccctccag tccacaaaat ctagctaatt ttagctgagt ggactgatta ctctcatcac
 421 acgctaacta ctaagggttt acctgagagc ctacaacatg gataaacggg tgagaggttc
 481 atgggccctg ggaggacaat ctgaagttga tcttgactac cacaaaatat aacagccgg
 541 gctttcggtc caacaaggga ttgtgcgaca aagagtcatc ccggtatatg ttgtgagtga
 601 tcttgagggt atttgtcaac atatcattca ggcctttgaa gcaggcgtag atttccaaga
 661 taatgctgac agcttccttt tactttatg tttacatcat gcttaccaag gagatcatag
 721 gctcttcctc aaaagtgatg cagtcaata cttagagggc catggtttca ggtttgaggt
 781 ccgagaaaag gagaatgtgc accgtctgga tgaattgttg cccaatgtca ccggtggaaa
 841 aaatcttagg agaacattgg ctgcaatgcc tgaagaggag acaacagaag ctaatgctgg
 901 tcagtttta tcctttgcca gtttgttct acccaaactt gtcgttgggg agaaagcgtg
 961 tctggaaaaa gtacaaaggc agattcaggt ccatgcagaa caagggctca ttcaatatcc
1021 aacttcctgg caatcagttg gacacatgat ggtgatcttc cgtttgatga gaacaaactt
1081 tttaatcaag ttcctactaa tacatcaggg gatgcacatg gtcgcaggcc atgatgcgaa
1141 tgacacagta atatctaatt ctgttgccca agcaaggttc tctggtcttc tgattgtaaa
1201 gactgttctg gaccacatcc tacaaaaaac agatcttgga gtacgacttc atccactggc
1261 caggacagca aaagtcaaga atgaggtcag ttcattcaag gcagctcttg gtcacttgc
1321 caagcatgga gaatatgctc catttgcacg tctcctcaat ctttctggag tcaacaactt
1381 ggaacatggg ctttatccac aactctcagc cattgctttg ggtgttgcaa ctgcccacgg
1441 gagcacgctg gctggtgtta atgtagggga gcaatatcag caactgcgtg aggctgctac
1501 tgaagctgaa aagcaactcc aacaatatgc tgaaacacgt gagttggaca accttgggct
1561 tgatgaacag gaaaagaaga ttctcatgag cttccaccag aagaagaatg agatcagctt
1621 ccagcaaact aacgcaatgg taaccctgag gaaaagagcg ctggccaaac tgaccgaagc
1681 catcacgact gcatcaaaga tcaaggttgg agatcgttat cctgatgaca atgatattcc
1741 attccccggg ccgatctatg atgaaaccca ccccaacct tctgatgata atcctgatga
1801 ttcacgtgat acaactatcc caggtggtgt tgttgacccg tatgatgatg agagtaataa
1861 ttatcctgac tacgaggatt cggctgaagg caccacagga gatcttgatc tcttcaattt
1921 ggacgacgac gatgacgaca gccaaccagg accaccagac agggggcaga gcaaggaaag
1981 agcggctcgg acacatggcc tccaagatcc gaccttggac ggagcgaaaa aggtgccgga
2041 gttgacccca ggttcccacc aaccaggcaa cctccacatc accaagccgg gttcaaacac
2101 caaccaacca caaggcaata tgtcatctac tctccagagt atgacccta tacaggaaga
2161 atcagagccc gatgatcaga aagatgatga tgacgagagt ctcacatccc ttgactctga
2221 aggtgacgaa gatgttgaga gcgtatcagg ggagaacaac ccaactgtag ctccaccagc
2281 accagtctac aaagatactg gagtagacac taatcagcaa aatggaccaa gcaatgctgt
2341 agatggtcaa ggttctgaaa gtgaagctct cccaatcaac cccgaaaagg gatctgcact
2401 ggaagaaaca tattatcatc tcctaaaaac acagggtcca tttgaggcaa tcaattatta
2461 tcacctaatg agtgatgagc ccattgcttt tagcactgaa agtggcaagg aatatatctt
```

2521 cccagattct cttgaagaag cctacccgcc ttggttgagt gagaaggagg ccttagagaa
2581 agaaaatcgt tatctggtca ttgatggcca gcaattcctc tggccagtaa tgagcctaca
2641 ggacaagttc cttgctgttc ttcaacatga ctgaggaccc atgattagta gattttgttt
2701 attctgagct tgattataat tgttttgata attcaagtat gagcaaccaa cccgaaatat
2761 aaaccctatt ttagttatga ggaaattaaa taaataatct gtaagttgta ggactatgaa
2821 gagctgcttg tgtcaattta tcacgggcta ataccatac cgcaagaata attatttagt
2881 aattttgatc agcttatgat atgtaccaat aggaaaacat tatagcatta aaacataaag
2941 tatccttcga tgagcttagg aggataatat cctgatgaat tctatagaac ttaggattaa
3001 gaaaaaattc atgatgaaga ttaaaaccttt catcatcctt taaaagaga gctattcttt
3061 atctgaatgt ccttattaat gtctaagagc tattatttg taccctctta gctagacac
3121 tgcccagcat ataagccatg cagcaggata ggactatag acatcatgga cccgaagtgt
3181 ctggctggtt ttctgagcaa ttaatgaccg gcaaaatacc gctaacagag gtgtttgttg
3241 atgttgaaaa caaaccaagt cctgccccga taaccattat tagtaagaat cccaagacaa
3301 cacgtaaaag tgataagcaa gtccaaacag atgatgccag tagcttattg acagaagaag
3361 tcaaggctgc cataaattcg gtgatatcag ctgtgcgtcg gcaaaccaat gctattgaat
3421 cactagaagg tcgagtaaca actcttgagg ccagcttaaa accgttcaa gacatggcaa
3481 agaccatatc atccctgaat cgcagctgtg ccgaaatggt tgcaaaatac gacctactgg
3541 tgatgaccac tgggcgagca actgccactg ctgcagcaac agaagcatat tggaatgaac
3601 atggacaagc cctccaggc ccatcattgt acgaggatga tgctattaag gctaaattga
3661 aagatccgaa cgggaaggtt ccagaaagtg tcaaacaggc ctacataaat ctagatagca
3721 caagtgccct caatgaggaa aatttcgggc gaccttacat tcagcaaaa gatctcaagg
3781 aaatcatcta tgaccatctc ccaggatttg ggacagcttt tcatcagttg gtgcaggtta
3841 tctgcaaaat tggtaaggat aataatatcc tagacataat tcatgcagaa ttccaagcaa
3901 gcttggctga gggagactcc ccccagtgtg cattaatcca gataacaaaa cggatccctg
3961 ctttccaaga tgcctctcct ccaattgtgc atatcaagtc tcgaggagat atacccaaag
4021 cctgtcagaa aagcctccgg ccggtcccac cgtcaccaaa gatcgataga ggttgggtct
4081 gtatttttca attccaagac gggaaggccc ttgggctaaa atatgatac agaagcaagg
4141 taagctcatt ttgcgatggc caaatgatac ttatgactgt ttaaaatcaa gttagactaa
4201 tagtctattg tgtcataagc ttataagtca gttttaaatt tccctctat cctaatcaat
4261 tgataatgct gtcaataggg aaattcccct gtattgtaat aagacctcat taacatattt
4321 cccctgctta gtactatgca gaaaccccg agcaaattaa aattgatgaa gattaagaaa
4381 aagagggatt ttctcaggaa aaatctttt tcttacctc atctcattta aacaaattta
4441 ggactcagga aaaatgagaa gggtcactgt gccgactgca ccacctgcct atgctgacat
4501 tggctatcct atgagcatgc ttcccatcaa gtcaagcagg gctgtgagtg gaattcaaca
4561 gaaacaagag gtccttcctg gaatggatac accatcaaat tctatgagac ctgttgctga
4621 tgataacatt gatcatacaa gtcatacccc gaacggagtg gcctcagcat tcatcttgga
4681 ggcaactgtc aatgtgatct cggggcccaa agtcctcatg aaacaaatcc ctatttggtt
4741 gccactcgga attgctgacc aaaaaacgta cagttttgac tcaacaacag cagcaattat
4801 gctcgcatct tatacgatca cccatttgg aaaggccaac aacccctcg ttagagtgaa
4861 tcgacttggt cagggaatac cggatcaccc actcagattg ctcaggatgg ggaaccaggc
4921 tttccttcaa gagtttgtgc taccaccagt tcaactgccg caatatttca cttttgatct
4981 gactgcactc aaactagtga cacagcctct ccctgctgca acatggacag atgagactcc
5041 gagcaaccttt tcaggagccc ttcgtcccgg gctttcattt cacccaaagc tgagacccgt
5101 tctacttcca ggcaagacgg gaaagaaagg gcatgtttct gatctgactg cccagacaa
5161 aattcagaca attgtgaacc tgatgcaaga tttcaaaatc gtgccaattg atccagctaa
5221 gagtatcatt gggatcgagg ttcagaatt gctggtccac aagctcactg ggaagaaaat

FIG. 2 CONTINUED

```
5281 gagtcagaag aatggacagc ctataattcc tgtcttactc ccaaaataca ttgggctaga
5341 tccaatctca cctggagacc tgactatggt cataacacca gattatgatg attgtcattc
5401 acctgccagt tgctcttatc tcagtgaaaa gtgattctca caaagtgaga gaaacacctc
5461 cagtaaagaa atcaaatctt atctatagca actcaatcga cttttaggaa gctagcagtc
5521 catatactat gggacaactc aaccctcttg ttaaaatgta ctaatcgggt caaggaactc
5581 tcactgatca agcctgaatc caagatagaa ccagcccaaa gggcctcccc agagtctctt
5641 acaagcttag ccaatcaatt aacatgcata agcgatccat acttcgccca atcagtgtcc
5701 gatgttcacc ccttcaagcc tccttcctag caaattgacc tagctgtacc aagagattcc
5761 ctcagcctcc ttctcaaata acctgatcct cgagggttac accttcacca ctctatgctc
5821 atttcaccca aacataaaat gaaatgtctt aacatgattg caccattaag aaaaacaaat
5881 ctgatgaaga ttaagcctga tgaaggccca accttcatct ttttaccata atcttgttct
5941 cagtaccatt tgataagggt acacttgcca atacgccccc atcctaaggg tctcgcaatg
6001 gggggtctta gcctactcca attgcccagg gacaaatttc ggaaaagctc tttctttgtt
6061 tgggtcatca tcttattcca aaaggccttt tccatgcctt tgggtgttgt gactaacagc
6121 actttagaag taacagagat tgaccagcta gtctgcaagg atcatcttgc atctactgac
6181 cagctgaaat cagttggtct caacctcgag gggagcggag tatctactga tatcccatct
6241 gcaacaaagc gttggggctt cagatctggt gttcctccca aggtggtcag ctatgaagcg
6301 ggagaatggg ctgaaaattg ctacaatctt gaaataaaga agccggacgg gagcgaatgc
6361 ttaccccccac cgccagatgg tgtcagaggc tttccaaggt gccgctatgt tcacaaagcc
6421 caaggaaccg ggccctgccc aggtgactac gcctttcaca aggatggagc tttcttcctc
6481 tatgacaggc tggcttcaac tgtaatttac agaggagtca attttgctga gggggtaatt
6541 gcattcttga tattggctaa accaaaagaa acgttccttc agtcaccccc cattcgagag
6601 gcagtaaact acactgaaaa tacatcaagt tattatgcca catcctactt ggagtatgaa
6661 atcgaaaatt ttggtgctca acactccacg acccttttca aaattgacaa taatactttt
6721 gttcgtctgg acaggcccca cacgcctcag ttccttttcc agctgaatga taccattcac
6781 cttcaccaac agttgagtaa tacaactggg agactaattt ggacactaga tgctaatatc
6841 aatgctgata ttggtgaatg ggcttttttgg gaaaataaaa aaatctctcc gaacaactac
6901 gtggagaaga gctgtctttc gaagctttat cgctcaacga gacagaagac gatgatgcgg
6961 catcgtcgag aattacaaag gaagaatct ccgaccgggc caccaggaag tattcggacc
7021 tggttccaaa gaattcccct gggatggttc cattgcacat accagaaggg gaaacaacat
7081 tgccgtctca gaattcgaca gaaggtcgaa gagtaggtgt gaacactcag gagaccatta
7141 cagagacagc tgcaacaatt ataggcacta acggcaacca tatgcagatc tccaccatcg
7201 ggataagacc gagctccagc caaatcccga gttcctcacc gaccacggca ccaagccctg
7261 aggctcagac ccccacaacc cacacatcag gtccatcagt gatggccacc gaggaaccaa
7321 caacaccacc gggaagctcc cccggcccaa caacagaagc acccactctc accacccag
7381 aaaatataac aacagcggtt aaaactgtcc tgccacagga gtccacaagc aacggtctaa
7441 taacttcaac agtaacaggg attcttggga gtcttgggct tcgaaaacgc agcagaagac
7501 aaactaacac caaagccacg ggtaagtgca atcccaactt acactactgg actgcacaag
7561 aacaacataa tgctgctggg attgcctgga tcccgtactt tggaccgggt gcggaaggca
7621 tatacactga aggcctgatg cataaccaaa atgccttagt ctgtggactt aggcaacttg
7681 caaatgaaac aactcaagct ctgcagcttt tcttaagagc cacaacggag ctgcggacat
7741 ataccatact caataggaag gccatagatt tccttctgcg acgatggggc gggacatgca
7801 ggatcctggg accagattgt gcattgagc cacatgattg gacaaaaaac atcactgata
7861 aaatcaaccca aatcatccat gatttcatcg acaaccccctt acctaatcag gataatgatg
7921 ataattggtg gacgggctgg agacagtgga tccctgcagg aataggcatt actggaatta
7981 ttattgcaat tattgctctct ctttgcgttt gcaagctgct ttgctgaata tcaatttgaa
```

FIG. 2 CONTINUED

```
8041 tcatcaattt aagcttgata catttctagc attttaaatt ataaaccgat actgatactt
8101 gaaaatcagg ctaatgccaa gttctgtgca aaacttgaaa gtaggtttac aaaaatcctt
8161 tggactggaa tgctttgata ctctttctca atactatata agttccttcc caagaataat
8221 attgatgaag attaagaaaa agtgacattg tgcccactt tgtaatcttc atccacctac
8281 acattcatat tcaggaatct ttgaattaac cctcacactt gcttaggaaa gagcctatcc
8341 tctacaagaa tcccgaggcg gcaattcagt taatttcata tcaagataac atccatttcc
8401 aagaccacag ataactatat tattaatctt taccacaaat atggagaggg gtcgtgagcg
8461 cgggagatca aggaattcac gtgccgacca gcaaaattca acaggtcctc aatttaggac
8521 aagatccatt tcccgggata agacaacaac agactaccgt agtagtcgaa gtacttcgca
8581 agttagagtc cctacggttt tccataagaa aggtactggg acccttactg tccctccagc
8641 acctaaggat gtttgtccta ctctcagaaa aggatttcta tgtgatagta atttctgtaa
8701 aaaggaccat caacttgaaa gcctaaccga ccgggagctc ctacttctta tagcacggaa
8761 gacctgtgga tcaactgatt catcgcttaa tatagctgct cctaaagacc taagactagc
8821 aaatcctacg gctgatgact tcaagcaaga cggcagtcca aaattaaccc taaaattact
8881 agtcgagact gctgagtttt gggccaatca gaatattaat gaagtagatg atgcaaaact
8941 ccgtgctctc ttgacgttga gtgctgtctt agtgcggaaa ttctctaagt cacagcttag
9001 tcaattatgt gagagtcatc ttaggaggga aaacttagga caagaccaag ctgaatcagt
9061 tctcgaggtt tatcaacgtt tacatagtga caaaggaggt gcttttgagg cagcactatg
9121 gcaacagtgg gatagacaat cattaactat gtttatatct gctttcctcc atgtagcatt
9181 gcaactttcc tgtgagagct ccactgtagt gatatcaggc ctacgcttac ttgccccccc
9241 aagcgttaat gaagggctcc ctcctgcacc agggggaatat acttggtcag aagatagtac
9301 aacttagcct gtagggagga caagtaaaac aagatgccct tatcctctat agatggtatt
9361 tttagagagg gggacaggat aggaataaag ataatgacta agccaatat aaagatacga
9421 acacaagtag aaattaaaat agaaatcaaa acaatctccc cttattcaat atgaaatata
9481 atagtgagta tttgtttcat gatgtcaatc atttattgtt aaaataaac aaagtcagta
9541 agagtgttag gatcgttata ttgcaaggat cctccctaga agcgttgaat catctcaagt
9601 agcctagaac aagaacagca gagcattaaa ttgaaataga taataaggat attgcttgtt
9661 tttaagatag ttttaggaag tttaaaatta agaaaaagaa cccatggaca cactctagca
9721 ttgaggatgg ggttcccttg atgatagtat agtcttaggt atagggtagt cctacacgta
9781 ctatattata cagtctaaac ttgtaaaatt aaactacaag aacatgatga aaattaatga
9841 gaaggttcca agattgactt caatccaaac accttgctct gccaattttc atctccttaa
9901 gatatatgat tttgttcctg cgagataagg ttatcaaata gggtgtgtat ctctttaca
9961 tatttgggct cccactaggc tagggtttat agttaaggaa gactcatcac attttttatt
10021 gaactagtct actcgcagaa tcctaccggg aatagaaatt agaacatttg tgatactttg
10081 actataggaa ataattttca acactacctg agatcaggtt attcttccaa cttattctgc
10141 aagtaattgt ttagcatcat aacaacaacg ttataattta agaatcaagt cttgtaacag
10201 aaataaagat aacagaaaga accttatta tacgggtcca ttaatttat aggagaagct
10261 ccttttacaa gcctaagatt ccattagaga taaccagaat ggctaaagcc acaggccggt
10321 acaacttggt aacaccaaaa cgggagctag agcaaggagt tgtgtttagc gacctatgca
10381 acttcctagt gactccaact gtgcaaggat ggaaggttta ctgggctgga cttgagtttg
10441 atgtcaacca aaagggtatt accctgttaa atcgtcttaa agtgaatgat tttgctcctg
10501 catgggcgat gacccggaac ctcttccac acttgttcaa aaaccaacag tctgaagtcc
10561 aaactcccat tgggccttg agggtaattc ttgccgccgg gattcttgac caattaatgg
10621 atcattccct cattgagccg ctatcagggg ccctgaacct aattgctgat tggttactaa
10681 caacatctac taatcacttc aacatgagaa ctcaacgagt aaaggaccaa ctgagcatga
10741 ggatgttatc tcttataagg tcaaatatta ttaactttat aaataagctc gagactcttc
```

FIG. 2 CONTINUED

```
10801 atgtcgttaa ttacaaggga cttctaagca gtgttgagat aggaacacca agctatgcaa
10861 tcatcattac caggactaat atgggttatc ttgtcgaggt tcaggaacca gataaatctg
10921 cgatggatat acgacaccct ggtcctgtca aattctcctt actacatgaa tcgacactta
10981 aacctgttgc cactcctaaa ccatcaagca ttacttcatt gatcatggag ttcaacagtt
11041 ctttggcaat ttaattgccg taataaaaat tgtacgatag ggctaacatt gattccataa
11101 tccatcgtag gacagaatca ttttcctgta tgatcttagt ttaatctctc tttatacaat
11161 gattaataag gagcctgttt aaaatgttac aaaagtatac tgtttgaacc cctagtatcc
11221 ctgtaaatat cctcattcaa ttttttgctt ttacatgtgt agtcacctgt atagcatgac
11281 cctagtcatg cctttaatta atacttaatc taacagttaa tataatgtat aactttccat
11341 gttcaaagag tagtcaaaac aatgtgagat ccagtttcac tcacagcatc tattcactat
11401 ttacagtatg atgagcccaa attaacacgg tagaggtcta gatttattaa tagaacgagg
11461 aagattaaga aaaagtccat aatgctgggg aggcaatcct tgccaccata ggactttttc
11521 aattcctcta ttttatgatg gctacccaac atacacaata tcctgatgca agattgtctt
11581 ccccaattgt cttagaccaa tgtgacctag tgacaagagc atgtggactt tactctgagt
11641 attcgctgaa ccctaaacta aagacatgcc gtttaccgaa acatatctat agattaaaat
11701 atgacactat tgttttacga tttattagtg atgtccctgt agctacaatc ccaatagact
11761 acattgctcc gatgttaata aatgttctgg cagataqtaa aaatgtacca ttggaacctc
11821 cctgcttgag tttcttggat gaaatagtca attataccgt gcaggatgca gccttcctta
11881 attattacat gaatcagatt aaaacacagg aaggagtaat tacagatcaa ttaaaacaga
11941 acattcgtag ggtcattcac aaaaacagat atctatctgc tctattcttc tggcatgatc
12001 ttgccatcct cacccgtcga gggagaatga accgaggaaa tgtgcgctcc acttggtttg
12061 taacgaatga ggttgttgac attctaggat atggtgatta tatcttctgg aagatcccta
12121 ttgctctatt accaatgaac acagctaatg ttccacatgc atcaactgac tggtaccaac
12181 ctaatatctt caaggaggct attcaaggac acacacatat tatttcagtc tctacagccg
12241 aggtccttat tatgtgtaag gatcttgtca caagtcgttt taatacccct ctgattgctg
12301 agttagccag gttggaagat ccagtgtctg ctgattatcc actagtagat aatattcaat
12361 ctctgtataa cgcaggagac tacctgttgt ccatattggg atcagagggg tacaaaataa
12421 tcaaatatct cgaacctctg tgtttggcta agattcaact atgttcccaa tatacagaac
12481 gaaaagggcg gttttaacc cagatgcatc ttgcagttat tcagacattg cgtgaactcc
12541 tccttaatag agggttgaaa aaatcacaat tgtctaaaat ccgcgagttt caccaactgt
12601 tgctcagact ccgatctaca ccacaacaat tatgtgaatt attttcaatc caaaaacact
12661 ggggccaccc agttctgcat agtgaaaagg ccatccaaaa ggttaaaaat catgcaacag
12721 ttctaaaggc attgcggccg attatcatct ttgaaacgta ttgtgtattc aagtatagtg
12781 ttgcaaaaca tttctttgat agtcaaggca cttggtacag tgtgatatca gaccgatgtt
12841 taacgccggg attgaattcc tacattaggc gaaatcaatt ccctccactt ccaatgatca
12901 aagatctttt atgggaattt taccatttgg atcatcctcc attattctcc acgaagatca
12961 ttagtgacct cagcattttc attaaagacc gcgcaacagc agttgaacaa acctgttggg
13021 atgcagtttt tgagcctaac gtttttgggct acagtccacc ttatcgattc aataccaaac
13081 gtgtacctga acaattcctg gagcaagagg attttctat tgagagtgtc ttacaatacg
13141 cccaagaact taggtactta ttgccccaga atcgaaaatt ttcttttca ttgaaggaaa
13201 aagaattaaa tgttggtagg acattggaa aattgcctta tttaaccagg aatgtccaaa
13261 ccctctgcga agcattactt gcagatggtt tggctaaagc cttccaagc aatatgatgg
13321 ttgtcacaga gagggaacaa aaggagagcc tccttcacca agcatcctgg caccatacaa
13381 gtgatgattt cggagagcat gccacagttc gtggaagtag tttgtcaca gacctggaaa
13441 aatacaatct ggccttcagg tatgaattca cagctccctc catcaaatat tgcaaccaat
13501 gctatggggt tcgcaatgtc tttgattgga tgcacttcct aattccgcaa tgttacatgc
```

FIG. 2 CONTINUED

```
13561 atgttagtga ttattataac ccaccacata atgtaacctt agagaatagg gaatatcccc
13621 ccgaaggacc aagtgcttat agaggccacc ttggcggtat tgaggggctt caacaaaagt
13681 tatggactag tatctcatgt gctcaaatct cattggtaga gatcaagacc gggttcaaat
13741 tgcgatcagc agtcatgggg gataatcaat gtattacagt attatcagtc tttccactag
13801 aatctagtcc gaatgagcag gagagatgcg cagaagacaa tgcagccaga gtggctgcta
13861 gcttggccaa agtcacaagt gcctgtggga tattcctcaa gcctgatgag actttcgtac
13921 actcaggctt tatctatttt ggcaaaaagc aatacttgaa cggaattcaa ttacctcaat
13981 cactcaagac agcagctagg atggcccctc tctcagatgc aatttttgat gacttgcaag
14041 gtacacttgc cagtatagga actgcctttg agcgatcaat ctccgaaact agacatattt
14101 taccatgccg tgttgcagct gcctttcata catatttctc tgttcggatc ttacaacatc
14161 atcaccttgg tttccataag ggttcagacc ttggacaatt ggcaatcaat aaacctcttg
14221 atttcgggac cattgcacta tccttagcag ttcctcaggt attgggtgga ttatccttcc
14281 taaatccaga aaagtgcctt tatcgcaact tgggtgatcc tgtaacttca ggcctatttc
14341 agttgaagca ttatctgtca atggtgggta tgagtgatat ctttcatgca cttattgcaa
14401 aaagcccagg gaattgtagc gcaattgact ttgttctaaa cccaggcggg ttaaatgtcc
14461 ctggatcaca ggatttaaca tctttccttc gtcagattgt cagaaggagt atcacacttt
14521 cggcaaggaa caagttaatc aacacgttat ttcacgcttc tgcagatctt gaagacgaat
14581 tagtatgtaa atggttactt tcttcaacgc ccgtgatgag ccgtttgca gccgatattt
14641 tctcacgaac accaagcggg aaaagattac aaatcttggg ataccctcgag ggaaccagaa
14701 ctttattagc atccaaaatg ataagcaata atgcagagac accaatccttg agaggctca
14761 gaaaaataac acttcaaaga tggaatctat ggtttagtta cctagaccat tgtgacccag
14821 ctttaatgga agcaattcaa ccaattaagt gtactgttga tattgctcaa attcttagag
14881 aatactcctg ggctcatatc cttgatggta gacagttaat aggggcaaca ctgccatgta
14941 tacctgagca gttccaaacc acatggttaa aacctacga gcaatgtgtg gaatgttcat
15001 ccacaaacaa ttctagtcca tatgtatcag ttgcattaaa aaggaacgtg gttagtgctt
15061 ggcctgatgc atctagattg gggtggacga ttggtgatgg gattccctac ataggctcaa
15121 gaactgagga caaaataggt cagcccgcta ttaagccgag gtgcccatca gctgcattaa
15181 gagaagctat tgaattgacc tctaggttga cctgggtcac tcaaggtagt gcaaacagcg
15241 atcagttaat tcgcccttt cttgaggcaa gagtaaactt gagtgtacaa gagattcttc
15301 aaatgacccc ctcacattac tccggtaata ttgtgcatcg gtataatgat cagtatagcc
15361 ctcactcctt tatggctaac cgcatgagta acacagcaac gcgcttgatg gtatctacca
15421 acacactagg agagttttcc ggaggggggtc aggctgcacg tgatagcaac attatatttc
15481 aaaatgtgat taacttgca gtggccttgt atgacattag gttcggaac acttgtacat
15541 cttctattca atatcacagg gcccatattc acctgacgaa ttgttgtacg agggaagtac
15601 cggcccaata cttaacatac acaaccacgc taaatctaga tttgagtaag taccgtaata
15661 atgaactgat ttatgattca gatccactaa gaggaggtct caactgcaac ttatcgattg
15721 acagtccttt gatgaagggc ccacgtttaa atattattga ggatgactta atacggttgc
15781 cacatttatc cggctgggaa ttagcaaaaa cagtcttgca atcaataatc tctgatagta
15841 gcaattcatc aacagatccc attagcagcg gtgaaacaag atcttcaca acccacttct
15901 taacgtatcc caaaataggg cttctataca gttttggagc cctcataagt ttttatttgg
15961 gtaatactat tctatgcacg aaaaagatcg gactcacaga atttctatac tatctccaga
16021 atcagatcca caactatca catagatccc ttcgaatctt caaaccgaca tttagacact
16081 caagtgtcat gtccaggttg atggatatag accccaactt ctcaatatat attggtggga
16141 ctgcaggtga ccgtggatta tcggacgctg caagattatt ctccgaatt gcaatttcaa
16201 ctttcttgag ctttgttgag gagtgggtta tctttaggaa ggcaaacatc ccactatggg
16261 ttatctatcc tctcgaaggc caacgctctg atcctcctgg cgaattttg aaccgagtaa
```

FIG. 2 CONTINUED

```
16321 aatctctaat tgttgggact gaagatgata aaaataaagg ctctatactt tcaagatctg
16381 gagagaaatg ctcttcaaat ctagtttata attgcaagag tacagcaagc aatttttcc
16441 atgcatcatt ggcttactgg agaggtcgac atagacctaa gaagactata ggtgcaacta
16501 acgcgacaac agctccacat atcattttgc cactgggaaa ttctgatcga ccgcctggcc
16561 tagaccttaa taggaacaat gatactttca ttcctaccag aattaaacag atagtccaag
16621 gagactctag aaacgacaga acgaccacca cgagatttcc acccaaaagt aggtccactc
16681 caacatcagc aaccgagcct cctacaaaaa tgtatgaggg ttcgacaacc caccaaggga
16741 aattaacaga tacacatttg gatgaggatc acaatgccaa agagttccca tccaatccgc
16801 atcgtttagt agtaccattc tttaaattaa caaaagatgg ggaatacagc atcgaacctt
16861 ctcctgaaga aagccgcagt aatataaaag ggttacttca acatttaaga accatggttg
16921 atactaccat atattgtcgc ttcactggaa ttgtttcatc aatgcattat aagttagatg
16981 aagtactatg ggaatataat aaatttgaat cagctgtaac cctagcagaa ggggaggtt
17041 caggtgcctt actactgatc caaaaatacg gcgttaagaa gttattttg aatacacttg
17101 ctactgaaca tagtattgag agtgaagtga tatcaggtta caccactcca aggatgctac
17161 tcccaattat gcctaaaaca catcgtggtg agctagaggt catattaaat aactcagcta
17221 gtcaaataac tgatattaca catcgagatt ggtttcaaa tcaaaaaaat aggattccaa
17281 atgatgctga tattattacc atggatgctg aaactacaga aaacttagat cgttccagat
17341 tatatgaagc agtatatacg attatttgta atcatatcaa tcctaaaact ttgaaagtgg
17401 tcatcttaaa agtcttcctc agcgatttgg atgggatgtg ctggattaac aattatcttg
17461 ctcctatgtt tggatcagga tatttaatca aacctataac atcaagtgca aagtcaagtg
17521 agtggtattt atgcttatct aatctactt caaccttgag aactactcag catcaaaccc
17581 aggcaaactg tctccatgtc gtacaatgtg ctcttcaaca gcaagtacaa agagggtcat
17641 attggctaag tcatcttacc aaatacacca caagtagatt gcacaatagt tatattgcat
17701 ttggttttcc ttcattagag aaggtcctat atcataggta taaccttgtt gattcgagaa
17761 atggaccatt agtttctata acgagacacc ttgccctcct ccaaactgag atccgggagt
17821 tggtaactga ttataatcag ctgcgacaaa gtcgaaccca gacttatcat ttcataaaaa
17881 catccaaggg acggataact aaaactagtga atgattatct aagatttgag ttggtatatac
17941 gggctcttaa aaataattct acatggcacc atgagttata cttgctacca gaacttatag
18001 gtgtttgcca tcgatttaat catacacgta actgtacatg cagtgaaagg ttcctggttc
18061 aaactttata tctacaccga atgagtgatg ctgagataaa acttatggac cggctcacca
18121 gcctagtcaa tatgttttct gaaggtttca ggtctagttc agtctaattc taactgcacc
18181 aaaggctcta aaatatttt aaataaccag gtgtatatca aagtcaatac aagtgtaaaa
18241 acaatatgca agggaccaca tttaggatca gtttattgac tcttccaata cacagagttg
18301 gaagcaccga ttcaaggttt ctaagacgcc ctatcgatta tgttgataat gtaaataata
18361 gcttttcctg tctattatga cttaaataat catatctata acgaccatca cagctaagtc
18421 gttgccctag ttcatatatt aaattaaaat ttagaagcta ggttgactct aattacataa
18481 gtattaagaa aaaattacta agactaatac tctcatgcca agaactagta atgtgtttca
18541 catgacagat tatttctaac actaaattgc aatttcaatt ttaaagctaa gtttaacacc
18601 tatacagcca aaatatttca tagggccgat gggaataaca taagaggaac atgatcaatg
18661 aacccttat tccaactagg cagttgattg ataatctaca aattccataa gatgttctta
18721 cgatattctt ttgttttaa tctcaatgtc aatgatttaa taagtaataa taaaaaaatc
18781 acattaaaga tgcaggaaga tcttgacctc gccaggaaaa ttaagcgcac acaaataaat
18841 taaaaaatct gtatttctc tttttgtgt gtcca
```

(SEQ ID NO:1)

MAKATGRYNLVTPKRELEQGVVFSDLCNFLVTPTVQGWKVYWAG
LEFDVNQKGITLLNRLKVNDFAPAWAMTRNLFPHLFKNQQSEVQTPIWALRVIL
AAGI
LDQLMDHSLIEPLSGALNLIADWLLTTSTNHFNMRTQRVKDQLSMRMLSLIRSNI
INF
INKLETLHVVNYKGLLSSVEIGTPSYAIIITRTNMGYLVEVQEPDKSAMDIRHPGP
VK
FSLLHESTLKPVATPKPSSITSLIMEFNSSLAI (SEAPOND: 2)

NC_004161

1    cggacacaca aaaagaaaaa aggtttttta agactttttg tgtgcgagta actatgagga
61   agattaacag ttttcctcag tttaagatat acactgaaat tgagattgag attctcctct
121  ttgctattct gtaactttcc ctggttgtga caattgaatc agtttatct attaccaatt
181  accatcaaca tggtatgtct agtgatcttg ggactcttct tcatctggtt tttcctagag
241  ctctgaatcc attttgcgag aagttcatcc aaacgaccca gtgtctgaaa atacaaaagg
301  ttcccctttc cgtcaagttt aaggggttgt tttgattgtg tgtagatttt ataatcctag
361  agtgccaagg agttgcgtgt catcattgat tgggaagatc aaggaaacaa tttgttccaa
421  taatatcgta catcttgact aagtcgaaca aggggaagtc gatatggatc gtgggaccag
481  aagaatctgg gtgtcgcaaa atcaaggtga tactgattta gattatcata aaattttgac
541  agctggcctt actgttcaac agggaattgt caggcagaaa ataatttctg tatatcttgt
601  tgataacttg gaggctatgt gtcaattggt aatacaagcc tttgaggccg gaattgattt
661  ccaagaaaat gccgacagct tccttctgat gctttgccta catcatgctt accaaggtga
721  ctataaattg ttcttggaga gcaatgctgt acagtatttg gaaggtcatg gattcaaatt
781  tgagctccgg aagaaggacg gtgtcaatcg gctcgaggaa ttgcttcctg ctgcaacgag
841  tggaaaaaac atcaggcgta cgttggccgc actgcctgaa gaggagacta cagaagcaaa
901  tgcagggcaa tttctctcat ttgcgagttt gtttcttccc aaactggttg tgggagagaa
961  ggcttgcttg gaaaaagtcc agcgacaaat tcaggttcat gcagaacagg gtttaattca
1021 atatcccact gcatggcaat cagttggaca catgatggta atcttcagat tgatgaggac
1081 taatttcttg attaaatatt tactgatcca ccagggtatg catatggtag ctggccacga
1141 tgccaatgat gctgtcattg ctaattcagt tgctcaggct cgcttttcag gactcctaat
1201 tgtcaaaacc gttcttgatc atattctgca aaaaaccgac caaggagtaa gacttcaccc
1261 tttggcccga acagccaaag tgcgtaatga ggttaatgca tttaaggccg ccctaagctc
1321 acttgctaag catggggaat atgccccttt tgctcgcctt ctcaatctct cgggagttaa
1381 caacctagaa catggtctct acccacagtt atcagcaatt gtcttggag ttgccacagc
1441 acatggtagc acccttgcag gagttaatgt tggtgagcag tatcagcagc ttagagaggc
1501 tgccactgaa gctgagaagc aactccaaca atatgctgag tccagagaac tgacagcct
1561 aggcctggac gatcaggaaa gaagaatact aatgaacttc atcagaaga aaaacgaaat
1621 tagtttccag cagaccaatg caatggtaac ccttaggaaa gagcgactgg ctaaattaac
1681 agaagctata acgctggcct caagacctaa cctcgggtct agacaagacg acggcaatga
1741 aataccgttc cctgggccta taagcaacaa cccagaccaa gatcatctgg aggatgatcc
1801 tagagactcc agagacacca tcattcctaa tggtgcaatt gaccccgagg atggtgattt
1861 tgaaaattac aatggctatc atgatgatga agttgggacg gcaggtgact tggtcctgtt
1921 cgatcttgac gatcatgagg atgacaataa agcttttgag ccacaggaca gctcgccaca
1981 atcccaaagg gaaatagaga gagaaagatt aattcatcca cccccaggca acaacaagga

FIG. 2 CONTINUED

```
2041 cgacaatcga gcctcagaca acaatcaaca atcagcagat tctgaggaac aaggaggtca
2101 atacaactgg caccgaggcc cagaacgtac gaccgccaat cgaagactct caccagtgca
2161 cgaagaggac acccttatgg atcaaggtga tgatgatccc tcaagcttac ctccgctgga
2221 atctgatgat gacgatgcat caagtagcca acaagatccc gattatacag ctgttgcccc
2281 tcctgctcct gtataccgca gtgcagaagc ccacgagcct ccccacaaat cctcgaacga
2341 gccagctgaa acatcacaat tgaatgaaga ccctgatatc ggtcaatcaa agtctatgca
2401 aaaattagaa gagacatatc accatctgct gagaactcaa ggtccatttg aagccatcaa
2461 ttattatcac atgatgaagg atgagccggt aatatttagc actgatgatg ggaaggaata
2521 cacctacccg gattcacttg aggaagccta tcctccatgg ctcaccgaga aagaacgact
2581 ggacaaagag aatcgctaca tttacataaa taatcaacag ttcttctggc ctgtcatgag
2641 tcccagagac aaatttcttg caatcttgca gcaccatcag taaccacagc acaaagcgcg
2701 gtccacttcg taaagctaaa tacacttaag acttgaccga ttcatctaca aaaactaatc
2761 cattataact tattagtgct acttttctat aagtgattct taatctaagg ccattaagag
2821 tttaagtaat atacatatac acttacaccg gtctatccaa gatgtggctc aatgttcttg
2881 atttgaacat agtcataagg ggataaataa tactttatat ttctgattgt ggattgaccc
2941 attctgctta aaatgcttcg cccattgaaa atgtgatcta atagatagcc ctgactagac
3001 aaattaagaa aaacatttga tgaagattaa aaccttcatc gccagtaaat gattatattg
3061 tctgtaggca ggtgtttact ccaccttaaa tttggaaata tcctaccta ggaccattgt
3121 caagaggtgc ataggcatta ccacccttga gaacatgtac aataataaat tgaaggtatg
3181 ttcaggccca gaaacgactg gatggatttc tgagcaactt atgacaggta agattccagt
3241 aactgatata ttcattgata ttgataacaa gccagatcaa atggaagtcc gactcaaacc
3301 atcatcaagg agctcaacaa gaacttgtac aagtagcagt cagacggagg tcaactatgt
3361 acctctcctt aaaaaggttg aggatacatt aactatgcta gtgaatgcca ccagtcgtca
3421 gaatgctgca atcgaggccc ttgaaaaccg cctcagcaca cttgagagta gcttaaagcc
3481 aatccaagac atgggtaaag tgatttcatc attgaatcgc agttgtgccg aaatggttgc
3541 aaaatatgat cttctagtta tgacaactgg acgggctact tcaactgcag ctgcagtaga
3601 tgcgtattgg aaaagagcaca aacagccacc accagggcca gcgttgtatg aagagaatgc
3661 gcttaaagga aaaatcgatg atccaaacag ctatgtacca gatgctgtgc aagaggctta
3721 caagaaccct gacagtacat cgaccctgac cgaggaaaat tttgggaaac cttatatatc
3781 tgctaaagac ctgaaggaga tcatgtatga tcatctacct ggttttggga ctgcctttca
3841 ccaacttgtt caagtgattt gtaaaatagg aaaggataac aacccttttgg acacaatcca
3901 tgctgagttc caggcaagtc tagcagatgg tgactctccc caatgtgcac tcatacagat
3961 aaccaaaagg gtcccaatct ttcaggatgt gccgcccccg ataatccata ttagatcccg
4021 tggtgacatc ccacgagcat gccaaaagag tctccgacca gcaccaccat caccaaaat
4081 tgatcgtggt tgggtttgtt tgtttaagat gcaagatggt aaaacgcttg gacttaagat
4141 ctaagaatca agattatttt aacaaggcaa gccacaacct tagatggaac ctcagccaga
4201 ctattgaact attgacgctg ttgatgataa tatataatta atggtcttat ttgaatatga
4261 caacatcttg cttcttgttc tgccttgtag ctctttgaat tggaagatca ttccaaactt
4321 acaaacatgc acaagatgtt atggtttagc aaagaattga taggagtact ggtatataat
4381 gtaaatataa caagtgatga agattaagaa aaaccagtcg gtattttcca gacttggcat
4441 ttcttatctt catcttctaa agtgagatat tttatcatca aaaatgagg cgcggagtgt
4501 taccaacggc tcctccagca tataatgata ttgcataccc tatgagcata ctcccaaccc
4561 gaccaagtgt catagtcaat gagaccaaat cagatgtact ggcagtgcca ggggcagatg
4621 ttccatcaaa ctccatgaga ccagtggctg atgataacat tgatcactca gccatactc
4681 caagcggagt agcttctgcc tttatattgg aagctacagt gaatgtaatt tcgggaacaa
4741 aagtcctgat gaagcaaata cctatttggc ttccactggg tgtagctgat cagaagatat
```

FIG. 2 CONTINUED

```
4801 acagctttga ttcaacaaca gccgcaatta tgttggcttc ctacacagtg acacacttcg
4861 ggaagatatc taaccgctg gtacgtgtca acaggctagg cccaggaata cccgatcatc
4921 cgctacgact cctaaggttg ggcaatcagg cattccttca agagtttgtt cttccaccag
4981 tccagcttcc ccagtatttc acatttgatc taacagctct aaagctcatc actcaaccat
5041 tgccagctgc aacctggaca gacgaaactc cagcaggagc agtcaatgct cttcgtcctg
5101 ggctctcact ccatcccaag cttcgtccaa ttctcctgcc ggggaagaca ggaaagaaag
5161 gacatgcttc agacttaaca tcacctgaca agattcaaac aatcatgaat gcaataccgg
5221 acctcaaaat tgtcccgatt gatccaacca agaacatagt tggaattgag gttccagaat
5281 tactagttca aaggctgacc ggcaaaaaac cacaacccaa aaatggccaa ccaattattc
5341 cagttcttct tccgaaatat gttggacttg atcctatatc gccaggggac ttaactatgg
5401 ttatcaccca ggattgtgat tcatgccact ctccagccag ccatccgtat cacatggaca
5461 agcagaatag ttaccaataa tttaaattcc attcgagcta ttattctgct agtaattccg
5521 acgggatcaa tagactaaaa atctgattgt atagaattat aaaagaatca agcagaggca
5581 acagactcac agcttacgcc tagataacta atattaagga gttttttaat ctaattttcc
5641 agtcttgagt aataatcatt tcttttgtaa ttaattatgc atttgttaac ttatcggtgc
5701 gagatttcct tgagaacccg gcggagcttc tactatctgc agtaaccaga agagaagttc
5761 aacccagtca aaactaaacc aagcaatatt ctgaatgctc tatagtctat tctaatcaga
5821 ggtataacaa tggctaagat ttcaatgact cgttaacaat cgctagtaat tttaatctcc
5881 agattaagaa aaagatatac gatgaagatt aaggcgacaa cgagccgaaa cttcatctct
5941 tttaaagatc taacattatc tgttccaaag tcatacaagg acacattcaa atcagggatt
6001 gtaagctgct atttcttacc tccccaaatt acctatacaa catgggggtca ggatatcaac
6061 ttctccaatt gcctcgggaa cgtttcgta aaacttcgtt cttagtatgg gtaatcatcc
6121 tcttccagcg agcaatctcc atgccgcttg gtatagtgac aaatagcact ctcaaagcaa
6181 cagaaattga tcaattggtt tgtcgggaca aactgtcatc aaccagtcag ctcaagtctg
6241 tggggctgaa tctggaagga aatggaattg caaccgatgt cccatcagca acaaaacgct
6301 ggggatttcg ttcaggtgtg cctcccaagg tggtcagcta tgaagccgga gaatgggcag
6361 aaaattgcta caatctggag atcaaaaagt cagacggaag tgaatgcctc cctctccctc
6421 ccgacggtgt acgaggattc cctagatgtc gctatgtcca caaagttcaa ggaacaggtc
6481 cttgtcctgg tgacttagct ttccataaaa atggggcttt tttcttgtat gatagattgg
6541 cctcaactgt catctaccga gggacaactt tgctgaagg tgtcgtagct tttttaattc
6601 tgtcagagcc caagaagcat ttttggaagg ctacaccagc tcatgaaccg gtgaacacaa
6661 cagatgatcc acaagctac tacatgaccc tgacactcag ctacgagatg tcaaattttg
6721 ggggcaatga aagcaacacc cttttaagg tagacaacca cacatatgtg caactagatc
6781 gtccacacac tccgcagttc cttgttcagc tcaatgaaac acttcgaaga aataatcgcc
6841 ttagcaacag tacagggaga ttgacttgga cattggatcc taaaattgaa ccagatgttg
6901 gtgagtgggc cttctgggaa actaaaaaaa cttttcccaa caacttcatg gagaaaactt
6961 gcatttccaa attccatcaa cccacaccaa caactcctca gatcagagcc cggcgggaac
7021 tgtccaagga aaaattagct accaccccacc cgccaacaac tccgagctgg ttccaacgga
7081 ttcccctcca gtggtttcag tgctcactgc aggacggaca gaggaaatgt cgacccaagg
7141 tctaaccaac ggagagacaa tcacaggttt caccgcgaac ccaatgacaa ccaccattgc
7201 cccaagtcca accatgacaa gcgaggttga taacaatgta ccaagtgaac agccgaacaa
7261 cacagcatcc attgaagact ccccccatc ggcaagcaac gagacaattt accactccga
7321 gatggatccg atccaaggct cgaacaactc cgcccagagc ccacagacca agaccacgcc
7381 agcaccaca acatcccga tgacccagga cccgcaagag acggccaaca gcagcaaacc
7441 aggaaccagc ccaggaagcg cagccggacc aagtcagccc ggactcacta taaatacagt
7501 aagtaaggta gctgattcac tgagtccac caggaaacaa aagcgatcgg ttcgacaaaa
```

FIG. 2 CONTINUED

```
7561 caccgctaat aaatgtaacc cagatcttta ctattggaca gctgttgatg aggggcagc
7621 agtaggattg gcatggattc catatttcgg acctgcagca gaaggcatct acattgaggg
7681 tgtaatgcat aatcagaatg ggcttatttg cgggctacgt cagctagcca atgaaactac
7741 ccaggctctt caattatttc tgcgggccac aacagaactg aggacttact cacttcttaa
7801 cagaaaagct attgattttc ttcttcaacg atggggaggt acctgtcgaa tcctaggacc
7861 atcttgttgc attgagccac atgattggac aaaaaatatt actgatgaaa ttaaccaaat
7921 taaacatgac tttattgaca atccectacc agaccacgga gatgatctta atctatggac
7981 aggttggaga caatggatcc cggctggaat tgggattatt ggagttataa ttgctataat
8041 agccctactt tgtatatgta agattttgtg ttgatttatt ctgagatctg agagagaaaa
8101 atctcagggt tactctaagg agaaatatta ttttaaaat ttacttgaat gctgaccact
8161 tatcttaaat gagcaattaa taatatgttt ttctgcttct ttgcttgatt tacaatatga
8221 tatttctctt aataatgatt aatatattaa gaaaaactta tgacgaagat taaaggagag
8281 gatcgttaac gggaaaacct cccatctcgt tcgtcgaagc cacgttggtg gtgcttgcag
8341 ctgagaacaa ctccagagat tgtaggtaga aaggaccaac atttataggt aggggtcaga
8401 aagcaacaat aaccataaaa ggagagcctg acattgctat ttaatatcct agaacctgat
8461 ttctaggttc tagctttaaa atccggatga tggagcattc aagagaacgg ggtagatcta
8521 gcaacatgcg acataatagc cgggaaccat acgaaaatcc atcaaggtct cgctcattat
8581 ctcgggaccc taatcaggtt gatcgtagac agcctcgaag tgcatcccaa attcgtgttc
8641 cgaatctgtt ccatcggaaa aagactgatg cactcatagt tcctccggct cctaaagata
8701 tatgcccaac actcaaaaaa ggattcctct gcgatagcaa attttgcaaa aagatcacc
8761 aattggatag cttaaatgat catgaattac tactgctaat tgcaagaaga acatgtggaa
8821 ttatcgagag caattcgcag attacatccc caaaagatat gcggttagcg aatccaacag
8881 ctgaagactt ctcacaaggt aatagtccta aattaacact tgcagtcctt cttcaaattg
8941 ctgaacattg ggcaaccaga gacctaaggc aaattgagga ctctaaactt agagctcttt
9001 taaccctttg tgccgtatta acaaggaaat tttctaaatc ccaactgggt cttctatgtg
9061 agacccacct acggcatgag ggcctcggac aggaccaagc tgattctgta ttagaggtct
9121 accaaagact ccacagtgat aaaggaggga attttgaggc tgccctgtgg caacaatggg
9181 accgacagtc attaataatg ttcatctctg cttttctcaa cattgctctc cagataccttt
9241 gtgaaagttc tagtgtcgta gtctcaggtc ttgccacatt gtacccagca caagacaatt
9301 ctacaccatc cgaggcaact aatgatacca cctggtcaag tacagttgaa tagaaaacca
9361 ctggagctat ttccacga ttgctctcag tcaataaatt aatatagata taatacgact
9421 tcggtgtgca attgtcaaga gttccatta gtaataatga ttcttaaaac aatctactat
9481 cgcaattatc gatggatcta ccctatttga cggtacatga cttgaatgta ataaggtaag
9541 ttggtatctg aggtatttg tctagagtat actcaaaatc gtatgtctag caaattatca
9601 atagcaaagt taattctcc taacctcata ttttgatcaa gtaatcatga ttatgata
9661 attctttca gattatcggt ttaatcttta ttaagaaaaa atcatgattg tagacaattt
9721 actggtagtc cttgggtatc caagttatg aatagagcta gagagaattt gctacttccg
9781 aggtataact ttattatttg ctacttcgaa tgcctaaaac cagtaatgca ggatgaagat
9841 taattgcgga ggaatcagga attcaacttt agttccttaa ggcctcgtcc gaatcttcat
9901 cagttcgtaa gttctttat agaagtcatt agcttctaag gtgattatat tttagtatta
9961 aattttgcta attgcttgct ataaagttga aatgtctaat gcttaaatga acactttttt
10021 gaagctgaca tacgaataca tcatatcata tgaaaacatc gcaattagag cgtccttgaa
10081 gtctggcatt gacagtcacc aggctgttct cagtagtctg tccttggaag ctcttgggga
10141 gacaaaaaga ggtcccagag agtcccaaca ggttggcata aggtcattaa caccagcata
10201 gtcggctcga ccaagactgt aagcgagtcg atttcaacta aaagattat ttcttgttgt
10261 ttaaacaaat tccttttgtg tgagacatcc tcaaggcaca agatggctaa agccacaggc
```

FIG. 2 CONTINUED

```
10321 cgatacaatc tcgtgccccc aaagaaagat atggaaaagg gagtgatttt tagtgatctt
10381 tgtaatttct tgattactca aaccctgcaa ggttggaagg tttattgggc aggaattgag
10441 tttgatgtaa gtcaaaaagg catggctctt ctgacaagac tcaaaacaaa tgactttgct
10501 cctgcctggg cgatgacaag aaatcttttc ccacatctgt tccagaaccc aaattcggtt
10561 attcaatctc ccatctgggc tttgagggta attttggcag ccggattgca ggatcagttg
10621 ttagaccatt cattggttga gccattgaca ggggctctcg gtctaatttc tgattggctc
10681 ctaactacaa cgtcaacaca tttcaatctt cgtactagaa gcgtaaagga ccagcttagt
10741 cttcgtatgt tatctttgat caggtcaaac atcttgcagt tcatcaacaa gcttgacgcc
10801 ctgcatgttg tcaattacaa tggtttactc agtagtattg agatcgggac ttctacacac
10861 acaatcatta taactcgtac aaatatgggt tttctcgtgg aagttcaaga gcctgacaaa
10921 tcagctatga attctaagcg cccaggacca gtcaagttct cattactica tgagtctgcc
10981 ttcaaaccttt tcactcgtgt tccacaatct gggatgcaat cattaataat ggagttcaac
11041 agtttgttgg caatttaaca aggtaatctt aaaataagta catgaatgag aattagttgt
11101 gggtcttatc tagcattgtt gagttaacta tctaatctat tttcgctaat tgcattgagc
11161 actgctaata ggtttgtatc acgttaaaga tttagagtgt atgaattgtg cagatttaaa
11221 cttgggtttt gcctatgct tcataggtgg tcttttttgaa atggagatta tcagcatttc
11281 ttaaatggga ggagttagca atcagaaatt ggagataaat ggacatcggg atagaacaat
11341 gcctaactat tgggcggctt ccatttttac atgtgtatat aaccaatctt ttcctatctt
11401 tgcttatatt ggtgtaactt tatttaata acatgtcaat gctatactgt taagagaagg
11461 tctgaggaag attaagaaaa aggcctcgtg ttcacttggt tgccgtcaag tatcctgtgg
11521 ttttttcta cctaacttcc tcatgccata tggctaccca gcatacccag tacccggatg
11581 cacgtttatc ctcacctata gtcctggatc aatgtgattt ggtaactcga gcatgtgggt
11641 tatattcatc ttattctcta aatcctcaac taaggcaatg taaattacca aaacatatat
11701 atcgacttaa gttcgacaca atagtatcca aattcctaag tgatacacct gtagcaacac
11761 tgccgataga ctatttagta ccaattctcc tgcgttccct aacggggcac ggtgatagge
11821 cattgaccce gacttgcaat caattccttg atgaaattat taattacact cttcatgatg
11881 cagcctttct tgattactat ctcaaggcaa caggtgcaca ggaccatttg acaaacattg
11941 caactagaga gaagcttaaa aacgaaattc taaacaatga ttatgtccat caattgttct
12001 tctggcatga cctttctatt ttggctcgac gtgggcgtct gaatcgcggg aacaaccgtt
12061 caacctggtt tgttcatgat gaattcattg atatttttagg atatggcgat tatattttt
12121 ggaaaatacc tttatcatta ttaccagtta ctatagacgg ggtcccacac gcagcaactg
12181 actggtatca accgactctt tttaaagaat ccatcctagg gcatagccaa atcctatctg
12241 tgtcaacagc tgaaatacta attatgtgta aagatatatt cacctgtagg tttaatacat
12301 cactgattgc atccattgca aaattagagg atgtagatgt gtctgattat cctgacccga
12361 gtgatattct taagatatac aatgctggag actatgtaat atctattctt ggctcagagg
12421 gttataagat aataaagtac cttgaaccac tttgtttggc caaaatccaa ctttgctcta
12481 aattcacaga aagaaaaggt cgttcctca cacagatgca tttatcagta ataatgatc
12541 ttcgggagtt gatttctaac cgcaggttaa aggactatca gcaagagaag attagagatt
12601 ttcacaaaat attattacaa ttgcaattat ctcctcaaca gttttgtgaa ttattctctg
12661 ttcaaaaaca ttgggggcat ccaattttac atagtgagaa agctatacaa aaagtaaaac
12721 ggcatgcaac catccttaag gctctcagac ctaatgtcat ctttgagaca tattgtgtat
12781 tcaagtacaa tattgccaag cactatttcg acagccaagg aacttggtac agtgtaatct
12841 cagacaggaa tttaactcca ggactcaact ccttcataaa acgtaatcac tttccttcac
12901 tacccatgat taaggatctt ctatgggaat tctatcatct taatcaccct ccgttattct
12961 ctacaaaggt gattagtgac ttaagtattt tcatcaaaga tagggccaca gctgttgaac
13021 agacatgttg ggatgcagtc tttgaaccca atgtgctagg ttacaatcct ccaaacaaat
```

FIG. 2 CONTINUED

```
13081 tctccactaa aagggtgccg gaacaatttc tagaacaaga ggattttca atcgaaagtg
13141 tcctgaatta tgcacaggaa ttacattatt tattaccaca gaataggaat ttttcctttt
13201 ctctcaaaga aaaggaatta aatattggac gaacatttgg gaagctacca tatctcacac
13261 ggaatgtcca aactttatgt gaggctctgt tagcagatgg actggccaag gccttcccca
13321 gtaacatgat ggtagtaact gaacgtgaac aaaaagagag ccttcttcat caggcatcat
13381 ggcaccacac cagtgatgat tttggagaga atgctaccgt tcgagggagt agttttgtaa
13441 ctgatttaga gaagtacaat cttgcatttc gctatgagtt cactgcacca tttattgagt
13501 actgcaacca ttgctatggt gtgcgtaatg tctttaattg gatgcattat ttaatcccgc
13561 agtgttacat gcatgtaagt gattattata atccgcctca caatgttaat cttagcaatc
13621 gagaatatcc tcctgaaggc ccagttcgt accgagggca cttaggaggc atagagggat
13681 tacaacaaaa actgtggacg agtatatcct gtgcacaaat ctccttagtg gaaattaaaa
13741 ctggttttaa gttacgatca gcggtcatgg gagacaatca gtgtataacc gtattgtctg
13801 tttttccact taaaacagac cctgaagagc aggagcaaag cgccgaagac aatgctgcaa
13861 gagtagcagc aagtcttgca aaagtaacca gtgcatgtgg gatctttctt aaaccagatg
13921 agacatttgt acactcaggt ttcatttatt tcggaaaaaa acaatatctc aatggtgtac
13981 aattaccgca atcactcaaa acagcagcaa gaatggcacc actctctgat gctatattcg
14041 atgatctaca aggaacactt gccagtattg gaactgcctt cgaacgtgct atatcggaaa
14101 cgcgacatat cctcccatgt cgtattgtag cagcttccaa tacgtatttc gccgttcgga
14161 ttttacaata tcaccatctt ggatttaata aaggcatcga tttaggacag ttgtcactta
14221 gtaaaccatt agactatggg actattactc taacattggc ggttccacaa gtccttgggg
14281 gattgtcttt tctaaatcca gaaaagtgtt tttatcgaaa cttcggagat cctgtgactt
14341 ctggactttt ccagctacgg gtgtacctag aaatggttaa catgaaagac ctattttgtc
14401 cattaatatc gaaaaatcca ggaaattgta gtgccattga ttttgtctta aatccatccg
14461 gattaaatgt tccaggatca caagacttga catccttttt gcgacaaatc gttaggcgta
14521 gtattaccct aactgctaga aataagttaa ttaacactct cttccatgcc tctgctgatt
14581 tggaagatga gatggtttgt aagtggctcc tttcatcaaa ccctgtcatg agtcgctttg
14641 cagcggatat ttttccagg acaccgagtg gtaaacgtct ccaaatatta ggttatcttg
14701 aagggaccag gactctattg gcctccaaaa tcataaacaa caacagtgag acacctgtac
14761 ttgataagct gaggaagatc accctacaaa gatggaatct gtggttcagt tatttggacc
14821 attgtgacca attactagca gatgctctac agaaaattag ttgcacggtg gatttggccc
14881 agattttgcg tgagtataca tggtcacaca tcttagaggg tagatcattg atcggagcga
14941 cattaccatg tatggtggag caattcaaag ttaagtggct aggacaatat gaaccttgtc
15001 cagaatgtct caacaaaaaa ggctcaaatg cttatgtctc agttgcagtc aaagatcaag
15061 tggtcagtgc ttggcctaat acttctcgaa taagttggac aataggggagt ggtgtcccct
15121 atataggtgtc aagaaccgag gataaaatcg gacagcctgc tatcaagccg cgatgcccct
15181 catctgccct caaggaggct atagaattag catcaaggct cacttgggtt acacaaggag
15241 gttctaatag tgaacaatta atccggcctt tcttggaagc gagagtcaac cttagtgtca
15301 gtgaagtcct gcaaatgaca ccatcacatt attcaggaaa tattgtccat cgatataacg
15361 accaatacag cccgcactca tttatggcga atcgcatgag caatactgcg acccgtctca
15421 tagtgtcaac taatacactt ggagaatttt caggtggagg gcaggccgcc agggatagca
15481 atataatttt ccagaatgtt ataaatttag cagttgccct tatgatatt agattccgga
15541 atacaaaac ctctgatata aggcataata gggctcatct tcacctgaca gagtgctgta
15601 ctaaagaggt cccggcccag tatttgacat atacaagtgc acttaatctg gatttaagcc
15661 gttatcgtga taatgaacta atatatgact caaatccact gaagggagga ttgaactgca
15721 atttaacaat agatagtcct tagtgaagg gtcctaggct taacatgatt gaagatgatc
15781 ttctccgctt tccacacctt tctggatggg agttagcgaa aacggtggta caatccatca
```

FIG. 2 CONTINUED

```
15841 tctcagacaa tagcaactca tcaacagatc caatcagtag cggagaaaca cgctctttca
15901 caactcattt tctcacttac cctcagattg gccttcttta cagtttcgga gcagtattat
15961 gctttatct aggcaatact atcctatgga ctaaaaaact tgattacgaa cagttctat
16021 attatttgca taaccagctg cacaacttac ctcatcgagc actccgtgtt tttaaaccaa
16081 catttaagca tgccagtgtg atgtcccgat taatggaaat tgattctaac ttctcaattt
16141 atattggcgg gacatctgga gatcgagggc tgtctgatgc tgctcgactg tttcttcgga
16201 cagcaatcgc gagtttttta caatttctta aaagctggat catcgatcgc caaaagacaa
16261 ttcctttatg gatagtatat ccgcttgaag gtcaacagcc ggaatccatc aatgaatttc
16321 tacataaaat tttgggtctg ctcaaacaag gccccaaaag tattccaaag gaggtcagca
16381 tccaaaatga tggacatttg gatttggcag aaaataatta tgtttacaat agtaagagca
16441 ctgctagtaa tttcttccat gcatccttag cttactggag aagtaggaaa tctcggaaaa
16501 ctcaagacca taatgatttc tcaagagggg atggaacact tacagaaccc gtgcgtaagt
16561 tttcaagcaa tcatcagtca gatgaaaagt actacaatgt gacatgtgga aagtcaccga
16621 agccgcaaga acgcaaagac ttctcgcaat acagactcag caataacggg caaacaatga
16681 gtaatcatcg taagaaaggg aagttccaca agtggaatcc ctgcaaaatg ttaatggaga
16741 gtcaaagggg aactgttcta acagagggtg actactttca aaacaatact ccaccaacag
16801 atgatgtatc aagtcctcac cgactcattc taccatttt taaattggga aatcacaacc
16861 atgcacatga tcaagatgcc caagaattga tgaatcaaaa tattaaacag tacctacatc
16921 agctaaggtc tatgttggac accactatat attgtagatt cacagggatt gtctcatcca
16981 tgcattacaa attggacgaa gttcttctag aatacaatag tttcgattca gctatcacat
17041 tagctgaagg tgaggggtca ggggctctat tactttgca aaaatatagt acaaggttat
17101 tatttttgaa cacattggca acagaacaca gtatagaatc agaagttgta tcaggttttt
17161 ctactccgag aatgttgtta ccaataatgc aaaaggttca tgaaggacaa gtcactgtta
17221 tcttaaataa ttcagcaagt cagataactg acataactag ctcaatgtgg ttaagtaatc
17281 aaaaatataa tctaccttgt caagttgaaa tcattatgat ggatgctgaa acaacagaga
17341 acttaaacag gtcccaactc taccgagcag tatataactt aatacttgat cacattgatc
17401 cgcagtatct caaggtggtg gtactcaaag tatttctgag tgatatagaa ggaatatat
17461 ggattaatga ttacttggct ccattattcg gggctggtta cttgattaaa ccgattacat
17521 caagtgcccg gtcaagtgaa tggtaccttt gcttatcaaa tttgatatct actaacagga
17581 gatcggccca tcagactcac aaggcatgtc ttggtgttat cagagatgct ttgcaagcac
17641 aagtccagcg aggcgtgtac tggttgagtc acatcgcaca gtatgctaca aagaatctcc
17701 attgtgaata cataggcctt ggtttccat ctctagaaaa ggtcctatat cacaggtata
17761 atctagttga tactggactc ggtccattgt cgtcagttat tagacattta actaacctcc
17821 aggcagagat acgagactta gtattagatt ataacctgat gagggagagt cgcactcaaa
17881 cgtaccattt tattaagact gcaaaaggca gaatcacaaa gttagtcaat gactttctga
17941 agttttcttt aattgtccag gcactcaaaa ataattcttc ttggtatact gagcttaaaa
18001 aattacctga ggttattaat gtgtgtaatc gatttttatca tactcacaat tgcgaatgtc
18061 aggaaaaatt ctttgtccag acgctttatt tacaacgcct acgcgatgca gaaatcaagc
18121 taattgaacg ccttaccggg ttaatgcgat tttatccaga agggttaata tattccaatc
18181 acacataggt actaaatcat catagtatga ggaataagat aatgataatt cctgacgaca
18241 gttttagttc cgattctaag tatatcggaa gagagtatgc caatcttaat tgttagaggt
18301 aacaagctat tagttattac ttattgataa gaatacactt tatcatagcg taacacatca
18361 taactttata acgattttgc atttctaatc ctagtatttta ttagaatgta ctaccagaga
18421 aatgacccca gttcctatct ttaaataatg attgtgtgta ttaaattatt agtttattag
18481 gtttatgagt tggtacaca gtgagtatta gtaattgagg attatgtaga taggtaatct
18541 aacactgaat cacccatctg atgtcaccat atccaaatgt tgtgctagtc gcatttaaac
```

FIG. 2 CONTINUED 18601 atgctatctt cagttaagta acatagactg aaaatgctaa gaagagattg gagtaaaagt
18661 ataaaataaa tttaattaaa cttcaaagtg attaaatgat aatgatcttg ggaactcgat
18721 atgacctcaa gtcaaaaata atgtcaatat aattgtttag taatatgagt gataatgtaa
18781 attttgataa ctaactagct ttagtagtta agatcaaatg caaacattat aagaatgtta
18841 agcgcacaca aaaacattat aaaaaaccaa ttttttcctt tttgtgtgtc c (SEQ ID NO: 3)

VP30

MEHSRERGRSSNMRHNSREPYENPSRSRSLSRDPNQVDRRQPRS
ASQIRVPNLFHRKKTDALIVPPAPKDICPTLKKGFLCDSKFCKKDHQLDSLNDHE
LLL
LIARRTCGIIESNSQITSPKDMRLANPTAEDFSQGNSPKLTLAVLLQIAEHWATRD
LR
QIEDSKLRALLTLCAVLTRKFSKSQLGLLCETHLRHEGLGQDQADSVLEVYQRL
HSDK
GGNFEAALWQQWDRQSLIMFISAFLNIALQIPCESSSVVVSGLATLYPAQDNSTPS
EA
TNDTTWSSTVE (SEQ ID NO: 4)

AY769362

1 cggacacaca aaaagaaaaa aggtttttta agacttttg tgtgcgagta actatgagga
61 agattaacag ttttcctcag tttaagatat acactgaaat tgagattgag attctcctct
121 ttgctattct gtaactttcc ctggttgtga caattgaatc agtttatct attaccaatt
181 accatcaaca tggtatgtct agtgatcttg ggactcttct tcatctggtt tttcctagag
241 ctctgaatcc atttcgcgag aagttcatcc aaacgaccca gtgtctgaaa atacaaaagg
301 ttcccctttc cgtcaagttt aaggggttgt tttgattgtg tgtagatttt ataatcctag
361 agtgccaagg agttgcgtgt catcattgat tgggaagatc aaggaaacaa tttgttccaa
421 taatatcgta catcttgact aagtcgaaca cggggaagtc gatatggatc gtgggaccag
481 aagaatctgg gtgtcgcaaa atcaaggtga tactgattta gattatcata aaattttgac
541 agctgtcctt actgttcaac agggaattgt caggcagaaa ataatttctg tatatcttgt
601 tgataacttg gaggctatgt gtcaattggt aatacaagcc tttgaggccg gaattgattt
661 ccgagaaaat gccgacagct tccttctgat gctttgccta catcatgctt accaaggtga
721 ctataaattg ttcttggaga gcaatgctgt acagtatttg gaaggtcatg gattcaaatt
781 tgagctccgg aagaaggacg gtgtcaatcg gctcgaggaa ttgcttcctg ctgcaacgag
841 tggaaaaaac atcaggcgta cgttggccgc actgcctgaa gaggagacta cagaagcaaa
901 tgcagggcaa tttctctcat ttgcgagtct gtttcttccc aaactggttg tgggagagaa
961 ggcttgcttg gaaaaagtcc agcgacaaat tcaggttcat gcagaacagg gtttaattca
1021 atatcccact gcatggcaat cagttggaca catgatggta atcttcagat tgatgaggac
1081 taatttcttg attaaatatt tactgatcca ccagggtatg catatggtag ctggccacga
1141 tgccaatgat gctgtcattg ctaattcagt tgctcaggct cgcttttcag gactcctaat
1201 tgtcaaaacc gttcttgatc atattctgca aaaaaccgac caaggagtaa gacttcaccc
1261 tttggcccga acagccaaag tgcgtaatga ggttaatgca tttaaggccg ccctaagctc
1321 acttgctaag catggggaat atgcccctt tgctcgcctt ctcaatctct cgggagttaa
1381 caacctagaa catggtctct acccacagtt atcagcaatt gctcttggag ttgccacagc
1441 acatggtagc accctgcag gagttaatgt tggtgagcag tatcagcagc ttagagaggc

FIG. 2 CONTINUED

```
1501 tgccactgaa gctgagaagc aactccaaca atatgctgag tccagagaac tgacagcct
1561 aggcctggac gatcaggaag gaagaatact aatgaacttc catcagaaga aaaacgaaat
1621 tagtttccag cagaccaatg caatggtaac ccttaggaaa gagcgactgg ctaaattaac
1681 agaagctata acgctggcct caagacctaa cctcgggtct agacaagacg acggcaatga
1741 aataccgttc cctgggccta taagcaacaa cccagaccaa gatcatctgg aggatgatcc
1801 tagagactcc agagacacca tcattcctaa tggtgcaatt gaccccgagg atggtgattt
1861 tgaaaattac aatggctatc atgatgatga agttgggacg gcaggtgact gggtcctgtt
1921 cgatcttgac gatcatgagg atgacaataa agcttttgag ccacaggaca gctcgccaca
1981 atcccaaagg gaaatagaga gagaaagatt aactcatcca ccccaggca acaacaagga
2041 cgacaatcga gcctcagaca acaatcaaca atcagcagat tctgaggaac aaggaggtca
2101 atacaactgg caccgaggcc cagaacgtac gaccgccaat cgaagactct caccagtgca
2161 cgaagaggac acccttatgg atcaaggtga tgatgatccc tcaagcttac ctccgctgga
2221 atctgatgat gacgatgcat caagtagcca acaagatccc gattatacag ctgttgcccc
2281 tcctgctcct gtataccgca gtgcagaagc ccacgagcct ccccacaaat cctcgaacga
2341 gccagctgaa acatcacaat tgaatgaaga ccctgatatc ggtcaatcaa agtctatgca
2401 aaaattagaa gagacatatc accatctgct gagaactcaa ggtccatttg aagccatcaa
2461 ttattatcac atgatgaagg atgagccggt aatatttagc actgatgatg ggaaggaata
2521 cacctacccg gattcacttg aggaagccta tcctccatgg ctcaccgaga agaacgact
2581 ggacaaagag aatcgctaca tttacataaa taatcaacag ttctcctggc ctgtcatgag
2641 tccagagac aaatttcttg caatcttgca gcaccatcag taaccacagc acaaagcgcg
2701 gtccacttcg taaagctaaa tacacttaag acttgaccga ttcatctaca aaaactaatc
2761 cattataact tattagtgct actttctat aagtgattct taatctaagg ccattaagag
2821 tttaagtaat atacatatac acttacaccg gtctatccaa gatgtggctc aatgttcttg
2881 atttgaacat agtcataagg ggataaataa tactttatat ttctgattgt ggattgaccc
2941 attctgctta aaatgcttcg cccattgaaa atgtgatcta atagatagcc ctgactagac
3001 aaattaagaa aaacatttga tgaagattaa aaccttcatc gccagtaaat gattatattg
3061 tctgtaggca ggtgtttact ccaccttaaa tttggaaata tcctaccta ggaccattgt
3121 caagaggtgc ataggcatta ccacccttga gaacatgtac aataataaat tgaaggtatg
3181 ttcaggccca gaaacgactg gatggatttc tgagcaactt atgacaggta agattccagt
3241 aactgatata ttcattgata ttgataacaa gccagatcaa atggaagtcc gactcaaacc
3301 atcatcaagg agctcaacaa gaacttgtac aagtagcagt cagacggagg tcaactatgt
3361 acctctcctt aaaaaggttg aggatacatt aactatgcta gtgaatgcca ccagtcgtca
3421 gaatgctgca atcgaggccc ttgaaaaccg cctcagcaca cttgagagta gcttaaagcc
3481 aatccaagac atgggtaaag tgatttcatc attgaatcgc agttgtgccg aaatggttgc
3541 aaaatatgat cttctagtta tgacaactgc acgggctact tcaactgcag ctgcagtaga
3601 tgcgtattgg aaagagcaca aacagccacc accagggcca gcgttgtatg aagagaatgc
3661 gcttaaagga aaaatcgatg atcctaacag ctatgtacca gatgctgtgc aagaggctta
3721 caagaaccct gacagtacat cgaccctgac cgaggaaaat tttgggaaac cttatatatc
3781 tgctaaagac ctgaaggaga tcatgtatga tcatctacct ggttttggga ctgcctttca
3841 ccaacttgtt caagtgattt gtaaaatagg aaaggataac aacctttgg acacaatcca
3901 tgctgagttc caggcaagtc tagcagatgg tgactctccc caatgtgcac tcatacagat
3961 aaccaaaagg gtcccaatct ttcaggatgt gccgccccg ataatccata ttagatcccg
4021 tggtgacatc ccacgagcat gccaaaagag tctccgacca gcaccaccat cacccaaaat
4081 tgatcgtggt tgggtttgtt tgtttaagat gcaagatggt aaaacgcttg gacttaagat
4141 ctaagaatca agattattt aacaaggcaa gccacaacct tagatggaac ctcagccaga
4201 ctattgaact attgacgctg ttgatgataa tatataatta atggtcttat ttgaatatga
```

FIG. 2 CONTINUED 4261 caacatcttg cttcttgttc tgccttgtag ctctttgaat tggaagatca ttccaaactt
4321 acaaacatgc acaagatgtt atggtttagc aaagaattga taggagtact ggtatataat
4381 gtaaatataa caagtgatga agattaagaa aaaccagtcg gtattttcca gacttggcat
4441 ttcttatctt catcttctaa agtgagatat tttatcatca aaaaatgagg cgcggagtgt
4501 taccaacggc tcctccagca tataatgata ttgcataccc tatgagcata ctcccaaccc
4561 gaccaagtgt catagtcaat gagaccaaat cagatgtact ggcagtgcca ggggcagatg
4621 ttccatcaaa ctccatgaga ccagtggctg atgataacat tgatcactca agccatactc
4681 caagcggagt agcttctgcc tttatattgg aagctacagt gaatgtaatt tcgggaacaa
4741 aagtcctgat gaagcaaata cctattggc ttccactggg tgtagctgat cagaagatat
4801 acagctttga ttcaacaaca gccgcaatta tgttggcttc ctacacagtg acacacttcg
4861 ggaagatatc taacccgctg gtacgtgtca acaggctagg cccaggaata cccgatcatc
4921 cgttccggct cctgaggttg ggcaaaaaag cgttccttcc cgggtttgtt cttccaccag
4981 tccagcttcc ccagtatttc acatttgatc taacagctct aaagctcatc actcaaccat
5041 tgccagctgc aacctggaca gacgaaactc cagcaggagc agtcaatgct cttcgtcctg
5101 ggctctcact ccatcccaag cttcgtccaa ttctcctgcc ggggaagaca ggaaagaaag
5161 gacatgcttc agacttaaca tcacctgaca agattcaaac aatcatgaat gcaataccgg
5221 acctcaaaat tgtcccgatt gatccaacca agaacatagt tggaattgag gttccagaat
5281 tactagttca aaggctgacc ggcaaaaaac cacaacccaa aaatggccaa ccaattattc
5341 cagttcttct tccgaaatat gttggacttg atcctatatc gccaggggac ttaactatgg
5401 ttatcaccca ggattgtgat tcatgccact ctccagccag ccatacgtat cacatggaca
5461 agcagaatag ttaccaataa tttaaattcc attcgagcta ttattctgct agtaattccg
5521 acgggatcaa tagactaaaa atctgattgt atagaattat aaaagaatca agcagaggca
5581 acagactcac agcttacgcc tagataacta atattaagga gttttttaat ctaattttcc
5641 agtcttgagt aataatcatt tcttttgtaa ttaattatgc atttgttaac ttatcggtgc
5701 gagatttcct tgagaacccg gcggagcttc tactatctgc agtaaccaga agagaagttc
5761 aacccagtca aaactaaacc aagcaatatt ctgaatgctc tatagtctat tctaatcaga
5821 ggtataacaa tggctaagat ttcaatgact cgttaacaat cgctagtaat tttaatctcc
5881 agattaagaa aaagatatac gatgaagatt aaggcgacaa cgagccgaaa cttcatctct
5941 tttaaagatc taacattatc tgttccaaag tcatacaagg acacattcaa atcagggatt
6001 gtaagctgct atttcttacc tccccaaatt acctatacaa catggggtca ggatatcaac
6061 ttctccaatt gcctcgggaa cgttttcgta aaacttcgtt cttagtatgg gtaatcatcc
6121 tcttccagcg agcaatctcc atgccgcttg gtatagtgac aaatagcact ctcaaagcaa
6181 cagaaattga tcaattggtt tgtcgggaca aactgtcatc aaccagtcag ctcaagtctg
6241 tggggctgaa tctggaagga aatggaattg caaccgatgt cccatcagca acaaaacgct
6301 ggggatttcg ttcaggtgtg cctcccaagg tggtcagcta tgaagccgga gaatgggcag
6361 aaaattgcta caatctggag atcaaaaagt cagacggaag tgaatgcctc cctctccctc
6421 ccgacggtgt acgaggattc cctagatgtc gctatgtcca caaagttcaa ggaacaggtc
6481 cttgtcctgg tgacttagct ttccataaaa atggggcttt ttcttgtat gatagattgg
6541 cctcaactgt catctaccga gggacaactt tgctgaagg tgtcgtagct tttttaattc
6601 tgtcagagcc caagaagcat ttttggaagg ctacaccagc tcatgaaccg gtgaacacaa
6661 cagatgattc cacaagctac tacatgaccc tgacactcag ctacgagatg tcaaattttg
6721 ggggcaatga agtaacacc cttttaagg tagacaacca cacatatgtg caactagatc
6781 gtccacacac tccgcagttc cttgttcagc tcaatgaaac acttcgaaga aataatcgcc
6841 ttagcaacag tacagggaga ttgacttgga cattggatcc taaaattgaa ccagatgttg
6901 gtgagtgggc cttctgggaa actaaaaaaa cttttcccaa caacttcatg gagaaaactt
6961 gcattccaa attctatcaa cccacaccaa caactcctca gatcagagcc cggcgggaac

FIG. 2 CONTINUED

```
7021 tgtccaagga aaaattagct accacccacc cgccaacaac tccgagctgg ttccaacgga
7081 ttcccctcca gtggtttcag tgctcactgc aggacggaca gaggaaatgt cgacccaagg
7141 tctaaccaac ggagagacaa tcacaggttt caccgcgaac ccaatgacaa ccaccattgc
7201 cccaagtcca accatgacaa gcgaggttga taacaatgta ccaagtgaac aaccgaacaa
7261 cacagcatcc attgaagact cccccccatc ggcaagcaac gagacaattt accactccga
7321 gatggatccg atccaaggct cgaacaactc cgcccagagc ccacagacca agaccacgcc
7381 agcacccaca acatcccga tgacccagga cccgcaagag acggccaaca gcagcaaacc
7441 aggaaccagc ccaggaagcg cagccggacc aagtcagccc ggactcacta taaatacagt
7501 aagtaaggta gctgattcac tgagtcccac caggaaacaa aagcgatcgg ttcgacaaaa
7561 caccgctaat aaatgtaacc cagatcttta ctattggaca gctgttgatg aggggcagc
7621 agtaggattg gcatggattc catatttcgg acctgcagca gaaggcatct acattgaggg
7681 tgtaatgcat aatcagaatg ggcttatttg cgggctacgt cagctagcca atgaaactac
7741 ccaggctctt caattatttc tgcgggccac aacagaactg aggacttact cacttcttaa
7801 cagaaaagct attgattttc ttcttcaacg atggggaggt acctgtcgaa tcctaggacc
7861 atcttgttgc attgagccac atgattggac aaaaaatatt actgatgaaa ttaaccaaat
7921 taaacatgac tttattgaca atcccctacc agaccacgga gatgatctta atctatggac
7981 aggttggaga caatggatcc cggctggaat tgggattatt ggagttataa ttgctataat
8041 agccctactt tgtatatgta agatttgtg ttgatttatt ctgagatctg agagagaaaa
8101 atctcagggt tactctaagg agaaatatta tttttaaaat ttacttgaat gctgaccact
8161 tatcttaaat gagcaattaa taatatgttt ttctgcttct ttgcttgatt tacaatatga
8221 tatttctctt aataatgatt aatatattaa gaaaaactta tgacgaagat taaaggagag
8281 gatcgttaac gggaaaacct cccatctcgt tcgtcgaagc cacgttggtg gtgcttgcag
8341 ctgagaacaa ctccagagat tgtaggtaga aaggaccaac atttataggt aggggtcaga
8401 aagcaacaat aaccataaaa ggagagcctg acattgctat ttaatatcct agaacctgat
8461 ttctaggttc tagctttaaa atccggatga tggagcattc aagagaacgg ggtagatcta
8521 gcaacatgcg acataatagc cgggaaccat acgaaaatcc atcaaggtct cgctcattat
8581 ctcgggaccc taatcaggtt gatcgtagac agcctcgaag tgcatcccaa attcgtgttc
8641 cgaatctgtt ccatcggaaa aagactgatg cactcatagt tcctccgact cctaaagata
8701 tatgcccaac actcaaaaaa ggattcctct gcgatagcaa attttgcaaa aaagatcacc
8761 aattggatag cttaaatgat catgaattac tactgctaat tgcaagaaga acatgtggaa
8821 ttatcgagag caattcgcag attacatccc caaaagatat gcggttagcg aatccaacag
8881 ctgaagactt ctcacatggt aatagtccta aattaacact tgcagtcctt cttcaaattg
8941 ctgaacattg ggcaaccaga gacctaaggc aaattgagga ctctaaactt agagctcttt
9001 taaccctttg tgccgtatta acaaggaaat ttctaaatc ccaactgggt cttctatgtg
9061 agacccacct acggcatgag ggcctcggac aggaccaagc tgattctgta ttagaggtct
9121 accaaagact ccacagtgat aaaggagga attttgaggc tgccctgtgg caacaatggg
9181 accgacagtc attaataatg ttcatctctg cttttctcaa cattgctctc cagatacctt
9241 gtgaaagttc tagtgtcgta gtctcaggtc ttgccacatt gtacccagca caagacaatt
9301 ctacaccatc cgaggcaact aatgatacca cctggtcaag tacagttgaa tagaaaacca
9361 ctggagctat ttttccacga ttgctctcag tcaataaatt aatatagata taatacgact
9421 tcggtgtgca attgtcaaga gttccattta gtaataatga ttcttaaaac aatctactat
9481 cgcaattatc gatggatcta ccctatttga cggtacatga cttgaatgta ataaggtaag
9541 ttggtatctg aggtattttg tctagagtat actcaaaatc gtatgtctag caaattatca
9601 atagcaaagt taaattctcc taacctcata ttttgatcaa gtaatcatga ttttatgata
9661 attctttca gattatcggt ttaatctttta ttaagaaaaa atcatgattg tagacaattt
9721 actggtagtc cttgggtatc caagtttatg aatagagcta gagagaattt gctacttccg
```

FIG. 2 CONTINUED 9781 aggtataact ttattatttg ctacttcgaa tgcctaaaac cagtaatgca ggatgaagat
9841 taattgcgga ggaatcagga attcaacttt agttccttaa ggcctcgtcc gaatcttcat
9901 cagttcgtaa gttcttttat agaagtcatt agcttctaag gtgattatat tttagtatta
9961 aattttgcta attgcttgct ataaagttga aatgtctaat gcttaaatga acactttttt
10021 gaagctgaca tacgaataca tcatatcata tgaaaacatc gcaattagag cgtccttgaa
10081 gtctggcatt gacagtcacc aggctgttct cagtagtctg tccttggaag ctcttgggga
10141 gacaaaaaga ggtcccagag agtcccaaca ggttggcata aggtcattaa caccagcata
10201 gtcggctcga ccaagactgt aagcgggtcg atttcaacta aaaagattat ttcttgttgt
10261 ttaaacaaat tcctttttgtg tgagacatcc tcaaggcaca agatggctaa agccacaggc
10321 cgatacaatc tcgtgccccc aaagaaaagat atggaaaagg gagtgatttt tagtgatctt
10381 tgtaatttct tgattactca aaccctgcaa ggttggaagg tttattgggc aggaattgag
10441 tttgatgtaa gtcaaaaagg catggctctt ctgacaagac tcaaaacaaa tgactttgct
10501 cctgcctggg cgatgacaag aaatctttc ccacatctgt tccgaaccc aaattcggtt
10561 attcaatctc ccatctgggc tttagggta attttggcag ccggattgca ggatcagttg
10621 ttagaccatt cattggttga gccattgaca gggggctctcg gtctaatttc tgattggctc
10681 ctaactacaa cgtcaacaca tttcaatctt cgtactagaa gcgtaaagga ccagcttagt
10741 cttcgtatgt tatctttgat caggtcaaac atcttgcagt tcatcaacaa gcttgacgcc
10801 ctgcatgttg tcaattacaa tggtttactc agtagtattg agatcgggac ttctacacac
10861 acaatcatta taactcgtac aaatatgggt tttctcgtgg aagttcaaga gcctgacaaa
10921 tcagctatga attctaagcg cccaggacca gtcaagtctt cattacttca tgagtctgcc
10981 ttcaaacctt tcactcgtgt tccacaatct gggatgcaat cattaataat ggagttcaac
11041 agtttgttgg caatttaaca aggtaatctt aaaataagta catgaatgag aattagttgt
11101 gggtcttatc tagcattgtt gagttaacta tctaatctat tttcgctaat tgcattgagc
11161 actgctaata ggtttgtatc acgttaaaga tttggagtgt atgaattgtg cagatttaaa
11221 cttgggttt gccttatgct tcataggtgg tcttttttgaa atggagatta tcagcatttc
11281 ttaaatggga ggagttagca atcagaaatt ggagataaat ggacatcggg atagaacaat
11341 gcctaactat tgggcggctt ccattttttac atgtgtatat aaccaatctt ttcctatctt
11401 tgcttatatt ggtgtaactt tatttttaata acatgtcaat gctatactgt taagagaagg
11461 tctgaggaag attaagaaaa aggcctcgtg ttcacttggt tgccgtcaag tatcctgtgg
11521 tttttttcta cctaacttcc tcatgccata tggctaccca gcatacccag tacccggatg
11581 cacgtttatc ctcacctata gtcctggatc aatgtgattt ggtaactcga gcatgtgggt
11641 tatattcatc ttattctcta aatcctcaac taaggcaatg taaattacca aaacatatat
11701 atcgacttaa gttcgacaca atagtatcca aattcctaag tgatacacct gtagcaacac
11761 tgccgataga ctatttagta ccaattctcc tgcgttccct aacggggcac ggtgataggc
11821 cattgacccc gacttgcaat caattcctg atgaaattat taattacact cttcatgatg
11881 cagcctttct tgattactat ctcaaggcaa caggtgcaca ggaccatttg acaaacattg
11941 caactagaga gaagcttaaa aacgaaattc taaacaatga ttatgtccat caattgttct
12001 tctggcatga cctttctatt tggctcgac gtgggcgtct gaatcgcggg aacaaccgtt
12061 caacctggtt tgttcatgat gaattcattg atattttagg atatggcgat tatatttttt
12121 ggagaatacc tttatcatta ttaccagtta ctagacacgg ggtcccacac gcagcaactg
12181 actggtatca accgactctt tttaaagaat ccatcctagg gcatagccaa atcctatctg
12241 tgtcaacagc tgaaatacta attatgtgta agatattat cacctgtagg tttaatacat
12301 cactgattgc atccattgca aaattagagg atgtagatgt gtctgattat cctgacccga
12361 gtgatattct taagatatac aatgctggag actatgtaat atctattctt ggctcagagg
12421 gttataagat aataagtac cttgaaccac tttgtttggc caaaatccaa ctttgctcta
12481 aattcacaga aagaaaaggt cgtttcctca cacagatgcg tttatcagta ataaatgatc 12541 ttcgggagtt gatttctaac cgcaggttaa aggactatca gcaagagaag attagagatt
12601 ttcacaaaat attattacaa ttgcaattat ctcctcaaca gttttgtgaa ttattctctg
12661 ttcaaaaaca ttgggggcat ccaatttac atagtgagaa agctatacaa aaagtaaaac
12721 ggcatgcaac catccttaag gctctcagac ctaatgtcat ctttgagaca tattgtgtat
12781 tcaagtacaa tattgccaag cactatttcg acagccaagg aacttggtac agtgtaatct
12841 cagacaggaa tttaactcca ggactcaact ccgtcataaa acgtaatcac tttccttcac
12901 tacccatgat taaggatctt ctatgggaat tctatcatct taatcaccct ccgttattct
12961 ctacaaaggt gattagtgac ttaagtattt tcatcaaaga tagggccaca gctgttgaac
13021 agacatgttg ggatgcagtc tttgaaccca atgtgctagg ttacaatcct ccaaacaaat
13081 tctccactaa aagggtgccg gaacaatttc tagaacaaga ggattttca atcgaaagtg
13141 tcctgaatta tgcacaggaa ttcattattt tattaccaca gaataggaat tttcctttt
13201 ctctcaaaga aaaggaatta aatattggac gaacatttgg gaagctacca tatctcacac
13261 ggaatgtcca aactttatgt gaggctctgt tagcagatgg actggccaag gccttcccca
13321 gtaacatgat ggtagtaact gaacgtggac aaaaagagag ccttcttcat caggcatcat
13381 ggcaccacac cagtgatgat tttggagaga atgctaccgt tgagggagt agttttgtaa
13441 ctgatttaga gaagtacaat cttgcatttc gctatgagtt cactgcacca tttattgagt
13501 actgcaacca ttgctatggt gtgcgtaatg tctttaattg gatgcattat taatcccgc
13561 agtgttacat gcatgtaagt gattattata atccgcctca caatgttaat cttagcaatc
13621 gagaatatcc tcctgaaggc ccgagttcgt accgagggca cttaggaggc atagagggat
13681 tacaacaaaa actgtggacg agtatatcct gtgcacaaat ctccttagtg gaaattaaaa
13741 ctggttttaa gttacgatca gcggtcatgg gagacaatca gtgtataacc gtattgtctg
13801 tttttccact tgaaacagac cctgaagagc aggagcaaag cgccgaagac aatgctgcaa
13861 gagtagcagc aagtcttgca aaagtaacca gtgcatgtgg gatcttct aaaccagatg
13921 agacatttgt acactcaggt ttcatttatt tcggaaaaaa acaatatctc aatggtgtac
13981 aattaccgca atcactcaaa acagcagcaa gaatggcacc actctctgat gctatattcg
14041 atgatctaca aggaacactt gccagtattg gaactgcctt cgaacgtgct atatcggaaa
14101 cgcgacatat cctcccatgt cgtattgtag cagctttcca tacgtatttc gccgttcgga
14161 ttttacaata tcaccatctt ggatttaata aaggcatcga tttaggacag ttgtcactta
14221 gtaaaccatt agactatggg actattactc taacattggc ggttccacaa gtccttgggg
14281 gattgtctttt tctaaatcca gaaaagtgtt tttatcgaaa cttcggagat cctgtgactt
14341 ctggactttt ccagctacgg gtgtacctag aaatggttaa catgaaagac ctattttgtc
14401 cattaatatc gaaaaatcca ggaaattgta gtgccattga ttttgtctta aatccatccg
14461 gattaaatgt tccaggatca caagacttga catccttttt gcgacaaatc gttaggcgta
14521 gtattaccct aactgctaga aataagttaa ttaacactct cttccatgcc tctgctgatt
14581 tggaagatga gatggtttgt aagtggctcc tttcatcaaa ccctgtcatg agtcgctttg
14641 cagcggatat ttttccagg acaccgagtg gtaaacgtct ccaaatatta ggttatcttg
14701 aagggaccag gactctattg gcctccaaaa tcataaacaa caacagtgag acacctgtac
14761 ttgataagct gaggaagatc accctacaaa gatggaatct gtggttcagt tatttggacc
14821 attgtgacca attactagca gatgctctac agaaaattag ttgcacggtg gatttggccc
14881 agattttgcg tgagtataca tggtcacaca tcttagaggg tagatcattg atcggagcga
14941 cattaccatg tatggtggag caattcaaag ttaagtggct aggacaatat gaaccttgtc
15001 cagaatgtct caacaaaaaa ggctcaaatg cttatgtctc agttgcagtc aaagatcaag
15061 tggtcagtgc ttggcctaat acttctcgaa taagttggac aataggggagt ggtgtcccct
15121 atataggtc aagaaccgag gataaaatcg gacagcctgc tatcaagccg cgatgccctt
15181 catctgccct caaggaggct atagaattag catcaaggct cacttgggtt acacaaggag
15241 gttctaatag tgaacaatta atccggccct tcttggaagc gagagtcaac cttagtgtca

```
15301 gtgaagtcct gcaaatgaca ccatcacatt attcaggaaa tattgtccat cgatataacg
15361 accaatacag cccgcactca tttatggcga atcgcatgag caatactgcg acccgtctca
15421 tagtgtcaac taatacactt ggagaatttt caggtggagg gcaggccgcc agggatagca
15481 atataatttt ccagaatgtt ataaatttag cagttgccct ttatgatatt agattccgga
15541 atacaaacac ctctgatata aggcataata gggctcatct tcacctgaca gagtgctgta
15601 ctaaagaggt cccggcccag tatttgacat atacaagtgc acttaatctg gatttgagcc
15661 gttatcgtgg taatgaacta atatatgact caaatccact gaagggagga ttgaactgca
15721 atttaacaat agatagtcct ttagtgaagg gtcctaggct taacatgatt gaagatgatc
15781 ttctccgctt tccacacctt tctggatggg agttagcgaa aacggtggta caatccatca
15841 tctcagacaa tagcaactca tcaacagatc caatcagtag cggagaaaca cgctctttca
15901 caactcattt tctcacttac cctcagattg gccttcttta cagtttcgga gcagtattat
15961 gcttttatct aggcaatact atcctatgga ctaaaaaact tgattacgac cagtttctat
16021 attatttgca taaccagctg cacaacttac ctcatcgagc actccgtgtt tttaaaccaa
16081 catttaagca tgccagtgtg atgtcccgat taatggaaat tgattctaac ttctcaattt
16141 atattggcgg gacatctgga gatcgagggc tgtctgatgc tgctcgactg tttcttcgga
16201 cagcaatcgc gagttttta caatttctta aaagctggat catcgatcgc caaaagacaa
16261 ttcctttatg gatagtatat ccgcttgaag gtcaacagcc ggaatccatc aatgaatttc
16321 tacataaaat tttgggtctg ctcaaacaag gcccaaaag tattccaaag gaggtcagca
16381 tccaaaatga tggacatttg gatttggcag aaaataatta tgtttacaat agtaagagca
16441 ctgctagtaa tttcttccat gcatccttag cttactggag aagtaggaaa tctcggaaaa
16501 ctcaagacca taatgatttc tcaagagggg atggaacact tacagaaccc gtgcgtaagt
16561 tttcaagcaa tcatcagtca gatgcaaagt actacaatgt gacatgtgga aagtcaccga
16621 agccgcaaga acgcaaagac ttctcgcaat acagactcag caataacggg caaacaatga
16681 gtaatcatcg taagaaaggg aagttccaca agtggaatcc ctgcaaaatg ttaatggaga
16741 gtcaaagggg aactgttcta acagagggtg actactttca aaacaatact ccaccaacag
16801 atgatgtatc aagtcctcac cgactcattc taccatttt taaattggga aatcacaacc
16861 atgcacatga tcaagatgcc caagaattga tgaatcaaaa tattaagcag tacctacatc
16921 agctaaggtc tatgttggac accactatat attgtagatt cacagggata gtctcatcca
16981 tgcattacaa attggacgaa gttcttctag aatacaaatag tttcgattca gctatcacat
17041 tagctgaagg tgaggggtca ggggctctat tactttgca aaaatatagt acaaggttat
17101 tattttgaa cacattggca acagaacaca gtatagaatc agaagttgta tcaggtttt
17161 ctactccgag aatgttgtta ccaataatgc aaaaggttca tgaaggacaa gtcactgtta
17221 tcttaaataa ttcatcaagt cacataactg acataactag ctcaatgtgg ctaagtagta
17281 atcaaaaata taatctacct tgtcaagttg aaatcattat gatggatgct gaaacaacag
17341 agaacttaaa caggtcccaa ctctaccgag cagtatataa cttaatactt gatcacattg
17401 atccgcagta tctcaaggtg gtggtactca agtatttct gagtgatata gaaggaatat
17461 tatggattaa tgattacttg gctccattat tcggggctgg ttacttgatt aaaccgatta
17521 catcaagtgc ccgtgtcaagt gaatggtacc tttgcttatc aaatttgata tctactaaca
17581 ggagatcggc ccatcagact cacaaggcat gtcttggtgt tatcagagat gctttgcaag
17641 cacaagtcca gcgaggcgtg tactggttga gtcacatcgc acagtatgct acaaagaatc
17701 tccattgtga atacatagcc cttggtttcc catctctaga aaaggtccta tatcacaggt
17761 ataatctagt tgatactgga ctcggtccat tgtcgtcagt tattagacat ttaactaacc
17821 tccaggcaga gatacgagac ttagtattag attataacct gatgagggag agtcgcactc
17881 aaacgtacca ttttattaag actgcaaaag gcagaatcac aaagttagtc aatgactttc
17941 tgaagttttc tttaattgtc caggcactca aaaataattc ttcttggtat actgagctta
18001 aaaaattacc tgaggttatt aatgtgtgta atcgatttta tcatactcac aattgcgaat
```

FIG. 2 CONTINUED 18061 gtcaggaaaa attctttgtc cagacgcttt atttacaacg cctacgcgat gcagaaatca
18121 agctaattga acgccttacc gggttaatgc gattttatcc agaagggtta atatattcca
18181 atcacacata ggtactaaat catcatagta tgaggaataa gataatgata attcctgacg
18241 acagttttag ttccgattct aagtatatcg gaagagagta tgccaatctt aattgttaga
18301 ggtaacaagc tattagttat tacttattga taagaataca ctttatcata gcgtaacaca
18361 tcataacttt ataacgattt tgcatttcta atcctagtat ttattagaat gtactaccag
18421 agaaatgacc ccagttccta tctttaaata atgattgtgt gtattaaatt attagtttat
18481 taggtttatg agttggttac acagtgagta ttagtaattg aggattatgt agataggtaa
18541 tctaacactg aatcacccat ctgatgtcac catatccaaa tgttgtgcta gtcgcattta
18601 aacatgctat cttcagttaa gtaacatagg ctgaaaatgc taagaagaga ttggagtaaa
18661 agtataaaat aaatttaatt aaacttcaaa gtgattaaat gataatgatc ttgggaactc
18721 gatatgacct caagtcaaaa ataatgtcaa tataattgtt tagtaatatg agtgataatg
18781 taaattttga taactaacta gctttagtag ttaagatcaa atgcaaacat tataagaatg
18841 ttaagcgcac acaaaaacat tataaaaaac caattttttc cttttgtgt gtcca (SEQ ID NO:5)

VP 30

MMEHSRERGRSSNMRHNSREPYENPSRSRSLSRDPNQVDRRQPR
SASQIRVPNLFHRKKTDALIVPPTPKDICPTLKKGFLCDSKFCKKDHQLDSLNDHE
LL
LLIARRTCGIIESNSQITSPKDMRLANPTAEDFSHGNSPKLTLAVLLQIAEHWATR
DL
RQIEDSKLRALLTLCAVLTRKFSKSQLGLLCETHLRHEGLGQDQADSVLEVYQRL
HSD
KGGNFEAALWQQWDRQSLIMFISAFLNIALQIPCESSSVVVSGLATLYPAQDNST
PSE
ATNDTTWSSTVE (SEQ ID NO:6)

AY142960

1 cggacacaca aaaagaaaga agaatttttta ggatcttttg tgtgcgaata actatgagga
61 agattaataa ttttcctctc attgaaattt atatcggaat ttaaattgaa attgttactg
121 taatcacacc tggtttgttt cagagccaca tcacaaagat agagaacaac ctaggtctcc
181 gaagggagca agggcatcag tgtgctcagt tgaaaatccc ttgtcaacac ctaggtctta
241 tcacatcaca agttccacct cagactctgc agggtgatcc aacaacctta atagaaacat
301 tattgttaaa ggacagcatt agttcacagt caaacaagca agattgagaa ttaaccttgg
361 ttttgaactt gaacacttag ggggattgaag attcaacaac cctaaagctt ggggtaaaac
421 attggaaata gttaaaagac aaattgctcg gaatcacaaa attccgagta tggattctcg
481 tcctcagaaa atctggatgg cgccgagtct cactgaatct gacatggatt accacaagat
541 cttgacagca ggtctgtccg ttcaacaggg gattgttcgg caaagagtca tcccagtgta
601 tcaagtaaac aatcttgaag aaatttgcca acttatcata caggcctttg aagcaggtgt
661 tgattttcaa gagagtgcgg acagtttcct tctcatgctt tgtcttcatc atgcgtacca
721 gggagattac aaactttttct tggaaagtgg cgcagtcaag tatttggaag ggcacgggtt
781 ccgttttgaa gtcaagaagc gtgatggagt gaagcgcctt gaggaattgc tgccagcagt
841 atctagtgga aaaaacatta agagaacact tgctgccatg ccggaagagg agacaactga
901 agctaatgcc ggtcagtttc tctcctttgc aagtctattc cttccgaaat tggtagtagg

FIG. 2 CONTINUED 961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgactttga acctttctgg
1381 agtaaataat cttgagcatg gtctttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt cccttccag gacccatcaa tgatgacgac aatcctggcc atcaagatga
1801 tgatccgact gactcacagg atacgaccat tccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca acaccccagtc
2401 agaacactct tttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact ccctttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttatttttg
2821 aatttaaagc tagcttatta ttactagccg ttttttcaaag ttcaatttga gtcttaatgc
2881 aaataggcgt taagccacag ttatagccat aattgtaact caatattcta actagcgatt
2941 tatctaaatt aaattacatt atgctttat aacttaccta ctagcctgcc caacatttac
3001 acgatcgttt tataattaag aaaaaactaa tgatgaagat taaaaccttc atcatccta
3061 cgtcaattga attctctagc actcgaagct tattgtcttc aatgtaaaag aaaagctggt
3121 ctaacaagat gacaactaga acaaagggca ggggccatac tgcggccacg actcaaaacg
3181 acagaatgcc aggccctgag cttttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aaccgaaga cgcgcaacag tcaaacccaa acggacccaa
3361 tttgcaatca tagtttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca cttatgaag
3661 aaagtgcgat tcggggtaag attgaatcta gagatgagac cgtccctcaa agtgttaggg 3721 aggcattcaa caatctaaac agtaccactt cactaactga ggaaaatttt gggaaacctg
3781 acatttcggc aaaggatttg agaaacatta tgtatgatca cttgcctggt tttggaactg
3841 cttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt tcagcttca agatggtaaa acacttggac
4141 tcaaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
4381 accaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcacccat ttcggcaagg
4861 caaccaatcc acttgtcaga gtcaatcggc tgggtcctgg aatccggat catcccctca
4921 ggctcctgcg aattggaaac caggctttcc tccaggagtt cgttcttccg ccagtccaac
4981 tacccagta tttcaccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aaggggaaca
5161 gtgccgatct aacatctccg gagaaaatcc aagcaataat gacttcactc caggactta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt cttttttctc tcctaaatgt agaacttaac aaaagactca taatatactt
5641 gttttaaag gattgattga tgaaagatca taactaataa cattacaaat aatcctacta
5701 taatcaatac ggtgattcaa atgttaatct ttctcattgc acatacttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atcctttttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa gatgggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttccccggg tgccggtatg tgcacaaagt atcaggaacg ggaccgtgtg

FIG. 2 CONTINUED

```
6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg ggaaactaaa aaaacctcac tagaaaaatt cgcagtgaag agttgtcttt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccgaggga atttacacag aggggctaat
7681 gcacaatcaa gatggtttaa tctgtgggtt gagacagctg ccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacatctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
7981 gagacaatgg ataccggcag gtattggagt tacaggcgtt ataattgcag ttatcgcttt
8041 attctgtata tgcaaatttg tcttttagtt ttctttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tcttttcgatt atcttttaatc ttcatccttg
8341 attctacaat catgacagtt gtctttagtg acaagggaaa gaagcctttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gatttttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaaccccgttc tcgaagtata tcaacgatta cacagtgata aaggaggcag ttttgaagct
9181 gcactatggc aacaatggga ccgacaatcc ctaattatgt ttatcactgc attcttgaat
```

FIG. 2 CONTINUED

```
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa ccttctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca acctaacag tgatcaaaga aaatcataat ctcgtatcgc tcgtaatata
9601 acctgccaag catacctctt gcacaaagtg attcttgtac acaaataatg tttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatattgt
9841 tcttgtttca agaggtagat tgtgaccgga aatgctaaac taatgatgaa gattaatgcg
9901 gaggtctgat aagaataaac cttattattc agattaggcc ccaagaggca ttcttcatct
9961 cctttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattagggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaatagga acgtcgttcc aacaatcgag
10261 cgcaaggttt caaggttgaa ctgagagtgt ctagacaaca aaatattgat actccagaca
10321 ccaagcaaga cctgagaaaa aaccatggct aaagctacgg gacgatacaa tctaatatcg
10381 cccaaaaagg acctggagaa agggggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg ccctgcatg gtcaatgaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaacccttag caggagccct tggtctgatc tctgattggc tgctaacaac caacactaac
10741 catttcaaca tgcgaacaca acgtgtcaag gaacaattga gcctaaaaat gctgtcgttg
10801 attcgatcca atattctcaa gttattaac aaattggatg ctctacatgt cgtgaactac
10861 aacggattgt tgagcagtat tgaaattgga actcaaaatc atacaatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagttttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacataccca ataccagac gctaggtat catcaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt
```

FIG. 2 CONTINUED

```
12001 cagggcaatg aattttaca tcaaatgttt ttctggtatg atctggctat tttaactcga
12061 aggggtagat taaatcgagg aaactctaga tcaacatggt ttgttcatga tgatttaata
12121 gacatcttag gctatggga ctatgtttt tggaagatcc caatttcaat gttaccactg
12181 aacacacaag gaatccccca tgctgctatg gactggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaaaatagc agagattgag
12361 gatccagttt gttctgatta tcccaatttt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
12661 acgccacaac aactttgtga gctattttcc attcaaaaac actgggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aagaaatca attccctccg ttgccaatga ttaaagaact actatgggaa
12961 ttttaccacc ttgaccaccc tccactttc tcaaccaaaa ttattagtga cttaagtatt
13021 tttataaaag acagagctac cgcagtagaa aggacatgct gggatgcagt attcgagcct
13081 aatgttctag gatataatcc acctcacaaa tttagtacta aacgtgtacc ggaacaattt
13141 ttagagcaag aaaactttc tattgagaat gttctttcct acgcacaaaa actcgagtat
13201 ctactaccac aatatcggaa ctttctttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gctattgca tcaagcatca tggcaccaca caagtgatga ttttggtgaa
13441 catgccacag ttagagggag tagcttgta actgatttag agaaatacaa tcttgcattt
13501 agatatgagt ttacagcacc ttttatagaa tattgcaacc gttgctatgg tgttaagaat
13561 gttttttaatt ggatgcatta tacaatccca cagtgttata tgcatgtcag tgattattat
13621 aatccaccac ataaactcac actggagaat cgagacaacc ccccgaagg gcctagttca
13681 tacaggggtc atatgggagg gattgaagga ctgcaacaaa aactctggac aagtatttca
13741 tgtgctcaaa tttctttagt tgaaattaag actggtttta agttacgctc agctgtgatg
13801 ggtgacaatc agtgcattac tgttttatca gtcttcccct tagagactga cgcagacgag
13861 caggaacaga gcgccgaaga caatgcagcg agggtggccg ccagcctagc aaaagttaca
13921 agtgcctgtg gaatctttt aaaacctgat gaaacatttg tacattcagg tttatctctat
13981 tttggaaaaa aacaatattt gaatggggtc caattgcctc agtcccttaa aacggctaca
14041 agaatggcac cattgtctga tgcaatttt gatgatcttc aagggaccct ggctagtata
14101 ggcactgctt ttgagcgatc catctctgag acacgacata tctttccttg caggataacc
14161 gcagcttcc atacgttttt tcggtgaga atcttgcaat atcatcatct cgggttcaat
14221 aaaggttttg acctggaca gttaacactc ggcaaaacct tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tcttttcacg cacgccgagc
14701 gggaagcgat tgcaaattct aggatacctg gaaggaacac gcacattatt agcctctaag
```

FIG. 2 CONTINUED

```
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaaccata cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgacccct
15361 tcacattact caggaaatat tgttcacagg tacaacgatc aatacagtcc tcattcttc
15421 atggccaatc gtatgagtaa ttcagcaacg cgattgattg tttctacaaa cactttaggt
15481 gagttttcag gaggtggcca gtctgcacgc gacagcaata ttattttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttgggggcc tttgtaagtt attatcttgg caatacaatt
16021 cttcggacta agaaattaac acttgacaat tttttatatt acttaactac tcaaattcat
16081 aatctaccac atcgctcatt gcgaatactt aagccaaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccattcatc ttttcttaca
16261 tttgtaaaag aatggataat taatcgcgga acaattgtcc ctttatggat agtatatccg
16321 ctagagggtc aaaacccaac acctgtgaat aattttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
16744 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagattac cggtatagtc tcgtccatgc attacaaaact tgatgaggtc
17041 ctttgggaaa tagagagttt caagtcggct gtgacgctag cagagggaga aggtgctggt
17101 gccttactat tgattcagaa ataccaagtt aagacctat ttttcaacac gctagctact
17161 gagtccagta tagagtcaga aatagtatca ggaatgacta ctccaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagccccg
```

FIG. 2 CONTINUED

```
17521 tttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcactttat tcgtactgca
17941 aaaggacgaa tcacaaaact agtcaatgat tatttaaaat tctttcttat tgtgcaagca
18001 ttaaaacata atgggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
18601 ctttaagatt aagtttttta taattatcat tactttaatt tgtcgtttta aaaacggtga
18661 tagccttaat ctttgtgtaa aataagagat taggtgtaat aaccttaaca ttttgtcta
18721 gtaagctact atttcataca gaatgataaa attaaaagaa aaggcaggac tgtaaaatca
18781 gaaataccct ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttcttttt gtgtgtcca  (SEQ ID NO:7)
```

VP30

MEASYERGRPRAARQHSRDGHDHHVRARSSSRENYRGEYRQSRS
ASQVRVPTVFHKKRVEPLTVPPAPKDICPTLKKGFLCDSSFCKKDHQLESLTDRE
LLL
LIARKTCGSVEQQLNITAPKDSRLANPTADDFQQEEGPKITLLTLIKTAEHWARQ
DIR
TIEDSKLRALLTLCAVMTRKFSKSQLSLLCETHLRREGLGQDQAEPVLEVYQRLH
SDK
GGSFEAALWQQWDRQSLIMFITAFLNIALQLPCESSAVVVSGLRTLVPQSDNEEA
STN
PGTCSWSDEGTP  (SEQ ID NO:8)

AF522874

```
  1 cggacacaca aaaagaaaaa aggttttta agacttttg tgtgcgagta actatgagga
 61 agattaacag ttttcctcag tttaagatat acactgaaat tgagattgag attctcctct
121 ttgctattct gtaacttttcc ctggttgtga caattgaatc agttttatct attaccaatt
181 accatcaaca tggtatgtct agtgatcttg ggactcttct tcatctggtt tttcctagag
241 ctctgaatcc atttgcgag aagttcatcc aaacgaccca gtgtctgaaa atacaaaagg
301 ttccccttt cgtcaagttt aagggggttgt tttgattgtg tgtagatttt ataatcctag
```

FIG. 2 CONTINUED

```
 361 agtgccaagg agttgcgtgt catcattgat tgggaagatc aaggaaacaa tttgttccaa
 421 taatatcgta catcttgact aagtcgaaca agggaagtc gatatggatc gtgggaccag
 481 aagaatctgg gtgtcgcaaa atcaaggtga tactgattta gattatcata aaattttgac
 541 agctggcctt actgttcaac agggaattgt caggcagaaa ataatttctg tatatcttgt
 601 tgataacttg gaggctatgt gtcaattggt aatacaagcc tttgaggccg gaattgattt
 661 ccaagaaaat gccgacagct tccttctgat gctttgccta catcatgctt accaaggtga
 721 ctataaattg ttcttggaga gcaatgctgt acagtatttg gaaggtcatg gattcaaatt
 781 tgagctccgg aagaaggacg gtgtcaatcg gctcgaggaa ttgcttcctg ctgcaacgag
 841 tggaaaaaac atcaggcgta cgttggccgc actgcctgaa gaggagacta cagaagcaaa
 901 tgcagggcaa tttctctcat ttgcgagttt gtttcttccc aaactggttg tgggagagaa
 961 ggcttgcttg gaaaaagtcc agcgacaaat tcaggttcat gcagaacagg gtttaattca
1021 atatcccact gcatggcaat cagttggaca catgatggta atcttcagat tgatgaggac
1081 taatttcttg attaaatatt tactgatcca ccagggtatg catatggtag ctggccacga
1141 tgccaatgat gctgtcattg ctaattcagt tgctcaggct cgcttttcag gactcctaat
1201 tgtcaaaacc gttcttgatc atattctgca aaaaaccgac caaggagtaa gacttcaccc
1261 tttggcccga acagccaaag tgcgtaatga ggttaatgca tttaaggccg ccctaagctc
1321 acttgctaag catggggaat atgccccttt tgctcgcctt ctcaatctct cgggagttaa
1381 caacctagaa catggtctct acccacagtt atcagcaatt gtcttggag ttgccacagc
1441 acatggtagc acccttgcag gagttaatgt tggtgagcag tatcagcagc ttagagaggc
1501 tgccactgaa gctgagaagc aactccaaca atatgctgag tccagagaac tcgacagcct
1561 aggcctggac gatcaggaaa gaagaatact aatgaacttc catcagaaga aaacgaaat
1621 tagtttccag cagaccaatg caatggtaac ccttaggaaa gagcgactgc ctaaattaac
1681 agaagctata acgctggcct caagacctaa cctcgggtct agacaagacg acggcaatga
1741 aataccgttc cctgggccta taagcaacaa cccagaccaa gatcatctgg aggatgatcc
1801 tagagactcc agagacacca tcattcctaa tggtgcaatt gaccccgagg atggtgattt
1861 tgaaaattac aatggctatc atgatgatga agttgggacg gcaggtgact tggtcctgtt
1921 cgatcttgac gatcatgagg atgacaataa agctttgag ccacaggaca gctcgccaca
1981 atcccaaagg gaaatagaga gagaaagatt aattcatcca ccccaggca acaacaagga
2041 cgacaatcga gcctcagaca acaatcaaca atcagcagat tctgaggaac aaggaggtca
2101 atacaactgg caccgaggcc cagaacgtac gaccgccaat cgaagactct caccagtgca
2161 cgaagaggac accctatgg atcaaggtga tgatgatccc tcaagcttac ctccgctgga
2221 atctgatgat gacgatgcat caagtagcca acaagatccc gattatacag ctgttgcccc
2281 tcctgctcct gtataccgca gtgcagaagc ccacgagcct ccccacaaat cctcgaacga
2341 gccagctgaa acatcacaat tgaatgaaga ccctgatatc ggtcaatcaa agtctatgca
2401 aaaattagaa gagacatatc accatctgct gagaactcaa ggtccatttg aagccatcaa
2461 ttattatcac atgatgaagg atgagccggt aatatttagc actgatgatg ggaaggaata
2521 cacctacccg gattcacttg aggaagccta tcctccatgg ctcaccgaga aagaacgact
2581 ggacaaagag aatcgctaca tttacataaa taatcaacag ttcttctggc ctgtcatgag
2641 tcccagagac aaatttcttg caatcttgca gcaccatcag taaccacagc acaaagcgcg
2701 gtccacttcg taaagctaaa tacacttaag acttgaccga ttcatctaca aaaactaatc
2761 cattataact tattagtgct acttttctat aagtgattct taatctaagg ccattaagag
2821 tttaagtaat atacatatac acttacaccg gtctatccaa gatgtggctc aatgttcttg
2881 atttgaacat agtcataagg ggataaataa tactttatat ttctgattgt ggattgaccc
2941 attctgctta aaatgcttcg cccattgaaa atgtgatcta atagatagcc ctgactagac
3001 aaattaagaa aaacatttga tgaagattaa aaccttcatc gccagtaaat gattatattg
3061 tctgtaggca ggtgtttact ccaccttaaa tttggaaata tcctaccttaa ggaccattgt
```

FIG. 2 CONTINUED

```
3121 caagaggtgc ataggcatta ccacccttga gaacatgtac aataataaat tgaaggtatg
3181 ttcaggccca gaaacgactg gatggatttc tgagcaactt atgacaggta agattccagt
3241 aactgatata ttcattgata ttgataacaa gccagatcaa atggaagtcc gactcaaacc
3301 atcatcaagg agctcaacaa gaacttgtac aagtagcagt cagacggagg tcaactatgt
3361 acctctcctt aaaaaggttg aggatacatt aactatgcta gtgaatgcca ccagtcgtca
3421 gaatgctgca atcgaggccc ttgaaaaccg cctcagcaca cttgagagta gcttaaagcc
3481 aatccaagac atgggtaaag tgatttcatc attgaatcgc agttgtgccg aaatggttgc
3541 aaaatatgat cttctagtta tgacaactgg acgggctact tcaactgcag ctgcagtaga
3601 tgcgtattgg aaagagcaca aacagccacc accagggcca gcgttgtatg aagagaatgc
3661 gcttaaagga aaaatcgatg atccaaacag ctatgtacca gatgctgtgc aagaggctta
3721 caagaaccttc gacagtacat cgaccctgac cgaggaaaat tttgggaaac cttatatatc
3781 tgctaaagac ctgaaggaga tcatgtatga tcatctacct ggtttttggga ctgcctttca
3841 ccaacttgtt caagtgattt gtaaaatagg aaaggataac aaccttttgg acacaatcca
3901 tgctgagttc caggcaagtc tagcagatgg tgactctccc caatgtgcac tcatacagat
3961 aaccaaaagg gtcccaatct ttcaggatgt gccgccccg ataatccata ttagatcccg
4021 tggtgacatc ccacgagcat gccaaaagag tctccgacca gcaccaccat cacccaaaat
4081 tgatcgtggt tgggtttgtt tgtttaagat gcaagatggt aaaacgcttg gacttaagat
4141 ctaagaatca agatttattt aacaaggcaa gccacaacct tagatggaac ctcagccaga
4201 ctattgaact attgacgctg ttgatgataa tatataatta atggtcttat ttgaatatga
4261 caacatcttg cttcttgttc tgccttgtag ctctttgaat tggaagatca ttccaaactt
4321 acaaacatgc acaagatgtt atggtttagc aaagaattga taggagtact ggtatataat
4381 gtaaatataa caagtgatga agattaagaa aaaccagtcg gtattttcca gacttggcat
4441 ttcttatctt catctctaa agtgagatat tttatcatca aaaaatgagg cgcggagtgt
4501 taccaacggc tcctccagca tataatgata ttgcataccc tatgagcata ctcccaaccc
4561 gaccaagtgt catagtcaat gagaccaaat cagatgtact ggcagtgcca ggggcagatg
4621 ttccatcaaa ctccatgaga ccagtggctg atgataacat tgatcactca agccatactc
4681 caagcggagt agcttctgcc tttatattgg aagctacagt gaatgtaatt tcgggaacaa
4741 aagtcctgat gaagcaaata cctatttggc ttccactggg tgtagctgat cagaagatat
4801 acagctttga ttcaacaaca gccgcaatta tgttggcttc ctacacagtg acacacttcg
4861 ggaagatatc taacccgctg gtacgtgtca acaggctagg cccaggaata cccgatcatc
4921 cgctacgact cctaaggttg ggcaatcagg cattccttca agagtttgtt cttccaccag
4981 tccagcttcc ccagtatttc acatttgatc taacagctct aaagctcatc actcaaccat
5041 tgccagctgc aacctggaca gacgaaactc cagcaggagc agtcaatgct cttcgtcctg
5101 ggctctcact ccatcccaag cttcgtccaa ttctcctgcc ggggaagaca ggaaagaaag
5161 gacatgcttc agacttaaca tcacctgaca agattcaaac aatcatgaat gcaataccgg
5221 acctcaaaat tgtcccgatt gatccaacca agaacatagt tggaattgag gttccagaat
5281 tactagttca aaggctgacc ggcaaaaaac cacaacccaa aaatggccaa ccaattattc
5341 cagttcttct tccgaaatat gttggacttg atcctatatc gccaggggac ttaactatgg
5401 ttatcaccca ggattgtgat tcatgccact ctccagccag ccatccgtat cacatggaca
5461 agcagaatag ttaccaataa tttaaattcc attcgagcta ttattctgct agtaattccg
5521 acgggatcaa tagactaaaa atctgattgt atagaattat aaaagaatca agcagaggca
5581 acagactcac agcttacgcc tagataacta atattaagga gtttttaat ctaattttcc
5641 agtcttgagt aataatcatt tctttttgtaa ttaattatgc atttgttaac ttatcggtgc
5701 gagatttcct tgagaacccg gcggagcttc tactatctgc agtaaccaga agagaagttc
5761 aacccagtca aaactaaacc aagcaatatt ctgaatgctc tatagtctat tctaatcaga
5821 ggtataacaa tggctaagat ttcaatgact cgttaacaat cgctagtaat tttaatctcc
```

FIG. 2 CONTINUED

```
5881 agattaagaa aaagatatac gatgaagatt aaggcgacaa cgagccgaaa cttcatctct
5941 tttaaagatc taacattatc tgttccaaag tcatacaagg acacattcaa atcagggatt
6001 gtaagctgct atttcttacc tccccaaatt acctatacaa catggggtca ggatatcaac
6061 ttctccaatt gcctcgggaa cgttttcgta aaacttcgtt cttagtatgg gtaatcatcc
6121 tcttccagcg agcaatctcc atgccgcttg gtatagtgac aaatagcact ctcaaagcaa
6181 cagaaattga tcaattggtt tgtcgggaca aactgtcatc aaccagtcag ctcaagtctg
6241 tggggctgaa tctggaagga aatggaattg caaccgatgt cccatcagca acaaaacgct
6301 ggggatttcg ttcaggtgtg cctcccaagg tggtcagcta tgaagccgga gaatgggcag
6361 aaaattgcta caatctggag atcaaaaagt cagacggaag tgaatgcctc cctctccctc
6421 ccgacggtgt acgaggattc cctagatgtc gctatgtcca caaagttcaa ggaacaggtc
6481 cttgtcctgg tgacttagct ttccataaaa atggggcttt tttcttgtat gatagattgg
6541 cctcaactgt catctaccga gggacaactt ttgctgaagg tgtcgtagct tttttaattc
6601 tgtcagagcc caagaagcat ttttggaagg ctacaccagc tcatgaaccg gtgaacacaa
6661 cagatgattc cacaagctac tacatgaccc tgacactcag ctacgagatg tcaaattttg
6721 ggggcaatga aagcaacacc cttttaagg tagacaacca cacatatgtg caactagatc
6781 gtccacacac tccgcagttc cttgttcagc tcaatgaaac acttcgaaga aataatcgcc
6841 ttagcaacag tacagggaga ttgacttgga cattggatcc taaaattgaa ccagatgttg
6901 gtgagtgggc cttctgggaa actaaaaaaa cttttcccaa caacttcatg gagaaaactt
6961 gcatttccaa attccatcaa cccacaccaa caactcctca gatcagagcc cggcgggaac
7021 tgtccaagga aaaattagct accaccacc cgccaacaac tccgagctgg ttccaacgga
7081 ttcccctcca gtggtttcag tgctcactgc aggacggaca gaggaaatgt cgacccaagg
7141 tctaaccaac ggagagacaa tcacaggttt caccgcgaac ccaatgacaa ccaccattgc
7201 cccaagtcca accatgacaa gcgaggttga taacaatgta ccaagtgaac agccgaacaa
7261 cacagcatcc attgaagact ccccccccatc ggcaagcaac gagacaattt accactccga
7321 gatggatccg atccaaggct cgaacaactc cgcccagagc ccacagacca agaccacgcc
7381 agcacccaca acatcccga tgacccagga cccgcaagag acggccaaca gcagcaaacc
7441 aggaaccagc ccaggaagcg cagccggacc aagtcagccc ggactcacta taaatacagt
7501 aagtaaggta gctgattcac tgagtcccac caggaaacaa aagcgatcgg ttcgacaaaa
7561 caccgctaat aaatgtaacc cagatcttta ctattggaca gctgttgatg aggggggcagc
7621 agtaggattg gcatggaatc catatttcgg acctgcagca gaaggcatct acattgaggg
7681 tgtaatgcat aatcagaatg ggctatttg cgggctacgt cagctagcca atgaaactac
7741 ccaggctctt caattatttc tgcgggccac aacagaactg aggacttact cacttcttaa
7801 cagaaaagct attgattttc ttcttcaacg atggggaggt acctgtcgaa tcctaggacc
7861 atcttgttgc attgagccac atgattggac aaaaaatatt actgatgaaa ttaaccaaat
7921 taaacatgac tttattgaca atcccctacc agaccacgga gatgatctta atctatggac
7981 aggttggaga caatggatcc cggctggaat tgggattatt ggagttataa ttgctataat
8041 agccctactt tgtatatgta agattttgtg ttgatttatt ctgagatctg agagagaaaa
8101 atctcagggt tactctaagg agaaatatta tttttaaaat ttacttgaat gctgaccact
8161 tatcttaaat gagcaattaa taatatgttt ttctgcttct ttgcttgatt tacaatatga
8221 tatttctctt aataatgatt aatatattaa gaaaaactta tgacgaagat taaaggagag
8281 gatcgttaac gggaaaacct cccatctcgt tcgtcgaagc cacgttggtg gtgcttgcag
8341 ctgagaacaa ctccagagat tgtaggtaga aaggaccaac atttataggt aggggtcaga
8401 aagcaacaat aaccataaaa ggagagcctg acattgctat ttaatatcct agaacctgat
8461 ttctaggttc tagctttaaa atccggatga tggagcattc aagagaacgg ggtagatcta
8521 gcaacatgcg acataatagc cgggaaccat acgaaaatcc atcaaggtct cgctcattat
8581 ctcgggaccc taatcaggtt gatcgtagac agcctcgaag tgcatcccaa attcgtgttc
```

FIG. 2 CONTINUED

```
8641 cgaatctgtt ccatcggaaa aagactgatg cactcatagt tcctccggct cctaaagata
8701 tatgcccaac actcaaaaaa ggattcctct gcgatagcaa attttgcaaa aaagatcacc
8761 aattggatag cttaaatgat catgaattac tactgctaat tgcaagaaga acatgtggaa
8821 ttatcgagag caattcgcag attacatccc caaaagatat gcggttagcg aatccaacag
8881 ctgaagactt ctcacaaggt aatagtccta aattaacact tgcagtcctt cttcaaattg
8941 ctgaacattg ggcaaccaga gacctaaggc aaattgagga ctctaaactt agagctcttt
9001 taacccttg tgccgtatta acaaggaaat tttctaaatc ccaactgggt cttctatgtg
9061 agacccacct acggcatgag ggcctcggac aggaccaagc tgattctgta ttagaggtct
9121 accaaagact ccacagtgat aaaggaggga attttgaggc tgccctgtgg caacaatggg
9181 accgacagtc attaataatg ttcatctctg cttttctcaa cattgctctc cagatacctt
9241 gtgaaagttc tagtgtcgta gtctcaggtc ttgccacatt gtacccagca caagacaatt
9301 ctacaccatc cgaggcaact aatgatacca cctggtcaag tacagttgaa tagaaaacca
9361 ctggagctat ttttccacga ttgctctcag tcaataaatt aatatagata taatacgact
9421 tcggtgtgca attgtcaaga gttccattta gtaataatga ttcttaaaac aatctactat
9481 cgcaattatc gatggatcta ccctatttga cggtacatga cttgaatgta ataaggtaag
9541 ttggtatctg aggtattttg tctagagtat actcaaaatc gtatgtctag caaattatca
9601 atagcaaagt taaattctcc taacctcata ttttgatcaa gtaatcatga ttatgata
9661 attctttca gattatcggt ttaatcttta ttaagaaaaa atcatgattg tagacaattt
9721 actggtagtc cttgggtatc caagtttatg aatagagcta gagagaattt gctacttccg
9781 aggtataact ttattatttg ctacttcgaa tgcctaaaac cagtaatgca ggatgaagat
9841 taattgcgga ggaatcagga attcaacttt agttccttaa ggcctcgtcc gaatcttcat
9901 cagttcgtaa gttcttttat agaagtcatt agcttctaag gtgattatat tttagtatta
9961 aattttgcta attgcttgct ataaagttga aatgtctaat gcttaaatga acacttttt
10021 gaagctgaca tacgaataca tcatatcata tgaaaacatc gcaattagag cgtccttgaa
10081 gtctggcatt gacagtcacc aggctgttct cagtagtctg tccttggaag ctcttgggga
10141 gacaaaaaga ggtcccagag agtcccaaca ggttggcata aggtcattaa caccagcata
10201 gtcggctcga ccaagactgt aagcgagtcg atttcaacta aaaagattat ttcttgttgt
10261 ttaaacaaat tccttttgtg tgagacatcc tcaaggcaca agatggctaa agccacaggc
10321 cgatacaatc tcgtgccccc aaagaaagat atggaaaagg gagtgatttt tagtgatctt
10381 tgtaatttct tgattactca aaccctgcaa ggttggaagg tttattgggc aggaattgag
10441 tttgatgtaa gtcaaaaagg catggctctt ctgacaagac tcaaaacaaa tgactttgct
10501 cctgcctggg cgatgacaag aaatcttttc ccacatctgt tccagaaccc aaattcggtt
10561 attcaatctc ccatctgggc tttgagggta attttggcag ccggattgca ggatcagttg
10621 ttagaccatt cattggttga gccattgaca ggggctctcg gtctaatttc tgattggctc
10681 ctaactacaa cgtcaacaca tttcaatctt cgtactagaa gcgtaaagga ccagcttagt
10741 cttcgtatgt tatctttgat caggtcaaac atcttgcagt tcatcaacaa gcttgacgcc
10801 ctgcatgttg tcaattacaa tggtttactc agtagtattg agatcgggac ttctacacac
10861 acaatcatta taactcgtac aaatatgggt tttctcgtgg aagttcaaga gcctgacaaa
10921 tcagctatga attctaagcg cccaggacca gtcaagttct cattacttca tgagtctgcc
10981 ttcaaacctt tcactcgtgt tccacaatct gggatgcaat cattaataat ggagttcaac
11041 agtttgttgg caatttaaca aggtaatctt aaaataagta catgaatgag aattagttgt
11101 gggtcttatc tagcattgtt gagttaacta tctaatctat tttcgctaat tgcattgagc
11161 actgctaata ggtttgtatc acgttaaaga tttagagtgt atgaattgtg cagatttaaa
11221 cttgggtttt gccttatgct tcataggtgg tcttttgaa atggagatta tcagcatttc
11281 ttaaatggga ggagttagca atcagaaatt ggagataaat ggacatcggg atagaacaat
11341 gcctaactat tgggcggctt ccattttac atgtgtatat aaccaatctt ttcctatctt
```

FIG. 2 CONTINUED 11401 tgcttatatt ggtgtaactt tattttaata acatgtcaat gctatactgt taagagaagg
11461 tctgaggaag attaagaaaa aggcctcgtg ttcacttggt tgccgtcaag tatccgtgg
11521 tttttttcta cctaacttcc tcatgccata tggctaccca gcatacccag tacccggatg
11581 cacgtttatc ctcacctata gtcctggatc aatgtgattt ggtaactcga gcatgtgggt
11641 tatattcatc ttattctcta aatcctcaac taaggcaatg taaattacca aaacatatat
11701 atcgacttaa gttcgacaca atagtatcca aattcctaag tgatacacct gtagcaacac
11761 tgccgataga ctatttagta ccaattctcc tgcgttccct aacggggcac ggtgataggc
11821 cattgacccc gacttgcaat caattccttg atgaaattat taattacact cttcatgatg
11881 cagccttct tgattactat ctcaaggcaa caggtgcaca ggaccatttg acaaacattg
11941 caactagaga gaagcttaaa aacgaaattc taaacaatga ttatgtccat caattgttct
12001 tctggcatga cctttctatt ttggctcgac gtgggcgtct gaatcgcggg aacaaccgtt
12061 caacctggtt tgttcatgat gaattcattg atattttagg atatggcgat tatattttt
12121 ggaaaatacc tttatcatta ttaccagtta ctatagacgg ggtcccacac gcagcaactg
12181 actggtatca accgactctt tttaaagaat ccatcctagg gcatagccaa atcctatctg
12241 tgtcaacagc tgaaatacta attatgtgta aagatattat cacctgtagg tttaatacat
12301 cactgattgc atccattgca aaattagagg atgtagatgt gtctgattat cctgacccga
12361 gtgatattct taagatatac aatgctggag actatgtaat atctattctt ggctcagagg
12421 gttataagat aataaagtac cttgaaccac tttgtttggc caaaatccaa ctttgctcta
12481 aattcacaga aagaaaaggt cgttcctca cacagatgca tttatcagta ataaatgatc
12541 ttcgggagtt gatttctaac cgcaggttaa aggactatca gcaagagaag attagagatt
12601 ttcacaaaat attattacaa ttgcaattat ctcctcaaca gttttgtgaa ttattctctg
12661 ttcaaaaaca ttggggggcat ccaattttac atagtgagaa agctatacaa aaagtaaaac
12721 ggcatgcaac catccttaag gctctcagac ctaatgtcat ctttgagaca tattgtgtat
12781 tcaagtacaa tattgccaag cactatttcg acagccaagg aacttggtac agtgtaatct
12841 cagacaggaa tttaactcca ggactcaact ccttcataaa acgtaatcac tttccttcac
12901 tacccatgat taaggatctt ctatgggaat tctatcatct taatcaccct ccgttattct
12961 ctacaaaggt gattagtgac ttaagtattt tcatcaaaga tagggccaca gctgttgaac
13021 agacatgttg ggatgcagtc tttgaaccca atgtgctagg ttacaatcct ccaaacaaat
13081 tctccactaa aagggtgccg gaacaatttc tagaacaaga ggatttttca atcgaaagtg
13141 tcctgaatta tgcacaggaa ttacattatt tattaccaca gaataggaat tttcctttt
13201 ctctcaaaga aaaggaatta aatattggac gaacatttgg gaagctacca tatctcacac
13261 ggaatgtcca aactttatgt gaggctctgt tagcagatgg actggccaag gccttcccca
13321 gtaacatgat ggtagtaact gaacgtgaac aaaaagagag ccttcttcat caggcatcat
13381 ggcaccacac cagtgatgat tttggagaga atgctaccgt tcgagggagt agttttgtaa
13441 ctgatttaga gaagtacaat cttgcatttc gctatgagtt cactgcacca tttattgagt
13501 actgcaacca ttgctatggt gtgcgtaatg tctttaattg gatgcattat ttaatcccgc
13561 agtgttacat gcatgtaagt gattattata atccgcctca caatgttaat cttagcaatc
13621 gagaatatcc tcctgaaggc ccgagttcgt accgagggca cttaggaggc atagagggat
13681 tacaacaaaa actgtggacg agtatatcct gtgcacaaat ctccttagtg gaaattaaaa
13741 ctggttttaa gttacgatca gcggtcatgg gagacaatca gtgtataacc gtattgtctg
13801 tttttccact taaaacagac cctgaagagc aggagcaaag cgccgaagac aatgctgcaa
13861 gagtagcagc aagtcttgca aaagtaacca gtgcatgtgg gatctttctt aaaccagatg
13921 agacatttgt acactcaggt ttcatttatt tcggaaaaaa acaatatctc aatggtgtac
13981 aattaccgca atcactcaaa acagcagcaa gaatggcacc actctctgat gctatattcg
14041 atgatctaca aggaacactt gccagtattg gaactgcctt cgaacgtgct atatcggaaa
14101 cgcgacatat cctcccatgt cgtattgtag cagctttcca tacgtatttc gccgttcgga

FIG. 2 CONTINUED 14161 ttttacaata tcaccatctt ggatttaata aaggcatcga tttaggacag ttgtcactta
14221 gtaaaccatt agactatggg actattactc taacattggc ggttccacaa gtccttgggg
14281 gattgtcttt tctaaatcca gaaaagtgtt tttatcgaaa cttcggagat cctgtgactt
14341 ctggactttt ccagctacgg gtgtacctag aaatggttaa catgaaagac ctattttgtc
14401 cattaatatc gaaaaatcca ggaaattgta gtgccattga ttttgtctta aatccatccg
14461 gattaaatgt tccaggatca caagacttga catccttttt gcgacaaatc gttaggcgta
14521 gtattaccct aactgctaga aataagttaa ttaacactct cttccatgcc tctgctgatt
14581 tggaagatga gatggtttgt aagtggctcc tttcatcaaa ccctgtcatg agtcgctttg
14641 cagcggatat ttttccagg acaccgagtg gtaaacgtct ccaaatatta ggttatcttg
14701 aagggaccag gactctattg gcctccaaaa tcataaacaa caacagtgag acacctgtac
14761 ttgataagct gaggaagatc acctacaaa gatggaatct gtggttcagt tatttggacc
14821 attgtgacca attactagca gatgctctac agaaaattag ttgcacggtg gatttggccc
14881 agattttgcg tgagtataca tggtcacaca tcttagaggg tagatcattg atcggagcga
14941 cattaccatg tatggtggag caattcaaag ttaagtggct aggacaatat gaaccttgtc
15001 cagaatgtct caacaaaaaa ggctcaaatg cttatgtctc agttgcagtc aaagatcaag
15061 tggtcagtgc ttggcctaat acttctcgaa taagttggac aatagggagt ggtgtcccct
15121 atataggggtc aagaaccgag gataaaatcg gacagcctgc tatcaagccg cgatgcccctt
15181 catctgcctt caaggaggct atagaattag catcaaggct cacttgggtt acacaaggag
15241 gttctaatag tgaacaatta atccggcctt tcttggaagc gagagtcaac cttagtgtca
15301 gtgaagtcct gcaaatgaca ccatcacatt attcaggaaa tattgtccat cgatataacg
15361 accaatacag cccgcactca tttatggcga atcgcatgag caatactgcg acccgtctca
15421 tagtgtcaac taatacactt ggagaatttt caggtggagg gcaggccgcc agggatagca
15481 atataatttt ccagaatgtt ataaatttag cagttgccct ttatgatatt agattccgga
15541 atacaaacac ctctgatata aggcataata gggctcatct tcacctgaca gagtgctgta
15601 ctaaagaggt cccggcccag tatttgacat atacaagtgc acttaatctg gatttaagcc
15661 gttatcgtga taatgaacta atatatgact caaatccact gaagggagga ttgaactgca
15721 atttaacaat agatagtcct ttagtgaagg gtcctaggct taacatgatt gaagatgatc
15781 ttctccgctt tccacacctt tctggatggg agttagcgaa aacggtggta caatccatca
15841 tctcagacaa tagcaactca tcaacagatc caatcagtag cggagaaaca cgctctttca
15901 caactcattt tctcacttac cctcagattg gccttcttta cagttcgga gcagtattat
15961 gcttttatct aggcaatact atccatggga ctaaaaaact tgattacgaa cagtttctat
16021 attatttgca taaccagctg cacaacttac ctcatcgagc actccgtgtt tttaaaccaa
16081 catttaagca tgccagtgtg atgtcccgat taatggaaat tgattctaac ttctcaattt
16141 atattggcgg gacatctgga gatcgagggc tgtctgatgc tgctcgactg tttcttcgga
16201 cagcaatcgc gagttttta caattcttta aagctggat catcgatcgc caaagacaa
16261 ttcctttatg gatagtatat ccgcttgaag gtcaacagcc ggaatccatc aatgaatttc
16321 tacataaaat tttgggtctg ctcaaacaag gccccaaaag tattccaaag gaggtcagca
16381 tccaaaatga tggacatttg gattggcag aaaataatta tgtttacaat agtaagagca
16441 ctgctagtaa tttcttccat gcatccttag cttactggag aagtaggaaa tctcggaaaa
16501 ctcaagacca taatgatttc tcaagagggg atggaacact tacagaaccc gtgcgtaagt
16561 tttcaagcaa tcatcagtca gatgaaaagt actacaatgt gacatgtgga aagtcaccga
16621 agccgcaaga acgcaaagac ttctcgcaat acagactcag caataacggg caaacaatga
16681 gtaatcatcg taagaaaggg aagttccaca gtggaatcc ctgcaaaatg ttaatggaga
16741 gtcaaaggggg aactgttcta acagagggtg actactttca aaacaatact ccaccaacag
16801 atgatgtatc aagtcctcac cgactcattc taccattttt taattggga aatcacaacc
16861 atgcacatga tcaagatgcc caagaattga tgaatcaaaa tattaaacag tacctacatc

```
16921 agctaaggtc tatgttggac accactatat attgtagatt cacagggatt gtctcatcca
16981 tgcattacaa attggacgaa gttcttctag aatacaatag tttcgattca gctatcacat
17041 tagctgaagg tgagggtca ggggctctat tacttttgca aaatatagt acaaggttat
17101 tattttgaa cacattggca acagaacaca gtatagaatc agaagttgta tcaggttttt
17161 ctactccgag aatgttgtta ccaataatgc aaaaggttca tgaaggacaa gtcactgtta
17221 tcttaaataa ttcagcaagt cagataactg acataactag ctcaatgtgg ttaagtaatc
17281 aaaaatataa tctaccttgt caagttgaaa tcattatgat ggatgctgaa acaacagaga
17341 acttaaacag gtcccaactc taccgagcag tatataactt aatacttgat cacattgatc
17401 cgcagtatct caaggtggtg gtactcaaag tatttctgag tgatatagaa ggaatattat
17461 ggattaatga ttacttggct ccattattcg gggctggtta cttgattaaa ccgattacat
17521 caagtgcccg gtcaagtgaa tggtaccttt gcttatcaaa tttgatatct actaacagga
17581 gatcggccca tcagactcac aaggcatgtc ttggtgttat cagagatgct ttgcaagcac
17641 aagtccagcg aggcgtgtac tggttgagtc acatcgcaca gtatgctaca aagaatctcc
17701 attgtgaata cataggcctt ggtttcccat ctctagaaaa ggtcctatat cacaggtata
17761 atctagttga tactggactc ggtccattgt cgtcagttat tagacattta actaacctcc
17821 aggcagagat acgagactta gtattagatt ataacctgat gagggagagt cgcactcaaa
17881 cgtaccattt tattaagact gcaaaaggca gaatcacaaa gttagtcaat gactttctga
17941 agtttctttt aattgtccag gcactcaaaa ataattcttc ttggtatact gagcttaaaa
18001 aattacctga ggttattaat gtgtgtaatc gatttatca tactcacaat tgcgaatgtc
18061 aggaaaaatt ctttgtccag acgcttatt tacaacgcct acgcgatgca gaaatcaagc
18121 taattgaacg ccttaccggg ttaatgcgat tttatccaga agggttaata tattccaatc
18181 acacataggt actaaatcat catagtatga ggaataagaa aatgataatt cctgacgaca
18241 gttttagttc cgattctaag tatatcggaa gagagtatgc caatcttaat tgttagaggt
18301 aacaagctat tagttattac ttattgataa gaatacactt tatcatagcg taacacatca
18361 taacttata acgattttgc atttctaatc ctagtattta ttagaatgta ctaccagaga
18421 aatgacccca gttcctatct ttaaataatg attgtgtgta ttaaattat agtttattag
18481 gtttatgagt tggttacaca gtgagtatta gtaattgagg attatgtaga taggtaatct
18541 aacactgaat cacccatctg atgtcaccat atccaaatgt tgtgctagtc gcatttaaac
18601 atgctatctt cagttaagta acatagactg aaaatgctaa gaagagattg gagtaaaagt
18661 ataaaataaa tttaattaaa cttcaaagtg attaaatgat aatgatcttg ggaactcgat
18721 atgacctcaa gtcaaaaata atgtcaatat aattgtttag taatatgagt gataatgtaa
18781 attttgataa ctaactagct ttagtagtta agatcaaatg caaacattat aagaatgtta
18841 agcgcacaca aaaacattat aaaaaaccaa ttttttcctt tttgtgtgtc c
```
(SEQ ID NO:10)

VP30

MEHSRERGRSSNMRHNSREPYENPSRSRSLSRDPNQVDRRQPRS
ASQIRVPNLFHRKKTDALIVPPAPKDICPTLKKGFLCDSKFCKKDHQLDSLNDHE
LLL
LIARRTCGIIESNSQITSPKDMRLANPTAEDFSQGNSPKLTLAVLLQIAEHWATRD
LR
QIEDSKLRALLTLCAVLTRKFSKSQLGLLCETHLRHEGLGQDQADSVLEVYQRL
HSDK
GGNFEAALWQQWDRQSLIMFISAFLNIALQIPCESSSVVVSGLATLYPAQDNSTPS
EA
TNDTTWSSTVE (SEQ ID NO:11)

1 cggacacaca aaaagaaaga agaatttta ggatcttttg tgtgcgaata actatgagga
   61 agattaataa ttttcctctc attgaaattt atatcggaat ttaaattgaa attgttactg
  121 taatcacacc tggtttgttt cagagccaca tcacaaagat agagaacaac ctaggtctcc
  181 gaagggagca agggcatcag tgtgctcagt tgaaaatccc ttgtcaacac ctaggtctta
  241 tcacatcaca agttccacct cagactctgc agggtgatcc aacaacctta atagaaacat
  301 tattgttaaa ggacagcatt agttcacagt caaacaagca agattgagaa ttaaccttgg
  361 ttttgaactt gaacacttag gggattgaag attcaacaac cctaaagctt ggggtaaaac
  421 attggaaata gttaaaagac aaattgctcg gaatcacaaa attccgagta tggattctcg
  481 tcctcagaaa atctggatgg cgccgagtct cactgaatct gacatggatt accacaagat
  541 cttgacagca ggtctgtccg ttcaacaggg gattgttcgg caaagagtca tcccagtgta
  601 tcaagtaaac aatcttgaag aaatttgcca acttatcata caggcctttg aagcaggtgt
  661 tgattttcaa gagagtgcgg acggtttcct tctcatgctt tgtcttcatc atgcgtacca
  721 gggagattac aaactttct tggaaagtgg cgcagtcaag tatttggaag ggcacgggtt
  781 ccgttttgaa gtcaagaagc gtgatggagt gaagcgcctt gaggaattgc tgccagcagt
  841 atctagtgga aaaaacatta agagaacact tgctgccatg ccggaagagg agacaactga
  901 agctaatgcc ggtcagtttc tctcctttgc aagtctattc cttccgaaat tggtagtagg
  961 agaaaaggct tgccttgaga aggttcaaag gcaaattcaa gtacatgcag agcaaggact
 1021 gatacaatat ccaacagctt ggcaatcagt aggacacatg atggtgattt tccgtttgat
 1081 gcgaacaaat tttctgatca aatttctcct aatacaccaa gggatgcaca tggttgccgg
 1141 gcatgatgcc aacgatgctg tgatttcaa ttcagtggct caagctcgtt ttcaggctt
 1201 attgattgtc aaaacagtac ttgatcatat cctacaaaag acagaacgag gagttcgtct
 1261 ccatcctctt gcaaggaccg ccaaggtaaa aaatgaggtg aactccttta aggctgcact
 1321 cagctccctg gccaagcatg gagagtatgc tccttccgcc cgactttga acctttctgg
 1381 agtaaataat cttgagcatg gtcttttccc tcaactatcg gcaattgcac tcggagtcgc
 1441 cacagcacac gggagtaccc tcgcaggagt aaatgttgga gaacagtatc aacaactcag
 1501 agaggctgcc actgaggctg agaagcaact ccaacaatat gcagagtctc gcgaacttga
 1561 ccatcttgga cttgatgatc aggaaaagaa aattcttatg aacttccatc agaaaaagaa
 1621 cgaaatcagc ttccagcaaa caaacgctat ggtaactcta agaaaagagc gcctggccaa
 1681 gctgacagaa gctatcactg ctgcgtcact gccaaaaaca agtggacatt acgatgatga
 1741 tgacgacatt cccttccag gacccatcaa tgatgacgac aatcctggcc atcaagatga
 1801 tgatccgact gactcacagg atacgaccat tcccgatgtg gtggttgatc ccgatgatgg
 1861 aagctacggc gaataccaga gttactcgga aaacggcatg aatgcaccag atgacttggt
 1921 cctattcgat ctagacgagg acgacgagga cactaagcca gtgcctaata gatcgaccaa
 1981 gggtggacaa cagaagaaca gtcaaaaggg ccagcatata gagggcagac agacacaatc
 2041 caggccaatt caaaatgtcc caggccctca cagaacaatc caccacgcca gtgcgccact
 2101 cacggacaat gacagaagaa atgaaccctc cggctcaacc agccctcgca tgctgacacc
 2161 aattaacgaa gaggcagacc cactggacga tgccgacgac gagacgtcta gccttccgcc
 2221 cttggagtca gatgatgaag agcaggacag ggacggaact tccaaccgca caccactgt
 2281 cgccccaccg gctcccgtat acagagatca ctctgaaaag aaagaactcc cgcaagacga
 2341 gcaacaagat caggaccaca ctcaagaggc caggaaccag gacagtgaca acacccagtc
 2401 agaacactct tttgaggaga tgtaccgcca cattctaaga tcacaggggc catttgatgc

FIG. 2 CONTINUED

```
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttattttg
2821 aatttaaagc tagcttatta ttactagccg tttttcaaag ttcaatttga gtcttaatgc
2881 aaataggcgt taagccacag ttatagccat aattgtaact caatattcta actagcgatt
2941 tatctaaatt aaattacatt atgcttttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaaagctggt
3121 ctaacaagat gacaactaga acaagggca ggggccatac tgtggccacg actcaaaacg
3181 acagaatgcc aggccctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacaggggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaattt gggaaacctg
3781 acatttcggc aaaggatttg agaaacatta tgtatgatca cttgcctggt tttggaactg
3841 ctttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaattg agccaatctc ccttccctcc gaaagaggcg aataatagca gaggcttcaa
4201 ctgctgaact ataggggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta gtaacccaa
4381 accaaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcccccat ttcggcaagg
4861 caaccaatcc acttgtcaga gtcaatcggc tgggtcctgg aatcccggat catcccctca
4921 ggctcctgcg aattggaaac caggcttttcc tccaggagtt cgttcttccg ccagtccaac
4981 taccccagta tttcacctttt gatttgacag cactcaaact gatcacccaa ccactgcctg
5041 ctgcaacatg gaccgatgac actccaacag gatcaaatgg agcgttgcgt ccaggaattt
5101 catttcatcc aaaaacttcgc cccattcttt tacccaacaa aagtgggaag aaggggaaca
5161 gtgccgatct aacatctccg gagaaaatcc aagcaataat gacttcactc caggacttca
```

FIG. 2 CONTINUED

```
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt cttttttctc tcctaaatgt agaacttaac aaaagactca taatatactt
5641 gttttttaaag gattgattga tgaaagatca taactaataa cattacaaat aatcctacta
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga ccagtggac
6241 tgaatctcga agggaatgga gtggcaactg acgtgccatc tgcaactaaa agatggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttcccccgg tgccggtatg tgcacaaagt atcaggaacg ggaccgtgtg
6481 ccggagactt tgccttccat aaagagggtg cttctttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaaccaagat
6781 tcacaccaca gtttctgctc cagctgaatg agacaatata tacaagtggg aaaaggagca
6841 ataccacggg aaaaactaat tggaaggtca acccgaaat tgatacaaca atcggggagt
6901 gggcttctg ggaaactaaa aaaacctcac tagaaaaatt cgcagtgaag agttgtcttt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccgaggga atttacacag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgatttgtt gataaaaccc ttccggacca ggggacaat gacaattggt ggacaggatg
```

FIG. 2 CONTINUED

```
7981  gagacaatgg ataccggcag gtattggagt tacaggcgtt ataattgcag ttatcgcttt
8041  attctgtata tgcaaatttg tcttttagtt tttcttcaga ttgcttcatg gaaaagctca
8101  gcctcaaatc aatgaaacca ggatttaatt atatggatta cttgaatcta agattacttg
8161  acaaatgata atataataca ctggagcttt aaacatagcc aatgtgattc taactccttt
8221  aaactcacag ttaatcataa acaaggtttg acatcaatct agttatctct ttgagaatga
8281  taaacttgat gaagattaag aaaaaggtaa tctttcgatt atctttaatc ttcatccttg
8341  attctacaat catgacagtt gtctttagtg acaagggaaa gaagccttt tattaagttg
8401  taataatcag atctgcgaac cggtagagtt tagttgcaac ctaacacaca taaagcattg
8461  gtcaaaaagt caatagaaat ttaaacagtg agtggagaca acttttaaat ggaagcttca
8521  tatgagagag gacgcccacg agctgccaga cagcattcaa gggatggaca cgaccaccat
8581  gttcgagcac gatcatcatc cagagagaat tatcgaggtg agtaccgtca atcaaggagc
8641  gcctcacaag tgcgcgttcc tactgtattt cataagaaga gagttgaacc attaacagtt
8701  cctccagcac ctaaagacat atgtccgacc ttgaaaaaag gattttgtg tgacagtagt
8761  ttttgcaaaa aagatcacca gttggagagt ttaactgata gggaattact cctactaatc
8821  gcccgtaaga cttgtggatc agtagaacaa caattaaata taactgcacc caaggactcg
8881  cgcttagcaa atccaacggc tgatgatttc cagcaagagg aaggtccaaa aattaccttg
8941  ttgacactga tcaagacggc agaacactgg gcgagacaag acatcagaac catagaggat
9001  tcaaaattaa gagcattgtt gactctatgt gctgtgatga cgaggaaatt ctcaaaatcc
9061  cagctgagtc ttttatgtga gacacaccta aggcgcgagg ggcttgggca agatcaggca
9121  gaacccgttc tcgaagtata tcaacgatta cacagtgata aaggaggcag ttttgaagct
9181  gcactatggc aacaatggga ccgacaatcc ctaattatgt ttatcactgc attcttgaat
9241  attgctctcc agttaccgtg tgaaagttct gctgtcgttg tttcagggtt aagaacattg
9301  gttcctcaat cagataatga ggaagcttca accaacccgg ggacatgctc atggtctgat
9361  gagggtaccc cttaataagg ctgactaaaa cactatataa ccttctactt gatcacaata
9421  ctccgtatac ctatcatcat atatttaatc aagacgatat cctttaaaac ttattcagta
9481  ctataatcac tctcgtttca aattaataag atgtgcatga ttgccctaat atatgaagag
9541  gtatgataca acccctaacag tggtcaaaga aaatcataat ctcgtatcgc tcgtaatata
9601  acctgccaag catacctctt gcacaaagtg attcttgtac acaaataatg ttttactcta
9661  caggaggtag caacgatcca tcccatcaaa aaataagtat ttcatgactt actaatgatc
9721  tcttaaaata ttaagaaaaa ctgacggaac ataaattctt tatgcttcaa gctgtggagg
9781  aggtgtttgg tattggctat tgttatatta caatcaataa caagcttgta aaaatattgt
9841  tcttgtttca agagtagat tgtgaccgga aatgctaaac taatgatgaa gattaatgcg
9901  gaggtctgat aagaataaac cttattattc agattaggcc ccaagaggca ttcttcatct
9961  ccttttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaaatagga acgtcgttcc aacaatcgag
10261 cgcaaggttt caaggttgaa ctgagagtgt ctagacaaca aaatattgat actccagaca
10321 ccaagcaaga cctgagaaaa aaaccatggc taaagctacg ggacgataca atctaatatc
10381 gcccaaaaag gacctggaga aagggggttgt cttaagcgac ctctgtaact tcttagttag
10441 ccaaactatt caggggtgga aggtttattg ggctggtatt gagtttgatg tgattcacaa
10501 aggaatggcc ctattgcata gactgaaaac taatgacttt gcccctgcat ggtcaatgac
10561 aaggaatctc tttcctcatt tatttcaaaa tccgaattcc acaattgaat caccgctgtg
10621 ggcattgaga gtcatccttg cagcagggat acaggaccag ctgattgacc agtctttgat
10681 tgaacccta gcaggagccc ttggtctgat ctctgattgg ctgctaacaa ccaacactaa
```

FIG. 2 CONTINUED

```
10741 ccatttcaac atgcgaacac aacgtgtcaa ggaacaattg agcctaaaaa tgctgtcgtt
10801 gattcgatcc aatattctca agtttattaa caaattggat gctctacatg tcgtgaacta
10861 caacggattg ttgagcagta ttgaaattgg aactcaaaat cataacatca tcataactcg
10921 aactaacatg ggttttctgg tggagctcca agaacccgac aaatcggcaa tgaaccgcat
10981 gaagcctggg ccggcgaaat tttccctcct tcatgagtcc acactgaaag catttacaca
11041 aggatcctcg acacgaatgc aaagtttgat tcttgaattt aatagctctc ttgctatcta
11101 actaaggtag aatacttcat attgagctaa ctcatatatg ctgactcaat agttatcttg
11161 acatctctgc tttcataatc agatatataa gcataataaa taaatactca tatttcttga
11221 taatttgttt aaccacagat aaatcctcac tgtaagccag cttccaagtt gacacccta
11281 caaaaaccag gactcagaat ccctcaaaca agagattcca agacaacatc atagaattgc
11341 tttattatat gaataagcat tttatcacca gaaatcctat atactaaatg gttaattgta
11401 actgaacccg caggtcacat gtgttaggtt tcacagattc tatatattac taactctata
11461 ctcgtaatta acattagata agtagattaa gaaaaaagcc tgaggaagat taagaaaaac
11521 tgcttattgg gtctttccgt gttttagatg aagcagttga aattcttcct cttgatatta
11581 aatggctaca caacataccc aataccaga cgctaggtta tcatcaccaa ttgtattgga
11641 ccaatgtgac ctagtcacta gagcttgcgg gttatattca tcatactccc ttaatccgca
11701 actacgcaac tgtaaactcc cgaaacatat ctaccgtttg aaatacgatg taactgttac
11761 caagttcttg agtgatgtac cagtggcgac attgcccata gattcatag tccagttct
11821 tctcaaggca ctgtcaggca atggattctg tcctgttgag ccgcggtgcc aacagttctt
11881 agatgaaatc attaagtaca caatgcaaga tgctctcttc ttgaaatatt atctcaaaaa
11941 tgtgggtgct caagaagact gtgttgatga acactttcaa gagaaaatct tatcttcaat
12001 tcagggcaat gaattttac atcaaatgtt tttctggtat gatctggcta ttttaactcg
12061 aagggggtaga ttaaatcgag gaaactctag atcaacatgg tttgttcatg atgatttaat
12121 agacatctta ggctatgggg actatgtttt ttggaagatc ccaatttcaa tgttaccact
12181 gaacacacaa ggaatccccc atgctgctat ggactggtat caggcatcag tattcaaaga
12241 agcggttcaa gggcatacac acattgtttc tgtttctact gccgacgtct tgataatgtg
12301 caaagattta attacatgtc gattcaacac aactctaatc tcaaaaatag cagagattga
12361 ggatccagtt tgttctgatt atcccaattt taagattgtg tctatgcttt accagagcgg
12421 agattactta ctctccatat tagggtctga tgggtataaa attattaagt tcctcgaacc
12481 attgtgcttg gccaaaaatc aattatgctc aaagtacact gagaggaagg gccgattctt
12541 aacacaaatg catttagctg taaatcacac cctagaagaa attacagaaa tgcgtgcact
12601 aaagccttca caggctcaaa agatccgtga attccataga acattgataa ggctggagat
12661 gacgccacaa caacttgtg agctatttc cattcaaaaa cactggggc atcctgtgct
12721 acatagtgaa acagcaatcc aaaaagttaa aaaacatgct acggtgctaa aagcattacg
12781 ccctatagtg attttcgaga catactgtgt ttttaaatat agtattgcca aacattattt
12841 tgatagtcaa ggatcttggt acagtgttac ttcagatagg aatctaacac cgggtcttaa
12901 ttcttatatc aaaagaaatc aattccctcc gttgccaatg attaaagaac tactatggga
12961 attttaccac cttgaccacc ctccactttt ctcaaccaaa attattagtg acttaagtat
13021 ttttataaaa gacagagcta ccgcagtaga aaggacatgc tgggatgcag tattcgagcc
13081 taatgttcta ggatataatc cacctcacaa atttagtact aaacgtgtac cggaacaatt
13141 tttagagcaa gaaaacttt ctattgagaa tgttctttcc tacgcacaaa aactcgagta
13201 tctactacca caatatcgga acttttcttt ctcattgaaa gagaaagagt tgaatgtagg
13261 tagaaccttc ggaaaattgc cttatccgac tcgcaatgtt caaacactt gtgaagctct
13321 gttagctgat ggtcttgcta aagcatttcc tagcaatatg atggtagtta cggaacgtga
13381 gcaaaaagaa agcttattgc atcaagcatc atggcaccac acaagtgatg attttggtga
13441 acatgccaca gttagaggga gtagctttgt aactgattta gagaaataca atcttgcatt
```

FIG. 2 CONTINUED

```
13501 tagatatgag tttacagcac cttttataga atattgcaac cgttgctatg gtgttaagaa
13561 tgtttttaat tggatgcatt atacaatccc acagtgttat atgcatgtca gtgattatta
13621 taatccacca cataacctca cactggagaa tcgagacaac cccccgaag ggcctagttc
13681 atacaggggt catatgggag ggattgaagg actgcaacaa aaactctgga caagtatttc
13741 atgtgctcaa atttctttag ttgaaattaa gactggtttt aagttacgct cagctgtgat
13801 gggtgacaat cagtgcatta ctgttttatc agtcttcccc ttagagactg acgcagacga
13861 gcaggaacag agcgccgaag acaatgcagc gagggtggcc gccagcctag caaaagttac
13921 aagtgcctgt ggaatctttt taaaacctga tgaaacattt gtacattcag gttttatcta
13981 ttttggaaaa aaacaatatt tgaatggggt ccaattgcct cagtcccta aaacggctac
14041 aagaatggca ccattgtctg atgcaatttt tgatgatctt caagggaccc tggctagtat
14101 aggcactgct tttgagcgat ccatctctga gacacgacat atctttcctt gcaggataac
14161 cgcagctttc catacgtttt tttcggtgag aatcttgcaa tatcatcatc tcgggttcaa
14221 taaaggtttt gaccttggac agttaacact cggcaaacct ctggatttcg gaacaatatc
14281 attggcacta gcggtaccgc aggtgcttgg agggtatcc ttcttgaatc ctgagaaatg
14341 tttctaccgg aatctaggag atccagttac ctcaggctta ctccagttaa aaacttatct
14401 ccgaatgatt gagatggatg atttattctt acctttaatt gcgaagaacc ctgggaactg
14461 cactgccatt gactttgtgc taaatcctag cggattaaat gtccctgggt cgcaagactt
14521 aacttcattt ctgcgccaga ttgtacgcag gaccatcacc ctaagtgcga aaaacaaact
14581 tattaatacc ttatttcatg cgtcagctga cttcgaagac gaaatggttt gtaaatggct
14641 attatcatca actcctgtta tgagtcgttt tgcggccgat atcttttcac gcacgccgag
14701 cgggaagcga ttgcaaattc taggatacct ggaaggaaca cgcacattat tagcctctaa
14761 gatcatcaac aataatacag agacaccggt tttggacaga ctgaggaaaa taacattgca
14821 aaggtggagc ctatggttta gttatcttga tcattgtgat aatatcctgg cggaggcttt
14881 aacccaaata acttgcacag ttgatttagc acagattctg agggaatatt catgggctca
14941 tattttagag ggaagacctc ttattggagc cacactccca tgtatgattg agcaattcaa
15001 agtgttttgg ctgaaaccct acgaacaatg tccgcagtgt tcaaatgcaa agcaaccagg
15061 tgggaaacca ttcgtgtcag tggcagtcaa gaaacatatt gttagtgcat ggccgaacgc
15121 atcccgaata agctggacta tcggggatgg aatcccatac attggatcaa ggacagaaga
15181 taagatagga caacctgcta ttaaaccaaa atgtccttcc gcagccttaa gagaggccat
15241 tgaattggcg tcccgtttaa catgggtaac tcaaggcagt tcgaacagtg acttgctaat
15301 aaaaccattt ttggaagcac gagtaaattt aagtgttcaa gaatacttc aaatgacccc
15361 ttcacattac tcaggaaata ttgttcacag gtacaacgat caatacagtc ctcattcttt
15421 catggccaat cgtatgagta attcagcaac gcgattgatt gtttctacaa acactttagg
15481 tgagttttca ggaggtggcc agtctgcacg cgacagcaat attattttcc agaatgttat
15541 aaattatgca gttgcactgt tcgatattaa atttagaaac actgaggcta cagatatcca
15601 atataatcgt gctcaccttc atctaactaa gtgttgcacc cgggaagtac cagctcagta
15661 tttaacatac acatctacat tggatttaga tttaacaaga taccgagaaa acgaattgat
15721 ttatgacagt aatcctctaa aaggaggact caattgcaat atctcattcg ataatccatt
15781 tttccaaggt aaacggctga acattataga agatgatctt attcgactgc ctcacttatc
15841 tggatgggag ctagccaaga ccatcatgca atcaattatt tcagatagca acaattcatc
15901 tacagaccca attagcagtg gagaaacaag atcattcact acccatttct taacttatcc
15961 caagatagga cttctgtaca gttttggggc ctttgtaagt tattatcttg gcaatacaat
16021 tcttcggact aagaaattaa cacttgacaa ttttttatat tacttaacta ctcaaattca
16081 taatctacca catcgctcat tgcgaatact taagccaaca ttcaaacatg caagcgttat
16141 gtcacggtta atgagtattg atcctcattt ttctgtttac ataggcggtg ctgcaggtga
16201 cagaggactc tcagatgcgg ccaggttatt tttgagaacg tccatttcat cttttcttac
```

FIG. 2 CONTINUED 16261 atttgtaaaa gaatggataa ttaatcgcgg aacaattgtc cctttatgga tagtatatcc
16321 gctagagggt caaaacccaa cacctgtgaa taattttctc tatcagatcg tagaactgct
16381 ggtgcatgat tcatcaagac aacaggcttt taaaactacc ataagtgatc atgtacatcc
16441 tcacgacaat cttgtttaca catgtaaagag tacagccagc aatttcttcc atgcatcatt
16501 ggcgtactgg aggagcagac acagaaacag caaccgaaaa tacttggcaa gagactcttc
16561 aactggatca agcacaaaca acagtgatgg tcatattgag agaagtcaag aacaaaccac
16621 cagagatcca catgatggca ctgaacggaa tctagtccta caaatgagcc atgaaataaa
16681 aagaacgaca attccacaag aaaacacgca ccagggtccg tcgttccagt cctttctaag
16741 tgactctgct tgtgggacag caaatccaaa actaaatttc gatcgatcga gacacaatgt
16801 gaaatttcag gatcataact cggcatccaa gagggaaggt catcaaataa tctcacaccg
16861 tctagtccta cctttcttta cattatctca agggacacgc caattaacgt catccaatga
16921 gtcacaaacc caagacgaga tatcaaagta cttacggcaa ttgagatccg tcattgatac
16981 cacagtttat tgtagattta ccggtatagt ctcgtccatg cattacaaac ttgatgaggt
17041 cctttgggaa atagagagtt tcaagtcggc tgtgacgcta gcagagggag aaggtgctgg
17101 tgccttacta ttgattcaga aataccaagt taagacctta tttttcaaca cgctagctac
17161 tgagtccagt atagagtcag aaatagtatc aggaatgact actcctagga tgcttctacc
17221 tgttatgtca aaattccata atgaccaaat tgagattatt cttaacaact cagcaagcca
17281 aataacagac ataacaaatc ctacttggtt taaagaccaa agagcaaggc tacctaagca
17341 agtcgaggtt ataaccatgg atgcagagac aacagagaat ataaacagat cgaaattgta
17401 cgaagctgta tataaattga tcttacacca tattgatcct agcgtattga aagcagtggt
17461 ccttaaagtc tttctaagtg atactgaggg tatgttatgg ctaaatgata attagcccc
17521 gttttttgcc actggttatt taattaagcc aataacgtca agtgctagat ctagtgagtg
17581 gtatctttgt ctgacgaact tcttatcaac tacacgtaag atgccacacc aaaaccatct
17641 cagttgtaaa caggtaatac ttacggcatt gcaactgcaa attcaacgaa gcccatactg
17701 gctaagtcat ttaactcagt atgctgactg tgagttacat ttaagttata tccgccttgg
17761 ttttccatca ttagagaaag tactatacca caggtataac ctcgtcgatt caaaaagagg
17821 tccactagtc tctatcactc agcacttagc acatcttaga gcagagattc gagaattaac
17881 taatgattat aatcaacagc gacaaagtcg gactcaaaca tatcacttta ttcgtactgc
17941 aaaaggacga atcacaaaac tagtcaatga ttatttaaaa ttctttctta ttgtgcaagc
18001 attaaaacat aatgggacat ggcaagctga gtttaagaaa ttaccagagt tgattagtgt
18061 gtgcaatagg ttctaccata ttagagattg caattgtgaa gaacgtttct tagttcaaac
18121 cttatattta catagaatgc aggattctga agttaagctt atcgaaaggc tgacagggct
18181 tctgagttta tttccggatg gtctctacag gtttgattga attaccgtgc atagtatcct
18241 gatacttgca aaggttggtt attaacatac agattataaa aaactcataa attgctctca
18301 tacatcatat tgatctaatc tcaataaaca actatttaaa taacgaaagg agtccctata
18361 ttatatacta tatttagcct ctctccctgc gtgataatca aaaaattcac aatgcagcat
18421 gtgtgacata ttactgccgc aatgaattta acgcaacata ataaactctg cactcttat
18481 aattaagctt taacgaaagg tctgggctca tattgttatt gatataataa tgttgtatca
18541 atatcctgtc agatggaata gtgtttttggt tgataacaca acttcttaaa acaaaattga
18601 tctttaagat taagttttt ataattatca ttactttaat ttgtcgtttt aaaaacggtg
18661 atagcctaa tctttgtgta aaataagaga ttaggtgtaa taaccttaac attttttgtct
18721 agtaagctac tatttcatac agaatgataa aattaaaaga aaaggcagga ctgtaaaatc
18781 agaaatacct tctttacaat atagcagact agataataat cttcgtgtta atgataatta
18841 agacattgac cacgctcatc agaaggctcg ccagaataaa cgttgcaaaa aggattcctg
18901 gaaaaatggt cgcacacaaa aatttaaaaa taaatctatt tcttctttt tgtgtgtcca (SEQ ID NO: 12)

MEASYERGRPRAARQHSRDGHDHHVRARSSSRENYRGEYRQSRS
ASQVRVPTVFHKKRVEPLTVPPAPKDICPTLKKGFLCDSSFCKKDHQLESLTDRE
LLL
LIARKTCGSVEQQLNITAPKDSRLANPTADDFQQEEGPKITLLTLIKTAEHWARQ
DIR
TIEDSKLRALLTLCAVMTRKFSKSQLSLLCETHLRREGLGQDQAEPVLEVYQRLH
SDK
GGSFEAALWQQWDRQSLIMFITAFLNIALQLPCESSAVVVSGLRTLVPQSDNEEA
STN
PGTCSWSDEGTP (SEQ ID NO:13)

L11365

```
   1 cggacacaca aaaagaaaga agaattttta ggatcttttg tgtgcgaata actatgagga
  61 agattaataa ttttcctctc attgaaattt atatcggaat ttaaattgaa attgttactg
 121 taatcacacc tggtttgttt cagagccaca tcacaaagat agagaacaac ctaggtctcc
 181 gaagggagca agggcatcag tgtgctcagt tgaaaatccc ttgtcaacac ctaggtctta
 241 tcacatcaca agttccacct cagactctgc agggtgatcc aacaacctta atagaaacat
 301 tattgttaaa ggacagcatt agttcacagt caaacaagca agattgagaa ttaaccttgg
 361 ttttgaactt gaacacttag gggattgaag attcaacaac cctaaagctt ggggtaaaac
 421 attggaaata gttaaaagac aaaattgctcg gaatcacaaa attccgagta tggattctcg
 481 tcctcagaaa atctggatgg cgccgagtct cactgaatct gacatggatt accacaagat
 541 cttgacagca ggtctgtccg ttcaacaggg gattgttcgg caaagagtca tcccagtgta
 601 tcaagtaaac aatcttgaag aaatttgcca acttatcata caggcctttg aagcaggtgt
 661 tgattttcaa gagagtgcgg acagtttcct tctcatgctt tgtcttcatc atgcgtacca
 721 gggagattac aaacttttct tggaaagtgg cgcagtcaag tatttggaag gcacgggtt
 781 ccgttttgaa gtcaagaagc gtgatggagt gaagcgcctt gaggaattgc tgccagcagt
 841 atctagtgga aaaaacatta agagaacact tgctgccatg ccggaagagg agacaactga
 901 agctaatgcc ggtcagtttc tctcctttgc aagtctattc cttccgaaat tggtagtagg
 961 agaaaaggct tgccttgaga aggttcaaag gcaaattcaa gtacatgcag agcaaggact
1021 gatacaatat ccaacagctt ggcaatcagt aggacacatg atggtgattt ccgtttgat
1081 gcgaacaaat ttctgatca aatttctcct aatacaccaa gggatgcaca tggttgccgg
1141 gcatgatgcc aacgatgctg tgattcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgacttttga accttctgg
1381 agtaaataat cttgagcatg gtctttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaagaa
1621 cgaaatcagc ttccagcaaa caaacgctat ggtaactcta agaaagagc gcctggccaa
1681 gctgacagaa gctatcactg ctgcgtcact gcccaaaaca agtggacatt acgatgatga
1741 tgacgacatt cccttccag gacccatcaa tgatgacgac aatcctggcc atcaagatga
```

FIG. 2 CONTINUED

```
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca acacccagtc
2401 agaacactct tttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gattgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttattttg
2821 aatttaaagc tagccttatt attactagcc gttttcaaa gttcaatttg agtcttaatg
2881 caaataggcg ttaagccaca gttatagcca taattgtaac tcaatattct aactagcgat
2941 ttatctaaat taaattacat tatgcttta taacttacct actagcctgc ccaacattta
3001 cacgatcgtt ttataattaa gaaaaaacta atgatgaaga ttaaaaccctt catcatcctt
3061 acgtcaattg aattctctag cactcgaagc ttattgtctt caatgtaaaa gaaaagctgg
3121 tctaacaaga tgacaactag aacaaagggc aggggccata ctgcggccac gactcaaaac
3181 gacagaatgc caggccctga gctttcgggc tggatctctg agcagctaat gaccggaaga
3241 attcctgtaa gcgacatctt ctgtgatatt gagaacaatc caggattatg ctacgcatcc
3301 caaatgcaac aaacgaagcc aaacccgaag acgcgcaaca gtcaaaccca aacggaccca
3361 atttgcaatc atagttttga ggaggtagta caaacattgg cttcattggc tactgttgtg
3421 caacaacaaa ccatcgcatc agaatcatta gaacaacgca ttacgagtct tgagaatggt
3481 ctaaagccag tttatgatat ggcaaaaaca atctcctcat tgaacagggt ttgtgctgag
3541 atggttgcaa aatatgatct tctggtgatg acaaccggtc gggcaacagc aaccgctgcg
3601 gcaactgagg cttattgggc cgaacatggt caaccaccac ctggaccatc actttatgaa
3661 gaaagtgcga ttcggggtaa gattgaatct agagatgaga ccgtccctca aagtgttagg
3721 gaggcattca acaatctaaa cagtaccact tcactaactg aggaaaattt tgggaaacct
3781 gacatttcgg caaaggattt gagaaacatt atgtatgatc acttgcctgg ttttggaact
3841 gcttccacc aattagtaca agtgatttgt aaattgggaa aagatagcaa ctcattggac
3901 atcattcatg ctgagttcca ggccagcctg gctgaaggag actctcctca atgtgcccta
3961 attcaaatta caaaaagagt tccaatcttc caagatgctg ctccaccctgt catccacatc
4021 cgctctcgag gtgacattcc ccgagcttgc cagaaaagct tgcgtccagt cccaccatcg
4081 cccaagattg atcgaggttg ggtatgtgtt tttcagcttc aagatggtaa aacacttgga
4141 ctcaaaattt gagccaatct cccttccctc cgaaagaggc gaataatagc agaggcttca
4201 actgctgaac tatagggtac gttacattaa tgatacactt gtgagtatca gccctggata
4261 atataagtca attaaacgac caagataaaa ttgttcatat ctcgctagca gcttaaaata
4321 taaatgtaat aggagctata tctctgacag tattataatc aattgttatt aagtaaccca
4381 aaccaaaagt gatgaagatt aagaaaaacc tacctcggct gagagagtgt tttttcatta
4441 accttcatct tgtaaacgtt gagcaaaaatt gttaaaaata tgaggcgggt tatattgcct
4501 actgctcctc ctgaatatat ggaggccata taccctgtca ggtcaaattc aacaattgct
```

FIG. 2 CONTINUED 4561 agaggtggca acagcaatac aggcttcctg acaccggagt cagtcaatgg ggacactcca
4621 tcgaatccac tcaggccaat tgccgatgac accatcgacc atgccagcca cacaccaggc
4681 agtgtgtcat cagcattcat ccttgaagct atggtgaatg tcatatcggg ccccaaagtg
4741 ctaatgaagc aaattccaat ttggcttcct ctaggtgtcg ctgatcaaaa gacctacagc
4801 tttgactcaa ctacggccgc catcatgctt gcttcataca ctatcaccca tttcggcaag
4861 gcaaccaatc cacttgtcag agtcaatcgg ctgggtcctg gaatcccgga tcatcccctc
4921 aggctcctgc gaattggaaa ccaggctttc tccaggagt tcgttcttcc gccagtccaa
4981 ctaccccagt atttcacctt tgatttgaca gcactcaaac tgatcaccca accactgcct
5041 gctgcaacat ggaccgatga cactccaaca ggatcaaatg gggcgttgcg tccaggaatt
5101 tcatttcatc caaaacttcg ccccattctt ttacccaaca aaagtgggaa gaaggggaac
5161 agtgccgatc taacatctcc ggagaaaatc caagcaataa tgacttcact ccaggacttt
5221 aagatcgttc caattgatcc aaccaaaaat atcatgggaa tcgaagtgcc agaaactctg
5281 gtccacaagc tgaccggtaa gaaggtgact tctaaaaatg gacaaccaat catccctgtt
5341 cttttgccaa agtacattgg gttggacccg gtggctccag gagacctcac catggtaatc
5401 acacaggatt gtgacacgtg tcattctcct gcaagtcttc cagctgtgat tgagaagtaa
5461 ttgcaataat tgactcagat ccagttttat agaatcttct cagggatagt gcataacatc
5521 tatttagtaa tccgtccatt agaggagaca cttttaattg atcaatatac taaaggtgct
5581 ttacaccatt gtctttttc tctcctaaat gtagaactta acaaaagact cataatatac
5641 ttgtttttaa aggattgatt gatgaaagat cataactaat aacattacaa ataatcctac
5701 tataatcaat acggtgattc aaatgttaat ctttctcatt gcacatactt tttgccctta
5761 tcctcaaatt gcctgcatgc ttacatctga ggatagccag tgtgacttgg attggaaatg
5821 tggagaaaaa atcgggaccc atttctaggt tgttcacaat ccaagtacag acattgccct
5881 tctaattaag aaaaaatcgg cgatgaagat taagccgaca gtgagcgtaa tcttcatctc
5941 tcttagatta tttgttttcc agagtagggg tcgtcaggtc ctttcaatc gtgtaaccaa
6001 aataaactcc actagaagga tattgtgggg caacaacaca atgggcgtta caggaatatt
6061 gcagttacct cgtgatcgat tcaagaggac atcattcttt ctttgggtaa ttatcctttt
6121 ccaaagaaca ttttccatcc cacttggagt catccacaat agcacattac aggttagtga
6181 tgtcgacaaa ctagtttgtc gtgacaaact gtcatccaca aatcaattga gatcagttgg
6241 actgaatctc gaagggaatg gagtggcaac tgacgtgcca tctgcaacta aaagatgggg
6301 cttcaggtcc ggtgtcccac caaaggtggt caattatgaa gctggtgaat gggctgaaaa
6361 ctgctacaat cttgaaatca aaaaacctga cgggagtgag tgtctaccag cagcgccaga
6421 cgggattcgg ggcttcccc ggtgccggta tgtgcacaaa gtatcaggaa cgggaccgtg
6481 tgccggagac tttgccttcc ataaagaggg tgctttcttc ctgtatgatc gacttgcttc
6541 cacagttatc taccgaggaa cgactttcgc tgaaggtgtc gttgcatttc tgatactgcc
6601 ccaagctaag aaggacttct tcagctcaca ccccttgaga gagccggtca atgcaacgga
6661 ggaccccgtct agtggctact attctaccac aattagatat caggctaccg gttttggaac
6721 caatgagaca gagtacttgt tcgaggttga caattgacc tacgtccaac ttgaatcaag
6781 attcacacca cagtttctgc tccagctgaa tgagacaata tatacaagtg ggaaaaggag
6841 caataccacg ggaaaactaa tttggaaggt caacccccgaa attgataca caatcgggga
6901 gtgggccttc tgggaaacta aaaaaaaacct cactagaaaa attcgcagtg aagagttgtc
6961 tttcacagtt gtatcaaacg gagccaaaaa catcagtggt cagagtccgg cgcgaacttc
7021 ttccgaccca gggaccaaca caacaactga agaccacaaa atcatggctt cagaaaattc
7081 ctctgcaatg gttcaagtgc acagtcaagg aagggaagct gcagtgtcgc atctaacaac
7141 ccttgccaca atctccacga gtccccaatc cctcacaacc aaaccaggtc cggacaacag
7201 cacccataat acaccgtgt ataaacttga catctctgag gcaactcaag ttgaacaaca
7261 tcaccgcaga acagacaacg acagcacagc ctccgacact ccctctgcca cgaccgcagc

FIG. 2 CONTINUED

```
7321 cggaccccca aaagcagaga acaccaacac gagcaagagc actgacttcc tggacccgc
7381 caccacaaca agtcoccaaa accacagcga gaccgctggc aacaacaaca ctcatcacca
7441 agataccgga gaagagagtg ccagcagcgg gaagctaggc ttaattacca atactattgc
7501 tggagtcgca ggactgatca caggcgggag aagaactcga agagaagcaa ttgtcaatgc
7561 tcaacccaaa tgcaacccta atttacatta ctggactact caggatgaag gtgctgcaat
7621 cggactggcc tgataccat atttcgggcc agcagccgag ggaatttaca tagaggggct
7681 aatgcacaat caagatggtt taatctgtgg gttgagacag ctggccaacg agacgactca
7741 agctcttcaa ctgttcctga gagccacaac tgagctacgc acctttcaa tcctcaaccg
7801 taaggcaatt gatttcttgc tgcagcgatg gggcggcaca tgccacattc tgggaccgga
7861 ctgctgtatc gaaccacatg attggaccaa gaacataaca gacaaaattg atcagattat
7921 tcatgatttt gttgataaaa cccttccgga ccaggggggac aatgacaatt ggtggacagg
7981 atggagacaa tggataccgg caggtattgg agttacaggc gttataattg cagttatcgc
8041 tttattctgt atatgcaaat ttgtcttta gttttcttc agattgcttc atggaaaagc
8101 tcagcctcaa atcaatgaaa ccaggattta attatatgga ttacttgaat ctaagattac
8161 ttgacaaatg ataatataat acactggagc tttaaacata gccaatgtga ttctaactcc
8221 tttaaactca cagttaatca taaacaaggt ttgacatcaa tctagttatc tctttgagaa
8281 tgataaactt gatgaagatt aagaaaaagg taatctttcg attatcttta atcttcatcc
8341 ttgattctac aatcatgaca gttgtcttta gtgacaaggg aaagaagcct ttttattaag
8401 ttgtaataat cagatctgcg aaccggtaga gtttagttgc aacctaacac acataaagca
8461 ttggtcaaaa gtcaatagaa atttaaacag tgagtggaga caacttttaa atggaagctt
8521 catatgagag aggacgccca cgagctgcca gacagcattc aagggatgga cacgaccacc
8581 atgttcgagc acgatcatca tccagagaga attatcgagg tgagtaccgt caatcaagga
8641 gcgcctcaca agtgcgcgtt cctactgtat ttcataagaa gagagttgaa ccattaacag
8701 ttcctccagc acctaaagac atatgtccga ccttgaaaaa aggattttg tgtgacagta
8761 gttttgcaa aaaagatcac cagttggaga gtttaactga tagggaatta ctcctactaa
8821 tcgcccgtaa gacttgtgga tcagtagaac aacaattaaa tataactgca cccaaggact
8881 cgcgcttagc aaatccaacg gctgatgatt ccagcaaga ggaaggtcca aaaattacct
8941 tgttgacact gatcaagacg gcagaacact gggcgagaca agacatcaga accatagagg
9001 attcaaaatt aagagcattg ttgactctat gtgctgtgat gacgaggaaa ttctcaaaat
9061 cccagctgag tctttatgt gagacacacc taaggcgcga gggggcttggg caagatcagg
9121 cagaacccgt tctcgaagta tatcaacgat tacacagtga taaaggaggc agttttgaag
9181 ctgcactatg gcaacaatgg gaccgacaat ccctaattat gtttatcact gcattcttga
9241 atattgctct ccagttaccg tgtgaaagtt ctgctgcgtt gtttcagggt taagaacatt
9301 ggttcctcaa tcagataatg aggaagcttc aaccaacccg gggacatgct catggtctga
9361 tgagggtacc ccttaataag gctgactaaa acactatata accttctact tgatcacaat
9421 actccgtata cctatcatca tatatttaat caagacgata tcctttaaaa cttattcagt
9481 actataatca ctctcgtttc aaattaataa gatgagcatg attgccctaa tatatgaaga
9541 ggtatgatac aacccctaaca gtgatcaaag aaaatcataa tctcgtatcg ctcgtaatat
9601 aacctgccaa gcatacctct tgcacaaagt gattcttgtc cacaaataat gttttactct
9661 acaggaggta gcaacgatcc atcccatcaa aaaataagta ttcatgact tactaatgat
9721 ctcttaaaat attaagaaaa actgacggaa cataaattct ttatgcttca agctgtggag
9781 gaggtgtttg gtattggcta ttgttatatt acaatcaata acaagcttgt aaaaatattg
9841 ttcttgtttc aagaggtaga ttgtgaccgg aaatgctaaa ctaatgatga agattaatgc
9901 ggaggtctga taagaataaa ccttattatt cagattaggc cccaagaggc attcttcatc
9961 tccttttagc aaagtactat ttcagggtag tccaattagt ggcacgtctt ttagctgtat
10021 atcagtcgcc cctgagatac gccacaaaag tgtctctaag ctaaattggt ctgtacacat
```

FIG. 2 CONTINUED

10081 cccatacatt gtattagggg caataatatc taattgaact tagccgttta aaatttagtg
10141 cataaatctg ggctaacacc accaggtcaa ctccattggc tgaaaagaag cttacctaca
10201 acgaacatca ctttgagcgc cctcacaatt aaaaaatagg aacgtcgttc caacaatcga
10261 gcgcaaggtt tcaaggttga actgagagtg tctagacaac aaaatattga tactccagac
10321 accaagcaag acctgagaaa aaaacatggc taaagctacg ggacgataca atctaatatc
10381 gcccaaaaag gacctggaga aagggggttgt cttaagcgac ctctgtaact tcttagttag
10441 ccaaactatt caggggtgga aggtttattg ggctggtatt gagtttgatg tgactcacaa
10501 aggaatggcc ctattgcata gactgaaaac taatgactttt gccctgcat ggtcaatgac
10561 aaggaatctc tttcctcatt tatttcaaaa tccgaattcc acaattgaat caccgctgtg
10621 ggcattgaga gtcatccttg cagcagggat acaggaccag ctgattgacc agtctttgat
10681 tgaaccctta gcaggagccc ttggtctgat ctctgattgg ctgctaacaa ccaacactaa
10741 ccatttcaac atgcgaacac aacgtgtcaa ggaacaattg agcctaaaaa tgctgtcgtt
10801 gattcgatcc aatattctca gtttattaa caattggat gctctacatg tcgtgaacta
10861 caacggattg ttgagcagta ttgaaattgg aactcaaaat catacaatca tcataactcg
10921 aactaacatg ggttttctgg tggagctcca agaacccgac aaatcggcaa tgaaccgcat
10981 gaagcctggg ccggcgaaat ttccctcct tcatgagtcc acactgaaag catttacaca
11041 aggatcctcg acacgaatgc aaagtttgat tcttgaattt aatagctctc ttgctatcta
11101 actaaggtag aatacttcat attgagctaa ctcatatatg ctgactcaat agttatcttg
11161 acatctctgc tttcataatc agatatataa gcataataaa taatactca tatttcttga
11221 taatttgttt aaccacagat aaatcctcac tgtaagccag cttccaagtt gacaccctta
11281 caaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaaccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacatacca ataccccagac gctaggttat catcaccaat tgtattggac
11641 caatgtgacc tagtcactag agcttgcggg ttatattcat catactcct taatccgcaa
11701 ctacgcaact gtaaactccc gaaacatatc taccgtttga aa (SEQ ID NO:14)

VP30

MEASYERGRPRAARQHSRDGHDHHVRARSSSRENYRGEYRQSRS
ASQVRVPTVFHKKRVEPLTVPPAPKDICPTLKKGFLCDSSFCKKDHQLESLTDRE
LLL
LIARKTCGSVEQQLNITAPKDSRLANPTADDFQQEEGPKITLLTLIKTAEHWARQ
DIR
TIEDSKLRALLTLCAVMTRKFSKSQLSLLCETHLRREGLGQDQAEPVLEVYQRLH
SDK
GGSFEAALWQQWDRQSLIMFITAFLNIALQLPCESSAALFQG (SEQ ID NO:15)

NC_001608

1 gacacacaaa aacaagagat gatgattttg tgtatcatat aaataaagaa gaatattaac
61 attgacattg agactgtca gtctgttaat attcttgaaa agatggattt acatagcttg
121 ttagagttgg gtacaaaacc cactgccccct catgttcgta ataagaaggt gatattattt
181 gacacaaatc atcaggttag tatctgtaat cagataatag atgcaataaa ctcagggatt

FIG. 2 CONTINUED

```
 241 gatcttggag atcttctaga aggggggtttg ctgacgttgt gtgttgaaca ttactataat
 301 tccgataaag ataaattcaa cacaagtcct atcgcaaaat acttgcgtga tgcgggctat
 361 gagtttgatg tcgtcaagaa tgcagatgca acccgctttc tggatgtgat tcctaacgaa
 421 cctcattaca gtcctttaat tttggcccttt aagacattgg aaagtactga atctcagagg
 481 gggagaattg ggctctttt gtcatttgc agtcttttc tcccgaaact tgttgtcgga
 541 gatcgggcta gtatcgaaaa ggcttaaga caagtaacag tacatcaaga acaggggatc
 601 gtcacatacc ctaatcactg gcttactaca ggccatatga aagtaatttt tgggatttg
 661 aggtctagct ttatcttaaa atttgtgtta attcatcaag gagtaaattt ggtgacaggt
 721 catgatgcct atgacagtat cattagtaat tcagtaggtc aaactagatt ctcaggactt
 781 cttattgtga aaacagttct tgagttcatc ttgcaaaaaa ctgattcagg ggtgacacta
 841 catcctttgg tgcggacctc caaagtaaaa aatgaagttg ctagtttcaa gcaggcgttg
 901 agcaacctag cccgacatgg agaatacgca ccgttcgcac gggtctgaa tttatcaggg
 961 attaacaacc tcgaacatgg actctatcct cagctttcgg cgattgcgct gggtgttgca
1021 acagcacacg gcagtacatt ggctggtgtc aatgttggcg aacagtatca acagctacga
1081 gaggcggcac atgatgcgga aataaaacta caaaggcgac atgaacatca ggaaattcaa
1141 gctattgcag aggatgatga ggagaggaag atattagaac aattccacct tcagaaaact
1201 gaaatcacac acagtcagac actagccgtc ctcagccaga aacgagaaaa attagctcgt
1261 cttgctgcag aaattgaaaa caatatattgtg gaagatcagg gatttaaaca atcacagaat
1321 caggtgtcac agtcgttttt gaatgacccct acacctgtgg aagtaacggt tcaagccagg
1381 cccataaatc gaccaactgc tctgcctccc ccagttgaca acaaaattga gcacgaatct
1441 acagaagata gctcttcttc aagcagcttt gttgatctta atgatccatt tgcgctgctg
1501 aatgaggacg aagacactct tgacgcacagt gtcatgatcc cgagcacaac atcgagagaa
1561 tttcaaggga ttccagcacc accaagacaa tctcaggacc tcaacaacag ccaaggaaag
1621 caggaagatg aatcaacaaa tccgattaag aaacagtttc tgagatatca agaactgcct
1681 ccggttcaag aggatgatga atcggaatac acaaccgact ctcaggagag tatcgaccaa
1741 ccaggatctg acaatgaaca aggagttgat cttccacctc ctccattgta cgctcaggaa
1801 aaaaggcaag atccaataca gcacccagca gtaagctctc aggatccctt tggcagtatt
1861 ggtgatgtaa atggtgatat cttagaaccc ataagatcac cttcttcacc atctgctcct
1921 caggaagaca caagggcaag agaagcctat gaattgtcgc ctgatttcac aaattatgag
1981 gacaatcagc agaattggcc acaaagagtg gtgacaaaga agggtaggac tttcctttat
2041 cctaatgatc ttctgcagac aaatcctcca gaatcactta taacagccct cgtagaggaa
2101 taccaaaatc ctgtctcagc taaggagctc caagcagatt ggcccgacat gtcatttgat
2161 gaaaggagac atgttgctat gaacttgtag tccagataac acagcacggt tacctactta
2221 tctactttga tccgattcgt cctcagatca cagtaatcaa atttatttga atattcaaac
2281 tacttttag gatcctatta cttgttacta ttgtgtgaga caacataagc tatcaaataa
2341 caatcacggg caagaaccgg gctactatg gtgatgcgag ggcattattc agtgctacaa
2401 attcttttt caattgctat aatgatacaa ctacgaacct ccatacattt gccgcaatac
2461 tgtaatcaac actgctgtat ctctccttca agccatctga tttaacttaa taaacatgac
2521 ttgattcaga gagtgtgctg aaaatgttat tgattgagct tctcaaatgg tgcactatcc
2581 tactgttttg ctcagcctag tatactgtaa catataagtg gactctccac ttctcttctc
2641 gagtattccc tataagtgat ttacttgata gaatgtcaag tccactggtt tggagtttcc
2701 ttactctaat gattgtaata attaactgtt ggcttagatg ataacagata cgaggttata
2761 taattactca tagtataaag tataattctt gcctctgttt cttctgtttt ctcttttcctt
2821 tgtaatatgc caattaagaa aaactaaaaa tcgaagaata ttaaaggttt tctttaatat
2881 tcagaaaagg tttttattc tcttctttct ttttgcaaac atattgaaat aataatttc
2941 acaatgtggg actcatcata tatgcaacaa gtcagtgagg ggttgatgac tggaaaagtt
```

FIG. 2 CONTINUED

```
3001 cccatagatc aagtgtttgg tgccaatccc tcagagaagt tacacaagag aaggaaacca
3061 aaaggcacag ttggactaca atgcagccct tgtctaatgt caaaggcgac aagcactgat
3121 gatattgttt gggaccaact gatcgtgaag aaaacactag ctgatctact tataccgata
3181 aataggcaga tatcggacat tcaaagcact ctaaacgaag taacaacaag agtccatgaa
3241 attgagcggc aattacatga gataacccca gtgttaaaaa tgggaaggac actggaagca
3301 atttccaagg ggatgtcaga aatgttagcc aaatacgacc acctcgtaat ttcaactgga
3361 agaaccactg caccagctgc tgcctttgat gcttacttaa atgagcatgc tgtccctccc
3421 ccccaacctg cgattttcaa agatcttggg gttgctcaac aagcttgtag taaggggacc
3481 atggttaaaa atgaaacaac agatgcagcc gacaagatgt cgaaagttct tgaactcagt
3541 gaggagacgt tctccaagcc aaatctttca gctaaggatt tagcccttt gttgtttacc
3601 catctacccg gcaacaacac tccattccat atcctagctc aagtcctttc aaaaattgct
3661 tacaagtcag gaaagtccgg agcattttg gatgcatttc accagattct aagtgaagga
3721 gagaatgctc aggcagcatt gactcgacta agcagaacat ttgatgcttt cctcggagta
3781 gttcctccag tgataagagt caaaaacttc caaacagtcc ctcgcccatg tcaaaaaagt
3841 cttcgggctg ttcctcccaa cccaacaatt gacaaaggat gggtctgtgt ttattcatct
3901 gagcaaggtg agacacgggc cctgaaaatc taattctcat tgttaacagt tgcaggggga
3961 gtgatctttc cgagttgata caaagacact aaacatttca aaagcatata tgtgggcaaa
4021 acgtgactag accatcttaa tagaagtagt aatttatttc tgtcttaagt gtgattttca
4081 ccttgaaaga gttaaatggt gatagattaa tccttgaagt aactttttta tatattatag
4141 aggaactaat attactaaca aaaggggtct acctaacagg tatgactgag tgatcagtat
4201 attttataaa ccaagcaatt gacttctcac tttttaagaa tcaactaaca acatagaaaa
4261 catatttatc cttgtgtaat tctcggctta gttggaatta acttttgttg caattcaaga
4321 cgcttattca tagtagatta tatgattttt tataagttta agatatctta aattataccc
4381 acaagagata ctgttttaat taagaaaaac tatgaagaac attaagaaga tctttctctc
4441 gtagtgttct tttactggaa ggagtatccc aatctcagct tgttgaatta attgttactt
4501 aagtcattct tttaaaatt aattcacaca aggtagtttg ggtttatatc tagaacaaat
4561 tttaatatgg ccagttccag caattacaac acatacatgc aatacttgaa ccccctcct
4621 tatgctgatc acggtgcaaa ccagttgatc ccggcggatc agctatcaaa tcagcagggt
4681 ataactccaa attatgtggg tgacttaaac ctagatgatc agttcaaagg gaatgtctgc
4741 catgctttca ctttagaggc aataattgac atatctgcgt ataatgaacc aacagtcaaa
4801 ggtgttccag catggctgcc tctcgggatt atgagcaatt ttgaatatcc tttagctcat
4861 actgtggctg cgttgctcac aggcagctat acaatcaccc aatttactca taatgggcaa
4921 aaattcgtcc gtgtaaatcg actcggtaca ggaatcccag cacacccact cagaatgttg
4981 cgtgaaggaa atcaagcttt tattcagaat atggtgatcc ccagaaattt ttccactaat
5041 caattcacct acaatctcac taacttagta ttgagtgtgc aaaagcttcc tgatgatgcc
5101 tggcgcccat ccaaggacaa attaattggg aacaccatgc atcccgcagt ctccatacac
5161 ccgaatttgc caccccattgt tctaccaaca gtcaagaagc aggcttatcg tcagcataaa
5221 aatcccaaca atggaccact gctggccata tctggcatcc ttcaccaact gagggtcgag
5281 aaagtcccag agaagacaag cctgtttagg atttcacttc ctgccgatat gtctcagta
5341 aaagaaggta tgatgaagaa aaggggagaa aattccccgg tggttatttt tcaagcacct
5401 gagaacttcc ctttgaatgg cttcaacaac agacaagttg tactagcgta tgcgaatcca
5461 acgctcagtg ccgtttgaaa taatgctcaa atgagacagg agtccatctg cataagaagc
5521 atggcctaaa tgggtgtctg ttaagttctc acaagattag tttgtattga ttcaataat
5581 gctttaacct tacattgctg ctttaaatgg ttaattaagc tgatcagctt gcaagatgta
5641 atctcttttg ggtcatcaga tctataatgg gtttactaga ttatataaaa gaatagtaa
5701 tgttttataa acaattcttg cttagtttta ctttgattta ctaacatata tcattgtgcc
```

FIG. 2 CONTINUED

```
5761 cttcattgct aagtaaactc aactgatgat gatattcctt ctgaaatagt aagaaaaact
5821 aatgaagaac attaattgcc gggtaagagt gattaagttc tttaaatttg accaaagtaa
5881 tgttttgtta gtgaatacat tcttatattg cttgattaaa aacaagaaat tatcctaaca
5941 tgaagaccac atgtctcttt atcagtcttta tcttaatcca agggataaaa actctcccta
6001 ttttagagat agctagtaac aatcaacccc aaaatgtgga ttcggtatgc tccggaactc
6061 tccagaagac agaagatgtc catctgatgg gattcacact gagtgggcaa aaagttgctg
6121 attccccttt ggaggcatcc aagcgatggg ctttcaggac aggtgtacct cccaagaatg
6181 ttgagtatac agaagggggag gaagccaaaa catgctacaa tataagtgta acggatccct
6241 ctggaaaatc cttgctgttg gatcctccta ccaacatccg tgactatcct aaatgcaaaa
6301 ctatccatca tattcaaggt caaaaccctc atgcgcaagg gatcgccctc catttgtggg
6361 gagcattttt cctgtatgat cgcattgcct ccacaacaat gtaccgaggc agagtcttca
6421 ctgaagggaa catagcagct atgattgtca ataagacagt gcacaaaatg attttctcga
6481 ggcaaggaca ggggtaccgt cacatgaatc tgacttctac taataaatat tggacaagta
6541 acaatggaac acaaacgaat gacactggat gcttcggtgc tcttcaagaa tacaactcca
6601 cgaagaatca aacatgtgct ccgtccaaaa tacctcacc actgccaca gccgtccag
6661 agatcaaacc cacaagcacc ccaactgatg ccaccacact caacaccaca gacccaaaca
6721 atgatgatga ggacctcata acatccggtt cagggtccgg agaacaggaa ccctatacaa
6781 cttcagatgc ggtcactaag caagggcttt catcaacaat gccacccact ccctcaccac
6841 aaccaagcac gccacagcaa gaaggaaaca acacagacca ttcccaaggt actgtgactg
6901 aacccaacaa aaccaacaca acggcacaac cgtccatgcc ccccacaac accactgcaa
6961 tctctactaa caaacctcc aagaacaact tcagcaccct ctctgtatca ctacaaaaca
7021 ccaccaatta cgacacacag agcacagcca ctgaaaatga acaaaccagt gcccctcga
7081 aaacaaccct gcctccaaca ggaaatctta ccacagcaaa gagcactaac aacacgaaag
7141 gccccaccac aacggcacca aatatgacaa atgggcattt aaccagtccc tcccccaccc
7201 ccaacccgac cacacaacat cttgtatatt tcagaaagaa acgaagtatc ctctggaggg
7261 aaggcgacat gtttccttt ctggacgggt taataaatgc tccaattgat tttgatccag
7321 ttccaaatac aaagacgatc tttgatgaat cttctagttc tggtgcttcg gctgaggaag
7381 atcaacatgc ctccccaat atcagtttaa ctttatccta tttctaat ataaatgaaa
7441 acactgccta ctctggagaa aatgagaacg attgtgatgc agagttaaga atttggagcg
7501 ttcaggagga tgacctggca gcagggctca gttggatacc gttttttggc cctggaatcg
7561 aaggacttta tactgctggt ttaattaaaa accaaaacaa tttggtctgc aggttgaggc
7621 gtctagccaa tcaaactgcc aaatccttgg aactcttatt aagagtcaca accgaggaaa
7681 ggacattttc cttaattaat agacatgcca ttgacttcta actcacaagg tggggaggaa
7741 catgcaaagt gcttggacct gattgttgca ttggaataga agacttgtcc aggaatattt
7801 cggaacaaat tgaccaaatc aaaaaagatg aacaaaaga ggggactggt tggggtctag
7861 gtggtaaatg gtggacatcc gactgggggt ttcttactaa cttgggcatt tgctactat
7921 tatccatagc tgtcttgatt gctctatcct gtatttgtcg tatctttacc aaatatatcg
7981 ggtaatatta agtgtgtatt gattaaagct ttaggacaat tgctactgag cccttcttct
8041 aatctactga aatcaacttg ggagattttt aagaagctga taatttaatg tgaatcagta
8101 gtttacgtat tgttgattgt tatggtttga tattcaattg ttatcatagt caagagtaac
8161 cttttctatt tgatgcatta atgttttaaa ctacctctta agcttttgtg gatggtttca
8221 atatgtgcgt agaggttaat ttaaagagat ttcttgttgc acagtttttt gtattactta
8281 cttgggcttg aagacatagt taagactggc cgaaaatgct ctccagtcaa ctccattccc
8341 cctcagaaga gacgtgccgt tcaaagagtc ttgatttata actaaccatt gtaagaatta
8401 atttactctt tccgttatac ttatctacat taattccttg aatgtccagc atcattaacg
8461 acttgtctta attcaatctt ttggatgcaa accataagga aaaatgagcc actttccctc
```

FIG. 2 CONTINUED

```
8521 tactctgaac taaggaaatt tctcttatca gcctaaaatc tgatccgtta ggtcatgggc
8581 ccttcataat ctgtttgagc atgaatgttg atcaaatgac caaataatag tgcatttgta
8641 tagattcaat tatcctttat taagaaaaag atagacagaa cacaaagaat tgataaaata
8701 ttactttgat caattttgcg aggaattata aaaatcttga gggacaaatt attgtaacgt
8761 agagtcgaag aacattaagt gttctttgtt agaattattc atccaagttg ttttgagtat
8821 actcgcttca atacaacttc ccttcatatt tgattcaaga tttaaaatgc aacaacccg
8881 tggaaggagt cgaactcgca accaccaaac cgcatcatct atatatcatg aaactcagtt
8941 gccctccaaa cctcactaca ccaatcatca tccacgtgca agatcgatga gctcaacccg
9001 cagtagtgca gaaagcagtc ccaccaatca tattcccccgt gctcgaccac cccaacatt
9061 caacttatcg aaaccccctc ctcctccaaa agacatgtgt aggaacatga aaattggatt
9121 gccgtgcact gatcccactt gtaatagaga tcatgaccttt gataatctaa caaatcgtga
9181 actttttgcta ttgatggccc gaaaaatgct ccccaataca gacaagactt ttagaagtct
9241 gcaggattgt gggtcaccgt ctctttctaa agggctctca aaagataaac aggagcaaac
9301 gaaagatgtg ttgaccttgg aaaaatctagg acacattctg aactacctcc acagatcaga
9361 tattgggaaa ttggatgaga catcactccg tgcagcatta agtttgacgt gcgctggaat
9421 tcgaaagacg aatagatcct tgatcaacac catgaccgaa ttacacatta accatgaaaa
9481 tctcccgcaa gaccaaaacg gtgttatcaa acagacatat acaggtattc accttgacaa
9541 aggaggtcaa ttcgaagccg ccttatggca aggttgggat aagagatcga tatctttatt
9601 cgtacaagca gctttatatg taatgaacaa tatcccttgt gaatcatcaa ccagtgtgca
9661 agcctcatac gatcatttta ttcttcctca aagtcaaagt aaaggacaat gattattgtt
9721 tgaaagttga caatcaaatc actttcagtt tttagtttca actcttattg cgagacttga
9781 acacaattct actaacttca ataagtgacc ccaaattcaa gtttactgaa gactacgacg
9841 ataataatca ccaattcatt gtaaattact cgattaaaat attcttaagc tatcttaaac
9901 ttgatgatgc agctctgttt caccttctg ttgatttcaa tgttacagct atatctaagt
9961 gtctaattaa caacttgtac ctctaaggaa aatcatgaag aacattaaga aaaaggatgt
10021 tcttattttt caactaaact tgcatatcct tgttgatac ccttgagaga caacttttga
10081 cactagatca cggatcaagc atatttcatt caaacacccc aaattttcaa tcatacacat
10141 aataaccatt ttagtagcgt tacctttcaa tacaatctag gtgattgtga aaagacttcc
10201 aaacatggca gaattatcaa cgcgttacaa cttgcctgca aatgttacgg aaaaaagcat
10261 aaatcttgac cttaattcca cagcacgatg gataaaagaa cccagtgttg ggggctggac
10321 agtgaagtgg ggaaactttg ttttccacat accaaatact gggatggcat tgttgcatca
10381 tttaaagtct aacttcgttg ttccagagtg gcaacaaaca aggaatctat tctcccacct
10441 ctttaaaaac ccaaagtcaa caattataga accgtcttg gctttgagga tcttgcttgg
10501 agttgctttg aaggatcaag aattacagca atcattaatt cctggattta gatctattgt
10561 tcatatgctt tcagaatggt tgctcctaga ggtaacgtcg gcaatccata ttagccccaa
10621 tctgttggga atctatttga cctcagacat gtttaagatt ctgatggcag gtgtgaaaaa
10681 tttctttaat aagatgttca ctcttcatgt tgtaaatgac cacggaaaac ccagcagtat
10741 tgaaataaag ttaactggac aacagatcat tatcactcgt gttaatatgg ggtttctagt
10801 ggaagtcagg aggattgata ttgaaccttg ttgtggtgag acagtcctct cagaatcagt
10861 tgttttgggg ctagtggctg aggcagttct aagagaacac agtcaaatgg agaagggcca
10921 accctcgat ctgacacaat acatgaacag caaaattgct atataagtgg cttaaattag
10981 catggatatt catagtttaa ccacataata atgttggagg cacagtacat tatagttaat
11041 tatccctgtat aacaaagaat ataccctaccc tgatttatat ttactggtat aaaatagtgg
11101 tatcatctta ttaaatagtt gtcatataac aggctgttcc tataatctga ttgtgagatt
11161 ataaacttgt agaattaccg tggatcacaa ctgttgcata tcttccaaaa tatatctttt
11221 gcaagcgatg tgtgcttgaa tacgtcgata taatacatac taataacgat tgattaagaa
```

FIG. 2 CONTINUED

```
11281 aaaccaatga tggatattaa atatccatca agcaggtgtc gcagaatacc aggggtttca
11341 tatgctgcca tatttactaa atcttacata ggattatatc attctcttcg atacacgtta
11401 tatctttagc aaagtaatga aaatagcctt gtcatgttag acgccagtta tccatcttaa
11461 gtgaatcctt tcttcaatat gcagcatcca actcaatatc ctgatgcaag gttgtcctcc
11521 cctataatcc tagaccagtg tgacttatta gccagaagtt tagggttgta tagtcattat
11581 tcacataatc cgaaattgcg taattgtagg attccacatc atatttaccg tttaaggaat
11641 tcgacagcat taaaaacatt tcttcagaac tgttcaatac tcaccgtccc ttttcattca
11701 atctgggatc atattttaac ttccattcaa tatgatgcaa ttaatcatgt tgatgatttt
11761 aaatacctat tgccctctga gctagtcaag tatgcaaatt gggacaacga gttcttgaag
11821 gcatatctta ataagatctt aggacttgac catgttttc cagcttctgc aaggtcacaa
11881 tgggaggatt tttctcctaa ggaaaatcct tattattggg ggatgctgtt actcgtgcat
11941 ttatctcaac ttgccaggag gataaaagga caaagagggt cattaagaag taactggaag
12001 tttataggaa cagatttaga gctgtttgga atagcagatt ttattatttt taaagttcca
12061 gtaaaaacaa taatccgaaa tgctgtaagc ttacaagctt caaaaccagg gttaagagta
12121 tggtaccgtg accaaaactt gaccccttat ctatgcgatg atgagtttat tgtaagcgtc
12181 gctagttatg aatgttttat catgattaaa gacgtcttca ttgagaggta taacacgtgg
12241 gaaatatgtg cccgcgcctg gctcgaagac agtgatggag ctgattatct ccctcttgat
12301 gtgttaggtg agttatacaa ccagggagat caaattattg ccatgtactt ggaagacggt
12361 ttcaaattga tcaaacactt ggaacccttg tgtgtcagct gtatacaaac acatggcatc
12421 tttacaccag gaaaatactg gttccaatca cagaggattg agtcatatta tgaggagctc
12481 tgtagtctca attggaaatt taaaatttca ggcaataaag ctgagtgtgc tcaaaacttt
12541 attaaaacta taattcaggg gaaattgact cctcaacaat actgtgaatt attctctcta
12601 caaaagcatt ggggtcaccc cgtttatac attgatgttg cactagataa ggttaaaaaa
12661 catgcgcaat ctgtaaaaat cttaaaacct aaagtcatgt ttgaaacttt ttgtgttttc
12721 aaatttatag tagcaaagaa tcattatcat tctcaaggat catggtataa aaccacaatg
12781 gatttgcatt taactccata tcttagacaa catattgtgt caaattcatt tccgtcacaa
12841 gccgaaattt atcagcatct ttgggagtgg tatttcgtgg agcatgaacc tcttttctca
12901 actaaaaataa taagtgattt aagtatttt ataaaagaca gggctactgc tgtgaaccag
12961 gagtgttggg acagtgtttt cgatagaagt gtattagggt ataaccctcc tgttagattt
13021 cagtcaaaga gagtgccaga gcaattttg ggccaagcag acttttcctt gaatcaaata
13081 ttggatttg ctgaaaagtt agaatatttg gctccttctt ataggaattt ttccttctca
13141 ttaaaagaaa aagagttgaa tataggaaga acttttggga aattaccata tcgtgtcaga
13201 aatgtccaaa cactcgcaga agccttgcta gcagatggac tagcaaaagc attccctagc
13261 aacatgatgg ttgttactga gagggaacag aaagaagcat tattgcatca ggcttcttgg
13321 caccacaatt cagcaagcat aggggaaaac gctatagtaa ggggtgcaag ttttgttact
13381 gatcttgaga aatacaacct tgccttccga tatgaattta acgacatttt catagactac
13441 tgtaatcgat gttatggtgt gaagaattta ttcgattgga tgcacttttt aataccacta
13501 tgttatatgc atgtcagtga tttttatagc ccaccacatt gcgtaacaga agataaccga
13561 aataacccac cggattgtgc taatgcttat cattatcact taggggtat agagggactt
13621 caacagaaat tgtggacatg tatatcatgt gcccagatca cccttgtaga gttaaaaact
13681 aaattaaaat taaaatccag tgttatgggt gataatcaat gtataacaac tctaagtctt
13741 tttccaattg atgctcccga cgattatcaa gagaacgaag ctgaattaaa tgcggcacga
13801 gttgctgtcg aattagctat tactacgggt tatgatggta tattttgaa gcctgaagaa
13861 acattgtcc attcagggtt catttatttt ggtaaaaagc aatacctcaa cggtgttcaa
13921 ctgccacaat cattgaaaac aatggcaaga tgtggaccct tatctgactc tatttttgat
13981 gatcttcaag gttccctggc cagtattggt acatcctttg agagaggaac aagtgagaca
```

FIG. 2 CONTINUED

```
14041 cggcacattt ttccgagtcg ttggatagct tcatttcatt caatgttagc aataaattta
14101 ttaaatcaga atcaccttgg gtttccccta gggttcagta ttgatatttc ttgtttcaaa
14161 aagcctctta ccttttcgga aaaattaatt gctcttataa cgcccaagt tctaggaggg
14221 ttatcatttt tgaatccgga gaaattgttc taccggaaca taagtgatcc gctcacttcg
14281 ggtctatttc aacttaagaa tgcattagaa tttcttgaaa aggaagaatt attctatatc
14341 ttgattgcta aaaaacctgg tttagcagat gcctcagatt tcgtcatgaa tccattaggc
14401 ttaaatgtac caggatcaag ggaaataata acgttcctta gacaaacagt tcgtgaaaat
14461 atcacgatca cgtcacaaaa tagaataata aattccctttt tcacatagg ttctgattta
14521 gaggaccaaa gggtgtgtga gtggcttta tcatcaaacc ccgtaatgag tcgatttgct
14581 gctgacatct tttcaagaac gcctagtgga aaacggcttc aggtcttagg ctatctggaa
14641 ggaacaagaa cattactagc ttctcggaca ataagtttaa ctacagaagg gacaatgttg
14701 atgaaattaa gggaattaac aagaaaccga tggaaaagct ggtttctta tattgatgca
14761 ttggacgatg atttatctga gtccttagaa aaattccacat gtactgttga tatagctaat
14821 ttcttgaggg catattcatg gctcgacgtc ttaaaaggga aaaggctaat tggtgccaca
14881 ttgccatgtt tactagagca atttaaggta aagtggatta atttgtctga ggatttaagg
14941 gaacaattta atatgtcttc agaatcagaa tcaactataa atttattgcc gtatgactgc
15001 aaggaactgc gacttggaag aagcaatgac acagagttaa actatgtcag ttgtgctctc
15061 gaccggaaag ttgtccagaa acatccctct gttaatcgtc tggcttggac aataggaaat
15121 cgagcaccgt ataggatc acggacagaa gacaagatcg gttatcctcc cttaagagta
15181 aattgtccat cagcggcact taagaagcc attgagatgg tttctagatt gttgtgggtg
15241 actcaaggca ctgcagaccg agaaaaattg cttattcctc tcctcaattc gagggtaaat
15301 ctggactatc agacagtgct taactttta cctacacact actcaggcaa catagttcat
15361 agatataatg accaatatgg acaacattcc tttatggcaa acaggatgag taatacatct
15421 acacgtgcaa ttatatcaac taacacactg ggcaaatatg ctggggggggg tcaagctgct
15481 gttgatagta atataatctt ccaaaatact atcaatttag gagtggcagt tttagatatt
15541 gcattatctc ttgctaaatt gtcgtcagca tcaaatgtca ctttccgttt gatgttaaat
15601 aagtgctgca cgcggcatgt gccatctgaa tacctatttt ttgataaacc tttagatgtg
15661 gatttgaaca agtatatgga caatgagtta gtttatgaca atgaccctct ttgcagtggg
15721 attaaaggga gattaggcag agtatcccga tcaacactct cgttgagttt gaatgtcagt
15781 gacattggtt cttatgactt tccaactatt gctgcatgga cactaggaga aactatagtc
15841 ggaagcattt tttctgatga gtcttctcaa agtacagatc caataagttc aggttgcaca
15901 aaaactttcg tcacacattt ccttgtgtat ccagttgaga gtattttta tgcattcggg
15961 gctaacttaa tagtagaaag tttaagtcta agtaggatca aatcaattaa gaacctctca
16021 gatttgacat tcctatatc atccacaatc aggaatttat cacatagatc acttcggatt
16081 cttcaatcta ccttccgaca tgaattggta ctcacccgac tagcccacca cataccgtta
16141 atttctttaa tgttaggggg ttctgcagga gagaaaagtt catcagatgc tgttcggcta
16201 tttctacag caagttacca gaatttcatc aacaacttca gttgtttgat gaaaaagggc
16261 cagtcatcac taccggtttg gctttacttt cctagtgaag ggcaacaatt aaaacctata
16321 ttaaaaatct tacagagatt atcagacttg ttatcacctg acaaagttca aaagcatcaa
16381 atcttagctg acacctgttg tccaattgac agcttttggg tctatccaag caagtccaca
16441 aggactaacc actattatgc aagcttaat tattggagag acaaagctaa taaggtcaag
16501 aatactcctt tttcgcattt gataaattgt tcatttcttg aacttcttc acacaccagt
16561 tcggtctctt ctaatcaaca agtgaccaat tcgaaatata ttgttcatcc agagaatatc
16621 cctgaaataa atgcaagaac caaattaata gattatggat caacagctct acaggggatg
16681 gatatcaaga tgccactctc ggagcaaaat ctggttggaa attgtcgacc atcaaagggc
16741 attagattca aggacaatcc aaaaacaaca aaacatgacc agggatttgt ggggaaggac
```

FIG. 2 CONTINUED 16801 tcttcaccgc gaccaatgtc ccctgaagac aacatgcaga ctcctgcata catacatagt
16861 tccccccat atcaaaccct tacaaaatca ccagatgtac atgaggactt tgatgcctcg
16921 aaggtaatct taaattctga aataaataac cttaaccta cggattgtac gcttaataca
16981 aagtcattga caactcctac cgggacagaa atcttaggta taagtccgtt cagatcctct
17041 agatattcat caacttccag ggaacggtct cgactatcta gagaacaagc ttcatatttg
17101 tatgttgatt gcagtaatat tccctctatc tctctagacc cgggttttca gaatatgtct
17161 gatcagaatc aagttcaaat gttaatcaat acctacaaac gtgatttaca tgcttgtttt
17221 gatagcaatc aattctgtcg gtttacaggg gtagtctcat caatgcatta caagctttat
17281 gatctcttgc ctccaggtga attgagaaag gcaatttgct tggccgaagg agaaggaagt
17341 ggtgctcggt tactttgaa gtggaagaag acggattatt tattttcaa cactttggct
17401 acggattcac agcaagaagc agagatttta agtggccggg taataccgag aatgttatat
17461 aacatagata ggttaaatgc tttgcttgaa tcaagaagat taatattgaa caacctaact
17521 atccaaatta cagatattac aagtccacta tggctagatt ctgtaataca atacttacct
17581 gaagatagcg acattcttac aatggacgca gagaccacta aagatgaaac aagggaacag
17641 ctttataaga ctattgtgaa tatttggaca cgtacttctc ctaatattcc aaaaattagc
17701 atcatcaagg tatttttatt agactatgaa gggactttgt tcttaatgag gaatgccatt
17761 cagtattatg ggcaggttca actcaagaaa ccatatagct caaatgcaaa aaactcagaa
17821 tggtacttgt gttgcggtaa acgaagaatt caacgactca aaattgattt ctcagaccag
17881 gtaggaattt ttctgatttg taaagcaatg tcgcgccaaa gacaagcaat tccttactgg
17941 ttaaaacata tagaaaagaa ttatcctgct tcattacata agttttcct aactttgggt
18001 ttcccttctt tagagtcatc tttctgccat cgttatacta ttccattcag tgaaggaaag
18061 gctcttttc ataaggtcca atctatgtt cgtcaaggca aacaacattt acattctctt
18121 atgttggatt atgaaaacaa ttcacctcta ctagacttga gaaatcactt tatttgctca
18181 ttgaggggaa agataactaa gtattacaat gatatattaa agttaaatct agttatcaag
18241 gcagtagaga aaggtaaaaa ttggtcacaa cttgttgaga ccctcctaa tatgcattca
18301 gtctgcatag tacacgtgga tcatgagtgc tttggatgtg agaaacggtc actactcaaa
18361 ttggatttta ttagaaacac aaagatcgca gaacaaaaat tacttaatag agtaatcggg
18421 tatatttat tcttccgtt cggtctgttt aaatctgaat cattaacagc ataactttaa
18481 caaagagaac ttcatttaat tcacgaaaat aatctatttta aaaatgaggg ttacattttc
18541 tagagtattg tatgagaaat aataaaataa acaagaagaa gaaaaaacta ttagacagct
18601 tgctttacac aagataatct tatatcgtct caaaccgtac acaagtaggg aaatcacgcg
18661 cacaaattaa cttgtgattg aacgttcggt cacaccagtg gtaactttc aatgttagtt
18721 actcaaatat tattgctcat aattggtatt gatattggta cattgggtga gtccttgagc
18781 tttatcctta atataatgta agaaattagg gaaatactga gatatactag ttgaattgag
18841 tttatgacata ccatatatca taaatataaa agaacgatct gctgtaatct ataagcatct
18901 cttttacata cattggggaa agaactaggt tatcgttgag attaaaaga ctacgttacg
18961 ttttctctga tgacaagtga caaaatttcg tagttaaatt tctagaatgt caatgtgaat
19021 gtaaattaag aaaaaccaat atataaaatt aaaaaattaa aaaactttga tataagtaac
19081 acaaaacatt cttcatcttt tttgtgtgtc ca (SEQ ID NO:18)

VP30

MQQPRGRSRTRNHQTASSIYHETQLPSKPHYTNHHPRARSMSST
RSSAESSPTNHIPRARPPPTFNLSKPPPPPKDMCRNMKIGLPCTDPTCNRDHDLDN
LT

NRELLLLMARKMLPNTDKTFRSLQDCGSPSLSKGLSKDKQEQTKDVLTLENLGHILNY
LHRSDIGKLDETSLRAALSLTCAGIRKTNRSLINTMTELHINHENLPQDQNGVIKQTY
TGIHLDKGGQFEAALWQGWDKRSISLFVQAALYVMNNIPCESSTSVQASYDHFILPQS
QSKGQ (SEQ ID NO: 14)

DQ447652

```
   1 agacacacaa aaacaagaga tgatgatttt gtgtatcata taaataaaga agaatattaa
  61 cattgacatt aagactagtc attttgttaa tattctttaa aagatggatt tacatagttt
 121 gctagaatta ggtacaaaac ccacagcccc tcatgttcgt aataagaagg tgatattgtt
 181 tgatacaaac catcaggtta gtatctgtaa ccagataata gatgcaataa actcagggat
 241 cgatttagga gatcttttgg aaggcggctt gttgacatta tgtgttgaac attattacaa
 301 ttctgacaaa gataaaattca atacaagtcc tattgcaaaa tatctgcggg acgcgggcta
 361 tgagtttgat gtcatcaaga atcctgatgc aactcgcttt ctagaggtta ttcccaatga
 421 acctcattac agcccttga ttttggctct caaaaccta gaaagcactg aatctcaaag
 481 ggggaggatt gggctctttc tgtcattttg cagtcttttt ctcccgaaac tcgttgtcgg
 541 agaccgagct agcatcgaaa aggccctgag acaagtaaca gtgcatcagg aacaagggat
 601 tgtaacatac cccaatcatt ggctcactac aggtcacatg aaagtaatct ttgggatttt
 661 aagatctagc ttcattttaa agtttgtctt aatccatcag ggagtaaact tggtgacagg
 721 tcatgatgcc tatgacagta tcatcagtaa ttcagtagga caaactagat tctcagggct
 781 tcttattgtg aaaacagttc tagagttcat cctacaaaaa actgattcag gggtggcatt
 841 gcatccactt gtgcggacct caaaagtaaa aaatgaagtt gcaagcttca acaggcatt
 901 gagtaactta gctcgtcatg gagagtacgc accatttgca cgggttttga atttatcagg
 961 gatcaataac cttgagcatg ggctctatcc tcagcttca gcaattgcac tgggcgttgc
1021 aacagcacat ggcagtacat tggctggtgt taacgttggc gaacaatacc aacaactgcg
1081 agaagcagca catgatgcag aagtaaaatt acaaaggcga catgaacacc aggaaattca
1141 ggccatcgcc gaggatgacg aagagagaaa aatattagaa cagttccatc tccagaagac
1201 tgagattaca cacagtcaga cattggccgt cctcagccag aaacgagaga aactagctcg
1261 tcttgctgca gaaattgaaa acaacattgc agaggatcag gggttcaaac aatcgcagaa
1321 tcaggtgtca caatcttct taaatgatcc cacacctgta gaagtgacag tccaagccag
1381 gtctataaat cgaccaacag ccctgccccc cccagtcgac aacaaaattg agcatgaaac
1441 tgaagaggac agctcctcat caagtagttt tgttgacttg aatgatccat ttgcactgct
1501 aaacgaagac gaggatactc ttgaaaatag tgtcatggcc ccaagcacta ctttgagaga
1561 acccaaagaa gtttccgaac cactaaggca aactcaggac cttgatatta gccaaaagaa
1621 acagggaaat gaatcaacag atccagcaag aaaacaattc ttgcgatatc aagaattacc
1681 tcctgttcaa gaagacgatg aatcagaata cacaactgat tctcaggaaa gtgacgatca
1741 accaggatct gataatgaac aaggcgttga tctcccacca cctccattat atgctcagga
1801 aaagagacag gatcccatac agcatccaga cgtgagctcc caagatccct ttggcagtat
1861 tggagatgta gatggtgata ttttggaacc tataagatcg ccttcttcac cgtctgctcc
1921 tcaggaggac acaaggatgg gagaagccta tgaattatca cctgatttta caagctatga
1981 ggataatcag cagaattggc cacagagagt ggtaacaaag aaaggcagga ccttcccttta
2041 tcctaatgac cttttacaga cgagtcctcc agagtcatta ataacagccc ttgttgaaga
2101 gtaccaaaac cctgtctcag caaaagagct tcaagcggat tggcctgaca tgtcatttga
```

FIG. 2 CONTINUED

```
2161 tgagaggagg catgttgcta tgaacttata atttcgacaa cacagcacga ctactcattt
2221 atttacttca atatatttta cctccgaaac ataatagtca aatttattta aatatctaga
2281 ccactttcaa ataccttgct atatatcact gttatgtgag atggtgcaaa cctagaatg
2341 ataaccaaag gtaggaactg gttatatgac agtacctcga aggtgttatt caatggttta
2401 gatctctcct ctaattgcta cgagaataca actacaaacc tctttaccttt ggttacaata
2461 ctgtaataga tatgattgta tttctttctt aaatcatctg attcaacttg atagatataa
2521 cttgattcag agaacatttt gggaacgtca ttaactaaat tctctaaatg atgtactgta
2581 ttactgtttc acccgactaa ttatatagta gcatattaat ggatcctta cctctcctcc
2641 tatgctcttc ttataagtca ctcaaccggt gaaacgccga gtttgttggc ttagagtttt
2701 cctgttttac tgaatgtagt aattaatgat tgacttgagt gttgatggaa tcaagatagt
2761 gcgatgattc atattataag gtacaatttc cattcctgtt ttgccaatgt atcttcttcc
2821 ttatcacatg ccaattaaga aaaacaaaga gtcgaagaat attaaagatt ctctttaata
2881 ttcaaaaaca gttcttaatt cttttccttt cctttattaa tataatatat cgataaatct
2941 tacaatgtgg gactcgtcat acatgcaaca agtgagtgag ggactgatga ctggaaaagt
3001 tccaatagat caagtgttcg gcactaatcc cttagaaaag ttatataaga gaagaaagcc
3061 gaaagggaca gtgggattac aatgtagtcc ttgcttaata tcaaaatcaa caagtactga
3121 cgacattgtt tgggatcagc taatcgtaaa gaaaacattg gctgacttgc ttatacctat
3181 aaataggcaa atgtcggaca ttcaaagcac cctaagcgaa atgacaacaa aagtccatga
3241 gatcgagcgt caactacatg atatcacccc agttgtaaaa atgggaaaaa cgctagaagc
3301 aatttccaaa ggaatgtcag agatgctagc taagtacgat catctcgtga tttcaactgg
3361 aagaaccacc gcaccagctg ctgcctttga tgcttactta aacgagcatg gagtcccccc
3421 ccctcagcct gcaatcttca aagatcttgg agttgcccaa caagcctaca gtcaaaagac
3481 tatggtcaaa aaccaaacaa cagatgcagc tgacaaaatg tcaaaggttc tggaactcag
3541 tgaagaaaca ttttccaagc caaacccttt agctaaggat ttggctctat tattatttac
3601 tcatctccct ggcaacaaca ctccattcca catactcgcc caagtccttt caaaaattgc
3661 ttacaaatca ggaaagtctg gagcattctt ggatgcattc catcagattt taagcgaagg
3721 ggagaatgct caggctgcat taactcgatt aagcagaaca ttcgatgctt tccttggagc
3781 agttcctcca gtaataaaag ttaaaaactt tcaaacggtc cccgcccctt gtcaaaaaag
3841 cctccgagct gttcccccaa atccaacaat tgacaaggga tgggtctgtg tctattcatc
3901 tgaacagggt gaaacccggg ctcttaaaat ctaatccttg cgattcattc ttgaacaaag
3961 aatgatcttt ctaggttaat aaaaaaccac taaacatttc aagagtttgt ggatgattta
4021 agcatatttg ggtaaattta atcagggtag tagtttaaat ttgttttaag cgtgattttc
4081 attaagagag ggttaattag ttatagattg atctttagtg tactccatat gcataatata
4141 gagaaattaa tattactaac aaaaagggtt ttttaaacgg atttgattaa tagatcagta
4201 tatctcaaaa gccaaataat tgacttctta ctctttggga atttactaac aatataggaa
4261 agatatttat tcttacgtaa tccttggccc aacggaaact aacctccatg gtcattcaat
4321 atgcttgctc atgatatatt cagagatttt ttataagttc aaaacgttgt aaattatact
4381 tgcataaaat actgttttaa ttaagaaaaa ctatgaagaa cattaagtgg attttccttt
4441 cttagtgttc tttttacaaag caaggttttt aaattcaagt agatcaagtc tactcttgct
4501 gaacttactt ctttaaaaat taattacac taaacaattc gtttttgttg acggaacaaa
4561 ttcagatatg gccagtccca gcaattataa tacgtatatg caatacctga accctccccc
4621 ttatgctgat catggtgcaa atcagttaat cccagcagat cagctatcaa atcaacatgg
4681 tataactccg aattatgtgg gcgatttgaa tctagatgat cagtttaaag ggaatgtttg
4741 tcacgccttc actttggaag caataattga tatatctgct tataatgagc ggacggtcaa
4801 aggagtccca gcgtggctgc ctcttgggat catgagcaat tttgaatacc ctttagccca
4861 cactgttgct gcattgctta cagggagcta cacgattacc caattcacgc acaatgggca
```

FIG. 2 CONTINUED

```
4921 aaaatttgtt cgtgttaatc gacttgggac aggaatccca gcacatccac tcagaatgct
4981 gcgggaagga aaccaagctt ttgtccaaaa catggtgatt cccaggaact tttctacaaa
5041 tcagtttacg tacaatctta ctaatctagt attgagcgtg caaaagcttc ctgatgatgc
5101 ttggcgcccg tccaaagaca aattaatcgg aaacaccatg caccctgcgg tttctgtaca
5161 cccaaacctg ccgcctattg tcctaccaac agttaaaaaa caagcctatc gtcagcataa
5221 gaatcctaac aatggaccac tgctggccat atctggcatc cttcatcaac tgagggttga
5281 aaaagtccca gagaagacga gcttattcag gatttcactt cctgccgaca tgttctcagt
5341 aaaagagggc atgatgaaga aaagaggaga aggttctccg gtagtttatt ccaagcgcc
5401 tgagaatttt cctttgaatg gcttcaacaa ccggcaagtt gtgctagcat atgctaaccc
5461 gacactcagt gctgtttaat aagataattg ggtaagacaa tggcccttct gtacaaaggg
5521 tctgattcag atagatattt gtcagattca tgcaggatca ttttaagttg attttaatag
5581 tgctttaacc cttcactgct acctaaagg attgattgag ctgattaacc tataatgtat
5641 aacttctttt aaaccgctaa atcaatcata agtttgtcag atcatatagg atgaatgtta
5701 atacgtgata aatggttcct attcagtttt actttaacct catagtaaat cttataagac
5761 tactcatctt caagttgatc aattcaaaga taatttccct tctaaaataa taagaaaaac
5821 taatgaagaa cattaattgc taggtaaagg caattaagtt ctttgaactt tgcaaaagta
5881 aggtttcact agtgagtaaa ttcctgtatt agcagattaa aaccaaggaa gcaccccgac
5941 atgaagacca tatacttct gattagtctc attttaatcc aaagtataaa aactctccct
6001 gttttagaaa ttgctagtaa cagccaacct caagatgtag attcagtgtg ctccggaacc
6061 ctccaaaaga cagaagatgt tcatctgatg ggatttacac tgagtgggca aaaagttgct
6121 gattcccctt tggaagcatc taaacgatgg gctttcagga caggtgttcc tccaagaac
6181 gttgagtata cggaaggaga agaagccaaa acatgttaca atataagtgt aacagaccct
6241 tctggaaaat ccttgctgct ggatcctccc agtaatatcc gcgattaccc taaatgtaaa
6301 actgttcatc atattcaagg tcaaaaccct catgcacagg ggattgccct ccatttgtgg
6361 ggggcatttt tcttgtatga tcgcgttgcc tctacaacaa tgtaccgagg caaggtcttc
6421 actgaaggaa atatagcagc tatgattgtt aataagacag ttcacagaat gatttttct
6481 aggcaaggac aaggttatcg tcacatgaac ttgacctcca ccaataata ttggacaagc
6541 agcaatgaaa cgcggagaaa tgatacggga tgttttggca tcctccaaga atacaactcc
6601 acaaacaatc aaacatgctc tccatctctt aaacctccat ccctgcccac agtaactccg
6661 agcattcact ctacaaatac tcaaattaat actgctaaat ctggaactat gaacccaagt
6721 agcgacgatg aggacctat gatttccggc tcaggatctg gagaacaggg gccccacaca
6781 actcttaatg tagtcactga acagaaacaa tcgtcaacaa tattgtccac tccttcacta
6841 catccaagca cctcacaaca tgagcaaaac agtacgaatc cttcccgaca tgctgtaact
6901 gagcacaatg gaaccgaccc aacaaacaca ccagcaacgc tcctcaacaa tactaatgca
6961 actcccacct ataacactct caagtacaac ctcagtactc cttccctcc aacccgcaac
7021 atcaccaata atgatacaca acgtgaacta gcagaaagcg aacaagccaa tgctcagttg
7081 aacacaactc tagatcctac agaaaatccc accacagcac aagacaccaa cagcacaacc
7141 aacatcgtca tgacgacatc agatataaca agcaaacacc ccacaaattc ttctccggat
7201 tctagtccga caacccgccc tcctatatac tttagaaaga aacgaagcat ttctggaaaa
7261 gaaggtgata tattcccgtt tttagatggg ttaataaata ctgaaattga tttgatcca
7321 atcccaaaca cagaaacaat ctttgatgaa tccccagct ttaatactc aactaatgag
7381 gaacaacaca ctttcccgaa tatcagttta actttctctt attttctga taaaaatgga
7441 gatactgcct actctgggga aaacgaggat gattgtgatg cagagttgag gatttggagt
7501 gtgcaggagg acgatttggc ggcagggctt agctggatac catttttggg ccctggaatc
7561 gaaggactct atactgccgg tttaatcaaa aatcagaaca atttagtttg taggttgagg
7621 cgcttagcta atcaaactgc taaatcctg gagctcttgt taagggtcac aactgaggaa
```

7681 aggacatttt ccttaatcaa taggcatgca attgactttt tgcttacgag gtggggcgga
7741 acatgcaagg tgctaggacc tgattgttgc ataggaatag aagatctatc taaaaatatc
7801 tcagaacaaa ttgacaaaat cagaaaggat gaacaaaagg aggaaactgg ctggggtcta
7861 ggtggcaaat ggtggacatc tgactggggt gttctcacca atttgggcat cctgctacta
7921 ttgtctatag ctgttctgat tgctctgtcc tgtatctgtc gtatcttcac taaatacatt
7981 ggatgacata aagtttacaa tggttagagc tttaggaaag ttgctgctga gcccttgtc
8041 taatctactg aaatcgactt aaagaatcct cagggagctt ataactcaat gtgaatcgat
8101 tccctatata ttgttgattg tgctgatata gcagtcaagt gtcaccatca ttaggagcaa
8161 ttcttctgat ccaatgcatt gaagtcacta attacttcta aaatccttat cttttaatccg
8221 aatattcaca tagaaatcaa tttttgggaaa attccagtag tgcgtctttt catgtcactt
8281 ctctgaacct aagaccataa taaatattgg ttaaagaggt cagctggtca atcttctatt
8341 ttcatattaa agatatactg ctcagaaact cctagtttgc aacccaatct tggaaaaaga
8401 aacctcctct tttgatcata actatctcta tcaatgtctt gaacacttaa tattattaac
8461 aacttatttt tatttaatct tttaaatgca aatcaaaaga ggacatgagc caccctcact
8521 ttacttcaat acgaaggaat tcttcttctc agcctacatt ttaatttacc aggtgataaa
8581 cttatggtaa tttaccttaa cataggtgct gataagatga ttggatgata acacatttac
8641 cgagatttaa tcgtatctca ttaagaaaaa gataattaga acactggaaa ttgataaact
8701 tctattttga tcaatgtaga aaagaattat aaaaatctta gtaaataaat tactgcaaag
8761 taaaaacgaa gaacattaag tgttctttat taaagttgtt catccttttt gcttttgatt
8821 atatttgatc aaatacaact tcatttggta ttcattccaa gattcagaat gcaacagcct
8881 cgtgggagaa gccgaaatcg tagccaccaa gttgcactat ccacatacca tgaaaatcaa
8941 ttaccctcta aacctcaata cattaaccat catccacgtg caagatcaat gagttcaacc
9001 cgtagtagta cagaaggtag ccctactaat catgcttccc gtgctcgacc actttcaaca
9061 tttaatctat cgaaacctcc tccccccccg aaagacatgt gcaggaacat gaaaattggg
9121 ttaccctgta ctgaccccgc ttgcaacagg gatcatgacc ttgataatct aacaaatcgt
9181 gaactcttgc tgttgatggc acggaagatg ctccccaata cagataaggc tttcaaaagt
9241 cagcaggact gtggatcgcc atctctttcc aaagggcttt caaaggacaa gcaggaacaa
9301 gcaaaggatg tactgacttt ggaaaatcta gggcacatat tgaattatct tcatagatca
9361 gaaatcggaa aattggacga gacatcactc cgtgcagcat tgagtttaac atgtgccgga
9421 atccgaaaga caaataggtc tttgattaat actatgacag aattgcatat caaccatgag
9481 aatcttccac aggaccaaaa tggtgttatt aagcagacat atacaggtat tcatcttgac
9541 aaaggggggtc aatttgaagc tgccttatgg cagggctggg acaagaagtc aatatctttg
9601 tttgtgcaag ctgcattata tgtgatgaat aatatcccct gtgaatcgtc catcagtgtg
9661 caggcctcat atgatcactt tattctcccct cgaaatcagg gtgaaagaca atgattgtca
9721 tttcaaaatc aacgatataa ttattgttaa cattctacct tggttcttat tgtaagactt
9781 gtacactctc ctatcaactg tgattactag ttcaaaatta aaactcacaa aaattcaatc
9841 gcattgtaat caattattta tcatcgatta tttagtttga gggattccac atcatcttaa
9901 atccaataac acgatttgt ttgattttc tttaattc tacaccataa caacatacaa
9961 gtgtctgacg aacaacctgt gtttctatgg aaaaacatga agaacattaa gaaaaaggat
10021 gttcttgtat ttcaaccaag gttgtatata tttggccgat atcctcggag aataattgtc
10081 aatatctgac aattgatcat acacattcca ataatacatt atagactttt tatcagatat
10141 agaactggga ttctaatagt tctacttctt agtgcagtac aggttttgc aaagaaactt
10201 ctgagtatgg cagaactgtc aacacgttac aacttaccaa caaatattac agagaagagc
10261 ataaatcttg atctcaattc tactgcacgg tgggtaaaag agcccagtgt tggggggctgg
10321 acagtgaaat gggggaattt tatctttcac atcccaaata ccggaatgac attgttgcat
10381 catttaaaat ctaattttgt tgttccagaa tggcaacaaa caaggagtct cttctcccat

FIG. 2 CONTINUED

```
10441 ctctttaaaa acccaaaatc aaccatcatg gagcctttct tggctttgag gatcttactt
10501 ggcgttgctt tgaaagatca agaattgcag caatcattga ttcccggatt tagatccatt
10561 gtgcatatgc tttcagaatg gctgctttta gaagttacgt cagctatcca tatcagtcct
10621 aacctgttgg ggatctattt gacctcagac atgtttaaaa tcctaatggc aggtgtgaaa
10681 aacttttta ataagctgtt taccctccat gttgtaaatg atcatggaaa acctagcagt
10741 attgaaataa aattaaccgg acaacagatc ataatcactc gagttaacat ggggttctta
10801 gtagaagtta ggaggattga cattgaacct tgctgcggcg agactgtcct ctcagaatca
10861 gttgtgtttg ggctagtagc tgaagcagtc ctaagggaac acagccagat tgagagaggt
10921 caacctctta atttgacaca atacatgaac agcaaaattg ctatttagac agcttgattc
10981 ggcatctaaa gctttaattc agctgtataa ggatattgag aagacagtgg atcataatca
11041 attgcccttt ataataaaag atgtagttgc cctaatttgt attcactaac ctaaaataat
11101 agtattatca cactagatag tcatcacata ataagttgtt tctatgaatt aatcatgata
11161 gtataatctt gtagaattac tatgggttct atatacggca tttattccgg actgtatcct
11221 ttgtaaacaa tgcatgctta agtattctca tatcatacat gttatcactg cctgattaag
11281 aaaaaccaat gatggatatt aaacatcctt caattgactg ttttgagact ttaaaatctt
11341 acaggctgtc ttgatcttta aattctctac gggattatac agtcaccttt agcatacatt
11401 atgcttctcg cgaaataata taagtgactc tatgacattc cgagccaggt cttatcttg
11461 aattaaccct cttttggta tgcaacaccc gactcaaatat ccagatgcaa gattatcttc
11521 tcccataatt ttagatcagt gtgatttatt gaccagaagt ctagggtgt atagtcatta
11581 ctcacacaat ccaaaactac gtaattgtag gattccatac cacatttatc gcttgaggaa
11641 ttctacagca ttaaagacat ttcttcagaa ctgttcgata ctcacagttc cttttcactc
11701 aatttgggat cacatcataa cttcaattca acacgatgca attaatcata tcaatgattt
11761 caaataccta ttaccatcag aactcataaa gtatgctaat tgggacaatg agttcttaag
11821 agtattcctt aacaagatct tgagactcga tcatgctttt acaaattctg caaagttaca
11881 acgtgaggat ttctctccca aagagaatcc ttattattgg gggatgttat tgctcgtgca
11941 tttatctcaa cttgccagaa ggattaaggg acaaagaggg tcttaaagga gcaactggaa
12001 gtttatagga gttgatttgg aactatttgg aatagcagat ttgttattt ttaaagttcc
12061 gctaaaagca ataattcgga atgctacaag tttacaggcc tcaaaaccag ggttaaagac
12121 atggtaccgt gatcaaaaact taactcctta tctgtgtgat gatgaatttg ttgtaagcat
12181 cgctagttat gaatgtttta tcatgattaa agatgtcttc atcgaaaggt acaacacatg
12241 ggagatctgt gctcgcgctt gggtcgaaga taatgaagaa gctgattacc cacctcttgg
12301 tatattaaga gatttgtaca atcaagggga ccaaattata accatgtatc tagaggatgg
12361 tttcaaatta ataaaacact tagaaccttt atgtgtcagt tgtatacaaa cgtacggtat
12421 ttttacgccg aggaagtact ggttcaatc tcagatgatt aaatcatatt atgacgaact
12481 tcgaagtctt aacctaaaac ttcagattcc ggataatagg actgaatgtg cacagaactt
12541 tattaaaacc ataattcagg caaaactgac tcctcaacaa tactgtgaat tgttctcttt
12601 acaaaaacat tggggtcacc cagtttttata caatgatgtt gcactagaca aagtgaagaa
12661 acatgcccaa tcaacaaaaa ttttaaaacc taaagtcatg tttgaaactt tttgtgtctt
12721 taagtttata gtggcaaaaa atcattatca ctctcaagga tcgtggtaca aaaccacaca
12781 tgatctacat ttgaccccat atctacggca gcacattgtg tcaaattcat tccatcgca
12841 agccgagatt tatcagcacc tctgggaatg gtactttgta gagcatgaac ctctttttc
12901 tacaaaaata ataagtgatt tgagtatttt cataaaagat agagctactg ctgtaaatcg
12961 agagtgttgg gacagcgttt ttgataggag tgtgctagga tacaatcccc ctgtcagatt
13021 tcaatcaaag agggtacctg agcaattctt aggtcaagca gatttctctt taaatcaaat
13081 actggatttt gctgagaaat tagagtatct agctccttca tatagaaact tttccttttc
13141 attaaaggaa aagaattga atattgggag aacattcggg aagttgccct atcgtgtcag
```

FIG. 2 CONTINUED

```
13201 aaatgtccaa acacttgcag aagccttatt agcagatgga ctagcgaagg cattccctag
13261 taatatgatg gttgttactg agagagagca gaaagaagct ctattgcatc aagcctcttg
13321 gcaccataat tcagcaagta taggggagaa tgccatagta agaggtgcaa gttttgttac
13381 tgatcttgag aaatacaatc ttgcctttag atatgagttt acacgacatt tcatagacta
13441 ctgtaataga tgttacggtg ttaaaaattt attcgactgg atgcatttct taataccact
13501 atgctatatg catgtcagtg acttttatag ccctcctcac tgcgtgacag aaaataaccg
13561 aaataaccca cctgattgtg ccaatgctta tcattatcat ttaggaggta tagaaggact
13621 acaacagaaa ttgtggacat gtatatcatg tgctcaaatc acgcttgtag aactgaaaac
13681 taagttaaaa ttgaaatcca gtgtcatggg tgataatcaa tgtataacaa ctctaagtct
13741 tttccctatt gatgctccca atgattatca agaaaatgag gcagaattaa atgctgcacg
13801 agttgctgtt gaattagcta ttactacagg ctatagtggg atattcttaa aacctgaaga
13861 gacatttgtg cattcagggt ttatttactt tggtaaaaag caatacctaa atggtgttca
13921 attaccacaa tcattgaaga caatggcaag gtgtggacct ttatcagatt ccattttcga
13981 tgatcttcaa ggttcactag ccagtattgg cacatcattt gagagagggg caagcgagac
14041 acggcatatt tttccaagtc gttggatagc tgcatttcat tccatgttaa cctaaaattt
14101 gttaaatcag aatcacctcg gatttcccct aggatttagt attgatgtat cctgttttaa
14161 aaagcctctt actttctcgg agaaattaat tgctttgatc acacctcaag tgctaggggg
14221 attatctttc ttaaacccgg agaaattatt ctatcggaac atcagtgatc ctcttacttc
14281 agggttattt caactcagga atgcattaga gttccttaga aaggaagagt tgttctacat
14341 cttgattgct aaaaaacccg gtttagctga tgcttcagat ttcgttatga atccattagg
14401 tttaaatgtg ccaggatcta gggaaataat aacgtttctc aggcaaacag ttcgtgaaaa
14461 cataacgatt acatcacaaa atagaataat aaattctctt tttcacatag gttccgactt
14521 agaggatcaa agagtatgtg aatggctttt atcatcaaac cccgtaatga gccgatttgc
14581 tgctgatatt ttttcacgaa cacctagtgg aaaaagactt caagttttag gttactgga
14641 agggaccaga acgttattag cttcccgcac gatcagttta accactgagg gtacaatgtt
14701 gatgagatta agagagttaa ctaagagtcg atggaagagt tggttttctt atattgatgc
14761 attagatgat gatttgtctg agtctcttga aaagttcata tgcactgttg atgtggctaa
14821 ttcttgaga gcatattcat ggtcagatgt cttgaaagga aagaagttaa ttggtgccac
14881 actaccatgt ttactggagc aattcaatgt aaagtgggtc aacttgtctg aagacttaaa
14941 ggagcaattt aagctatctt cagatctggg atcacctacg gatttattgc agtacgattg
15001 caatggactg cattcaaagg gggccgataa cgcagaatta aattatgtga gttgtgccct
15061 tgaccggaaa attgttcaaa agcatccatc tgacaatcgc ctggcatgga caataggaaa
15121 tcgagcaccg tatatagggt cacgaacaga agataaaatt ggttaccctc ctttaagagt
15181 aaactgccca tcggcagccc ttaaagaagc tattgaaatg gtctctagac tattgtgggt
15241 gactcaaggc accgcagatc gagaaaaatt gctcattcct cttctcaatt caagagttaa
15301 tttagactat cagacagtgc tcaacttcct gccccactcac tactcaggca atatagttca
15361 cagatacaat gatcaatatg gacaacactc ctttatggca aatagaatga gcaatacatc
15421 cactcgtgca atcatatcaa ctaacacact agggaaatat gctggagggg gtcaagctgc
15481 tgttgatagt aatatataatct tccagaacac tattaattta ggtgttgcag ttttggacat
15541 tgcattgtct ctttctaaat tgtcatcaac atcaaatgtt tctttccgtt taatgttaag
15601 taaatgttgc acacggcatg tacggtctga gtatttattc tttgataaac cttagatgt
15661 ggatttgaac aagtacatgg acaacgagtt agtttacgat aatgatcctc tctgtagtgg
15721 aataaaggga agattaggta gagtatcaag atcaacactc tcattgagtc taaatgtaag
15781 cgatattgga tcttacgact ttccgactat tgctgcgtgg actttaggag agacaattat
15841 tggaagtatt ttttctgatg aatcttctca aagtacagac cctataagtt caggctgtac
15901 aaaaacttt gtaacacact ttcttgtgta tccagttgag agtatttttt atgcctttgg
```

FIG. 2 CONTINUED

```
15961 agctaatcta atagtggaaa gtttaagttt aagcaggatc aattcaatca agagcctctc
16021 agatttaaca tttcttatat catccacaat cagaaatttg tcacacagat cacttcgaat
16081 tcttcaatct actttccgac atgaattggt attaactaga ctagctcatc atataccatt
16141 gatttcctta atgctaggag gttctgcggg tgagaaaagt tcatcggatg ctgtccgact
16201 atttcttacg gcaagttatc aaaactttat caataatttc agttgtttga tgagaaagaa
16261 ccaatcacca ttaccagttt ggctttattt cctagtgaa gggcaacaac taaacctat
16321 tttaaaaatt ttgcaaaggt tatcatgttt attaacaact aaaaaggctc aaaatcacag
16381 acctgtagct gatacttgtt ttttgactga taatttttgg gtctatccaa gcaaatcaac
16441 gagaactaat cattattatg caagtcttaa ttattggaga gacaaagcta ataagattaa
16501 gaatacttca ttttcacatt tgataaacta ttcattttct gaaccctctc tacatgcgag
16561 ctctatctct tctagtcaag aagtggtcaa tttaaaacac actagtcgtt tagatgaaac
16621 acctaatatg agtgaaaggg ctcaatcaac aaatcatgag ccaacagctt tacaagaggt
16681 gtgcactgag ataccctct cggaacaaga tccagccaaa agttatttgc tgttagagaa
16741 cactagattc agggataatc agaaaatatt aagcatgat cagaacgctg agaggggtga
16801 acctctttca ttgcaagtgt cttctagggg ttgcctgcag gctcttactt gccctcatca
16861 ccctcccca tctcaaacca ccacagaacc actaagcatg cttaggaatt gtgacgccat
16921 aaaagcagcc ttacgttctg agacgaatga tccccgtctt atgagcagta tccttgatat
16981 gagatcattg aaaactccca tgagaataga atctcgaaac acgagtctat tgcaaccttc
17041 tgagtgtctg tcaacttcta agggaaaatc tgtactgtct agagaacagg cttcatcct
17101 gtatgttgat tgcagtaata tctcttctat ttctctggat tcaggttttc gaaatatgtc
17161 tgatagaaat caagtccaaa tgctaataaa tacttacaaa cgcgacttat acacttgtt
17221 tgatagtaac caattctgca ggtttacagg ggtcgtttca tcaatgcatt ataagcttta
17281 tgatcttttg ccagcaggca aactcggaaa ggcaatctgc ctagccgaag gggaagggag
17341 tggcgctcga ctactcttga agtggaagga gacagattat ttattcttca atactttggc
17401 cacagattca caacaggaag cagaaatttt gagtggtcga gttattccaa ggatgttgta
17461 taacatagat aagctaagtg ttttacttga atccagaaaa ttaatcttga ataatctaac
17521 tattcaaatc acggatatta cacacccact atggctggac tctgtcatac aataccctacc
17581 tgaagatagt gacattctaa caatggatgc agagaccact aaagaagaga caagagagca
17641 actctataaa actatcataa atatttgggc acgtacttct cctaatatcc ctaaaaccag
17701 catcattaaa gtgttttat tagattatgg gggaaccttg ttcttaatga agaatgctat
17761 tcaatattat ggacaagttc aacttaagaa accatatagt tcaaatgcaa aaaattcaga
17821 atggtactta tgttgtggaa aacgaagagt tcaacgactc cgagttgatt ttccagacca
17881 agtaggaata ttcttgatct gtaaagcaat gtcacgtcag aggcaagcaa ttccttactg
17941 gctaaagcac atagaaaaga attaccctgc ttcattgcac gagttcttta acttttagg
18001 tttcttct ttagagtcat ctttctgcca tcgctacacc attccgttca ctgagggaac
18061 ggctctctttt cacaaggtcc agtcttacgt ccgacaaggt agacaacacc tacactctct
18121 tatgttagat tacgaaaata attcacccct cctagatctg agaaatcact tcatatgctc
18181 attgaggga aagatagcca agtattacaa tgacatattg aaattaagtt tagtagtgag
18241 agcagtagaa agagggaaaa attggtcgca actcgttgag tcccttccta atatgcactc
18301 agtatgcaata acacatgttg atcacgaatg tattggctgt gagagacggt tattacttaa
18361 attggacttt gtcagaaata caaagatagc agaacaaaag ttactcaata gggtaattgg
18421 gtatattcta ttcttcccctt ttggttttctc cagacccaag tgactacaga tatattcttc
18481 aataaaggaa gctcagtcta actcacagaa ataatccact tcaaaacaag gatcacccat
18541 tttggaacat tgtataagaa actgcaagac aaataataag gaaaggatac tactgtataa
18601 cttgttatat ccaaaaggat cttgggtcat tttaagcatg atgcaaataa aaaatcgtct
18661 acatagccga actgaccgct cagtacttat tcacaatcat gctaactttt agttttaat
```

FIG. 2 CONTINUED 18721 tgtgcaaaaa ttactaagaa taattaatat tgatattaaa acattaaatg gacatttgag
18781 ttttatgcct agaataatat aaagaaattt aagagatatt tagatatatc agttgaattg
18841 atttatgaca catagtgcat catgaataca aagagaaaaa tcgttgcaat tcaggaatat
18901 cttatttaaa tgtattagag agaaagtcag attattatca aaatcaagca aaatacaata
18961 ggttttttca aagaataggt ggtaaagcct tatggttatt tttaaagat gtcaatgtga
19021 attttatta agaaaaagta atgcatgaaa ttaaaaaatt aaagaactt gatataagta
19081 acacaaaaca ctcttcatct ttttagtgtg tcca (SEQ ID NO:30)

VP30

MQQPRGRSRNRSHQVALSTYHENQLPSKPQYINHHPRARSMSST
RSSTEGSPTNHASRARPLSTFNLSKPPPPPKDMCRNMKIGLPCTDPACNRDHDLD
NLT
NRELLLLMARKMLPNTDKAFKSQQDCGSPSLSKGLSKDKQEQAKDVLTLENLG
HILNY
LHRSEIGKLDETSLRAALSLTCAGIRKTNRSLINTMTELHINHENLPQDQNGVIKQ
TY
TGIHLDKGGQFEAALWQGWDKKSISLFVQAALYVMNNIPCESSISVQASYDHFIL
PRN
QGERQ (SEQ ID NO:31)

DQ447649

1 agacacacaa aaacaagaga tgatgatttt gtgtatcata taaataaaga agaatattaa
61 cattgacatt aagactagtc attttgttaa tattctttaa aagatggatt tacatagttt
121 gctagaatta ggtacaaaac ccacagcccc tcatgttcgt aataagaagg tgatattgtt
181 tgatacaaac catcaggtta gtatctgtaa ccagataata gatgcaataa actcagggat
241 cgatttagga gatcttttgg aaggcggctt gttgacatta tgtgttgaac attattacaa
301 ttctgacaaa gataaattca atacaagtcc tattgcaaaa tatctgcggg acgcgggcta
361 tgagtttgat gtcatcaaga atcctgatgc aactcgcttt ctagaggtta ttcccaatga
421 acctcattac agccctttga ttttggctct caaaacctta gaaagcactg aatctcaaag
481 ggggaggatt gggctctttc tgtcattttg cagtctttt ctcccgaaac tcgttgtcgg
541 agaccgagct agcatcgaaa aggccctgag acaagtaaca gtgcatcagg aacaagggat
601 tgtaacatac cccaatcatt ggctcactac aggtcacatg aaagtaatct ttgggatttt
661 aagatctagc ttcattttaa agtttgtctt aatccatcag ggagtaaact tggtgacagg
721 tcatgatgcc tatgacagta tcatcagtaa ttcagtagga caaactagat tctcagggct
781 tcttattgtg aaaacagttc tagagttcat cctacaaaaa actgattcag gggtggcatt
841 gcatccactt gtgcggacct caaaagtaaa aatgaagtt gcaagcttca acaggcatt
901 gagtaactta gctcgtcatg gagagtacgc accatttgca cgggttttga atttatcagg
961 gatcaataac cttgagcatg ggctctatcc tcagctttca gcaattgcac tgggcgttgc
1021 aacagcacat ggcagtacat ggctggtgt taacgttggc gaacaatacc aacaactgcg
1081 agaagcagca catgatgcag aagtaaaatt acaaaggcga catgaacacc aggaaaattca
1141 ggccatcgcc gaggatgacg aagagagaaa aatattagaa cagttccatc tccagaagac
1201 tgagattaca cacagtcaga cattggccgt cctcagccag aaacgagaga aactagcccg
1261 tcttgctgca gaaattgaaa acaacattgc agaggatcag gggttcaaac aatcgcagaa

FIG. 2 CONTINUED 1321 tcaggtgtca cagtctttct taaatgatcc cacacctgta gaagtgacag tccaagccag
1381 gtctataaat cgaccaacag ccctgccccc cccagtcgac aacaaaattg agcatgaaac
1441 tgaagaggac agctcctcat caagtagttt tgttgacttg aatgatccat ttgcactgct
1501 gaacgaagac gaggatactc ttgaaaatag tgtcatggcc ccaagcacta ctttgagaga
1561 acccaaagaa gtttccgaac cactaaggca aactcaggac cttgatatta gccaaaagaa
1621 acagggaaat gaatcaacag atccagcaag aaaacaattc ttacgatatc aagaattacc
1681 tcctgttcaa gaagacgatg aatcagaata cacaactgat tctcaggaaa gtgacgatca
1741 accaggatct gataatgaac aaggtgttga tctcccacca cctccattat atgctcagga
1801 aaagagacag gatcccatac agcatccagc cgtgagctcc caagatccct tggcagtat
1861 tggtgatgta gatggtgata ttttggaacc tataagatcg ccttcctcac cgtctgctcc
1921 tcaggaggac acaaggatgg gagaagccta tgaattatca cctgatttta caagctatga
1981 ggataatcag cagaattggc cacagagagt ggtaacaaag aaaggcagga ccttccttta
2041 tcctaatgac cttttacaga cgagtcctcc agagtcatta ataacagccc ttgttgaaga
2101 gtaccaaaac cctgtctcag caaaagagct tcaagcggat tggcctgaca tgtcatttga
2161 tgagaggagg catgttgcta tgaactgta atttcgacaa cacagcacga ctactcattt
2221 atttacttca atatatttta cctccgaaac ataatagtca aatttattta aatatctaga
2281 ccactttcaa ataccttgtt atatatcact gttatgtgag atggtgcaaa ccttagaatg
2341 ataaccaaag gtaggaactg gttatatgac agtacctcga aggtgttatt caatggttta
2401 gatctctcct ctaattgcta cgataataca actacaaacc tctttacctt ggttacaata
2461 ctgtaataga tatgattgta tttctttctt aaatcatctg attcaacttg atagatataa
2521 cttgattcag agaacatttt gggaacgtca ttaactaaat tctctaaatg atgtactgta
2581 ttactgtttc acccgactaa ttatatagta gcatattaat ggatccttta cctctcctcc
2641 tatgctcttc ttataagtca ctcaaccggt gaaacgccga gtttgttggc ttagagtttt
2701 cctgttttac tgaatgtagt aattaatgat tgacttgagt gttgatggaa tcaagatagt
2761 gcgatgattc atattataag gtacaatttc catttctgtt ttgccaatgt atcctcttcc
2821 ttatcacatg ccaatcaaga aaaacaaaga gtcgaagaat attaaagatt ctctttaata
2881 ttcaaaaaca gttcttaatt cttttccttt cctttattaa tataatatat cgataaatct
2941 tacaatgtgg gactcgtcat acatgcaaca agtgagtgag ggactgatga ctggaaaagt
3001 tccaatagat caagtgttcg gcactaatcc cttagaaaag ttatataaga gaagaaagcc
3061 gaaagggaca gtgggattac aatgtagtcc ttgcttaata tcaaaatcaa caagtactga
3121 cgacattgtt tgggatcagc taatcgtaaa gaaaacattg gctgacttgc ttatacctat
3181 aaataggcaa atgtcggaca ttcaaagcac cctaagcgaa atgacaacaa aagtccatga
3241 gatcgagcgt caactacatg atatcacccc agttgtaaaa atgggaaaaa cgctagaagc
3301 aatttccaaa ggaatgtcag agatgctagc taagtacgat catctcgtga tttcaactgg
3361 aagaaccacc gcaccagctg ctgcctttga tgcttactta aacgagcatg gagtccccc
3421 ccctcagcct gcaatcttca aagatcttgg agttgcccaa caagcctaca gtcaaaagac
3481 tatggtcaaa accaaacaa cagatgcagc tgacaaaatg tcaaaggttc tggaactcag
3541 tgaagaaaca ttttccaagc caaaccttc agctaaggat ttagctctat tattatttac
3601 tcatctccct ggcaacaaca ctccattcca catactcgcc caagtccttt caaaaattgc
3661 ttacaaatca ggaaagtctg gagcattctt ggatgcattc catcagattt aagcgaagg
3721 ggagaatgct caggctgcat taacccgatt aagcagaaca ttcgatgctt tccttggagc
3781 agttcctcca gtaataaaag ttaaaaactt tcaaacggtc cccgccctt gtcaaaaaag
3841 cctccgagct gttccccaa atccaacaat tgacaaggga tgggtctgtg tctattcatc
3901 tgaacagggt gaaacccggg ctcttaaaat ctaatccttg cgattcattc ttgaacaaag
3961 aatgatcttt ctaggttaat acaaaaacac taaacatttc aagagttgt ggatgattta
4021 agcatatttg ggtaaattta atcaggatag tagtttaaat ttgttttaag cgtgattttc

FIG. 2 CONTINUED

```
4081 attaagagag ggttaattag ttatagattg atctttagtg tactccatac gcataatata
4141 gagaaattaa tattactaac aaaaagggtt ttttaaacgg atttgattaa tagatcagta
4201 tatctcaaaa gccaaataat tgacttctta ctctttggga atttactaac aatataggaa
4261 agatatttat tcttacgtaa tccttggccc aacggaaact aacctcaatg gtcattcaat
4321 atgcttgctc atgatatatc cagagatttt ttataagttc aaaacgttgt aaattatact
4381 tgcataaaat actgttttaa ttaagaaaaa ctatgaagaa cattaagtgg attttttcctt
4441 cttagtgttc ttttacaaag caaggtttt aaattcaagt agatcaagtc tactcttgct
4501 gaacttactt ctttaaaaat taatttacac taaacaattc gttttttgttg acggaacaaa
4561 ttcagatatg gccagttcca gcaattataa tacgtatatg caatacctga accctccccc
4621 ttatgctgat catggtgcaa atcagttaat cccagcagac cagctatcaa atcaacatgg
4681 tataactccg aattatgtgg gcgacttgaa tctagatgat cagtttaaag ggaatgtttg
4741 tcacgccttc actttggaag caataattga tatatctgct tataatgagc ggacggtcaa
4801 aggagtccca gcgtggctgc ctcttgggat catgagcaat tttgaatacc ctttagccca
4861 cactgttgct gcattgctta cagggagcta cacgattacc caattcacgc acaatggaca
4921 aaaatttgtt cgtgttaatc gacttgggac aggaatccca gcacatccac tcagaatgct
4981 gcgggaagga aaccaagctt ttgtccaaaa catggtgatt cccaggaact tttctacaaa
5041 tcagtttacg tacaatctta ctaatctagt attgagcgtg caaaagcttc ctgatgatgc
5101 ttggcgcccg tccaaagaca aattaatcgg aaacaccatg caccctgcgg tttctgtaca
5161 cccaaacctg ccgcctattg tcctaccaac agttaaaaaa caagcctatc gtcagcataa
5221 gaatcctaac aatggaccac tgctggccat atctggcatc cttcatcaac tgagggttga
5281 aaaagtccca gagaagacga gcttattcag gatttcactt cctgccgaca tgttctcagt
5341 aaaagagggc atgatgaaga aaagaggaga aggttctccg gtagtttatt tccaagcgcc
5401 tgagaatttt cctttgaatg gcttcaacaa ccggcaagtt gtgctagcat atgctaaccc
5461 gacactcagt gctgtttaat aagataattg ggtaagacaa tggcccttct gtacaaaggg
5521 tctgattcag atagatattt gtcagattca tgcaggatca ttttaagttg attttaatag
5581 tgcttttaacc cttcactgct accctaaagg attgattgag ctgattaacc tataatgtat
5641 aacttctttt aaaccgctaa atcaatcata agtttgtcag atcatatagg atgaatgtta
5701 atacgtgata aatggttcct attcagtttt actttaacct catagtaaat cttataagac
5761 tactcatctt caagttgatc aattcaaaga taatttccct tctaaaataa taagaaaaac
5821 taatgaagaa cattaattgc taggtaaagg caattaagtt ctttgaactt tgcaaaagta
5881 aggtttcact agtgagtaaa ttcctgtatt agtagattaa aaccaaggaa gcaccccgac
5941 atgaagacca tatatttct gattagtctc attttaatcc aaagtataaa aactctccct
6001 gttttagaaa ttgctagtaa cagccaacct caagatgtag attcagtgtg ctccggaacc
6061 ctccaaaaga cagaagatgt tcatctgatg ggatttacac tgagtgggca aaaagttgct
6121 gattcccctt tggaagcatc taaacgatgg gcttcagga caggtgttcc tcccaagaac
6181 gttgagtata cggaaggaga agaagccaaa acatgttaca atataagtgt aacagaccct
6241 tctggaaaat ccttgctgct ggatcctccc agtaatatcc gcgattaccc taaatgtaaa
6301 actgttcatc atattcaagg tcaaaaccct catgcacagg ggattgccct ccatttgtgg
6361 ggggcatttt tcttgtatga tcgcgttgcc tctacaacaa tgtaccgagg caaggtcttc
6421 actgaaggaa atatagcagc tatgattgtt aataagacag ttcacagaat gatttttttct
6481 aggcaaggac aaggttatcg tcacatgaac ttgacctcca ccaataaata ttggacaagc
6541 agcaatgaaa cgcagagaaa tgatacggga tgttttggca tcctccaaga atacaactcc
6601 acaaacaatc aaacatgccc tccatctctt aaacctccat ccctgcccac agtaactccg
6661 agcattcact ctacaaatac tcaaattaat actgctaaat ctggaactat gaacccaagt
6721 agcgacgatg aggaccttat gatttccggc tcaggatctg gagaacaggg gccccacaca
6781 actcttaatg tagtcactga acagaaacaa tcgtcaacaa tattgtccac tccttcacta
```

FIG. 2 CONTINUED

```
6841 catccaagca cctcacaaca tgagcaaaac agtacgaatc cttcccgaca tgctgtaact
6901 gagcacaatg gaaccgaccc aacaacacaa ccagcaacgc tcctcaacaa tactaataca
6961 actcccacct ataacactct caagtacaac ctcagtactc cttcccctcc aacccgcaac
7021 atcaccaata atgatacaca acgtgaacta gcagaaagcg aacaaaccaa tgctcagttg
7081 aacacaactc tagatccaac agaaaatccc accacaggac aagacaccaa cagcacaacc
7141 aacatcatca tgacgacatc agatataaca agcaaacacc ccacaaattc ttctccggat
7201 tctagtccga caacccgccc tcctatatac tttagaaaga aacgaagcat tttctggaaa
7261 gaaggtgata tattcccgtt tttagatggg ttaataaata ctgaaattga ttttgatcca
7321 atcccaaaca cagaaacaat ctttgatgaa tctcccagct ttaatacttc aactaatgag
7381 gaacaacaca ctcccccgaa tatcagttta acttctctct attttcctga taaaaatgga
7441 gatactgcct actctgggga aaacgagaat gattgtgatg cagagttgag gatttggagt
7501 gtgcaggagg acgatttggc ggcagggctt agctggatac cattttttgg ccctggaatc
7561 gaaggactct atactgccgg tttaatcaaa aatcagaaca atttagtttg taggttgagg
7621 cgcttagcta atcaaactgc taaatccttg gagctcttgt taagggtcac aaccgaggaa
7681 aggacatttt ccttaatcaa taggcatgca attgactttt tgcttacgag gtggggcgga
7741 acatgcaagg tgctaggacc tgattgttgc ataggaatag aagatctatc taaaaatatc
7801 tcagaacaaa tcgacaaaat cagaaaggat gaacaaaagg aggaaactgg ctggggtcta
7861 ggtggcaaat ggtggacatc tgactgggggt gttctcacca atttgggcat cctgctacta
7921 ttatctatag ctgttctgat tgctctgtcc tgtatctgtc gtatcttcac taaatacatt
7981 ggatgacata aagtttacaa tggttagagc tttaggaaag ttgctgctga gcccttgtc
8041 taatctactg aaatcgactt aaagaatcct cagggagctt ataactcaat gtgaatcgat
8101 tccctatata ttgttgatcg tgatgatata gcagtcaagt gtcaccatca ttaggagcaa
8161 ttcttctgat ccaatgcatt gaagtcacta attacttcta aaatccttat ctttaatccg
8221 aatattcaca tagaaatcaa ttttgggaaa attccagtag tgcgtctttt catgtcactt
8281 ctctgaacct aagaccataa taaatattgg ttaaagaggt cagctggtca atcttctatt
8341 ttcatattaa agatatactg ctcagaaact cctagtttgc aacccaatct tggaaaaata
8401 aacctcctct tttgatcata actatctcta tcaatgtctt gaacacttaa tattattaac
8461 aacttatttt tatttaatct tttaaatgca aatcaaaaga ggacatgagc caccctcatt
8521 ttacttcaat acgaaggaat tcttcttctc agcctacatt ttaatttacc aggtgataaa
8581 cttttggtaa tttaccttaa cataggtgct gataagatga ttggatgata acacatttac
8641 cgagatttaa tcgtatctca ttaagaaaaa gataattaga acactggaaa ttgataaact
8701 tctatttga tcaatgtaga aaagaattat aaaaatctta gtaaataaat tactgcaaag
8761 taaaaacgaa gaacattaag tgttctttat taaaattgtt catcctttc gcttttgatt
8821 atatttgatc aaatacaact tcatttggta ttcattccaa gattcagaat gcaacagcct
8881 cgtgggagaa gccgaaatcg tagccaccaa gttgcactat ccacatacca tgaaaatcaa
8941 ttaccctcta aacctcagta cattaaccat catccacgtg caagatcaat gagttcaacc
9001 cgtagtagta cagaaggtag ccctactaat catgcttccc gtgctcgacc actttcaaca
9061 tttaatctat cgaaacctcc tccccccccg aaagacatgt gcaggaacat gaaaattggg
9121 ttaccctgta ctgaccccgc ttgcaacagg gatcatgacc ttgataatct aacaaatcgt
9181 gaacttttgc tgttgatggc acggaagatg ctccccaata cagataaggc tttcaaagt
9241 cagcaggact gtggatcgcc atctctttcc aaagggcttt caaaggacaa gcaggaacaa
9301 gcaaaggatg tactgacttt ggaaaatcta gggcacatat tgaattatct tcatagatca
9361 gaaatcggaa aattggacga gacatcactc cgtgcagcat tgagttttaac atgtgccgga
9421 atccgaaaga caaataggtc tttgattaat actatgacag aattgcatat caaccatgag
9481 aatcttccac aggaccaaaa tggtgttatt aagcagacat atacaggtat tcatcttgac
9541 aaagggggtc aatttgaagc tgccttatgg cagggctggg acaagaagtc aatatcgttg
```

FIG. 2 CONTINUED 9601 tttgtgcaag ctgcattata tgtgatgaat aatatcccct gtgaatcgtc catcagtgtg
9661 caggcctcat atgatcactt tattctccct cgaaatcagg gtgaaagaca atgattgtca
9721 tttcaaaatc aacgatataa ttattgttaa cattctacct tggttcttat tgtaagactt
9781 gtatactctc ctatcaactg tgactactag ttcaaaatta aaactcacaa aaattcaatc
9841 gcattgtaat caattattta tcatcgattg tttagtttga gggattccac atcatcttaa
9901 atccaataac acgatttttgt ttgatttttc ttttaatttc tacaccacaa caacatacaa
9961 gtgtctgacg aacgacctgt gtttctatgg aaaaacatga agaacattaa gaaaaaggat
10021 gttcttgtat ttcaaccaag gttgtatata tttggccgat atcctcggag aataattgtc
10081 aatatctgac aattgatcat acacattcca ataatacatt atagacttt tatcatatat
10141 agaactggga ttctaatagt tctacttctt agtgcagtac aggttttgc aaagaaactt
10201 ctgagtatgg cagaactgtc aacacgttac aacttaccaa caaatattac agagaagagc
10261 ataaatcttg atctcaattc tactgcacgg tgggtaaaag agcccagtgt tgggggctgg
10321 acagtgaaat gggggaattt tatctttcac atcccaaata ccggaatgac attgttgcat
10381 catttaaaat ctaattttgt tgttccagaa tggcaacaaa caaggagtct cttctcccat
10441 ctctttaaaa acccaaaatc aaccatcatg gagcctttct tggctttgag gatcttactt
10501 ggcgttgctt tgaaggatca agaattgcag caatcattga ttcctggatt tagatccatt
10561 gtgcatatgc tttcagaatg gctgctttta gaagttacgt cagctatcca tatcagtcct
10621 aacctgttgg ggatctattt gacctcagac atgtttaaaa tcctaatggc aggtgtgaaa
10681 aactttttca ataagctgtt taccctccat gttgtaaatg atcatggaaa acctagcagt
10741 attgaaataa aattaaccgg acaacagatc ataatcactc gagttaacat ggggttctta
10801 gtagaagtta ggaggattga cattgaacct tgctgcggcg agactgtcct ctcagaatca
10861 gttgtgtttg ggctagtagc tgaagcagtc ctaagggaac acagccagat tgagagaggt
10921 caacctctta atttgacaca atacatgaac agcaaaattg ctatttagac agcttgattc
10981 ggcatctaaa gctttaattc agctgtataa ggatattgag aagacagtgg atcataatca
11041 attgcccttt ataataaaag atgtagttgc cctaatttgt attcactaac ctaaaataat
11101 agtattatca cactagatag tcatcacata ataagttgtt tctatgaatt aatcatgata
11161 gtataatctt gtagaattac tatgggttct atatacggca tttattccgg actgtatcct
11221 ttgtaaacaa tgcatgctta agtattctca tatcatacat gttatcactg cctgattaag
11281 aaaaaccaat gatggatatt aaacatcctt caattgactg ttttgagact ttaaaatctt
11341 acaggctgtc ttgatttta aattctctac gggattatac agtcacctt agcatacatt
11401 atgcctctcg cgaaataata taagtgactc tatgacattc cgagccaggt ctttatcttg
11461 aattaaccct cttttttggta tgcaacaccc gactcaatat ccagatgcaa gattatcttc
11521 tcccataatt ttagatcagt gtgattatt gaccagaagt ctagggttgt atagtcatta
11581 ctcacacaat ccaaaactac gtaattgtag gattccatac cacatttatc gcttgaggaa
11641 ttctacagca ttaaagacat ttcttcagaa ctgttcgata ctcacagttc cttttcactc
11701 aatttgggat cacatcataa cttcaattca acacgatgca attaatcata tcaatgattt
11761 caaatacccta ttaccatcag aactcataaa gtatgctaat tgggacaatg agttcttaag
11821 agtattcctt aacaagatct tgagactcga tcatgctttt acaaattctg caaagttaca
11881 atgtgaggat ttctctccca aagagaatcc ttattattgg gggatgttat tgctcgtgca
11941 tttatctcaa cttgccagaa ggattaaggg acaaagaggg tctttaagga gcaactggaa
12001 gtttataggga gttgatttgg aactatttgg aatagcagat tttgttattt ttaaagttcc
12061 gataaaagca ataattcgga atgctacaag tttacaggcc tcaaaaccag ggttaaagac
12121 atggtaccgt gatcaaaaact taactcctta tctgtgtgat gatgaatttg ttgtaagcat
12181 cgctagttat gaatgtttta tcatgattaa agatgtcttc atcgaaaggt acaacacgtg
12241 ggagatctgt gctcgcgctt gggtcgaaga taatgaagaa gctgattacc cacctcttgg
12301 tatattaaga gatttgtaca atcaagggga ccaaattata accatgtatc tagaggatgg

FIG. 2 CONTINUED

```
12361 tttcaaatta ataaaacact tagaaccctt atgtgtcagt tgtatacaaa cgtacggtat
12421 ttttacgccg aggaagtact ggtttcaatc tcagatgatt aaatcatatt atgatgaact
12481 tcaaagtctt aacctaaaac ttcagattcc agataatagg actgaatgtg cacagaactt
12541 tattaaaacc ataattcagg caaaactgac tcctcaacaa tactgtgaat tgttctcttt
12601 acaaaaacat tggggtcacc cagtttata caatgatgtt gcactagaca aagtgaagaa
12661 acatgcccaa tcaacaaaaa ttttaaaacc taaggtcatg tttgaaactt tttgtgtctt
12721 taagtttata gtggcaaaaa atcattatca ctctcaagga tcgtggtaca aaaccacaca
12781 tgatctacat ttgaccccat atctacggca gcacattgtg tcaaattcat ttccatcgca
12841 agccgagatt tatcagcacc tctgggaatg gtactttgta gagcatgaac ctcttttttc
12901 tacaaaaata ataagtgatt tgagtatttt cataaaagat agagctactg ctgtaaatcg
12961 agagtgttgg gacagcgttt ttgataggag tgtgctagga tacaatcccc ctgtcagatt
13021 tcaatcaaag agggtacctg agcaattctt aggtcaagca gatttctctt taaatcaaat
13081 attggatttt gctgagaaat tagagtatct agctccttca tatagaaact tttcctttc
13141 attaaaggaa aaagaattga atattgggag aacattcggg aagttgccct atcgtgtcag
13201 aaatgtccaa acacttgcag aagccttatt agcagatgga ctagcgaagg cattccctag
13261 taatatgatg gttgttactg agagagagca gaaagaagct ctattgcatc aagcctcttg
13321 gcaccataat tcagcaagta taggggagaa tgccatagta agaggtgcaa gttttgttac
13381 tgatctgag aaatacaatc ttgcctttag atatgagttt acacgacatt tcatagacta
13441 ctgtaatcga tgttacggtg ttaaaaattt attcgactgg atgcatttct taataccact
13501 atgctatatg catgtcagtg acttttatag ccctcctcac tgcgtgacag aaaataaccg
13561 aaataaccca cctgattgtg ccaatgctta tcattatcat ttaggaggta tagaaggact
13621 acaacagaaa ttgtggacat gtatatcatg tgctcaaatc acgcttgtag aactgaaaac
13681 taagttaaaa ttgaaatcca gtgtcatggg tgataatcaa tgtataacaa ctctaagtct
13741 tttccctatt gatgctccca atgattatca agaaaatgag gcagaattaa atgctgcacg
13801 agttgctgtt gaattagcta ttactacagg ctatagtggg atattcttaa aacctgaaga
13861 gacatttgtg cattcagggt ttatttactt tggtaaaaag caataccctaa atggtgttca
13921 attaccacaa tcattgaaga caatggcaag gtgtggaccT ttatcagatt ccattttcga
13981 cgatcttcaa ggttcactag ccagtattgg cacatcattt gagagaggg caagcgagac
14041 acggcatatt ttccaagtc gttggatagc tgcatttcat tccatgttag ccgtaaattt
14101 gttaaatcag aatcacctcg gatttcccct aggatttagt attgatgtat cctgttttaa
14161 aaagcctctt acttctcgg agaaattaat tgctttgatc acacctcaag tgctaggggg
14221 attatctttc ttaaacccgg agaaattatt ctatcggaac atcagtgatc ctcttactc
14281 agggttattt caactcagga atgcattaga gttccttaga aaggaagagt tgtctacat
14341 cttgattgct aaaaaaaccg gtttagctga tgcttcagat ttcgttatga tccattagg
14401 tttaaatgtg ccaggatcta gggaaataat aacgttctc aggcaaacag ttcgtgaaaa
14461 cataacaatt acatcacaaa atagaatat aaatctctt ttcacatag gttccgactt
14521 agaggatcaa agagtatgtg aatggctttt atcatcaaac cctgtaatga gccgatttgc
14581 tgctgatatt ttttcacgaa cacctagtgg aaaaagactt caagtttag gttacttgga
14641 aggaaccaga acgttattag cttcccgcac gatcagttta accactgagg gtacaatgtt
14701 gatgagatta agagagttaa ctaagagtcg atggaagagt tggtttctt acattgatgc
14761 attagatgat gatttgtctg agtctctga aaagttcata tgcactgttg atgtggctaa
14821 tttcttgaga gcatattcat ggtcagatgt cttgaaggga aaaaggttaa ttggtgccac
14881 actaccatgt ttactggagc aattcaatgt aaagtgggtc aacttgtctg aagacttaaa
14941 ggagcaattt aagctatctt cagatctggg atcacctacg gatttattgc agtacgattg
15001 caatggactg cattcaaagg gggccgataa cgcagaatta aattatgtga gttgtgccct
15061 tgaccggaaa attgttcaaa agcatccatc tgacaatcgc ctggcatgga atataggaaa
```

FIG. 2 CONTINUED

```
15121 tcgagcaccg tatatagggt cacgaacaga agataaaatt ggttaccctc ctttaagagt
15181 aaactgccca tcggcagccc ttaagaagc tattgaaatg gtctctagac tattgtgggt
15241 gactcaaggc accgcagatc gagaaaaatt gctcattcct cttctcaatt caagagttaa
15301 tttagactat cagacagtgc tcaacttcct gccactcac tactcaggca atatagttca
15361 cagatacaat gatcaatatg gacaacactc ctttatggca aatagaatga gcaatacatc
15421 cactcgtgca atcatatcaa ctaacacact agggaaatat gctggagggg gtcaagctgc
15481 tgttgatagt aatataatct tccagaacac tattaattta ggtgttgcag ttttggacat
15541 tacattgtct ctttctaaat tgtcatcaac atcaaatgtt tctttccgtt taatgttaag
15601 taaatgttgc acacggcatg taccgtctga gtatttattc tttgataaac ctttagatgt
15661 ggatttgaac aagtacatgg acaacgagtt agtttacgat aatgatcctc tctgtagtgg
15721 aataaaggga agattaggta gagtatcaag atcaacactc tcattgagtc taaatgtaag
15781 cgatattgga tcttacgact ttccgactat tgctgcgtgg actttaggag agacaattat
15841 tggaagtatt ttttctgatg aatcttctca aagtacagac cctataagtt caggctgtac
15901 aaaaactttt gtaacacact ttcttgtgta tccagttgag agtatctttt atgcctttgg
15961 agctaatcta atagtggaaa gttaagttt aagcaggatc aattcaatca agagcctctc
16021 agatttaaca tttcttatat catccacaat cagaaatttg tcacacagat cacttcgaat
16081 tcttcaatct actttccgac atgaattggt attaactaga ctagctcatc atataccatt
16141 gatttcctta atgctaggag gttctgcggg tgagaaaagt tcgtcggatg ctgtccgact
16201 atttcttacg gcaagttatc aaaattttat caataatttc agttgtttga tgagaaagaa
16261 ccaatcacca ttaccagttt ggctttattt ccctagtgaa gggcaacaac taaaacctat
16321 tttaaaaatt ttgcaaaggt tatcatgttt attaacaact aaaaaggttc aaaatcacag
16381 acctgtagct gatactgtt ttttgactga taattttgg gtctatccaa gcaaatcaac
16441 gagaactaat cattattatg caagtcttaa ttattggaga gacaaagcta ataagattaa
16501 gaatacttca ttttcacatt tgataaacta ttcatttct gaaccctctc tacatgcgag
16561 ctctatctct tctagtcaag aagtggtcaa tttaaaacac accagtcgtt tagatgaaac
16621 acctaatatg agtgaaaggg ctcaatcaac aaatcatgag ccaacagctt tacaagaggt
16681 gtgcactgag ataccctact cggaacaaga tccagccaaa agttatttgc tgttagagaa
16741 tactagattc agggatgatc agaaaatatt aagacatgat cagaaagctg agaggggtga
16801 acctctttca ttgcaagtgt cttctagggg ttgcctgcag gctcttactt gccctcatca
16861 cccctcccca tctcaaacca ccacagaacc actaagcatg cttaggaatt gtgacgccat
16921 aaaagcagcc ttacgttctg agacgaatga tccccgtctt atgagcagta tccttgatat
16981 gagatcattg aaaactccca tgagaataga atctcgaaac acgagtctat tgcaaccttc
17041 tgagtgtctg tcaacttcta agggaaaatc tgtactgtct agagaacagg cttcataccct
17101 gtatgttgat tgcagtaata tctcttctat ttctctggat tcaggttttc gaaatatgtc
17161 tgatagaaat caagtccaaa tgctaataaa tacttacaaa cgtgactat acacttgttt
17221 tgatagtaac caattctgca ggtttacagg ggtcgtttca tcaatgcatt ataagcttta
17281 tgatcttttg ccagcaggca aactcggaaa ggcaatctgc ctagccgaag gggaagggag
17341 tggcgctcga ctactcttga agtggaagga gacagattat ttattcttca atacttggc
17401 cacagattca caacaggaag cagaaatttt gagtggtcga gttattccaa ggatgttgta
17461 taacatagat aagctaagtg ttttacttga atccagaaaa ttaatcttga ataatctaac
17521 tattcaaatc acggatatta caaacccact atggctggac tctgtcatac aatacctacc
17581 tgaagatagt gacattctaa caatggatgc agagaccact aaagaagaga caagagagca
17641 actctataaa actatcataa atatttgggc acgtacttct cctaatatcc ctaaaaccag
17701 catcattaaa gtgttttat tagattatgg gggaaccttg ttcttaatga agaatgctat
17761 tcaatattat ggacaagttc aacttaagaa accatatagt tcaaatgcaa aaaattcaga
17821 atggtactta tgttgtggaa aacgaagagt tcaacgactc cgagttgatt tccagacca
```

17881 agtaggaata ttcttgatct gtaaagcaat gtcacgtcag aggcaagcaa ttccttactg
17941 gctaaagcac atagaaaaga attaccctgc ttcattgcac gagttcttta taactttagg
18001 ttttccttct ttagagtcat ctttctgcca tcgctacacc attccgttca ctgagggaac
18061 ggctctcttt cacaaggtcc agtcttatgt ccgacaaggt agacaacacc tacactctct
18121 tatgttagat tacgaaaata attcacccct cctagatctg agaaatcact tcatatgctc
18181 attgagggga aagataacca agtattacaa tgacatattg aaattaaatc tagtagtgag
18241 agcagtagaa agagggaaaa attggtcgca actcgttgag tcccttccta atatgcactc
18301 agtatgcata acacatgttg atcacgaatg tattggctgt gagagacggt tattacttaa
18361 attggacttt gtcagaaata caaagatagc agaacaaaag ttactcaata gggtaattgg
18421 gtatattcta ttcttccctt ttggtttctc cagacccaag tgactacaga tatattcttc
18481 aataaaggaa gctcagtcta actcacagaa ataatctact tcaaaacaag gatcacccat
18541 tttggaacat tgtataagaa actgcaagac aaataataag gaaaggatac tactgtataa
18601 cttgttatat ccaaaaggat cttgggtcat tttaagcatg atgcaaataa aaaatcgtct
18661 acatagccga actgaccgct cagtacttat tcacaatcat gctaactttt agtttttaat
18721 tgtgcaaaaa ttactaagaa taattaatat tgatattaaa acattaaatg gacatttgag
18781 ttttatgcct agaataatat aaagaaattt aagagacatt tagatatatc agttgaattg
18841 atttatgaca catagtgcat catgaataca aagagaaaaa ttgttgcaat tcaggaatat
18901 cttatttaaa tgtattagag agaaagtcag attattatca aaatcaagca aaatacaata
18961 ggttttttca aagaataggt ggtaaagcct tatggttatt ttttaaagat gtcaatgtga
19021 atttttatta agaaaaagta atgcatgaaa ttaaaaaatt aaagaacttt gatataagta
19081 acacaaaaca ctcttcatct ttttagtgtg tcca (SEQ ID NO: 22)

VP30

MQQPRGRSRNRSHQVALSTYHENQLPSKPQYINHHPRARSMSST
RSSTEGSPTNHASRARPLSTFNLSKPPPPPKDMCRNMKIGLPCTDPACNRDHDLD
NLT
NRELLLLMARKMLPNTDKAFKSQQDCGSPSLSKGLSKDKQEQAKDVLTLENLG
HILNY
LHRSEIGKLDETSLRAALSLTCAGIRKTNRSLINTMTELHINHENLPQDQNGVIKQ
TY
TGIHLDKGGQFEAALWQGWDKKSISLFVQAALYVMNNIPCESSISVQASYDHFIL
PRN
QGERQ (SEQ ID NO: 23)

AB050936

1 gggacacaca aaagaaaaag gttttttaag atttttgtg tgcgagtaac tatgaggaag
61 attaacagtt ttcctcagtt taaggtatac actgaaattg agattgagat tctcctcttt
121 gctattctgt aactttccct ggttgtgaca attgaatcag ttttatctat taccaattac
181 catcaacatg gtatgtctag tgatcttggg actcttcttc atctggtttt tcctagagct
241 ctgaatctat tttgtgagaa gttcatccaa acgacccagt gtctgaaaat acaagaggtt
301 ccccttttccg tcaagtttaa ggggttgttt tgattgtgtg tagattttat aatcctagag
361 tgccaaggag ttgcgtgtca tcattaattg ggaagatcaa ggaaacaatt tgttccaata
421 atatcgtaca tcttgactaa gtcgaacaag gggaagtcga tatggatcgt gggaccagaa

FIG. 2 CONTINUED

```
 481 gaatctgggt gtcgcaaaat caaggtgata ctgatttaga ttatcataaa attttgacag
 541 ctggccttac tgttcaacag ggaattgtca ggcagaaaat aattctgta tatcttgttg
 601 ataacttgga ggctatgtgt caattggtaa tacaagcctt tgaggccgga attgatttcc
 661 aagaaaatgc cgacagcttc cttctgatgc tttgcctaca tcatgcttac caaggtgact
 721 ataaattgtt cttggagagc aatgctgtac agtatttgga aggtcatgga ttcaaatttg
 781 agctccggaa gaaggacggt gtcaatcggc tcgaggaatt gcttcctgct gcaacgagtg
 841 gaaaaaacat caggcgtacg ttggccgcac tgcctgaaga ggagactaca gaagcaaatg
 901 cagggcaatt tctctcattt gcgagtttgt ttcttcccaa actggttgtg ggagagaagg
 961 cttgcttgga aaaagtccag cgacaaattc aggttcatgc agaacagggt ttaattcaat
1021 atcccactgc atggcaatca gttggacaca tgatggtaat cttcagattg atgaggacta
1081 atttcttgat taaatatttta ctgatccacc agggtatgca tatggtagct ggccacgatg
1141 ccaatgatgc tgtcattgct aattcagttg ctcaggctcg cttttcagga ctcctaattg
1201 tcaaaaccgt tcttgatcat attctgcaga aaaccgacca aggagtaaga cttcacccct
1261 tggcccgaac agccaaagtg cgtaatgagg ttaatgcatt taaggccgcc ctaagctcac
1321 ttgctaagca tggggagtat gcccctttg ctcgccttct caatctctcg ggagttaaca
1381 acctagaaca tggtctctac ccacagttat cagcaattgc tcttggagtt gccacagcac
1441 atggtagcac ccttgcagga gttaatgttg gtgagcagta tcagcagctt agagaggctg
1501 ccactgaagc tgagaagcaa ctccaacaat atgctgagtc cagagaactc gacagcctag
1561 gcctagacga tcaggaaaga agaatactaa tgaacttcca tcagaagaaa aatgaaatta
1621 gtttccagca gaccaatgca atggtaaccc ttaggaaaga gcgactggct aaaattaacag
1681 aagctataac gctggcctca agacctaacc tcgggtctag acaagacgac gacaatgaaa
1741 taccgttccc tgggcctata agcaacaacc cagaccaaga tcatctggag gatgatccta
1801 gagactccag agacactatc attcctaata gtgcaattga ccccgaggat ggtgattttg
1861 aaaattacaa tggctatcat gatgatgaag ttgggacggc aggtgacttg gtcttgttcg
1921 atcttgacga tcatgaggat gacaataaag cttttgagct acaggacagc tcaccacaat
1981 cccaaaggga aatagagaga gaaagattaa ttcatccacc cccaggcaac aacaaggacg
2041 acaatcgggc ctcagacaac aatcaacaat cagcagattc tgaggaacaa gaaggtcaat
2101 acaacaggca ccgaggccca gaacgtacga ccgccaatcg aagactctca ccagtgcacg
2161 aagaggacac ccctatagat caaggcgatg atgatccctc aagcccacct ccgctggaat
2221 ctgatgatga cgatgcatca agtagccaac aagatcccga ttatacagct gttgccctc
2281 ctgctcctgt ataccgcagt gcagaagccc acgagcctcc ccacaaatcc tcgaacgagc
2341 cagctgaaac atcacaattg aatgaagacc ctgatatcgg tcaatcaaag tctatgcaaa
2401 aattaggaga gacatatcac catctgctga gaactcaagg tccatttgaa gctatcaatt
2461 attatcacat gatgaaggat gagccggtaa tatttagcac tgatgatggg aaggaataca
2521 cctacccgga ttcacttgag gaagcctatc ctccatggct caccgagaaa gaacgactgg
2581 acaatgaaaa tcgatacatt tacataaata atcaacagtt cttctggcct gtcatgagtc
2641 ccagagacaa atttcttgca atcttgcagc accatcagta accacagcac aaagcgcggt
2701 ccacttcgta aagctaaata cacttaaagc ttgaccgatt catctacaaa aactaatcca
2761 ttataactta ttagtgctac ttttctataa gtgattctca atctaaggcc attaagagtt
2821 taagcaatat acatatacac ttacaccggt ctatccaaga tgtggctcaa tgttcttaat
2881 ttgaacatag tcataagggg ataaataata cttatattt ctgattgtgg actgacccat
2941 tctgcttaaa atgcttcgcc cattaaaaat gtgatctaat agatagccct gactagacca
3001 attaagaaaa acatttgatg aagattaaaa ccttcatcgc cagtaaatga ttatattgtc
3061 tgtaggcagg tgtttactcc acctttaaagt cggaaatatc ctaccttagg accattgtta
3121 agaggtgcat aggcattacc atccttgaga acatgtataa tgataaattg aagatatgtt
3181 caggcccaga acaactggga tggatttctg agcaactaat gacaggtaag attccagtaa
```

FIG. 2 CONTINUED

```
3241 ctgatatatt cattgatatt gataacaagc cagatcaaat ggaagtccgg ctcaaaccat
3301 catcaaggag ctcaaccaga acttgtacaa gtagcagtca gacggaggtc aactatgtac
3361 ctctccttaa aaaggttgag gatacattaa ctatgctagt gagtgcaacc agtcgtcaga
3421 atgctgcaat cgaggccctt gaaaaccgcc tcagcacact tgagagtagc ttaaagccaa
3481 tccaagacat gggtaaagtg atttcatcat tgaatcgcag ttgtgccgaa atggtggcaa
3541 aatatgatct tctagttatg acaactggac gggctacttc aaccgcagct gcagtagatg
3601 cgtactggaa agagcacaaa cagccaccac cagggccagc gttgtatgaa gagaatgcgc
3661 ttaaaggaaa aatcgatgat ccaaacagct atgtaccaga tgctgtgcag gaggcttaca
3721 agaaccttga cagtacatcg accctgaccg aggaaaattt tgggaaacct tatatatctg
3781 ctaaagatct gaaggagatc atgtatgatc atctacctgg ttttgggact gccttttcacc
3841 aacttgttca agtgatttgt aaaataggaa aggataacaa cctcttggac acaatccatg
3901 ctgagttcca ggcaagtcta gcagatggtg actctcccca atgtgcactc atacagataa
3961 ccaaaagagt cccaatcttt caggatgtgc cgccccccgac aatccacatt agatcccgtg
4021 gtgatatccc acgagcatgc caaaagagtc tccgaccagc accaccatca cccaaaattg
4081 atcgtggttg ggtttgtttg tttaagatgc aagatggtaa aacgcttgga cttaagatct
4141 aaggatcaag atttatttaa caaggcaagc cacaaccctta gatagaaact cagccagact
4201 attgaactat tgacgctgtt gatgataata tataattaat ggtcatattt gaatatgaca
4261 acatcttgct tcttgttttg ccttgtatct ctttgagttg gaagatcatt ccaaacttac
4321 aaacatgcac aagatgttat ggtttagcaa agaattgata ggagtactgg tatataatgt
4381 aaatataaca agtgatgaag attaagaaaa accagtcggt attttccaga cttggcattt
4441 cttatcttca tcttctaaag tgagatattt tatcatcaaa aatgagacg cggagtgtta
4501 ccaacggctc ctccagcata taatgatatt gcatactcta tgagcatact cccaacccga
4561 ccaagtgtca tagtcaatga gaccaaatca gatgtactgg cagtgccagg agcagatgtt
4621 ccatcaaaact ccatgagacc agtggctgat gataacattg atcactcaag ccatactcca
4681 agcggagtag cttctgcctt tatattggaa gctaaagtga atgtaatttc gggaacaaaa
4741 gtcctgatga agcaaatacc tatttggctt ccactgggtg tagctgatca gaagatatac
4801 agctttgatt caacaacagc cgcaattatg ttggcttcct acacagtgac acacttcggg
4861 aagatatcta acccgctggt acgtgtcaac aggctaggcc caggaatacc cgatcatccg
4921 ctacgactcc taaggttggg caatcaggca ttccttcaag agtttgttct tccaccagtc
4981 cagcttcccc agtatttcac atttgatcta acagctctaa agctcatcac tcaaccattg
5041 ccagctgcaa cctggacaga cgaaactcca gcaggagcag tcaatgctct tcgtcctggg
5101 ctctcactcc atcccaagct tcgtccaatt cttctaccgg ggaagatagg aaagaaaggt
5161 catgcttcag acttaacatc acctgacaaa attcaaacaa tcatgaatgc aataccggac
5221 ctcaaaattg tcccgattga tccaatcaag aacatagttg gaattgaggt tccagaatta
5281 ctagttcaaa ggctgaccgg caaaaaacca caacccaaaa atggccaacc aattattcca
5341 gttcttcttc cgaaatatgt tggacttgat cctatatcgc caggggactt aactatggtt
5401 atcacccagg attgtgattc atgccacactct ccagccagcc atccgtatca catggacaag
5461 caggatagtt accaataatt taaattccat tcgagctatt attctgctag taattccgac
5521 gggatcaata gactaaaaat ctgattgtat agaattataa aagaatcaag cagaggcaac
5581 agactcacag cttacgccta gatgactaat attaaggagt tttttaatct aattttccag
5641 tcttaagtaa taatcatttc ttttgtaatt aattatgcat ttgttaactt atcggtgcga
5701 gatttccttg agaacccggc ggggcttcta ctatctgtag taaccagaag agaagttcaa
5761 cccagtcaaa actaaaccaa gcaatattct gaatgctcta tagtctattc taatcagagg
5821 tataacaatg gctaagattt caatgactcg ttaacaatcg ctagtaattt taatctccag
5881 attaagaaaa agatatacga tgaagattaa ggcgacaacg agccgaaact tcatctcttt
5941 taaagatcta acattatctg ttccaaagtc atacaaggac acattcaaat cagggattgt
```

FIG. 2 CONTINUED

```
6001 aagctgctat ttcttacctc cccaaatcac ctatacaaca tggggtcagg atatcaactt
6061 ctccaattgc ctcgggaacg ttttcgtaaa acttcgttct tagtatgggt aatcatcctc
6121 ttccagcgag caatctccat gccgcttggt atagtgacaa atagcactct caaagcaaca
6181 gaaattgatc aattggtttg tcgggacaaa ctgtcatcaa ccagtcagct caagtctgtg
6241 gggctgaatc tggaaggaaa tggaattgca accgatgtcc catcagcaac aaaacgctgg
6301 ggattccgtt caggtgtgcc tcccaaggtg gtcagctatg aagccggaga atgggcagaa
6361 aattgctaca atctggagat caaaaagtca gacggaagtg agtgcctccc tctccctccc
6421 gacggtgtac ggggattccc tagatgtcgc tatgtccaca aagttcaagg aacaggtcct
6481 tgtcccggtg acttagcttt ccataaaaat ggggcttttt tcttgtatga tagattggcc
6541 tcaactgtca tctaccgtgg gacaactttt gctgaaggtg tcatagcttt tttaattctg
6601 tcagagccca agaagcattt ttggaaggct acaccagctc atgaaccggg gaacacaaca
6661 gatgattcca caagctacta catgaccctg acactcagct acgagatgtc aaattttgga
6721 ggcgaggaaa gtaacaccct ttttaaggta gacaaccaca catatgtgca actagatcgt
6781 ccacacactc cgcagttcct tgttcagctc aatgaaacac ttcgaagaaa taatcgcctt
6841 agcaacagta cagggagatt gacttggaca gtggatccca aaattgaacc agatgttggt
6901 gagtgggcct ctgggaaac taaaaaaact tttcccaaca acttcatgga gaaaacttgc
6961 atttccaaat tctatcaacc cacaccaaca actcctcaga tcagagcccg gcgggaactg
7021 tccaaggaaa aattagctac cacccaccca ccaacaactc cgagctggtt ccaacggatt
7081 cccctccagt ggtttcagtg ctcactgcag gacggacaga ggaaatgtcg acccaaggtc
7141 taactaacgg agagacaatc acaggtttca ccgcgaaccc aatgacaacc accattgccc
7201 caagtccaac catgacaagc gaggttgata acaatgtacc aagtgaacaa ccgaacaaca
7261 cagcatccat tgaagactcc ccccatcgg caagcaacga gacaattgac cactccgaaa
7321 tgaattcgat ccaaggctcg aacaactccg cccagagccc acagaccaag gccacgccag
7381 cgcccacagc atccccgatg accctggacc cgcaagagac ggccaacatc agcaaaccag
7441 gaaccagccc aggaagcgca gccggaccaa gtcagcccgg actcactata aatacaataa
7501 gtaaggtagc tgattcactg agtcccacca ggaaacaaaa gcgatcggtt cgacaaaaca
7561 ccgctaataa atgtaaccca gatcttcact attggacagc tgttgatgag ggggcagcag
7621 caggattggc atggattcca tattttggac ctgcagcaga aggcatctac attgagggtg
7681 taatgcataa tcagaatggg cttatttgcg ggctacgtca gctagccaat gaaactaccc
7741 aggctcttca attattctg cggggccaca cagaactgag gacttactca cttcttaaca
7801 gaaaagctat tgattttctt cttcaacgat ggggaggtac ctgtcgaatc ctaggaccat
7861 cttgttgcat tgagccacat gattggacaa aaaatattac tgatgaaatt aaccaaatta
7921 aacatgactt tattgacaat cccctaccag accacggaga tgatcttaat ctatggacag
7981 gttggagaca atggatcccg gctggaattg ggattattgg agttataatt gctataatag
8041 ccctactttg tatatgtaag atttttgtgt gatttattct gagatctgag agaaaaaaat
8101 ctcagggtta ctctaaggag aaatatatt tttaaaattt acttaaatgc tgaccactta
8161 tcttaaatga gcaattaata atatgttttt ctgcttcttt gcttgattta caatatgata
8221 tttctcttaa taatgattaa tatattaaga aaaacttatg acgaagatta aagggggagga
8281 tcgttaacgg gaaaatctcc catctcgttc gtcgaagcca cgttggtggt gcttgcagct
8341 gagaacaact ccagagattg taggtagaaa ggaccagcat ttataggtag gggtcagaaa
8401 gcaacaatag ccataaaagg agagcctgac attgctattt aatatcctag aacctgattt
8461 ctaggttcta gttgtacaat ccggatgatg gagcattcaa gagaacgggg tagatctagc
8521 aacatgcgac ataatagccg ggaaccatac gaaaatccat caaggtctcg ctcattatct
8581 cgggacccta atcaggttga tcgtaggcag cctcgaagtg catcccaaat tcgtgttccg
8641 aatctgttcc atcggaaaaa gactgatgca ctcatagttc ctccggctcc caaagatata
8701 tgcccaacac tcaaaaaagg attcctctgc gatagtaaat tttgcaaaaa agatcaccaa
```

FIG. 2 CONTINUED

```
8761 ttggatagct taaatgatca tgaattacta ctgctaattg caagaagaac atgtggaatt
8821 atcgagagca attcgcagat tacatcccca aaagatatgc ggttagcgaa tccaacagct
8881 gaagacttct cacaaggtaa tagtcctaaa ttaacacttg cagtccttct tcaaattgct
8941 gaacattggg caaccagaga cctaaggcaa attgaggact ctaaacttag agctctttta
9001 acccttgtg ccgtattaac aaggaaattt tctaaatccc aactgggtct tctatgtgag
9061 acccacctac ggcatgaggg cctcggacag gaccaagctg attctgtatt agaggtctac
9121 caaagactcc acagtgataa aggagggaat tttgaggctg ccctgtggca acaatgggac
9181 cgacagtcgt taataatgtt catctctgct tttctcaaca ttgctctcca gacaccttgt
9241 gaaagttcta gtgtcgtagt ctcaggtctt gccacattgt acccagcaca agacaattct
9301 acaccgtccg aggcaactaa tgataccacc tggtcaagta cagttgaata gaaaaccact
9361 ggagctattt ttccacgatt gctctcagtc aataaattsa tatagatata atacgacttc
9421 ggtgtgcaat tgtcaagggt tccatttggt aataatgatt cttaaaacaa tctactatcg
9481 taattatcga tggatctacc ctatttgacg gtacatgact tgaatgtaat aaggtaagtt
9541 ggtatctgag gtattttgtc tagagtatac tcaaaatcgt atgtctagca aattatcaat
9601 agcaaagtta aattctccta acctcatatt ttgatcaagt aatcatgatt ttatggtaat
9661 tctttgcaga ttatcggttt aatcttttatt aagaaaaaat catgattgta gacaatttac
9721 tggtagtccc tgggtatcca agtttatgaa cagagctaga gagaatttgc tacttccgag
9781 gtataacttt attatttgct acttcgaatg cctaaaaacca gtaatgcagg atgaagatta
9841 attgcggagg aatcaggaat tcaactttag ttccttaagg cctcgtctga atcttcatca
9901 gttagtaagt tctttatag aagtcattag cttctaaggt gattatattt tagtattaaa
9961 ttttgttaat tgcttgctat aaagttgaaa tgtctaatgc ttaaatgaac atttctttga
10021 agctgacata cgaatacatc atatcatatg aaaacatcgc aattagagcg tccttgaagt
10081 ctggcattga cagtcaccag gctgttctca gtagtctgtc cttggaagct cttggggaga
10141 caagaagagg tcccagagag tcccaacagg ttggcataag gtcattaaca ccagcatagt
10201 cagctcgatc aagactgtaa gcgagtcgat tgcaactaaa aagattattt cttgttgttt
10261 aaacaaattc cttttgtgtg agacaccctc aaggcacaag atggctaaag ccacaggccg
10321 atacaatctc gtgcccccaa agaaagatat ggaaaaggga gtgattttta gtgatctttg
10381 taatttcttg attactcaaa ccctgcaagg ttggaaggtt tattgggcag gaattgagtt
10441 tgatgtaagt caaaaaggca tggctcttct gacaagactc aaaacaaatg actttgctcc
10501 tgcctgggcg atgacaagaa atctcttccc acatctgttc caaacccaa attcggttat
10561 tcaatctccc atctgggctt tgagggtgat tttggcagcc ggattgcagg atcagttgtt
10621 agaccattca ttggttgagc cattgacagg ggctctcggt ctaatttctg attggctcct
10681 aactacaacg tcaacacatt tcaatcttcg tactagaagc gtaaaggacc agcttagtct
10741 tcgtatgtta tctttgatca ggtcaaacat cttgcagttc atcaacaagc ttgacgccct
10801 gcatgttgtc aattacaatg gtttactcag tagtattgag atcgggactt ctacacacac
10861 aatcattata actcgtacaa atatgggttt tctcgtggaa gttcaggagc ctgcaaaatc
10921 agctatgaat tctaagcgcc caggaccagt caagttctca ttacttcatg agtctgcctt
10981 caaacctttc actcgtgttc cacaatctgg gatgcaatca ttaataatgg agttcaacag
11041 tttgttggca atttaacaag gtgatcttaa aataagtaca tgaatgagaa ttagttgtgg
11101 gtcttaccta gcattgttga gttagctatc taatctattt tcactaattg cattgagcac
11161 tgctagtagg tttgcaccac gttaaagatt cagagtgtat gaattgtgca gatttaaact
11221 tgggttttgc cttatgcttc acaggtggtc ttttttaaaat ggagattatc agcatttctt
11281 caatgggagg agttagcaat cagaaattgg agataaatgg acatcgggat agaacaatgc
11341 ctaactattg ggcggctttc attttttaaat gtgtatataa ccaatctttt cctatcttgc
11401 cttatattgg tgtaaacttta cttttaataac atgtcaatgc tatactgtta agagaaggtc
11461 tgaggaagat taagaaaaag gtctcgtgtt cacttggttg ccgtcaagta tcctgtggtt
```

FIG. 2 CONTINUED 11521 tttttctacc taacttcctc atgccatatg gctacccagc ataccagta cccggatgca
11581 cgtttatctt cacctatagt cctggatcaa tgtgatttgg taactcgagc atgtgggtta
11641 tattcatctt attctctaaa tcctcagcta aggcaatgta aattaccaaa acatatatat
11701 cgacttaagt tcgacacaat agtatccaaa ttcctaagtg atacacctgt agcaacactg
11761 ccgatagact atttagtacc aattctcctg cgttcccctaa cggggcacgg tgataggccg
11821 ttgaccccga cttgtaatca attccttgat ggaattatta attacactct tcatgatgca
11881 gcctttcttg attactatct caaggcaaca ggtgcacagg accatttgac aaacattaca
11941 actagagaga agcttaaaaa cgaaattcta aacaatgatt atgtccatca attgttcttc
12001 tggcatgacc tgtctatttt ggctcgacgt gggcgtctga atcgcgggaa caaccgttca
12061 acctggtttg ttcatgatga attcattgat attttaggat atggcgatta tattttttgg
12121 aaaataccctt tatcattatt accagtttact atagacgggg tcccacacgc ggcaactgac
12181 tggtatcaac cgactcttt taaagaatcc atcctagggc acagccaaat cctatctgtg
12241 tcgacagctg aaatactaat tatgtgtaaa gatattatca cctgtaggtt taatacatca
12301 ctgattgcat ccattgcaaa attagaggat gtagatgtgt ctgattatcc tgacccgagt
12361 gatattctta agatatacaa tgctggagac tatgtaatat ctattcttgg ctcagaaggt
12421 tataagataa taaagtaccc tgaaccactt tgtttggcca aaatccaact ttgctctaaa
12481 ttcacagaaa gaaaaggtcg tttcctcaca cagatgcatt tatcagtaat aaatgatctt
12541 cgggagttga tttctaaccg caggttaaag gactatcagc aagagaagat tagggatttt
12601 cacaaaatat tattacaatt gcaattatct cctcaacagt tttgtgaatt attctctgtt
12661 caaaaacatt gggggcatcc aattttacat agtgagaaag ctatacaaaa agtaaaacgg
12721 catgcaacca tccttaaggc tctcagacct aatgtcattt ttgagacata ttgtgtattc
12781 aagtacaata ttgccaagca ctattcgac agccaaggaa cttggtacag tgtaatctca
12841 gacaggaatt taactccagg actcaactcc ttcataaaac gtaatcactt tccttcacta
12901 cccatgatta aggatcttct atgggaattc tatcatctta atcaccctcc gttattctct
12961 acaaaggtga ttagtgactt aagtatttc atcaaggata gggccacagc tgttgaacag
13021 acatgttggg atgcagtctt tgaacccaat gtgctaggtt acaatcctcc aaacaaattc
13081 tccactaaaa gggtgccgga acaattctca gaacaggagg attttcaat cgaaagtgtc
13141 ctgaattatg cacaggaatt acattattta ttaccacaga ataggaattt tccttttct
13201 cttaaagaaa aagaattaaa tattggacga acatttggta agctaccata tctcacacgg
13261 aatgtccaaa cttttatgtga ggctctgtta gcagatggac tggctaaggc cttccccagt
13321 aacatgatgg tagtaactga acgtgaacaa aaagagagcc ttcttcatca ggcatcatgg
13381 caccacacca gtgatgattt tggagagaat gctaccgttc gagggagtag ttttgtaact
13441 gatttagaga agtacaatct tgcatttcgc tatgagttca ctgcaccatt tattgagtac
13501 tgcaaccatt gctatggtgt gcgtaatgtc tttaattgga tgcattatt aatccccgcag
13561 tgttacatgc atgtaagtga ttattataat ccgcctcaca atgttaatct tagcaatcga
13621 gaatatcctc ctgaaggccc gagttcgtac cgagggcact taggaggcat agagggatta
13681 caacaaaaac tgtggacgag tatatcctgt gcacaaatct ccttagtgga aattaaaact
13741 ggtttaagt tacgatcagc ggtcatggga gacaatcagt gtataaccgt attgtctgtt
13801 tttccactig aaacagaccc tgaagagcag gagcaaagcg ccgaagacaa tgctgcaaga
13861 gtagcagcaa gtcttgcaaa agtaaccagt gcatgtggga tctttcttaa accagaagag
13921 acattcgtac actcaggttt catttatttc ggaaaaaaac aatatctcaa tggtgtacaa
13981 ttaccgcaat cactcaaaac agcagcaaga atggcgccac tctctgatgc tatattcgat
14041 gatctacaag gaacacttgc cagtattgga actgccctcg aacgtgtcat atcggaaacg
14101 cgacatatcc tcccatgtcg tattgtagca gctttccata cgtatttcgc cgttcggatt
14161 ttacaatatc accatcttgg atttaataaa ggcatcgatt tagggcagtt gtcacttagt
14221 aaaccattag actatgggac tattactcta acattggcgg ttccacaagt ccttggggga

```
14281 ttgtcttttc taaatccaga aaagtgtttt tatcgaaact tcggagatcc tgtgacttct
14341 ggacttttcc agctacgggt gtacctagaa atggttaaca tgaaagacct attttatcca
14401 ttaatatcga aaaatccagg aaattgtagt gccattgatt ttgtcttaaa tccatccgga
14461 ttaaatgttc caggatcaca agacttgaca tccttttttgc gacagatcgt taggcgtagt
14521 attacactaa ctgcaagaaa taagttaatt aacactctct tccatgcctc tgctgatttg
14581 gaagatgaga tggtttgtaa atggctcctt tcatcaaacc ctgtcatgag tcgctttgca
14641 gcggatattt tttccaggac acctagtggt aaacgtctcc aaatattagg ttatcttgaa
14701 gggaccagga ctctattggc ctccaaaatc ataaacaaca acagtgagac acctgtactt
14761 gataagctga ggaagatcac cctacaaaga tggaatctgt ggttcagtta tttggaccat
14821 tgtgaccaat tactagcaga tgctctacag aaaattagtt gcacggtgga tttggcccag
14881 attttgcgtg agtatacatg gtcacacatc ttagagggta gaccattgat cggagcgaca
14941 ttaccatgta tggtggagca attcaaagtt aagtggctaa gacaatatga acctttgtcca
15001 gaatgcctca acaaaaaagg ctcaaatgct tatgtctcag ttgcagtcaa agatcaagtg
15061 gtcagtgctt ggcctaatac ttctcgaata agttggacaa tagggagtgg tgtcccctat
15121 ataggggtcaa gaaccgagga taaaatcgga cagcctgcaa tcaagccgcg atgccccttca
15181 tctgccctca aggaggctat agaattagca tcaaggctca cttgggttac acaaggaagt
15241 tctaatagtg aacaattaat ccggcctttc ttagaagcga gagtcaaacct tagtgtcagt
15301 gaagtcctgc aaatgacacc atcacattat tcaggaaata ttgtccatcg atataacgac
15361 caatatagcc cgcactcatt tatggcgaat cgcatgagca atactgcgac ccgtctcata
15421 gtgtcaacta atacacttgg agaattttca ggtggagggc aggccgccag ggatagcaat
15481 ataattttcc agaatgttat aaatttagca gttgcccttt atgatattag attccggaat
15541 acgaacacct ctgatataag gcataatagg gctcatcttc acctgacaga gtgctgtact
15601 aaagaggtcc cggcccagta tttgacatat acaagtgcac tcaatctgga tttaagccgt
15661 tatcgtgata atgaactaat atatgactca aatccactga ggggaggatt gaactgcaat
15721 ttaacaatgg atagtccttt agtgaagggt cctaggctta acatgattga agatgatctt
15781 ctccgctttc cacacctttc tggatgggag ttagcgaaaa cggtggtaca atccatcatc
15841 tcagacaata gcaactcatc aacagatcca atcagtagcg gagaaacacg ctcttcaca
15901 actcatttc tcacttaccc tcagattggc cttctttaca gtttcggggc agtattatgc
15961 ttttatctag gcaatactat cctatggact aaaaaacttg attatgaaca gtttctatat
16021 tatttgcata accagctgca caacttaccct catcgagcac tccgtgtttt taaaccaaca
16081 tttaagcatg ccagtgtgat gtcccgatta atggaaattg attccaactt ctcaatttat
16141 attggcggga catctggaga tcgagggctg tctgatgctg ctcgactgtt tcttcggaca
16201 gcaatcgcga gttttttaca atttcttaaa agctggatca tcgatcgcca aaaggcaatt
16261 cctttatgga tagtatatcc gcttgaaggt caacagccgg aatccatcaa tgaatttcta
16321 cataaaaattt ttggtctgct caaacaaggc cccaaaaata ttccaaagga ggtcagcatt
16381 caaaatgatg gacattttgga tttggcagaa aataattatg tttacaatag taagagcact
16441 gctagtaatt tcttccatgc atccttagct tactggagaa gtaggaaatc tcggaaaact
16501 caagaccata atgatttctc aagaggggat ggaacactta cagaacccgt gtgtaagttc
16561 tcaagcaatc atcagtcaga tgaaaagtac tacaatgtga catgtggaaa gtcaccgaag
16621 ccgcaagaac gcaaagactt ctcgcaatac agactcagca ataacgggca aacaatgagt
16681 aatcatcgta agaaagggaa gttccacaag tggaatccct gcaaagtgtt aatggagagt
16741 caaaggggaa ctgtctctaaa agagggtgac tactttcaaa acaatactcc accaacagat
16801 gatgtatcaa gtcctcaccg actcattcta ccattttta aattgggaaa tcacaaccat
16861 gcacatgatc aagatgccca agaattgata aatcaaaata ttaaacagta cctacatcag
16921 ctaaggtcta tgttggacac cactatatat tgtagattca cagggattgt ctcatccatg
16981 cattacaaat tggacgaagt tcttctagaa tacaatagtt tcgattcagc tatcacatta
```

FIG. 2 CONTINUED 17041 gctgaaggtg aggggtcagg ggctctatta cttttgcaga aatatagtac aaggttatta
17101 ttttgaaca cattggcaac agaacacagt atagagtcag aagttgtatc aggtttttct
17161 actccgagaa tgttgttacc aataatgcaa aaggttcatg aaggacaagt cactgttatc
17221 ttaaataatt cagcaagtca gataactgac ataactagct caatgtggtt aagtaatcaa
17281 aaatataatc taccttgtca agttgaaatc attacgatgg atgctgaaac aacagagaac
17341 ttaaacaggt cccaactcta ccgagcagta tataacttaa tacttgatca cattgatccg
17401 cagtatctca aggtggtggt actcaaagta tttctgagtg atatagaagg aatattatgg
17461 attaatgatt acttggctcc attattcggg gctggttact tgattaaacc gattacatca
17521 agtgcccggt caagtgaatg gtacctttgc ttatcaaatt tgatatctac taacaggaga
17581 tcggccccatc agactcacaa ggcatgtctt ggtgttatca gagatgcttt gcaagcacaa
17641 gtccagcgag gcgtgtactg gttgagtcac atcgcacagt atgctacaaa gaatctccat
17701 tgtgaataca tatgccttgg tttcccacct ctagaaaagg tcctatatca caggtataat
17761 ctagttgata ctggactcgg tccattgtcg tcagttatta gacatttaac taacctccag
17821 gcagagatac gagacttagt attagattat accctgatga gagagagtcg cactcaaacg
17881 taccatttta ttaagactgc aaaaggcaga atcacaaagt tagtcaatga ctttctgaag
17941 ttttctttaa ttgtccaggc actcaaaaat aattcttctt ggtatactga gcttaaaaaa
18001 ttacctgagg tgattaatgt gtgtaatcga ttttatcata ctcacagttg cgaatgtcag
18061 gaaaaattct ttgtccagac gctttattta caacgcctac gcgatgcaga aatcaagcta
18121 attgaacgcc ttaccgggtt aatgcgattt tatccagaag ggttaatata ttccaatcac
18181 acataggtac taaatcatca tagtatgagg aataaaataa tgataattcc tgacgacagt
18241 tttagttccg attctaagta tatcggaaga gagtatgcca atcttaatta ttaaaggtaa
18301 caagctatta gttattactt attgataaga ataaacttta tcatagcgta acacatcata
18361 actttatagc gattttgcat ttctaatcct agtatttatt agaatgtact atcagagaaa
18421 tgaccccagt tcctatcttt aaataatgat tgtgtgtatt aaattattag tttattaggt
18481 ttatgagttg gttacacagt gagtattagt aattgaggat tatgtagata ggtaatctaa
18541 cactgaatca cccatctgat gtcaccatat ccaaatattg tgctagtcgc atttaaacat
18601 gctatcttca gttaagtaac atagactgaa aatgctaaga agagattgga gtaaaagtat
18661 aaaataaatt taattaaact tcaaagtgat taaatgataa tgatcttggg aactcgatat
18721 gacctcaagt caaaaataat gtcaatataa ttgtttagta atatgagtta taatgtgaat
18781 tttgataact aactagcttt agtagttaag atcaaatgca aacattctaa gaatgttaag
18841 cgcacacaaa aacattataa aaaaccaatt ttttcctttt tgtgtgtccc (SEQ ID NO: 24)

VP30

MEHSRERGRSSNMRHNSREPYENPSRSRSLSRDPNQVDRRQPRSASQIRVPNLFH
RKKTDALIVPPAPKDICPTLKKGFLCDSKFCKKDHQLDSLNDHELLLLIARRTCGI
IESNSQITSPKDMRLANPTAEDFSQGNSPKLTLAVLLQIAEHWATRDLRQIEDSKL
RALLTLCAVLTRKFSKSQLGLLCETHLRHEGLGQDQADSVLEVYQRLHSDKGGN
FEAALWQQWDRQSLIMFISAFLNIALQTPCESSSVVVSGLATLYPAQDNSTPSEA
TNDTTWSSTVE (SEQ ID NO: 25)

NC002549

1 cggacacaca aaaagaaaga agaattttta ggatcttttg tgtgcgaata actatgagga
61 agattaataa ttttcctctc attgaaattt atatcggaat ttaaattgaa attgttactg
121 taatcacacc tggtttgttt cagagccaca tcacaaagat agagaacaac ctaggtctcc

FIG. 2 CONTINUED

```
 181 gaagggagca agggcatcag tgtgctcagt tgaaaatccc ttgtcaacac ctaggtctta
 241 tcacatcaca agttccacct cagactctgc agggtgatcc aacaacctta atagaaacat
 301 tattgttaaa ggacagcatt agttcacagt caaacaagca agattgagaa ttaaccttgg
 361 ttttgaactt gaacacttag gggattgaag attcaacaac cctaaagctt ggggtaaaac
 421 attggaaata gttaaaagac aaattgctcg gaatcacaaa attccgagta tggattctcg
 481 tcctcagaaa atctggatgg cgccgagtct cactgaatct gacatggatt accacaagat
 541 cttgacagca ggtctgtccg ttcaacaggg gattgttcgg caaagagtca tcccagtgta
 601 tcaagtaaac aatcttgaag aaatttgcca acttatcata caggcctttg aagcaggtgt
 661 tgattttcaa gagagtgcgg acagtttcct tctcatgctt tgtcttcatc atgcgtacca
 721 gggagattac aaactttct tggaaagtgg cgcagtcaag tatttggaag ggcacgggtt
 781 ccgttttgaa gtcaagaagc gtgatggagt gaagcgcctt gaggaattgc tgccagcagt
 841 atctagtgga aaaaacatta agagaacact tgctgccatg ccggaagagg agacaactga
 901 agctaatgcc ggtcagtttc tctcctttgc aagtctattc cttccgaaat tggtagtagg
 961 agaaaaggct tgccttgaga aggttcaaag gcaaattcaa gtacatgcag agcaaggact
1021 gatacaatat ccaacagctt ggcaatcagt aggacacatg atggtgattt ccgtttgat
1081 gcgaacaaat tttctgatca aatttctcct aatacaccaa gggatgcaca tggttgccgg
1141 gcatgatgcc aacgatgctg tgatttcaaa ttcagtgggt caagctctgt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgactttga accttctgg
1381 agtaaataat cttgagcatg gtctttccc tcaactatcg gcaattgcac tggagtcgc
1441 cacagcacac gggagtaccc tgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt cccttccag gacccatcaa tgatgacgac aatcctggcc atcaagatga
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca cacccagtc
2401 agaacactct tttgaggaga tgtatcgcca cattctaaga tcacaggggc catttgatgc
2461 tgttttgtat tatcatatga tgaaggatga gcctgtagtt tcagtacca gtgatggcaa
2521 agagtacacg tatccagact cccttgaaga ggaatatcca ccatggctca ctgaaaaaga
2581 ggctatgaat gaagagaata gattgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttatttttg
2821 aatttaaagc tagcttatta ttactagccg tttttcaaag ttcaatttga gtcttaatgc
2881 aaataggcgt taagccacag ttatagccat aattgtaact caatattcta actagcgatt
```

FIG. 2 CONTINUED

```
2941 tatctaaatt aaattacatt atgcttttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaaagctggt
3121 ctaacaagat gacaactaga acaaagggca ggggccatac tgcggccacg actcaaaacg
3181 acagaatgcc aggcctgag ctttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaatttt gggaaacctg
3781 acatttcggc aaaggatttg agaaacatta tgtatgatca cttgcctggt tttggaactg
3841 ctttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
4381 accaaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcccccat ttcggcaagg
4861 caaccaatcc acttgtcaga gtcaatcggc tgggtcctgg aatcccggat catcccctca
4921 ggctcctgcg aattggaaac caggctttcc tccaggagtt cgttcttccg ccagtccaac
4981 taccccagta tttcaccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc ccattcttt tacccaacaa aagtgggaag aaggggaaca
5161 gtgccgatct aacatctccg gagaaaatcc aagcaataat gacttcactc caggacttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgtc
5341 tttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt cttttttctc tcctaaatgt agaacttaac aaaagactca taatatactt
5641 gttttttaaag gattgattga tgaaagatca taactaataa cattacaaat aatcctacta
```

FIG. 2 CONTINUED

```
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgcccttc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttcccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg acttcgctg aaggtgtcgt tgcatttctg atactgcccc
6601 aagctaagaa ggacttcttc agctcacacc ccttgagaga gccggtcaat gcaacggagg
6661 accgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatcaaaca atcggggagt
6901 gggccttctg ggaaactaaa aaaacctcac tagaaaaatt cgcagtgaag agttgtcttt
6961 cacagttgta tcaaacggag ccaaaaacat cagtggtcag agtccggcgc gaacttcttc
7021 cgaccaaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 acccccaaaa gcagagaaca ccaaacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccgaggga atttacatag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttctgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
7981 gagacaatgg ataccggcag gtattggagt tacaggcgtt ataattgcag ttatcgcttt
8041 attctgtata tgcaaatttg tcttttagtt ttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct tgagaatga
8281 taaacttgat gaagattaag aaaaggtaa tcttcgatt atctttaatc ttcatccttg
8341 attctacaat catgacagtt gtctttagtg acaagggaaa gaagccttt tattaagtt
8401 taataatcag atctgcgaac cggtagagtt tagttgcaac ctaacacaca taaagcattg
```

FIG. 2 CONTINUED 8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gatttttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa ccttctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca accctaacag tgatcaaaga aaatcataat ctcgtatcgc tcgtaatata
9601 acctgccaag catacctctt gcacaaagtg attcttgtac acaaataatg ttttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatattgt
9841 tcttgtttca agaggtagat tgtgaccgga aatgctaaac taatgatgaa gattaatgcg
9901 gaggtctgat aagaataaac cttattattc agattaggcc ccaagaggca ttcttcatct
9961 ccttttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaaatagga acgtcgttcc aacaatcgag
10261 cgcaaggttt caaggttgaa ctgagagtgt ctagacaaca aaatattgat actccagaca
10321 ccaagcaaga cctgagaaaa aaccatggct aaagctacgg gacgatacaa tctaatatcg
10381 cccaaaaagg acctggagaa aggggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg cccctgcatg gtcaatgaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaacccttag caggagccct tggtctgatc tctgattggc tgctaacaac caacactaac
10741 catttcaaca tgcgaacaca acgtgtcaag gaacaattga gcctaaaaat gctgtcgttg
10801 attcgatcca atattctcaa gtttattaac aaattggatg ctctacatgt cgtgaactac
10861 aacggattgt tgagcagtat tgaaattgga actcaaaatc atacaatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat

FIG. 2 CONTINUED

```
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacataccca atacccagac gctaggttat catcaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt
12001 cagggcaatg aatttttaca tcaaatgttt ttctggtatg atctggctat tttaactcga
12061 aggggtagat taaatcgagg aaactctaga tcaacatggt ttgttcatga tgatttaata
12121 gacatcttag gctatgggga ctatgttttt tggaagatcc caatttcaat gttaccactg
12181 aacacacaag gaatccccca tgctgctatg gactggtatc aggcatcagt attcaaagaa
12241 gcggtcaag ggcatacaca cattgtttct gtttctactg ccgacgtctt gataatgtgc
12301 aaagatttaa ttacatgtcg attcaacaca actctaatct caaaaatagc agagattgag
12361 gatccagttt gttctgatta tcccaatttt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttcagaaat gcgtgcacta
12601 aagccttcac aggctcaaaa gatccgtgaa ttccatagaa cattgataag gctggagatg
12661 acgccacaac aacttgtga gctatttcc attcaaaaac actgggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aaagaaatca attccctccg ttgccaatga ttaaagaact actatgggaa
12961 ttttaccacc ttgaccaccc tccactttt tcaaccaaaa ttattagtga cttaagtatt
13021 tttataaaag acagagctac cgcagtagaa aggacatgct gggatgcagt attcgagcct
13081 aatgttctag gatataatcc acctcacaaa tttagtacta aacgtgtacc ggaacaattt
13141 ttagagcaag aaaacttttc tattgagaat gttcttttcct acgcacaaaa actcgagtat
13201 ctactaccac aatatcggaa cttttctttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgatttag agaaatacaa tcttgcattt
13501 agatatgagt ttacagcacc ttttatagaa tattgcaacc gttgctatgg tgttaagaat
13561 gttttaatt ggatgcatta tacaatccca cagtgttata tgcatgtcag tgattattat
13621 aatccaccac ataacctcac actggagaat cgagacaacc cccccgaagg gcctagttca
13681 tacagggggtc atatgggagg gattgaagga ctgcaacaaa aactctggac aagtatttca
13741 tgtgctcaaa tttctttagt tgaaattaag actggtttta agttacgctc agctgtgatg
13801 ggtgacaatc agtgcattac tgttttatca gtcttcccct tagagactga cgcagacgag
13861 caggaacaga gcgccgaaga caatgcagcg agggtggccg ccagcctagc aaaagttaca
13921 agtgcctgtg gaatcttttt aaaacctgat gaaacatttg tacattcagg ttttatctat
```

FIG. 2 CONTINUED 13981 tttggaaaaa aacaatattt gaatggggtc caattgcctc agtcccttaa aacggctaca
14041 agaatggcac cattgtctga tgcaattttt gatgatcttc aagggaccct ggctagtata
14101 ggcactgctt ttgagcgatc catctctgag acacgacata tctttccttg caggataacc
14161 gcagctttcc atacgttttt ttcggtgaga atcttgcaat atcatcatct cgggttcaat
14221 aaaggttttg accttggaca gttaacactc ggcaaacctc tggatttcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tctttcacg cacgccgagc
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaaccctà cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagataggac aacctgctat taaaccaaaa tgtcctccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgaccct
15361 tcacattact caggaaatat tgttcacagg tacaacgatc aatacagtcc tcattctttc
15421 atggccaatc gtatgagtaa ttcagcaacg cgattgattg tttctacaaa cacttaggt
15481 gagttttcag gaggtggcca gtctgcacgc gacagcaata ttattttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag tttgggggcc tttgtaagtt attatcttgg caatacaatt
16021 cttcggacta agaaattaac acttgacaat tttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccattcatc ttctcttaca
16261 tttgtaaaag aatggataat taatcgcgga acaattgtcc tttatggat agtatatccg
16321 ctagagggtc aaaacccaac acctgtgaat aatttttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac caggtccgt cgttccagtc ctttctaagt

FIG. 2 CONTINUED

```
16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagacctat ttttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagccccg
17521 tttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcactttat tcgtactgca
17941 aaaggacgaa tcaaaaact agtcaatgat tatttaaaat tctttcttat tgtgcaagca
18001 ttaaaacata atgggacatg gcaagctgag ttttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgttttggtt gataacacaa cttcttaaaa caaaattgat
18601 ctttaagatt aagtttttta taattatcat tacttaatt tgtcgtttta aaaacggtga
18661 tagccttaat cttgtgtaa aataagagat taggtgtaat aaccttaaca ttttgtcta
18721 gtaagctact atttcataca gaatgataaa attaaagaa aaggcaggac tgtaaaatca
18781 gaaataccttc cttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttcttttt gtgtgtccca (SEQ ID NO: 36)
```

VP30

MEASYERGRPRAARQHSRDGHDHHVRARSSSRENYRGEYRQSRSASQVRVPTV
FHKKRVEPLTVPPAPKDICPTLKKGFLCDSSFCKKDHQLESLTDRELLLLIARKTC
GSVEQQLNITAPKDSRLANPTADDFQQEEGPKITLLTLIKTAEHWARQDIRTIEDS
KLRALLTLCAVMTRKFSKSQLSLLCETHLRREGLGQDQAEPVLEVYQRLHSDKG
GSFEAALWQQWDRQSLIMFITAFLNIALQLPCESSAVVVSGLRTLVPQSDNEEAS
TNPGTCSWSDEGTP (SEQ ID NO: 37)

```
   1 agacacacaa aaacaagaga tgatgatttt gtgtatcata taaataaaga agaatattaa
  61 cattgacatt gagacttgtc agtctgttaa tattcttgaa gagatggatt tacacagttt
 121 gttggagttg ggtacaaaac ccactgcccc tcatgttcgt aataagaaag tgatattatt
 181 tgacacaaat catcaggtta gtatctgtaa tcagataata gatgcaataa actcagggat
 241 tgatcttgga gatctcctag aagggggttt gctgacgttg tgtgttgagc attactataa
 301 ttctgataag gataaattca acacaagtcc tatcgcgaag tacttacgtg atgcgggcta
 361 tgaatttgat gtcatcaaga atgcagatgc aacccgcttt ctggatgtga ttcctaatga
 421 acctcattac agccctttaa ttctagccct taagacattg gaaagtactg aatctcagag
 481 ggggagaatt gggctctttt tatcattttg cagtctttc ctcccaaaac ttgtcgtcgg
 541 agaccgagct agtatcgaaa aggcttaag acaagtaaca gtgcatcaag aacaggggat
 601 cgtcacatac cctaatcatt ggcttaccac aggccacatg aaagtaattt tcgggatttt
 661 gaggtccagc ttcattttaa agtttgtgtt gattcatcaa ggagtaaatt tggtgacagg
 721 tcatgatgcc tatgacagta tcattagtaa ttcagtaggt caaactagat tctcaggact
 781 tcttatcgtg aaaacagttc tcgagttcat cttgcaaaaa actgattcag gggtgacact
 841 acatcctttg gtgcggacct ccaaagtaaa aaatgaagtt gctagtttca agcaggcgtt
 901 gagcaaccta gcccgacatg gggaatacgc accatttgca cgggtctga atttatcagg
 961 gattaacaac ctcgaacatg gactctatcc tcagctttca gcaattgcgc tgggtgtggc
1021 aacagcacac ggcagtacat tggctggtgt caatgttggc gaacaatatc aacaactacg
1081 agaggcggca catgatgcgg aagtaaaaact acaaaggcga catgaacatc aggaaattca
1141 agctattgcc gaggatgacg aggaaaggaa gatattagaa caattccacc ttcagaaaac
1201 tgaaatcaca cacagtcaga cactagccgt cctcagccag aaacgagaaa aattagctcg
1261 tctcgctgca gaaattgaaa acaatattgt ggaagatcag ggatttaagc aatcacagaa
1321 tcgggtgtca cagtcgtttt tgaatgaccc tacacctgtg gaagtaacgg ttcaagccag
1381 gcccatgaat cgaccaactg ctctgcctcc cccagttgac gacaagattg agcatgaatc
1441 tacagaagat agctcttctt caagtagctt tgttgacttg aatgatccat ttgcactgct
1501 gaatgaggac gaggatactc ttgatgacag tgtcatgatc ccgggcacaa catcgagaga
1561 atttcaaggg attcctgaac cgccaagaca atcccaagac ctcaataaca gccaaggaaa
1621 gcaggaagat gaatccacaa atccgattaa gaaacagttt ctgagatatc aagaattgcc
1681 tcctgttcaa gaggatgatg aatcggaata cacaactgac tctcaagaaa gcatcgacca
1741 accaggatcc gacaatgaac aaggagttga tcttccacct cctccgttgt acgctcagga
1801 aaaaagacag gacccaatac agcacccagc agcaaaccct caggatccct tcggcagtat
1861 tggtgatgta aatggtgata tcttagaacc tataagatca ccttcttcac catctgctcc
1921 tcaggaagac acaaggatga gggaagccta tgaattgtcg cctgatttca caaatgatga
1981 ggataatcag cagaattggc cacaaagagt ggtgacaaag aagggtagaa ctttccttta
2041 tcctaatgat cttctgcaaa caaatcctcc agagtcactt ataacagccc tcgttgagga
2101 ataccaaaat cctgtctcag ctaaggagct tcaagcagat tggcccgaca tgtcatttga
2161 tgaaaggaga catgttgcga tgaacttgta gtccagataa cacagcacgg ttactcactt
2221 atctattttg tatgactca tcctcagatc acagcaatca aatttatttg aatatttgaa
2281 ccaccttta gtatcctatt acttgttact attgtgtgag acaacataag ccatcaaata
2341 acaatcacgg gcaaggactg ggcatactat ggtggtctta gagcattgtc cagtgctaca
2401 aattcttttt tcaattgcta taattataca actacaaacc tccatacatt tgccgcaaca
2461 ctgtaatcaa cactgctgta tctcttcttc aagccatctg atttaactta ataaacatga
2521 cttgattcaa agaatatact gacaatgtta ctgtttgaat ttctcaagtg gtgcactatc
```

FIG. 2 CONTINUED

```
2581 ctactgtttt gctcagctta gtatattgta atatgtaagt ggactctccc cttctcctct
2641 cgtgtattct ttataaatca cttactigat agaatgtcga gtctactggt ttggagtttc
2701 cttactctaa tggatgtaat aattaactgt tggcctagat gataacagat atgaggttat
2761 ataattactc atagtgtaaa gtataattct tacctctgtt tcttctgttt tcccttctt
2821 ttataatatg ccaattaaga aaaactaaaa atcgaagaat attaaagatt ttctttaata
2881 ttcagaaaag gctttttatt ctattctttc tttttacaaa cgtattgaaa tagtaattct
2941 cacaatgtgg gactcatcat acatgcagca agtcagcgaa gggttgatga ctggaaaagt
3001 acccatagat caagtgtttg gtgccaatcc cttagagaag ttatacaaga gaagaaaacc
3061 aaaaggcaca gttggactac aatgtagccc ttgtctaatg tcaaaggcga caagtactga
3121 tgatattatt tgggaccaac tgatcgtgaa gagaacacta gctgatctac ttataccgat
3181 aaataggcag atatcagaca ttcaaagcac tctaagcgaa gtaacaacaa gagtccatga
3241 aattgagcgg caattacatg agattacccc agttttaaaa atgggaagga cactggaagc
3301 aatttccaag gggatgtcag aaatgttagc caaatacgac caccttgtaa tttcaactgg
3361 aagaaccact gcaccagctg ctgcctttga tgcctactta aatgagcatg gtgtccctcc
3421 ccctcaaccc gcgattttca aagatcttgg ggttgcccaa caagcttgta gtaaggggac
3481 catggttaaa aatgcaacaa cagatgcagc cgacaagatg tcgaaggttc ttgaactcag
3541 tgaggaaacg ttctccaagc caaaccttc agctaaggat ttagcccttt tattgttac
3601 ccatctaccc ggcaacaaca ctccattcca tatcctagct caggtccttt caaaaattgc
3661 ttacaagtca ggaaaatccg gagcattctt ggatgcattt caccagattc taagtgaagg
3721 agagaatgct caggcggcat taactcgact aagcagaaca tttgacgctt tccttggagt
3781 ggttcctcca gtgataagag tcaaaaactt ccaaacagtc cctcgtccat gtcaaaaaag
3841 tcttcgggct gtccctccaa atccaacaat tgacaaagga tgggtctgtg tttattcatc
3901 tgagcaaggt gaaacacggg cccttaaaat ctaattctca ttgttcatag ttgcaaggga
3961 agtgatcttt ccgagttgat acaaagacac taaacatttc aaaagcatgt atgtggacaa
4021 aacataatta gaccatctta attggagtag taatttattt ctgtcttaaa tgtgattttc
4081 actttaaaag cgttaaatgg tgatagatta atccttgaag ttactcttct atatattata
4141 gagaaaccaa tgttactaac aaaaggggtc tacctaacgc atatgattga gtaatccgta
4201 tattttataa accaaacaat taacttctta cttttaaga atcaactaac aacatagaaa
4261 agacattat ccttatgtaa tcctcggctt agttgaaatt aacttttgtt ggacctcaag
4321 acgcttattc atagtatatt atatgatttt ttataagttt aagatatctt aaattatacc
4381 cacaaaagat actgttttaa ttaagaaaaa ctatgaagaa cattaagaag atctttcttt
4441 cgtagtgttc ttttactgga aggagtattc caatttcagc ttgttggatt aattgttact
4501 taaattgtcc ttttgaaat taattcacac aaggtagttt aaatttatat ccaaaataaa
4561 ttttgatatg gccagttcca gcaattacaa cacatacatg caatacttga accccctcc
4621 ttatgctgat cacggtgcaa accagttgat cccggcggat cagctatcaa atcagcaggg
4681 tataactcca aattacgtgg gtgatttaaa cctagatgat cagttcaaag ggaatgtctg
4741 ccatgctttc actttagagg caataattga catatctgca tataacgagc gaacagtcaa
4801 aggcgttccg gcatggctgc ctcttgggat tatgagcaat tttgaatatc ctttagctca
4861 tactgtggcc gcgttgctca caggcagcta tacaatcacc caatttactc acaacgggca
4921 aaaattcgtc cgtgttaatc gacttggtac aggaatccca gcacacccac tcagaatgtt
4981 gcgtgaagga aatcaagctt ttattcagaa tatggtgatc cccaggaatt tttcaactaa
5041 tcaattcacc tacaatctca ctaatttagt attgagtgtg caaaaacttc ctgatgatgc
5101 ctggcgccca tccaaggaca aattaattgg gaacactatg catcccgcag tctccatcca
5161 cccgaatctg ccgcctattg ttctaccaac agtcaagaag caggcttatc gtcagcacaa
5221 aaatcccaac aatggaccat tgctggccat atctggcatc ctccatcaac tgagggtcga
5281 aaaagtccca gagaagacga gcctgtttag gatctcgctt cctgccgaca tgttctcagt
```

FIG. 2 CONTINUED

```
5341 aaaagagggt atgatgaaga aaaggggaga aaattccccc gtggtttatt ttcaagcacc
5401 tgagaacttc cctttgaatg gcttcaataa cagacaagtt gtgctagcgt atgcgaatcc
5461 aacgctcagt gccgtttgaa atgatgctca aatgagacag gagtccatct gtataagaag
5521 tatggcttaa atggatattt gtcaaattct tacaagatta gtttgtattg atttcaacaa
5581 tgctttaacc ttacattgct gctttaaata gttgattaag ctgatcagct tgtaatatgt
5641 aatctcttct gggccatcag atccataatg ggtttactag actatataag agaaatagta
5701 atatttata aacaattctt gctcagtttt actgtgattt aataacatat gtcattgtgc
5761 cctccattgc taagtcaact caactgacga taatactcct tctgaaatag taagaaaaac
5821 taatgaagaa cattaattgc tgggtaaaag tgattaattt cttaaattt gaccagaata
5881 atattttgtc agtgaatata ttctcatatc acttgattaa aaacagaaaa ttaccctaac
5941 atgaagacca catgtttcct tatcagtctt atcttaattc aagggacaaa aaatctcccc
6001 attttagaga tagctagtaa taatcaaccc caaaatgtgg attcggtatg ctccggaact
6061 ctccagaaga cagaagacgt ccatctgatg ggattcacac tgagtgggca aaaagttgct
6121 gattcccctt tggaggcatc caagcgatgg gctttcagga caggtgtacc tccaagaat
6181 gttgagtaca cagaggggga ggaagccaaa acatgctaca atataagtgt aacggatccc
6241 tctggaaaat cctgctgtt agatcctcct accaacatcc gtgactatcc taaatgcaaa
6301 actatccatc atattcaagg tcaaaaccct catgcacagg ggatcgccct tcatttatgg
6361 ggagcatttt ttctgtatga tgcattgcc tccacaacaa tgtaccgagg caaagtcttc
6421 actgaaggga acatagcagc tatgattgtc aataagacag tgcacaaaat gattttctcg
6481 cggcaaggac aagggtaccg tcatatgaat ctgacttcta ctaataaata ttggacaagt
6541 agtaacggaa cgcaaacgaa tgacactgga tgtttcggcg ctcttcaaga atacaattct
6601 acaaagaacc aaacatgtgc tccgtccaaa ataccctccac cactgcccac agcccgtccg
6661 gagatcaaac tcacaagcac cccaactgat gccaccaaac tcaataccac ggacccaagc
6721 agtgatgatg aggacctcgc aacatccggc tcagggtccg gagaacgaga acccacaca
6781 acttctgatg cggtcaccaa gcaagggctt tcatcaacaa tgccacccac tccctcacca
6841 caaccaagca cgcacagca aggaggaaac aacacaaacc attcccaaga tgctgtgact
6901 gaactagaca aaaataacac aactgcacaa ccgtccatgc cccctcataa cactaccaca
6961 atctctacta acaacacctc caaacacaac ttcagcactc tctctgcacc attacaaaac
7021 accaccaatg acaacacaca gagcacaatc actgaaaatg agcaaaccag tgcccctcg
7081 ataacaaccc tgcctccaac gggaaatccc accacagcaa agagcaccag cagcaaaaaa
7141 ggccccgcca caacggcacc aaacacgaca aatgagcatt tcaccagtcc tccccccacc
7201 cccagctcga ctgcacaaca tcttgtatat tcagaagaa agcgaagtat cctctggagg
7261 gaaggcgaca tgttcccttt tctggatggg ttaataaatg ctccaattga ttttgaccca
7321 gttccaaata caaaacaat ctttgatgaa tcctctagtt ctggtgcctc ggctgaggaa
7381 gatcaacatg cctccccaa tattagttta actttatctt atttcctaa tataaatgag
7441 aacactgcct actctggaga aaatgagaat gattgtgatg cagagttaag aatttggagc
7501 gttcaggagg atgacctggc cgcaggctc agttggatac cgttttttgg ccctggaatt
7561 gaaggacttt acactgctgt tttaattaaa aatcaaaaca atttggtctg caggttgagg
7621 cgtctagcca atcaaactgc caaatccttg gaactcttat tgagagtcac aactgaggaa
7681 agaacattct ccttaatcaa tagacatgct attgactttc tactcacaag atggggagga
7741 acatgcaaag tgcttggacc tgattgttgc atcgggatag aagacttgtc caaaatatt
7801 tcagagcaaa ttgaccaaat taaaaggac gaacaaaaag agggggactgg ttggggtctg
7861 ggtggtaaat ggtggacatc cgactggggt gttcttacta acttgggcat tttgctacta
7921 ttatccatag ctgtccttgat tgctctatcc tgtatttgtc gtatctttac taaatatatc
7981 ggataacgtt aaatgtgtaa tgattaggac tttaggacaa ttgctactga gccctttttc
8041 taatctactg aaatcaactt gggagatttt taagaagctg ataacttaat gtgaatcaat
```

FIG. 2 CONTINUED

```
8101 agtttatgta ttatcgatta ttatggtttg atattcaatt gttattattg tcaggagtga
8161 cctttctat ttgatgcatt aatgttttaa actacctctt aagcctttga gggcggtccc
8221 aatatgtgcg taggggttaa tttaaaggga tttcttattg tacagttttc tgtattactt
8281 atttgggctt gaagacatag ttaagatttg ccgaaaatgc tctccagtca attccatccc
8341 ctctcagaaa agacgtgctg ttcaaagagt cttaatttat aaccaactat tgcaagaatt
8401 aatttacttt ttccgttata cttagttaca ttaatctttt gactgttcag cattattaac
8461 gacttgtctt aattcaatcg ttcggatgaa attcataagg aaaaatgagc ctccttcccc
8521 ctattctggg ctgagaaaat ttctcttatc cgcctaaaat ctgatctgtt aggtcatggg
8581 tccttcataa tctgtttgag catgaatatt gatcaaatga ccaaatgata gtgcatttgt
8641 atagactcaa ttatccttta ttaagaaaaa gataaataga acacaaagaa ttgacaaaat
8701 ttactttga ttgatttgc aaggagttat aaaaatcttg aaggataaat tgttataaag
8761 tagagtcgaa gaacattaaa tgttctttgt tagaattatt catctaagtt gttttgagt
8821 atattcgctt caatacaact cctctttata tttgatttaa gttttaaaat gcaacaacct
8881 cgcggaagaa gtcgaacccg caaccaccaa gtcacaccga ctatatatca tgaaactcaa
8941 ttgccctcca aacctcatta taccaattat catccacgtg caagatcgat gagctcaacc
9001 cgtagtagtg cagaaagtag tcccaccaat catattcccc gtgctcgacc accctcaaca
9061 ttcaacttat cgaaacccc tcctcctcca aaagacatgt gcaggaacat gaaaattgga
9121 ttgccgtgcg ctgatcccac ttgtaataga gatcatgacc ttgataatct aacaaatcgt
9181 gaactttgc tattgatggc ccgaaaaatg ctccccaata cagacaagac ctttagaagt
9241 ccgcaggact gtggatcacc gtctcttct aaaggtctct caaaagataa acaggagcaa
9301 acgaaagatg tgttgacctt ggaaaatcta ggacacattc tgagctatct ccacagatca
9361 gaaattggga aattggatga gacatcactt cgtgcagcat taagtctgac gtgtgctgga
9421 attcgaaaga cgaatagatc cttgatcaac accatgacag aattacacat gaaccatgaa
9481 aatctcccgc aagaccaaaa cggtgttatc aagcagacct atacaggtat tcaccttgac
9541 aaaggaggtc aattcgaagc cgccttatgg caaggttggg ataagagatc gatatctcta
9601 ttcgtacaag cagctttata tgtaatgaac aatatcccct gtgaatcatc aatcagtgtg
9661 caagcctcat acgatcattt tattcttcct caaagtcaag gtaaaggaca gtgattattg
9721 ttcgaaagtt gacaatttga tcactttcag ttttcagttt caaccctat cgcgagactt
9781 gaatacaatc ctactaactt caataagtga ccccaaattc aagtttgctg aaagctaaga
9841 tgacaatgat cactagttca ttgtaaaatta ctcgatcaaa atgttcttaa gctatcttaa
9901 gcttactgat gcggctctgc ttcactttc ttttgatttt aaagccatag ctatatctaa
9961 gtgtctaatt aacaacttgt accctctaagg aaaaacatga agaacattaa gaaaaaggat
10021 gttcttattc tttgactaaa cctgcatatt ctttgttgat accctcgaga gacaacttt
10081 gacaccagat cacggatcaa gcacacttca atcaagcacc ctaaattttc aatcatacac
10141 ataataacca ttttagtagc gttgcctttc agtacagtct aggtgattgt tgaaagactt
10201 ccaagcatgg cagaattatc aacgcgttac aacttgcctg caaatgttac ggaaaatagt
10261 ataaatcttg accttaattc cacagcacga tggataaaag aacccagtgt tggggggctgg
10321 acagtgaagt ggggaaactt tgttttccat ataccaaata ctggaatgac attgttgcat
10381 catttaaagt ctaacttcgt tgttccagag tggcaacaaa caaggaatct attctcccac
10441 ctcttaaaa acccaaaatc aacaattata gaaccgtttt tggccctgag gattttgctt
10501 ggagttgctt tgaaggatca agaattacag caatcattga ttcctggatt tagatctatt
10561 gttcatatgc tatcagaatg gctgctcctg gaggtcacgt cggcaatcca tattagccct
10621 aatctgttgg gaatctattt gacttcagac atgttaaaa ttctgatggc aggtgtgaaa
10681 aatttcttca ataagatgtt cactcttcat gttgtaaatg accacggaaa acccagcagt
10741 attgaaataa agttaactgg acaacagatc attatcactc gtgttaatat ggggtttcta
10801 gtggaagtca ggaggattga tattgaacct tgctgtggtg agacagtcct ctcagaatca
```

FIG. 2 CONTINUED

```
10861 gttgtttttg gactagtggc tgaggcagtt ctaagagaac acagtcaaat ggagaagggc
10921 caacctctca atctgacaca atacatgaac agcaaaattg ctatataagt ggcttaaatt
10981 agcatgggta ttcctagttc gaccacataa taatgttgga ggcacagtac attatagtta
11041 attgtcttgt atactaaggg atatacctaa cctgatttat atttactggt ataaaatagt
11101 agcatcatct tattgaatag ttatcataca ataggctgtt cctataatct gattgtgaga
11161 ttataaactt gtagaattac cgtgggtcac aactgttgca tatcctccaa aatatatctt
11221 ttgcaagtga tgtgtgcttg aatacttcga tataatacat actaataacg attgattaag
11281 aaaaatcaat gatggatatt aaatgtccat caagcaagtg ttgtagaata ccaggggttt
11341 cacaggctgc taaacttact aaattttaca taggattata taattctttt cgatacacgt
11401 tatatcttta gcaaagtgag gaaaacagct ttatcatgtt agatgccagt tatccatttt
11461 aagtgaatcc tttcctcaac atgcagcatc caactcaata tcctgatgca aggttgtcct
11521 ctcctataat cctagaccag tgtgacttat tagccagaag tttagggttg tatagtcatt
11581 attcacataa tccgaaattg cgtaattgta ggattccaca tcacatttac cgtttaagga
11641 attcgacagc attaaagaca tttcttcaga attgttcgat actcaccgtt cctttcatt
11701 caatttggga tcatatttta acttccattc aatatgatgc aattaatcat gttgatgatt
11761 ttaaataccct attgccatct gagctagtca agtatgcgaa ttgggacaac gagttcttaa
11821 aagcatatct taataagatc ttaggacttg accatgtttt ttcagcttct gcaaggtcac
11881 agtgtgagga tttttctcct aaggaaaaatc cttattattg ggggatgtta ttactcgtgc
11941 atctatctca acttgccagg aggataaaag gacaaagagg gtcattaaga agtaactgga
12001 aatttatagg aacagatttg gagctgtttg gaatagcaga ttttgttatt tttaaggttc
12061 cagtaaaaac aataatccga aatgctgtaa gctacaagc ttcaaaaccg ggattaagaa
12121 tatggtaccg tgaccaaaac ttgacccctt atctatgcga cgatgagttt attgtaagcg
12181 tcgctagtta tgaatgtttt atcatgatta aagacgtctt cattgagagg tataacacat
12241 gggaaatctg tgcccgcgct tggctcgaag acagtgatgg agctgattat cctcctcttg
12301 atgtgttagg tgaattatac aaccagggag accaaaattt tgccatgtac ctggaggacg
12361 gtttcaaatt gattaaacac ttagaaccct tgtgtgtcag ctgtatacaa acacatggca
12421 tctttacacc aagaaaaatac tggttccaat cacagatgat taagtcatat tatgatgaac
12481 tccatgatct caattttgaaa cttcaaattt cagacaataa ggctgagtgt gcccaaaact
12541 ttattaaaac tatagttcag gcgaaattga ctcctcaaca atactgtgaa ttattctccc
12601 tacaaaagca ttgggggtcat cccgttttat acaatgatgt tgcactagat aaggttaaaa
12661 aacatgcgca atcgacaaaa atcttaaaac ctaaagtcat gtttgaaact ttttgtgttt
12721 tcaaatttat agtagcaaag aatcattatc attctcaagg atcatggtat aaaaccacac
12781 atgatttgca tttgactcca tatcttagac aacatattgt gtcaaattca tttccatcac
12841 aagccgaaat ttatcagcat ctttgggagt ggtatttcgt ggagcatgaa cctcttttct
12901 caactaaaat aataagtgat ttaagtatct ttataaaaga cagggctacc gctgtgaacc
12961 aggagtgttg ggacagtgtc ttcgatagaa gtgtattagg atataaccct cctgttagat
13021 ttcaatcaaa gagagtgcca gagcaatttt tgggtcaagc agacttttcc ttgaatcaaa
13081 tattagagtt tgctgaaaag ttagagtatt tggctccttc ttataggaat ttttccttct
13141 cattaaaaga aaaagagttg aatataggaa gaactttggg gaagttaccg tatcgtgtca
13201 gaaatgtcca aacactcgca gaagccctgc tagcagatgg actggcaaaa gcattcccta
13261 gtaacatgat ggttgtcact gagagggaac agaaagaagc attattacat caggcttctt
13321 ggcaccacaa ttcagcaagc ataggggaga acgctatagt gaggggtgca agtttttgtta
13381 ctgatcttga gaaatacaac ctcgccttcc gatatgaatt tacacggcat ttcatagact
13441 actgtaatcg atgttatggt gtgaagaatt tatttgattg gatgcatttt ttaataccac
13501 tatgttatat gcatgtcagt gactttata gccaccaca ttgtgtgaca gaagataatc
13561 gaaataaccc acctgattgt gctaatgctt atcattatca cttaggaggt atagagggac
```

FIG. 2 CONTINUED

```
13621 ttcagcagaa attgtggaca tgcatatcat gtgcccaaat caccettgtg gagttaaaaa
13681 ctaaattaaa attgaagtcc agcgtcatgg gtgataatca atgtataaca actctaagtc
13741 tttttccaat tgatgctccc aacgattatc aagagaacga ggctgaattg aatgcggcac
13801 gagttgctgt cgaattagct attactacag gttatagtgg tatatttta aagcctgagg
13861 aaacatttgt ccattcaggg ttcatttatt ttggtaaaaa gcaatatctc aacggtgttc
13921 aactgccgca atcattgaaa acaatggcaa ggtgtggacc cttatctgac tctatttcg
13981 atgatcttca aggttctctg gccagtattg gtacatcctt tgagagagga acaagcgaga
14041 cacggcacat ttttccgagc cgttggatag cttcattcca ttcaatgtta gcaataaatt
14101 tattaaatca gaatcacctt gggtttcctc tagggttcaa tattgatatt tcttgtttca
14161 aaaagcctct taccttctcg gaaaaattaa ttgctctcat aacgccccaa gtttaggag
14221 ggttatcatt tttaaatcca gaaaaattgt tctaccggaa cataagtgat cctctcactt
14281 caggtctatt tcaactcaag aatgcattgg aatttcttga aaaggaagaa ttattctata
14341 tcttgatttc taaaaaacct ggtttagcag atgcctcaga ttttgtcatg aatccattag
14401 gcttaaatgt accaggatca aaggaaataa taacgttcct tagacaaaca gtcgcgaaa
14461 atatcacgat cacgtcacaa aatagaataa taattctct tttccacata ggttctgatt
14521 tagaggacca aagagtgtgt gagtggcttt tatcatcaaa ccctgtaatg agccgatttg
14581 ctgctgacat ctttcaaga acacctagtg gaaaacggct tcaagtctta ggctatctag
14641 aaggaacaag aacattacta gcttctcgga caatcagttt aactacagaa ggaacaatgt
14701 tgatgaaatt aagagaatta acgagaaacc gatggaaaag ttggttttct tatattgatg
14761 cactggacga tgatttatct gagtccttgg aaaagttcac atgtactgtt gatgtggcta
14821 atttcttgag ggcatattca tggtctgacg tcttaaaagg gaaaaggcta attggtgcca
14881 cactgccatg tttactagag caatttgagg taaagtggat taatttatct gaggatttaa
14941 gggaacaatt taatctatct tcagactcaa aatcaactat aaacttgttg ccgtatgact
15001 gtaaggaact gcgacttgaa ggaagcaatg acacagagtt aaattatgtc agttgtgctc
15061 ttgaccggaa agttgtccag aaacatccct ctgttaatcg tctagcttgg acgataggaa
15121 atcgagcacc gtatattggc tcacggacag aagataagat cggttatcct ccttaagag
15181 taaattgccc atcagcagca cttaaagaag ctattgagat ggtttctaga ttgttatggg
15241 tgactcaagg cactgcagac cgagaaaaat tgcttattcc tcttctcaat tcaagagtaa
15301 atctggacta tcagacggtg cttaactttt tacctacaca ctactcaggc aacatagttc
15361 atagatataa tgatcaatat ggacaacatt cctttatggc aaacaggatg agtaatacat
15421 ctacacgtgc aattatatca actaacacac tgggtaaata tgctggggga ggtcaagctg
15481 ctattgatag taatataatc tttcaaaata ctattaattt aggagttgca gtttagata
15541 ttgcattgtc tcttgctaaa ttgtcgtcag catcaaatgt cactttccgt ttaatgttaa
15601 ataagtgctg cacgcggcat gtaccgtccg aatacctata ttttgataaa cctttagatg
15661 tggatttgaa caagtatatg gacaatgagt tggtttatga caatgaccct ctttgcagtg
15721 ggattaaagg gagattaggc agagtatctc gatcaacact cacattgagt ttgaatgtca
15781 gtgacattgg ttcttatgac tttccaacta ttgctgcatg gacactagga gaaactatag
15841 tcggaagcat ttttctgat gaatcttctc aaagtacgga tccaataagc tcaggttgca
15901 caaaaacttt cgtcacacat ttccttgtgt atccagttga gagtatattt tatgcattcg
15961 gagctaactt aatagttgaa agtttaagtc taagtaggat caaatcaatt aagaacctct
16021 cagatttgac attccttata tcatccacaa tcaggaattt atcacataga tcacttcgga
16081 ttcttcaatc tactttccga catgaattgg tgctcacccg actagcccac cacataccgt
16141 taattcttt aatgttaggg ggctctgcag gagagaagag ttcatcagat gctgttcggc
16201 tatttcttac agcaagttat cagaattta tcaataattt cagttgtctg atgaagaagg
16261 gtcagtcatc gctaccggtt tggctttact ttcctagtga agggcaacaa ttaaagccta
16321 tattaaaaat cttacagaga ttatcagact tgttatcacc tgacaaaatt caaaagcgta
```

FIG. 2 CONTINUED

```
16381 aaattttggc tgacacctgt tgtccaattg gcagcttttg ggtctatcca agcaagtcca
16441 caaggactaa ccattattat gcaagcctta attattggag agacaaagct aataaggtta
16501 agaatactcc tttttcacac ttgataaatt gttcatttcc tgaattttct tcacatacca
16561 gttcagtctc ctctaatcaa caagtgacca attcgaagta tattgtttat ccagaaaata
16621 tcactgaaat aaatgcaaga accagattaa taaattatgg atcaacagct ctacagggga
16681 tggacaccaa gatgccactc tcagagcaaa atctagtcga aaattgtcga ccatcagagg
16741 gcatcagatt caaggacaat caaaaaataa caaaacatga ccagagatgt gagagggagg
16801 aatcttcacc gcaacagatg ttccctgaag ataacatgca gactcctgcg cacatacata
16861 gttcctcccc atttcaaatc cttataaaat cactagatgc acatgaggac tttgatgcct
16921 cgaagataat cttaaattct gaaataaata atcttaacct tacggagtat actcttaata
16981 caaagttatt gacaactcct accaggacag aaattttaga tacaagtccg ttacaatcct
17041 ctagatattc atcaacttcc agggaacggt ctctactatc cagagaacaa gcttcatatt
17101 tgtacgttga ttgcagtaat attccttcta tctctctaga cccaggtttt cggagtatgt
17161 ctgatcagaa tcaagttcaa atgttaatca atacctacaa acgtgattta catgcttgtt
17221 ttgatagcaa tcaattctgt cggtttacag gggtagtctc atcaatgcat tacaagcttt
17281 atgatctttt gcctccaggt aaattgaaaa aggcaatttg tttggccgaa ggggaaggaa
17341 gtggtgctcg gttacttttg aagtggaagg aaacggatta tttattcttc aacactttgg
17401 ctacggattc acaacaagaa gccgagattt tgagtggccg ggtaataccg agaatgttgt
17461 ataacataga cagattaagt gctttgcttg aatcaaggag actaatattg aacaacctaa
17521 ctatccaaat tacagatatt acaaatccat tatggctaga ttctgtaata caatatttac
17581 ctgaagatag tgacattctt acaatggacg cagagaccac caaggatgaa acaagggaac
17641 agctttataa aactattgtg aatatttgga cacgtacttc tcctaatatc ccaaaaatta
17701 gcatcatcaa ggtattttta ttagactatg aagggacttt attcttaatg aagaatgcta
17761 ttcagtatta tgggcaagtt caactcaaga aaccatatag ctcaaatgca aaaaactcag
17821 aatggtactt gtgttgcggt aaacgaagaa ttcaacggct ccaaattgat ttctcagacc
17881 aggtgggaat ttttctgatt tgtaaagcaa tgtcacgcca aagacaagca attccttact
17941 ggttaaaaca tatagaaaag aattatcctg cttcattaca cgagttttc ctaactttgg
18001 gtttcccttc tttagagtca tctttctgcc atcgttatac tattccattc agtgaaggaa
18061 aggctctttt tcacaaggtc cagtcttatg ttcgtcaagg caaacaacat ttacattctc
18121 ttatgttgga ttatgaaaac aattcacctc tactagactt gagaaatcac tttatttgct
18181 cattaagggg aaagataact aaatattaca atgatatatt aaagttaaat ctagtcatca
18241 aggcagtaga aaaagtaaa aattggtcac aacttgttga gatccttcct aatatgcatt
18301 cagtatgcat agtgcacgtg gatcatgagt gttctggatg cgagaaacgg ttattactta
18361 aattggattt tatcagaaat acaaagatcg cagaacaaaa attacttaac agagtaatcg
18421 ggtatatcct attctttcca ttcggtctgt ttaaatctgg atcattaagg gcataatttc
18481 aacagagaga acttcattta attcacaaaa acaatctatt taagagtgag ggttacattg
18541 tctaagatat tgtatgagaa gtaataaaat aaataagaaa acgaaaagac tattagacag
18601 cttattttat acaagataat cttatatcgc tttaggcctc acacaagtga gaaaattacg
18661 cgcacagatt aactagtgat tagtgtttgg tcacaccaga ggtaacttt taacgttaat
18721 tactcagatg ttattgctca taattagcat taatattggc acattgggtg aatccttgag
18781 ctttatccct aatatggtgt aagaaattaa ggaatactg agatacacta gttgaattga
18841 attatgacat accatatatc ataaatataa aaaagtgtct gctgtaatct acaagcacct
18901 cttttaaata cattaggaaa agaattaagt taccgttgag atcaaaaaaa ccacgtcatg
18961 ttttctctga tgacaagtga taaaacttcg tagttaaatt tctagaatgt cgatgtgaat
19021 gtaaattaag aaaaaccaat atataaaatt aaaaaattaa aaagctttga tataagtaac
19081 acaaaacatt cttcatcttt tttgtgtgtc c (SEQ ID NO: 28)
```

FIG. 2 CONTINUED

VP30
MQQPRGRSRTRNHQVTPTIYHETQLPSKPHYTNYHPRARSMSSTRSSAESSPTNH
IPRARPPSTFNLSKPPPPPKDMCRNMKIGLPCADPTCNRDHDLDNLTNRELLLLM
ARKMLPNTDKTFRSPQDCGSPSLSKGLSKDKQEQTKDVLTLENLGHILSYLHRSE
IGKLDETSLRAALSLTCAGIRKTNRSLINTMTELHMNHENLPQDQNGVIKQTYTG
IHLDKGGQFEAALWQGWDKRSISLFVQAALYVMNNIPCESSISVQASYDHFILPQ
SQGKGQ SEQ ID NO:201

AF086833

1 cggacacaca aaaagaaaga agaattttta ggatcttttg tgtgcgaata actatgagga
61 agattaataa ttttcctctc attgaaattt atatcggaat ttaaattgaa attgttactg
121 taatcacacc tggtttgttt cagagccaca tcacaaagat agagaacaac ctaggtctcc
181 gaagggagca agggcatcag tgtgctcagt tgaaaatccc ttgtcaacac ctaggtctta
241 tcacatcaca agttccacct cagactctgc agggtgatcc aacaacctta atagaaacat
301 tattgttaaa ggacagcatt agttcacagt caaacaagca agattgagaa ttaaccttgg
361 ttttgaactt gaacacttag ggattgaag attcaacaac cctaaagctt ggggtaaaac
421 attggaaata gttaaaagac aaattgctcg gaatcacaaa attccgagta tggattctcg
481 tcctcagaaa atctggatgg cgccgagtct cactgaatct gacatggatt accacaagat
541 cttgacagca ggtctgtccg ttcaacaggg gattgttcgg caaagagtca tcccagtgta
601 tcaagtaaac aatcttgaag aaatttgcca acttatcata caggcctttg aagcaggtgt
661 tgattttcaa gagagtgcgg acagtttcct tctcatgctt tgtcttcatc atgcgtacca
721 gggagattac aaacttttct tggaaagtgg cgcagtcaag tatttggaag ggcacgggtt
781 ccgttttgaa gtcaagaagc gtgatggagt gaagcgcctt gaggaattgc tgccagcagt
841 atctagtgga aaaaacatta agagaacact tgctgccatg ccggaagagg agacaactga
901 agctaatgcc ggtcagtttc tctcctttgc aagtctattc cttccgaaat tggtagtagg
961 agaaaaggct tgccttgaga aggttcaaag gcaaattcaa gtacatgcag agcaaggact
1021 gatacaatat ccaacagctt ggcaatcagt aggacacatg atggtgattt tccgtttgat
1081 gcgaacaaat tttctgatca aatttctcct aatacaccaa gggatgcaca tggttgccgg
1141 gcatgatgcc aacgatgctg tgatttcaaa ttcagtggct caagctcgtt tttcaggctt
1201 attgattgtc aaaacagtac ttgatcatat cctacaaaag acagaacgag gagttcgtct
1261 ccatcctctt gcaaggaccg ccaaggtaaa aaatgaggtg aactccttta aggctgcact
1321 cagctccctg gccaagcatg gagagtatgc tcctttcgcc cgacttttga acctttctgg
1381 agtaaataat cttgagcatg gtcttttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt ccctttccag gacccatcaa tgatgacgac aatcctggcc atcaagatga
1801 tgatccgact gactcacagg atacgaccat tcccgatgtg gtggttgatc ccgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatc

FIG. 2 CONTINUED 2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca acacccagtc
2401 agaacactct tttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttattttg
2821 aatttaaagc tagcttatta ttactagccg tttttcaaag ttcaatttga gtcttaatgc
2881 aaataggcgt taagccacag ttatagccat aattgtaact caatattcta actagcgatt
2941 tatctaaatt aaattacatt atgcttttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaagctggt
3121 ctaacaagat gacaactaga acaaagggca ggggccatac tgcggccacg actcaaaacg
3181 acagaatgcc aggccctgag cttcgggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagttttgag gaggtagtac aaacattggc ttcattggct actgttgtgc
3421 aacaacaaac catcgcatca gaatcattag aacaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcatcaa caatctaaac agtaccactt cactaactga ggaaaatttt gggaaacctg
3781 acatttcggc aaaggatttg agaaacatta tgtatgatca cttgcctggt tttggaactg
3841 cttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaacgacc aagataaaat tgttcatatc tcgctagcag cttaaaatat
4321 aaatgtaata ggagctatat ctctgacagt attataatca attgttatta agtaacccaa
4381 accaaaagtg atgaagatta agaaaaacct acctcggctg agagagtgtt ttttcattaa
4441 ccttcatctt gtaaacgttg agcaaaattg ttaaaaatat gaggcggggtt atattgccta
4501 ctgctcctcc tgaatatatg gaggccatat accctgtcag gtcaaattca acaattgcta
4561 gaggtggcaa cagcaataca ggcttcctga cacggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct

FIG. 2 CONTINUED

```
4801 ttgactcaac tacggccgcc atcatgcttg cttcatacac tatcacccat ttcggcaagg
4861 caaccaatcc acttgtcaga gtcaatcggc tgggtcctgg aatcccggat catcccctca
4921 ggctcctgcg aattggaaac caggctttcc tccaggagtt cgttcttccg ccagtccaac
4981 taccccagta tttcaccttt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aaggggaaca
5161 gtgccgatct aacatctccg gagaaaatcc aagcaataat gacttcactc caggacttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aagtgcttt
5581 acaccattgt cttttttctc tcctaaatgt agaacttaac aaaagactca taatatactt
5641 gttttaaag gattgattga tgaaagatca taactaataa cattacaaat aatcctacta
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgcccttc
5881 taattaagaa aaaatcggcg atgaagatta gccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattcttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttccccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg actttcgctg aaggtgtcgt tgcatttctg atactgcccc
6601 aagctaagaa ggacttcttc agctcacacc ccttgagaga gccggtcaat gcaacggagg
6661 accgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggccttctg gaaactaaa aaaaccctcac tagaaaaatt cgcagtgaag agttgtctt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
```

FIG. 2 CONTINUED

```
7561 acccaaatgc aaccctaatt tacattactg gactactcag gatgaaggtg ctgcaatcgg
7621 actggcctgg ataccatatt tcgggccagc agccgaggga atttacatag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
7981 gagacaatgg ataccggcag gtattggagt tacaggcgtt ataattgcag ttatcgcttt
8041 attctgtata tgcaaatttg tcttttagtt tttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtctttagtg acaagggaaa gaagccttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gattttgtgt tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa cctctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca acccctaacag tgatcaaaga aaatcataat ctcgtatcgc tcgtaatata
9601 acctgccaag catacctctt gcacaaagtg attcttgtac acaaataatg ttttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatatttgt
9841 tcttgtttca agaggtagat tgtgaccgga aatgctaaac taatgatgaa gattaatgcg
9901 gaggtctgat aagaataaac cttattattc agattaggcc ccaagaggca ttcttcatct
9961 ccttttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaatagga acgtcgttcc aacaatcgag
10261 cgcaaggttt caaggttgaa ctgagagtgt ctagacaaca aaatattgat actccagaca
```

FIG. 2 CONTINUED

```
10321 ccaagcaaga cctgagaaaa aaccatggct aaagctacgg gacgatacaa tctaatatcg
10381 cccaaaaagg acctggagaa agggggttgtc ttaagcgacc tctgtaactt cttagttagc
10441 caaactattc aggggtggaa ggtttattgg gctggtattg agtttgatgt gactcacaaa
10501 ggaatggccc tattgcatag actgaaaact aatgactttg ccctgcatg gtcaatgaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaacccttag caggagccct tggtctgatc tctgattggc tgctaacaac caacactaac
10741 catttcaaca tgcgaacaca acgtgtcaag gaacaattga gcctaaaaat gctgtcgttg
10801 attcgatcca atattctcaa gtttattaac aaattggatg ctctacatgt cgtgaactac
10861 aacggattgt tgagcagtat tgaaattgga actcaaaatc atacaatcat cataactcga
10921 actaacatgg gttttctggt ggagctccaa gaacccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
11221 aattgtttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacatacccca ataccccagac gctaggttat catcaccaat tgtattggac
11641 caatgtgacc tagtcactag agcttgcggg ttatattcat catactcccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cactttcaag agaaaatctt atcttcaatt
12001 cagggcaatg aattttttaca tcaaatgttt ttctggtatg atctggctat tttaactcga
12061 aggggtagat taaatcgagg aaactctaga tcaacatggt ttgttcatga tgatttaata
12121 gacatcttag gctatgggga ctatgttttt tggaagatcc caatttcaat gttaccactg
12181 aacacacaag gaatccccca tgctgctatg gactggtatc aggcatcagt attcaaagaa
12241 gcggttcaag ggcatacaca cattgtttct gtttctactg ccgacgtctt gataatgtgc
12301 aaagatttaa ttacatgtcg attcaacaca actctaatct caaaaatagc agagattgag
12361 gatccagttt gttctgatta tcccaatttt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
12661 acgccacaac aactttgtga gctattttcc attcaaaaac actgggggca tcctgtgcta
12721 catagtgaaa cagcaatcca aaaagttaaa aaacatgcta cggtgctaaa agcattacgc
12781 cctatagtga ttttcgagac atactgtgtt tttaaatata gtattgccaa acattatttt
12841 gatagtcaag gatcttggta cagtgttact tcagatagga atctaacacc gggtcttaat
12901 tcttatatca aaagaaatca attccctccg ttgccaatga ttaaagaact actatgggaa
12961 tttttaccacc ttgaccaccc tccacttttc tcaaccaaaa ttattagtga cttaagtatt
13021 tttataaaag acagagctac cgcagtagaa aggacatgct gggatgcagt attcgagcct
```

FIG. 2 CONTINUED

```
13081 aatgttctag gatataatcc acctcacaaa tttagtacta aacgtgtacc ggaacaattt
13141 ttagagcaag aaaacttttc tattgagaat gttctttcct acgcacaaaa actcgagtat
13201 ctactaccac aatatcggaa cttttcttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgatttag agaaatacaa tcttgcattt
13501 agatatgagt ttacagcacc ttttatagaa tattgcaacc gttgctatgg tgttaagaat
13561 gttttaatt ggatgcatta tacaatccca cagtgttata tgcatgtcag tgattattat
13621 aatccaccac ataacctcac actggagaat cgagacaacc ccccgaagg gcctagttca
13681 tacaggggtc atatgggagg gattgaagga ctgcaacaaa aactctggac aagtatttca
13741 tgtgctcaaa tttctttagt tgaaattaag actggtttta agttacgctc agctgtgatg
13801 ggtgacaatc agtgcattac tgtttatca gtcttcccct tagagactga cgcagacgag
13861 caggaacaga gcgccgaaga caatgcagcg agggtggccg ccagcctagc aaaagttaca
13921 agtgcctgtg gaatctttt aaaacctgat gaaacatttg tacattcagg ttttatctat
13981 tttggaaaaa aacaatattt gaatggggtc caattgcctc agtcccttaa aacggctaca
14041 agaatggcac cattgtctga tgcaattttt gatgatcttc aagggaccct ggctagtata
14101 ggcactgctt ttgagcgatc catctctgag acacgacata tcttcctg caggataacc
14161 gcagctttcc atacgttttt ttcggtgaga atcttgcaat atcatcatct cgggttcaat
14221 aaaggttttg accttggaca gttaacactc ggcaaaccc tggattcgg aacaatatca
14281 ttggcactag cggtaccgca ggtgcttgga gggttatcct tcttgaatcc tgagaaatgt
14341 ttctaccgga atctaggaga tccagttacc tcaggcttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tcttttcacg cacgccgagc
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatattc atgggctcat
14941 attttagagg gaagacctct tattggagcc acactcccat gtatgattga gcaattcaaa
15001 gtgttttggc tgaaacccta cgaacaatgt ccgcagtgtt caaatgcaaa gcaaccaggt
15061 gggaaaccat tcgtgtcagt ggcagtcaag aaaacatattg ttagtgcatg gccgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgttaac atgggtaact caaggcagtt cgaacagtga cttgctaata
15301 aaaccatttt tggaagcacg agtaaattta agtgttcaag aaatacttca aatgaccct
15361 tcacattact caggaaatat tgttcacagg tacaacgatc aatacagtcc tcattcttc
15421 atggccaatc gtatgagtaa ttcagcaacg cgattgattg ttctacaaa cactttaggt
15481 gagttttcag gaggtggcca gtctgcacgc gacagcaata ttattttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgacagta atcctctaaa aggaggactc aattgcaata tctcattcga taatccattt
15781 ttccaaggta aacggctgaa cattatagaa gatgatctta ttcgactgcc tcacttatct
```

FIG. 2 CONTINUED

```
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttggggcc tttgtaagtt attatcttgg caatacaatt
16021 cttcggacta agaaattaac acttgacaat ttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccatttcatc ttttcttaca
16261 tttgtaaaag aatggataat taatcgcgga acaattgtcc ctttatggat agtatatccg
16321 ctagagggtc aaaacccaac acctgtgaat aatttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgcaaa ttccacaaga aaacacgcac cagggtccgt cgttccagtc ctttctaagt
16741 gactctgctt gtggtacagc aaatccaaaa ctaaatttcg atcgatcgag acacaatgtg
16801 aaatttcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 ctttgggaaa tagagagttt caagtcggct gtgacgctag cagagggaga aggtgctggt
17101 gccttactat tgattcagaa ataccaagtt aagacctttat ttttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taatgataa tttagccccg
17521 tttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 tttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcactttat tcgtactgca
17941 aaaggacgaa tcacaaaaact agtcaatgat tatttaaaat tctttcttat tgtgcaagca
18001 ttaaaacata atgggacatg gcaagctgag tttaagaaat taccagagtt gattagtgtg
18061 tgcaataggt tctaccatat tagagattgc aattgtgaag aacgtttctt agttcaaacc
18121 ttatatttac atagaatgca ggattctgaa gttaagctta tcgaaaggct gacagggctt
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat attagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgtttttggtt gataacacaa cttcttaaaa caaaattgat
```

FIG. 2 CONTINUED

18601 ctttaagatt aagtttttta taattatcat tactttaatt tgtcgtttta aaaacggtga
18661 tagccttaat ctttgtgtaa aataagagat taggtgtaat aaccttaaca tttttgtcta
18721 gtaagctact atttcataca gaatgataaa attaaaagaa aaggcaggac tgtaaaatca
18781 gaaatacctt ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttctttttt gtgtgtcca (SEQ ID N°3)

VP30

MEASYERGRPRAARQHSRDGHDHHVRARSSSRENYRGEYRQSRSASQVRVPTV
FHKKRVEPLTVPPAPKDICPTLKKGFLCDSSFCKKDHQLESLTDRELLLLIARKTC
GSVEQQLNITAPKDSRLANPTADDFQQEEGPKITLLTLIKTAEHWARQDIRTIEDS
KLRALLTLCAVMTRKFSKSQLSLLCETHLRREGLGQDQAEPVLEVYQRLHSDKG
GSFEAALWQQWDRQSLIMFITAFLNIALQLPCESSAVVVSGLRTLVPQSDNEEAS
TNPGTCSWSDEGTP (SEQ ID N°31)

AF272001

1 cggacacaca aaaagaaaga agaattttta ggatcttttg tgtgcgaata actatgagga
61 agattaataa ttttcctctc attgaaattt atatcggaat ttaaattgaa attgttactg
121 taatcacacc tggtttgttt cagagccaca tcacaaagat agagaacaac ctaggtctcc
181 gaagggagca agggcatcag tgtgctcagt tgaaaatccc ttgtcaacac ctaggtctta
241 tcacatcaca agttccacct cagactctgc agggtgatcc aacaaccta atagaaacat
301 tattgttaaa ggacagcatt agttcacagt caaacaagca agattgagaa ttaaccttgg
361 ttttgaactt gaacacttag gggattgaag attcaacaac cctaaagctt ggggtaaaac
421 attggaaata gttaaaagac aaattgctcg gaatcacaaa attccgagta tggattctcg
481 tcctcagaaa atctggatgg cgccgagtct cactgaatct gacatggatt accacaagat
541 cttgacagca ggtctgtccg ttcaacaggg gattgttcgg caaagagtca tcccagtgta
601 tcaagtaaac aatcttgaag aaatttgcca acttatcata caggcctttg aagcaggtgt
661 tgatttcaa gagagtgcgg acagtttcct tctcatgctt tgtcttcatc atgcgtacca
721 gggagattac aaactttct tggaaagtgg cgcagtcaag tatttggaag ggcacgggtt
781 ccgttttgaa gtcaagaagc gtgatggagt gaagcgcctt gaggaattgc tgccagcagt
841 atctagtgga aaaaacatta agagaacact tgctgccatg ccggaagagg agacaactga
901 agctaatgcc ggtcagtttc tctcctttgc aagtctattc cttccgaaat tggtagtagg
961 agaaaaggct tgccttgaga aggttcaaag gcaaattcaa gtacatgcag agcaaggact
1021 gatacaatat ccaacagctt ggcaatcagt aggacacatg atggtgattt ccgtttgat
1081 gcgaacaaat ttctgatca aatttctcct aatacaccaa gggatgcaca tggttgccgg
1141 gcatgatgcc aacgatgctg tgattcaaa ttcagtggct caagctcgtt tttcaggctt
1201 attgattgtc aaaacagtac ttgatcatat cctacaaaag acagaacgag gagtcgtct
1261 ccatcctctt gcaggaccg ccaaggtaaa aaatgaggta aactccttta aggctgcact
1321 cagctccctg gccaagcatg gagagtatgc tcctttcgcc cgactttgga ccttctgg
1381 agtaaataat cttgagcatg gtctttccc tcaactatcg gcaattgcac tcggagtcgc
1441 cacagcacac gggagtaccc tcgcaggagt aaatgttgga gaacagtatc aacaactcag
1501 agaggctgcc actgaggctg agaagcaact ccaacaatat gcagagtctc gcgaacttga
1561 ccatcttgga cttgatgatc aggaaaagaa aattcttatg aacttccatc agaaaaagaa

FIG. 2 CONTINUED

```
1621 cgaaatcagc ttccagcaaa caaacgctat ggtaactcta agaaaagagc gcctggccaa
1681 gctgacagaa gctatcactg ctgcgtcact gcccaaaaca agtggacatt acgatgatga
1741 tgacgacatt cccttccag gacccatcaa tgatgacgac aatcctggcc atcaagatga
1801 tgatccgact gactcacagg atacgaccat tcccgatgtg gtggttgatc ctgatgatgg
1861 aagctacggc gaataccaga gttactcgga aaacggcatg aatgcaccag atgacttggt
1921 cctattcgat ctagacgagg acgacgagga cactaagcca gtgcctaata gatcgaccaa
1981 gggtggacaa cagaagaaca gtcaaaaggg ccagcatata gagggcagac agacacaatt
2041 caggccaatt caaaatgtcc caggccctca cagaacaatc caccacgcca gtgcgccact
2101 cacggacaat gacagaagaa atgaaccctc cggctcaacc agccctcgca tgctgacacc
2161 aattaacgaa gaggcagacc cactggacga tgccgacgac gagacgtcta gccttccgcc
2221 cttggagtca gatgatgaag agcaggacag ggacggaact tccaaccgca cacccactgt
2281 cgccccaccg gctcccgtat acagagatca ctctgaaaag aaagaactcc cgcaagacga
2341 gcaacaagat caggaccaca ctcaagaggc caggaaccag gacagtgaca cacccagtc
2401 agaacactcc cttgaggaga tgtatcgcca cattctaaga tcacaggggc catttgatgc
2461 tgttttgtat tatcatatga tgaaggatga gcctgtagtt ttcagtacca gtgatggcaa
2521 agagtacacg tatccagact cccttgaaga ggaatatcca ccatggctca ctgaaaaaga
2581 ggctatgaat gaagagaata gatttgttac attggatggt caacaatttt attggccggt
2641 gatgaatcac aagaataaat tcatggcaat cctgcaacat catcagtgaa tgagcatgga
2701 acaatgggat gattcaaccg acaaatagct aacattaagt agtcaaggaa cgaaaacagg
2761 aagaattttt gatgtctaag gtgtgaatta ttatcacaat aaaagtgatt cttattttg
2821 aatttaaagc tagcttatta ttactagccg tttttcaaag ttcaatttga gtcttaatgc
2881 aaataggcgt taagccacag ttatagccat aattgtaact caatattcta actagcgatt
2941 tatctaaatt aaattacatt atgctttat aacttaccta ctagcctgcc caacatttac
3001 acgatcgttt tataattaag aaaaaactaa tgatgaagat taaaaccttc atcatcctta
3061 cgtcaattga attctctagc actcgaagct tattgtcttc aatgtaaaag aaaagctggt
3121 ctaacaagat gacaactaga acaagggca ggggcctac tgcggccacg actcaaaacg
3181 acagaatgcc aggcctgag cttcggggct ggatctctga gcagctaatg accggaagaa
3241 ttcctgtaag cgacatcttc tgtgatattg agaacaatcc aggattatgc tacgcatccc
3301 aaatgcaaca aacgaagcca aacccgaaga cgcgcaacag tcaaacccaa acggacccaa
3361 tttgcaatca tagtttgag gaggtagtac aaacattgg ttcattggct actgttgtgc
3421 aacaacaaac catcgcatca gaatcattag acaacgcat tacgagtctt gagaatggtc
3481 taaagccagt ttatgatatg gcaaaaacaa tctcctcatt gaacagggtt tgtgctgaga
3541 tggttgcaaa atatgatctt ctggtgatga caaccggtcg ggcaacagca accgctgcgg
3601 caactgaggc ttattgggcc gaacatggtc aaccaccacc tggaccatca ctttatgaag
3661 aaagtgcgat tcggggtaag attgaatcta gagatgagac cgtccctcaa agtgttaggg
3721 aggcattcaa caatctaaac agtaccactt cactaactga ggaaaatttt gggaaacctg
3781 acatttcggc aaaggatttg agaaacatta tgtatgatca cttgcctggt tttggaactg
3841 ctttccacca attagtacaa gtgatttgta aattgggaaa agatagcaac tcattggaca
3901 tcattcatgc tgagttccag gccagcctgg ctgaaggaga ctctcctcaa tgtgccctaa
3961 ttcaaattac aaaaagagtt ccaatcttcc aagatgctgc tccacctgtc atccacatcc
4021 gctctcgagg tgacattccc cgagcttgcc agaaaagctt gcgtccagtc ccaccatcgc
4081 ccaagattga tcgaggttgg gtatgtgttt ttcagcttca agatggtaaa acacttggac
4141 tcaaaatttg agccaatctc ccttccctcc gaaagaggcg aataatagca gaggcttcaa
4201 ctgctgaact atagggtacg ttacattaat gatacacttg tgagtatcag ccctggataa
4261 tataagtcaa ttaaacgacc aagataaaat tgttcatatc tcgctagcag cttaaaatat
4321 aaatgtaata ggagctatat ctctgacagt attataatca attgttatta agtaacccaa
```

FIG. 2 CONTINUED

```
4381 accaaaagtg atgaagatta agaaaaacct acctcggctg agagagtgtt ttttcattaa
4441 ccttcatctt gtaaacgttg agcaaaattg ttaaaaatat gaggcgggtt atattgccta
4501 ctgctcctcc tgaatatatg gaggccatat accctgtcag gtcaaattca acaattgcta
4561 gaggtggcaa cagcaataca ggcttcctga caccggagtc agtcaatggg gacactccat
4621 cgaatccact caggccaatt gccgatgaca ccatcgacca tgccagccac acaccaggca
4681 gtgtgtcatc agcattcatc cttgaagcta tggtgaatgt catatcgggc cccaaagtgc
4741 taatgaagca aattccaatt tggcttcctc taggtgtcgc tgatcaaaag acctacagct
4801 ttgactcaac tacggccgcc atcatgcttg cttcatacac tatcacccat ttcggcaagg
4861 caaccaatcc acttgtcaga gtcaatcggc tgggtcctgg aatcccggat catcccctca
4921 ggctcctgcg aattggaaac caggctttcc tccaggagtt cgttcttccg ccagtccaac
4981 taccccagta tttcacctt gatttgacag cactcaaact gatcacccaa ccactgcctg
5041 ctgcaacatg gaccgatgac actccaacag gatcaaatgg agcgttgcgt ccaggaattt
5101 catttcatcc aaaacttcgc cccattcttt tacccaacaa aagtgggaag aaggggaaca
5161 gtgccgatct aacatctccg gagaaaatcc aagcaataat gacttcactc caggacttta
5221 agatcgttcc aattgatcca accaaaaata tcatgggaat cgaagtgcca gaaactctgg
5281 tccacaagct gaccggtaag aaggtgactt ctaaaaatgg acaaccaatc atccctgttc
5341 ttttgccaaa gtacattggg ttggacccgg tggctccagg agacctcacc atggtaatca
5401 cacaggattg tgacacgtgt cattctcctg caagtcttcc agctgtgatt gagaagtaat
5461 tgcaataatt gactcagatc cagttttata gaatcttctc agggatagtg ataacatcta
5521 tttagtaatc cgtccattag aggagacact tttaattgat caatatacta aaggtgcttt
5581 acaccattgt ctttttctc tcctaaatgt agaacttaac aaaagactca taatatactt
5641 gttttttaaag gattgattga tgaaagatca taactaataa cattacaaat aatcctacta
5701 taatcaatac ggtgattcaa atgttaatct ttctcattgc acatactttt tgcccttatc
5761 ctcaaattgc ctgcatgctt acatctgagg atagccagtg tgacttggat tggaaatgtg
5821 gagaaaaaat cgggacccat ttctaggttg ttcacaatcc aagtacagac attgccctc
5881 taattaagaa aaaatcggcg atgaagatta agccgacagt gagcgtaatc ttcatctctc
5941 ttagattatt tgttttccag agtaggggtc gtcaggtcct tttcaatcgt gtaaccaaaa
6001 taaactccac tagaaggata ttgtggggca acaacacaat gggcgttaca ggaatattgc
6061 agttacctcg tgatcgattc aagaggacat cattctttct ttgggtaatt atccttttcc
6121 aaagaacatt ttccatccca cttggagtca tccacaatag cacattacag gttagtgatg
6181 tcgacaaact agtttgtcgt gacaaactgt catccacaaa tcaattgaga tcagttggac
6241 tgaatctcga agggaatgga gtggcaactg acgtgccatc tgcaactaaa agatgggggct
6301 tcaggtccgg tgtcccacca aaggtggtca attatgaagc tggtgaatgg gctgaaaact
6361 gctacaatct tgaaatcaaa aaacctgacg ggagtgagtg tctaccagca gcgccagacg
6421 ggattcgggg cttccccccgg tgccggtatg tgcacaaagt atcaggaacg ggaccgtgtg
6481 ccggagactt tgccttccat aaagagggtg ctttcttcct gtatgatcga cttgcttcca
6541 cagttatcta ccgaggaacg actttcgctg aaggtgtcgt tgcattctg atactgcccc
6601 aagctaagaa ggacttcttc agctcacacc ccttgagaga gccggtcaat gcaacggagg
6661 acccgtctag tggctactat tctaccacaa ttagatatca ggctaccggt tttggaacca
6721 atgagacaga gtacttgttc gaggttgaca atttgaccta cgtccaactt gaatcaagat
6781 tcacaccaca gtttctgctc cagctgaatg agacaatata tacaagtggg aaaaggagca
6841 ataccacggg aaaactaatt tggaaggtca accccgaaat tgatacaaca atcggggagt
6901 gggcccttctg ggaaactaaa aaaaccctcac tagaaaaatt cgcagtgaag agttgtcttt
6961 cacagttgta tcaaacggag ccaaaaacat cagtggtcag agtccggcgc gaacttcttc
7021 cgacccaggg accaacacaa caactgaaga ccacaaaatc atggcttcag aaaattcctc
7081 tgcaatggtt caagtgcaca gtcaaggaag ggaagctgca gtgtcgcatc taacaaccct
```

FIG. 2 CONTINUED

7141 tgccacaatc tccacgagtc cccaatccct cacaaccaaa ccaggtccgg acaacagcac
7201 ccataataca cccgtgtata aacttgacat ctctgaggca actcaagttg aacaacatca
7261 ccgcagaaca gacaacgaca gcacagcctc cgacactccc tctgccacga ccgcagccgg
7321 accccaaaa gcagagaaca ccaacacgag caagagcact gacttcctgg accccgccac
7381 cacaacaagt ccccaaaacc acagcgagac cgctggcaac aacaacactc atcaccaaga
7441 taccggagaa gagagtgcca gcagcgggaa gctaggctta attaccaata ctattgctgg
7501 agtcgcagga ctgatcacag gcgggagaag aactcgaaga gaagcaattg tcaatgctca
7561 acccaaatgc aaccctaatt tacattactg gactactcag gatgaaggtg ctgcaatcgg
7621 actggcctgg ataccatatt tcgggccagc agccgaggga atttacatag aggggctaat
7681 gcacaatcaa gatggtttaa tctgtgggtt gagacagctg gccaacgaga cgactcaagc
7741 tcttcaactg ttcctgagag ccacaactga gctacgcacc ttttcaatcc tcaaccgtaa
7801 ggcaattgat ttcttgctgc agcgatgggg cggcacatgc cacattctgg gaccggactg
7861 ctgtatcgaa ccacatgatt ggaccaagaa cataacagac aaaattgatc agattattca
7921 tgattttgtt gataaaaccc ttccggacca gggggacaat gacaattggt ggacaggatg
7981 gagacaatgg ataccggcag gtattggagt tacaggcgtt ataattgcag ttatcgcttt
8041 attctgtata tgcaaatttg tcttttagtt tttcttcaga ttgcttcatg gaaaagctca
8101 gcctcaaatc aatgaaacca ggatttaatt atatggatta cttgaatcta agattacttg
8161 acaaatgata atataataca ctggagcttt aaacatagcc aatgtgattc taactccttt
8221 aaactcacag ttaatcataa acaaggtttg acatcaatct agttatctct ttgagaatga
8281 taaacttgat gaagattaag aaaaaggtaa tctttcgatt atctttaatc ttcatccttg
8341 attctacaat catgacagtt gtctttagtg acaagggaaa gaagcctttt tattaagttg
8401 taataatcag atctgcgaac cggtagagtt tagttgcaac ctaacacaca taaagcattg
8461 gtcaaaaagt caatagaaat ttaaacagtg agtggagaca acttttaaat ggaagcttca
8521 tatgagagag gacgcccacg agctgccaga cagcattcaa gggatggaca cgaccaccat
8581 gttcgagcac gatcatcatc cagagagaat tatcgaggtg agtaccgtca atcaaggagc
8641 gcctcacaag tgcgcgttcc tactgtattt cataagaaga gagttgaacc attaacagtt
8701 cctccagcac ctaaagacat atgtccgacc ttgaaaaaag gattttgtg tgacagtagt
8761 ttttgcaaaa aagatcacca gttggagagt ttaactgata gggaattact cctactaatc
8821 gcccgtaaga cttgtggatc agtagaacaa caattaaata taactgcacc caaggactcg
8881 cgcttagcaa atccaacggc tgatgatttc cagcaagagg aaggtccaaa aattaccttg
8941 ttgacactga tcaagacggc agaacactgg gcgagacaag acatcagaac catagaggat
9001 tcaaaattaa gagcattgtt gactctatgt gctgtgatga cgaggaaatt ctcaaaatcc
9061 cagctgagtc ttttatgtga gacacaccta aggcgcgagg ggcttgggca agatcaggca
9121 gaacccgttc tcgaagtata tcaacgatta cacagtgata aaggaggcag ttttgaagct
9181 gcactatggc aacaatggga ccgacaatcc ctaattatgt ttatcactgc attcttgaat
9241 attgctctcc agttaccgtg tgaaagttct gctgtcgttg tttcagggtt aagaacattg
9301 gttcctcaat cagataatga ggaagcttca accaacccgg ggacatgctc atggtctgat
9361 gagggtaccc cttaataagg ctgactaaaa cactatataa cctctactt gatcacaata
9421 ctccgtatac ctatcatcat atatttaatc aagacgatat cctttaaaac ttattcagta
9481 ctataatcac tctcgtttca aattaataag atgtgcatga ttgccctaat atatgaagag
9541 gtatgataca accctaacag tgatcaaaga aaatcataat ctcgtatcgc tcgaaatata
9601 acctgccaag catacctctt gcacaaagtg attcttgtac acaaataatg ttttactcta
9661 caggaggtag caacgatcca tcccatcaaa aaataagtat ttcatgactt actaatgatc
9721 tcttaaaata ttaagaaaaa ctgacggaac ataaattctt tatgcttcaa gctgtggagg
9781 aggtgtttgg tattggctat tgttatatta caatcaataa caagcttgta aaaatattgt
9841 tcttgtttca agaggtagat tgtgaccgga aatgctaaac taatgatgaa gattaatgcg

FIG. 2 CONTINUED

```
9901  gaggtctgat aagaataaac cttattattc agattaggcc ccaagaggca ttcttcatct
9961  cctttagca aagtactatt tcagggtagt ccaattagtg gcacgtcttt tagctgtata
10021 tcagtcgccc ctgagatacg ccacaaaagt gtctctaagc taaattggtc tgtacacatc
10081 ccatacattg tattaggggc aataatatct aattgaactt agccgtttaa aatttagtgc
10141 ataaatctgg gctaacacca ccaggtcaac tccattggct gaaaagaagc ttacctacaa
10201 cgaacatcac tttgagcgcc ctcacaatta aaaatagga acgtcgttcc aacaatcgag
10261 cgcaaggttt caaggttgaa ctgagagtgt ctagacaaca aatattgat actccagaca
10321 ccaagcaaga cctgagaaaa aaccatggct aaagctacgg gacgatacaa tctaatatcg
10381 cccaaaaagg acctggagaa aggggttgtc ttaagcgacc tctgtaactt cttagttagc
10441 caaactattc agggggtggaa ggtttattgg gctggtattg agtttgatgt gactcacaaa
10501 ggaatggccc tattgcatag actgaaaact aatgactttg ccctgcatg gtcaataaca
10561 aggaatctct ttcctcattt atttcaaaat ccgaattcca caattgaatc accgctgtgg
10621 gcattgagag tcatccttgc agcagggata caggaccagc tgattgacca gtctttgatt
10681 gaacccttag caggagccct tggtctgatc tctgattggc tgctaacaac caacactaac
10741 catttcaaca tgcgaacaca acgtgtcaag gaacaattga gcccaaaaat gctgtcgttg
10801 attcgatcca atattctcaa gtttattaac aaattggatg ctctacatgt cgtgaactac
10861 aacggattgt tgagcagtat tgaaattgga actcaaaatc atataatcat cataactcga
10921 actaacatgg gttttctggt ggagctccaa gaaccgaca aatcggcaat gaaccgcatg
10981 aagcctgggc cggcgaaatt ttccctcctt catgagtcca cactgaaagc atttacacaa
11041 ggatcctcga cacgaatgca aagtttgatt cttgaattta atagctctct tgctatctaa
11101 ctaaggtaga atacttcata ttgagctaac tcatatatgc tgactcaata gttatcttga
11161 catctctgct ttcataatca gatatataag cataataaat aaatactcat atttcttgat
11221 aatttgttta accacagata aatcctcact gtaagccagc ttccaagttg acacccttac
11281 aaaaaccagg actcagaatc cctcaaacaa gagattccaa gacaacatca tagaattgct
11341 ttattatatg aataagcatt ttatcaccag aaatcctata tactaaatgg ttaattgtaa
11401 ctgaacccgc aggtcacatg tgttaggttt cacagattct atatattact aactctatac
11461 tcgtaattaa cattagataa gtagattaag aaaaaagcct gaggaagatt aagaaaaact
11521 gcttattggg tctttccgtg ttttagatga agcagttgaa attcttcctc ttgatattaa
11581 atggctacac aacatacca ataccagac gctaggttat catcaccaat tgtattggac
11641 caatgtgacc tagtcactag agcttgcggg ttatattcat catactccct taatccgcaa
11701 ctacgcaact gtaaactccc gaaacatatc taccgtttga aatacgatgt aactgttacc
11761 aagttcttga gtgatgtacc agtggcgaca ttgcccatag atttcatagt cccagttctt
11821 ctcaaggcac tgtcaggcaa tggattctgt cctgttgagc cgcggtgcca acagttctta
11881 gatgaaatca ttaagtacac aatgcaagat gctctcttct tgaaatatta tctcaaaaat
11941 gtgggtgctc aagaagactg tgttgatgaa cacttcaag agaaaatctt atcttcaatt
12001 cagggcaatg aatttttaca tcaaatgttt ttctggtatg atctggctat ttaactcga
12061 agggtagat taaatcgagg aaactctaga tcaacatggt ttgttcatga tgatttaata
12121 gacatcttag gctatgggga ctatgttttt tggaagatcc caatttcaat gttaccactg
12181 aacacacaag gaatcccca tgctgctatg gactggtatc aggcatcagt attcaaagaa
12241 gcggttcaag ggcatacaca cattgttctt gtttctactg ccgacgtctt gataatgtgc
12301 aaagatttaa ttacatgtcg attcaacaca actctaatct caaaaatagc agagattgag
12361 gatccagttt gttctgatta tcccaattt aagattgtgt ctatgcttta ccagagcgga
12421 gattacttac tctccatatt agggtctgat gggtataaaa ttattaagtt cctcgaacca
12481 ttgtgcttgg ccaaaattca attatgctca aagtacactg agaggaaggg ccgattctta
12541 acacaaatgc atttagctgt aaatcacacc ctagaagaaa ttacagaaat gcgtgcacta
12601 aagccttcac aggctcaaaa gatccgtgaa ttccatagaa cattgataag gctggagatg
```

```
12661 acgccacaac aactttgtga gctatttcc attcaaaaac actgggggca tcctgtgcta
12721 catagtgaaa cagcaatcca aaaagttaaa aaacatgcta cggtgctaaa agcattacgc
12781 cctatagtga tttcgagac atactgtgtt tttaaatata gtattgccaa acattatttt
12841 gatagtcaag gatcttggta cagtgttact tcagatagga atctaacacc gggtcttaat
12901 tcttatatca aaagaaatca attccctccg ttgccaatga ttaagaact actatgggaa
12961 ttttaccacc ttgaccaccc tccactttc tcaaccaaaa ttattagtga cttaagtatt
13021 tttataaaag acagagctac cgcagtagaa aggacatgct gggatgcagt attcgagcct
13081 aatgttctag gatataatcc acctcacaaa ttagtacta aacgtgtacc ggaacaattt
13141 ttagagcaag aaaactttc tattgagaat gttctttcct acgcacaaaa actgagtat
13201 ctactaccac aatatcggaa cttttctttc tcattgaaag agaaagagtt gaatgtaggt
13261 agaaccttcg gaaaattgcc ttatccgact cgcaatgttc aaacactttg tgaagctctg
13321 ttagctgatg gtcttgctaa agcatttcct agcaatatga tggtagttac ggaacgtgag
13381 caaaaagaaa gcttattgca tcaagcatca tggcaccaca caagtgatga ttttggtgaa
13441 catgccacag ttagagggag tagctttgta actgattag agaaatacaa tcttgcattt
13501 agatatgagt ttacagcacc ttttatagaa tattgcaacc gttgctatgg tgttaagaat
13561 gtttttaatt ggatgcatta tacaatccca cagtgttata tgcatgtcag tgattattat
13621 aatccaccac ataacctcac actggagaat cgagacaacc ccccgaagg gcctagttca
13681 tacaggggtc atatggagg gattgaagga ctgcaacaaa aactctggac aagtatttca
13741 tgtgctcaaa tttctttagt tgaaattaag actggtttta agttacgctc agctgtgatg
13801 ggtgacaatc agtgcattac tgtttttatca gtcttcccct tagagactga cgcagacgag
13861 caggaacaga gcgccgaaga caatgcagcg agggtggccg ccagcctagc aaaagttaca
13921 agtgcctgtg gaatctttt aaaacctgat gaaacatttg tacattcagg tttatctat
13981 tttggaaaaa aacaatatttt gaatggggtc caattgcctc agtcccttaa aacggctgca
14041 agaatggcac cattgtctga tgcaatttttt gatgatcttc aagggaccct ggctagtata
14101 ggcactgctt ttgagcgatc catctctgag acacgacata tctttccttg caggataacc
14161 gcagctttcc atacgttttt ttcggtgaga atcttgcaat atcatcatct cgggtcaat
14221 aaaggttttg accttggaca gttaacactc ggcaaacctc tggattcgg aacaatatca
14281 ttggcactag cggtaccgca ggtgcttgga gggttatcct tcttgaatcc tgagaaatgt
14341 ttctaccgga atctaggaga tccagttacc tcaggttat tccagttaaa aacttatctc
14401 cgaatgattg agatggatga tttattctta cctttaattg cgaagaaccc tgggaactgc
14461 actgccattg actttgtgct aaatcctagc ggattaaatg tccctgggtc gcaagactta
14521 acttcatttc tgcgccagat tgtacgcagg accatcaccc taagtgcgaa aaacaaactt
14581 attaatacct tatttcatgc gtcagctgac ttcgaagacg aaatggtttg taaatggcta
14641 ttatcatcaa ctcctgttat gagtcgtttt gcggccgata tcttcacg cacgccgagc
14701 gggaagcgat tgcaaattct aggatacctg gaaggaacac gcacattatt agcctctaag
14761 atcatcaaca ataatacaga gacaccggtt ttggacagac tgaggaaaat aacattgcaa
14821 aggtggagcc tatggtttag ttatcttgat cattgtgata atatcctggc ggaggcttta
14881 acccaaataa cttgcacagt tgatttagca cagattctga gggaatatc atgggctcat
14941 attttagagg gaagaccctc tattggagcc acactcccat gtatgattga gcaattcaaa
15001 gtgtttttggc tgaaacccta cgaacaatgt ccgcagtgtt caaatgcaaa gcaaccaggt
15061 gggaaaccat tcgtgtcagt ggcagtcaag aaacatattg ttagtgcatg gccgaacgca
15121 tcccgaataa gctggactat cggggatgga atcccataca ttggatcaag gacagaagat
15181 aagataggac aacctgctat taaaccaaaa tgtccttccg cagccttaag agaggccatt
15241 gaattggcgt cccgtttaac atgggtaact caaggcagtt cgaacagtga cttgctaata
15301 aaaccatttt tggaagcacg agtaaattta agtgttcaag aaatacttca aatgaccct
15361 tcacattact caggaaatat tgttcacagg tacaacgatc aatacagtcc tcattctttc
```

FIG. 2 CONTINUED

```
15421 atggccaatc gtatgagtaa ttcagcaacg cgattgattg tttctacaaa cactttaggt
15481 gagttttcag gaggtggcca gtctgcacgc gacagcaata ttatttcca gaatgttata
15541 aattatgcag ttgcactgtt cgatattaaa tttagaaaca ctgaggctac agatatccaa
15601 tataatcgtg ctcaccttca tctaactaag tgttgcaccc gggaagtacc agctcagtat
15661 ttaacataca catctacatt ggatttagat ttaacaagat accgagaaaa cgaattgatt
15721 tatgcacagta atcctctaaa aggaggactc aattgcaata tctcattcga taatccattt
15781 ttccaaggta aacggctgaa cattatagaa gatgatctta ttcgactgcc tcacttatct
15841 ggatgggagc tagccaagac catcatgcaa tcaattattt cagatagcaa caattcatct
15901 acagacccaa ttagcagtgg agaaacaaga tcattcacta cccatttctt aacttatccc
15961 aagataggac ttctgtacag ttttgggggcc tttgtaagtt attatcttgg caatacaatt
16021 cttcggacta agaaattaac acttgacaat ttttatatt acttaactac tcaaattcat
16081 aatctaccac atcgctcatt gcgaatactt aagccaacat tcaaacatgc aagcgttatg
16141 tcacggttaa tgagtattga tcctcatttt tctatttaca taggcggtgc tgcaggtgac
16201 agaggactct cagatgcggc caggttattt ttgagaacgt ccattcatc ttttcttaca
16261 tttgtaaaag aatggataat taatcgcgga acaattgtcc ctttatggat agtatatccg
16321 ctagagggtc aaaaccccaac acctgtgaat aattttctct atcagatcgt agaactgctg
16381 gtgcatgatt catcaagaca acaggctttt aaaactacca taagtgatca tgtacatcct
16441 cacgacaatc ttgtttacac atgtaagagt acagccagca atttcttcca tgcatcattg
16501 gcgtactgga ggagcagaca cagaaacagc aaccgaaaat acttggcaag agactcttca
16561 actggatcaa gcacaaacaa cagtgatggt catattgaga gaagtcaaga acaaaccacc
16621 agagatccac atgatggcac tgaacggaat ctagtcctac aaatgagcca tgaaataaaa
16681 agaacgacaa ttccacaaga aaacacgcac cagggtccgt cgttccagtc ctttctaagt
16741 gactctgctt gtggtacagc aaatccaaaa ctaaatttcg atcgatcgag acacaatgtg
16801 aaattcagg atcataactc ggcatccaag agggaaggtc atcaaataat ctcacaccgt
16861 ctagtcctac ctttctttac attatctcaa gggacacgcc aattaacgtc atccaatgag
16921 tcacaaaccc aagacgagat atcaaagtac ttacggcaat tgagatccgt cattgatacc
16981 acagtttatt gtagatttac cggtatagtc tcgtccatgc attacaaact tgatgaggtc
17041 cttttgggaaa tagagagttt caagtcggct gtgacgctag cagagggaga aggtgctggt
17101 gccttactat tgattcagaa ataccaagtt aagacctttat tttcaacac gctagctact
17161 gagtccagta tagagtcaga aatagtatca ggaatgacta ctcctaggat gcttctacct
17221 gttatgtcaa aattccataa tgaccaaatt gagattattc ttaacaactc agcaagccaa
17281 ataacagaca taacaaatcc tacttggttt aaagaccaaa gagcaaggct acctaagcaa
17341 gtcgaggtta taaccatgga tgcagagaca acagagaata taaacagatc gaaattgtac
17401 gaagctgtat ataaattgat cttacaccat attgatccta gcgtattgaa agcagtggtc
17461 cttaaagtct ttctaagtga tactgagggt atgttatggc taaatgataa tttagcccccg
17521 ttttttgcca ctggttattt aattaagcca ataacgtcaa gtgctagatc tagtgagtgg
17581 tatctttgtc tgacgaactt cttatcaact acacgtaaga tgccacacca aaaccatctc
17641 agttgtaaac aggtaatact tacggcattg caactgcaaa ttcaacgaag cccatactgg
17701 ctaagtcatt taactcagta tgctgactgt gagttacatt taagttatat ccgccttggt
17761 ttccatcat tagagaaagt actataccac aggtataacc tcgtcgattc aaaaagaggt
17821 ccactagtct ctatcactca gcacttagca catcttagag cagagattcg agaattaact
17881 aatgattata atcaacagcg acaaagtcgg actcaaacat atcacttat tcgtactgca
17941 aaaggacgaa tcacaaaact agtcaatgat tatttaaaat tctttcttat tgtgcaagca
18001 ttaaaacata atgggacatg gcaagctgag tttaagaaat taccagagtt gattagtgtg
18061 tgcaataggt tctaccatat tagagattgc aattgtgaag aacgttctt agttcaaacc
18121 ttatatttac atagaatgca ggattctgaa gttaagctta tcgaaaggct gacagggctt
```

FIG. 2 CONTINUED

```
18181 ctgagtttat ttccggatgg tctctacagg tttgattgaa ttaccgtgca tagtatcctg
18241 atacttgcaa aggttggtta ttaacataca gattataaaa aactcataaa ttgctctcat
18301 acatcatatt gatctaatct caataaacaa ctatttaaat aacgaaagga gtccctatat
18361 tatatactat atttagcctc tctccctgcg tgataatcaa aaaattcaca atgcagcatg
18421 tgtgacatat tactgccgca atgaatttaa cgcaacataa taaactctgc actctttata
18481 attaagcttt aacgaaaggt ctgggctcat attgttattg atataataat gttgtatcaa
18541 tatcctgtca gatggaatag tgtttggtt gataacacaa cttcttaaaa caaaattgat
18601 ctttaagatt aagtttttta taattatcat tactttaatt tgtcgtttta aaaacggtga
18661 tagccttaat ctttgtgtaa aataagagat taggtgtaat aaccttaaca tttttgtcta
18721 gtaagctact atttcataca gaatgataaa attaaaagaa aaggcaggac tgtaaaatca
18781 gaaatacctt ctttacaata tagcagacta gataataatc ttcgtgttaa tgataattaa
18841 gacattgacc acgctcatca gaaggctcgc cagaataaac gttgcaaaaa ggattcctgg
18901 aaaaatggtc gcacacaaaa atttaaaaat aaatctattt cttctttttt gtgtgtcca  (SEQ ID NO: 32)
```

VP30
MEASYERGRPRAARQHSRDGHDHHVRARSSSRENYRGEYRQSRSASQVRVPTV
FHKKRVEPLTVPPAPKDICPTLKKGFLCDSSFCKKDHQLESLTDRELLLLIARKTC
GSVEQQLNITAPKDSRLANPTADDFQQEEGPKITLLTLIKTAEHWARQDIRTIEDS
KLRALLTLCAVMTRKFSKSQLSLLCETHLRREGLGQDQAEPVLEVYQRLHSDKG
GSFEAALWQQWDRQSLIMFITAFLNIALQLPCESSAVVVSGLRTLVPQSDNEEAS
TNPGTCSWSDEGTP (SEQ ID NO: 33)

Bundibugyo Ebola virus polymerase

```
   1 matqhtqypd arlsspivld qcdlvtracg lyssyslnpq lkncrlpkhi yrlkfdatvt
  61 kflsdvpivt lpidyltpll lrtlsgeglc pvepkcsqfl deivsyvlqd arflryyfrh
 121 vgvhddnvgk nfepkikali ydneflqqlf ywydlailtr rgrlnrgnnr stwfanddli
 181 dilgygdyif wkiplsllsl ntegiphaak dwyhasifke avqghthivs vstadvlimc
 241 kdiitcrfnt tliaalanle dsicsdypqp etisnlykag dylisilgse gykvikflep
 301 lclakiqlcs nyterkgrfl tqmhlavnht leeliegrgl ksqqdwkmre fhrilvnlks
 361 tpqqlcelfs vqkhwghpvl hsekaiqkvk khatvikalr pviifetycv fkysiakhyf
 421 dsqgswysvi sdkhltpglh syikrnqfpp lpmikdllwe fyhldhpplf stkiisdlsi
 481 fikdratave ktcwdavfep nvlgysppnk fstkrvpeqf leqenfsids vltyaqrldy
 541 llpqymfsf slkekelnvg rafgklpypt rnvqtlceal ladglakafp snmmvvtere
 601 qkesllhqas whhtsddfge natvrgssfv tdlekynlaf ryeftapfie ycnrcygvkn
 661 lfnwmhytip qcyihvsdyy npphgvslen redppegpss yrghlggieg lqqklwtsis
 721 caqislveik tgfklrsavm gdnqcitvls vfpletdsne qehssednaa rvaaslakvt
 781 sacgiflkpd etfvhsgfiy fgkkqylngv qlpqslktat riaplsdaif ddlqgtlasi
 841 gtafersise trhvypcrvv aafhtffsvr ilqyhhlgfn kgtdlgqlsl skpldfgtit
 901 lalavpqvlg glsflnpekc fyrnlgdpvt sglfqlrtyl qminmddifl pliaknpgnc
 961 saidfvlnps glnvpgsqdl tsflrqivrr titlsaknkl intlfhssad ledemvckwl
1021 lsstpvmsrf aadifsrtps gkrlqilgyl egtrtllask vinnnaetpi ldrlrkitlq
1081 rwslwfsyld hcdqvladal ikvsctvdla qilreytwah ilegrqliga tlpcmleqfn
1141 vfwlksyeqc pkcaksrnpk gepfvsiaik kqvvsawpnq srlnwtigdg vpyigsrted
1201 kigqpaikpk cpsaalreai eltsrltwvt qggansdllv kpfvearvnl svqeilqmtp
1261 shysgnivhr yndqysphsf manrmsnsat rlvvstntlg efsgggqsar dsniifqnvi
```

FIG. 2 CONTINUED

```
1321 nfsvalfdlr frntetssiq hnrahlhlsq cctrevpaqy ltytstlsld ltryreneli
1381 ydnnplkggl ncnlsfdnpl fkgqrlniie edlirfphls gwelaktiiq siisdsnnss
1441 tdpissgetr sftthfltyp kvgllysfga ivsyylgnti irtkkldlsh fmyylttqih
1501 nlphrslril kptfkhvsvi srlmsidphf siyiggtagd rglsdatrlf lrvaissflq
1561 fikkwiveyk taiplwviyp legqnpdpin sflhliiall qnespqnniq fqedrnnqql
1621 sdnlvymcks tasnffhasl aywrsrhkgr pknrsteeqt vkpipydnfh svkcasnpps
1681 ipksksgtqg ssaffekley dkerelptas tpaeqsktyi kalssriyhg ktpsnaakdd
1741 sttskgcdsk eenavqashr ivlpfftlsq ndyrtpsakk seyiteitkl irqlkaipdt
1801 tvycrftgvv ssmhykldev lwefdsfkta vtlaegegsg allllqkykv rtiffntlat
1861 ehsieaeivs gtttprmllp vmaklhddqi nvilnnsasq vtditnpawf tdqksriptq
1921 veimtmdaet teninrskly eaiqqlivsh idtrvlkivi ikvflsdieg llwlndhlap
1981 lfgsgylikp itsspkssew ylclsnflsa srrrphqgha tcmqviqtal rlqvqrssyw
2041 lshlvqyadi nlhlsyvnlg fpslekvlyh rynlvdsrkg plvsilyhlt hlqaeirelv
2101 cdynqqrqsr tqtyhfiktt kgritklvnd ylkfylvvqa lkhnclwqee lrtlpdllnv
2161 cnrfyhirdc scedrfliqt lyltrmqdse aklmerltgf lglypngina   (SEQ ID NO: 34)
```

Marburgvirus polymerase

```
   1 mqhptqypda rlsspiildq cdllarslgl yshyshnpkl mcriphhiy rlmstalkt
  61 flqncsiltv pfhsiwdhil tsiqydainh vddfkyllps elvkyanwdn eflkaylnki
 121 lgldhvfsas arsqcedfsp kenpyywgml llvhlsqlar rikgqrgslr snwkfigtdl
 181 elfgiadfvi fkvpvktiir navslqaskp glriwyrdqn ltpylcddef ivsvasyecf
 241 imikdvfier yntweicara wledsdgady ppldvlgely nqgdqiiamy ledgfklikh
 301 leplcvsciq thgiftprky wfqsqmiksy ydelhdlnlk lqisdnkaec aqnfiktivq
 361 akltpqqyce lfslqkhwgh pvlyndvald kvkkhaqstk ilkpkvmfet fcvfkfivak
 421 nhyhsqgswy ktthdlhltp ylrqhivsns fpsqaeiyqh lwewyfvehe plfstkiisd
 481 lsifikdrlt avnqecwdsv fdrsvlgynp pvrfqskrvp eqflgqadfs lnqilefaek
 541 leylapsyrn fsfslkekel nigrtfgklp yrvmvqtla ealladglak afpsnmmvvt
 601 ereqkeallh qaswhhnsas igenaivrga sfvtdlekyn lafryeftrh fidycnrcyg
 661 vknlfdwmhf liplcymhvs dfyspphcvt ednrmnppdc anayhyhlgg ieglqqklwt
 721 ciscaqitlv elktklklks svmgdnqcit tlslfpidap ndyqeneael naarvavela
 781 ittgysgifl kpeetfvhsg fiyfgkkqyl ngvqlpqslk tmarcgplsd sifddlqgsl
 841 asigtsferg tsetrhifps rwiasfhsml ainllnqnhl gfplgfnidi scfkkpltfs
 901 eklialitpq vlgglsflnp eklfyrnisd pltsglfqlk naleflekee lfyiliskkp
 961 gladasdfvm nplglnvprs keiitflrqt vrenititsq nriinslfhi gsdledqrvc
1021 ewllssnpvm srfaadifsr tpsgkrlqvl gylegtrtll asrtisltte gtmlmklrel
1081 tmrwkswfs yidaldddls eslekftctv dvanflrays wsdvlkgkrl igatlpclle
1141 qfevkwinls edlreqfnls sdskstinll pydckelrle gsndtelnyv scaldrkvvq
1201 khpsvnrlaw tignrapyig srtedkigyp plrvncpsaa lkeaiemvsr llwvtqgtad
1261 reklliplln srvnldyqtv lnflpthysg nivhryndqy gqhsfmanrm sntstraiis
1321 tntlgkyagg gqaaidsnii fqntinlgva vldialslak lssasnvtfr lmlnkcctrh
1381 vpseylyfdk pldvdlnkym dnelvydndp lcsgikgrlg rvsrstlsls lnvsdigsyd
1441 fptiaawtlg etivgsifsd essqstdpis sgctktfvth flvypvesif yafganlive
1501 slslsriksi knlsdltfli sstirnlshr slrilqstfr helvltrlah hiplislmlg
1561 gsagekssd avrlfltasy qnfinnfscl mkkgqsslpv wlyfpsegqq lkpilkilqr
1621 lsdllspdki qkrkiladtc cpigsfwvyp skstrtnhyy aslnywrdka nkvkntpfsh
```

FIG. 2 CONTINUED 1681 lincsfpefs shtssvssnq qvtnskyivy peniteinar trlinygsta lqgmdtkmpl
1741 seqnlvencr psegirfkdn qkitkhdqrc ereesspqqm fpednmqtpa hihssspfqi
1801 liksldahed fdaskiilns einnlnltey tlntkllttp trteildtsp lqssryssts
1861 rersllsreq asylyvdcsn ipsisldpgf rsmsdqnqvq mlintykrdl hacfdsnqfc
1921 rftgvvssmh yklydllppg klkkaiclae gegsgarlll kwketdylff ntlatdsqqe
1981 aeilsgrvip rmlynidrls allesrrlil nnltiqitdi tnplwldsvi qylpedsdil
2041 tmdaettkde treqlyktiv niwtrtspni pkisiikvfl ldyegtlflm knaiqyygqv
2101 qlkkpyssna knsewylccg krriqrlqid fsdqvgifli ckamsrqrqa ipywlkhiek
2161 nypaslheff ltlgfpsles sfchrytipf segkalfhkv qsyvrqgkqh lhslmldyen
2221 nsplldlrnh ficslrgkit kyyndilkln lvikavekgk nwsqlveilp nmhsvcivhv (SEQ ID NO: 35)
2281 dheccsgcekr lllkldfirn tkiaeqklln rvigyilffp fglfksgslr a Zaire Ebola virus polymerase 1 matqhtqypd arlsspivld qcdlvtracg lyssyslnpq lmcklpkhi yrlkydvtvt
  61 kflsdvpvat lpidfivpvl lkalsgngfc pveprcqqfl deiikytmqd alflkyylkn
 121 vgaqedcvde hfqekilssi qgneflhqmf fwydlailtr rgrlnrgnsr stwfvhddli
 181 dilgygdyvf wkipismlpl ntqgiphaam dwyqasvfke avqghthivs vstadvlimc
 241 kdlitcrfnt tliskiaeie dpvcsdypnf kivsmlyqsg dyllsilgsd gykiikflep
 301 lclakiqlcs kyterkgrfl tqmnhlavnht leeitemral kpsqaqkire fhrtlirlem
 361 tpqqlcelfs iqkhwghpvl hsetaiqkvk khatvlkalr pivifetycv fkysiakhyf
 421 dsqgswysvt sdrnltpgln syikrnqfpp lpmikellwe fyhldlhpplf stkiisdlsi
 481 fikdratave rtcwdavfep nvlgynpphk fstkrvpeqf leqenfsien vlsyaqkley
 541 llpqyrnfsf slkekelnvg rtfgklpypt rnvqtlceal ladglakafp snmmvvtere
 601 qkesllhqas whhtsddfge hatvrgssfv tdlekynlaf ryeftapfie ycnrcygvkn
 661 vfnwmhytip qcymhvsdyy npphnltlen rdnppegpss yrghmggieg lqqklwtsis
 721 caqislveik tgfklrsavm gdnqcitvls vfpletdade qeqsaednaa rvaaslakvt
 781 sacgiflkpd etfvhsgfiy fgkkqylngv qlpqslktat rmaplsdaif ddlqgtlasi
 841 gtafersise trhifpcrit aafhtffsvr ilqyhhlgfn kgfdlgqltl gkpldfgtis
 901 lalavpqvlg glsflnpekc fyrnlgdpvt sglfqlktyl rmiemddlfl pliaknpgnc
 961 taidfvlnps glnvpgsqdl tsflrqivrr titlsaknkl intlfhasad fedemvckwl
1021 lsstpvmsrf aadifsrtps gkrlqilgyl egtrtllask iinnntetpv ldrlrkitlq
1081 rwslwfsyld hcdnilaeal tqitctvdla qilreyswah ilegrpliga tlpcmieqfk
1141 vfwlkpyeqc pqcsnakqpg gkpfvsvavk khivsawpna sriswtigdg ipyigsrted
1201 kigqpaikpk cpsaalreai elasrltwvt qgssnsdlli kpflearvnl svqeilqmtp
1261 shysgnivhr yndqysphsf manrmsnsat rlivstntlg efsgggqsar dsniifqnvi
1321 nyavalfdik frnteatdiq ynrahlhltk cctrevpaqy ltytstldld ltryreneli
1381 ydsnplkggl ncnisfdnpf fqgkrlniie ddlirlphls gwelaktimq siisdsnnss
1441 tdpissgetr sftthfltyp kigllysfga fvsyylgnti lrtkkltldn flyylttqih
1501 nlphrslril kptfkhasvm srlmsidphf siyiggaagd rglsdaarlf lrtsissflt
1561 fvkewiinrg tivplwivyp legqnptpvn nflyqivell vhdssrqqaf kttisdhvhp
1621 hdnlvytcks tasnffhasl aywrsrhms nrkylardss tgsstnnsdg hiersqeqtt
1681 rdphdgtern lvlqmsheik rttipqenth qgpsfqsfls dsacgtanpk lnfdrsrhnv
1741 kfqdhnsask reghqiishr lvlpffftlsq gtrqltssne sqtqdeisky lrqlrsvidt
1801 tvycrftgiv ssmhykldev lweiesfksa vtlaegegag allliqkyqv ktlffntlat
1861 essieseivs gmttprmllp vmskfhndqi eiilnnsasq itditnptwf kdqrarlpkq

FIG. 2 CONTINUED 1921 vevitmdaet teninrskly eavyklilhh idpsvlkavv lkvflsdteg mlwlndnlap
1981 ffatgylikp itssarssew ylcltnflst trkmphqnhl sckqviltal qlqiqrspyw
2041 lshltqyadc elhlsyirlg fpslekvlyh rynlvdskrg plvsitqhla hlraeirelt
2101 ndynqqrqsr tqtyhfirta kgritklvnd ylkfflivqa lkhngtwqae fkklpelisv
2161 cnrfyhirdc nceerflvqt lylhrmqdse vklierltgl lslfpdglyr fd  SEQ ID NO: 36

Reston Ebola virus polymerase 1 matqhtqypd arlsspivld qcdlvtracg lyssyslnpq lrqcklpkhi yrlkfdtivs
61 kflsdtpvat lpidylvpil lrsltghgdr pltptcnqfl deiinytlhd aafldyylka
121 tgaqdhltni atreklknei lnndyvhqlf fwhdlsilar rgrlnrgnnr stwfvhdefi
181 dilgygdyif wkiplsllpv tidgvphaat dwyqptlfke silghsqils vstaeilimc
241 kdiitcrfnt sliasiakle dvdvsdypdp sdilkiynag dyvisilgse gykiikylep
301 lclakiqlcs kfterkgrfl tqmhlsvind lrelisnrrl kdyqqekird fhkillqlql
361 spqqfcelfs vqkhwghpil hsekaiqkvk rhatilkalr pnvifetycv fkyniakhyf
421 dsqgtwysvi sdrnltpgln sfikrnhfps lpmikdllwe fyhlnhpplf stkvisdlsi
481 fikdratave qtcwdavfep nvlgynppnk fstkrvpeqf leqedfsies vlnyaqelhy
541 llpqnrnfsf slkekelnig rtfgklpylt rnvqtlceal ladglakafp snmmvvtere
601 qkesllhqas whhtsddfge natvrgssfv tdlekynlaf ryeftapfie ycnhcygvrn
661 vfnwmhylip qcymhvsdyy npphnvnlsn reyppegpss yrghlggieg lqqklwtsis
721 caqislveik tgfklrsavm gdnqcitvls vfplktdpee qeqsaednaa rvaaslakvt
781 sacgiflkpd etfvhsgfiy fgkkqylngv qlpqslktaa rmaplsdaif ddlqgtlasi
841 gtaferaise trhilpcriv aafhtyfavr ilqyhhlgfn kgidlgqlsl skpldygtit
901 ltlavpqvlg glsflnpekc fyrnfgdpvt sglfqlrvyl emvnmkdlfc plisknpgnc
961 saidfvlnps glnvpgsqdl tsflrqivrr sitltarnkl intlfhasad ledemvckwl
1021 lssnpvmsrf aadifsrtps gkrlqilgyl egtrtllask iinnnsetpv ldklrkitlq
1081 rwnlwfsyld hcdqlladal qkisctvdla qilreytwsh ilegrsliga tlpcmveqfk
1141 vkwlgqyepc pecinkkgsn ayvsvavkdq vvsawpntsr iswtigsgvp yigsrtedki
1201 gqpaikpcrp ssalkeaiel asrltwvtqg gsnseqlirp flearvnlsv sevlqmtpsh
1261 ysgnivhryn dqysphsfma nrmsntatrl ivstntlgef sgggqaards niifqnvinl
1321 avalydirfr ntntsdirhn rahlhltecc tkevpaqylt ytsalnldls ryrdneliyd
1381 snplkgglnc nltidsplvk gprlnmiedd llrfphlsgw elaktvvqsi isdnsnsstd
1441 pissgetrsf tthfltypqi gllysfgavl cfylgntilw tkkldyeqfl yylhnqlhnl
1501 phralrvfkp tfkhasvmsr lmeidsnfsi yiggtsgdrg lsdaarlflr taiasflqfl
1561 kswiidrqkt iplwivyple gqqpesinef lhkilgllkq gpksipkevs iqndghldla
1621 ennyvynsks tasnffhasl aywrsrksrk tqdhndfsrg dgtltepvrk fssnhqsdek
1681 yynvtcgksp kpqerkdfsq yrlsnngqtm snhrkkgkfh kwnpckmlme sqrgtvlteg
1741 dyfqnntppt ddvssphrli lpffklgnhn hahdqdaqel mnqnikqylh qlrsmldtti
1801 ycrftgivss mhykldevll eynsfdsait laegegsgal lllqkystrl lflntlateh
1861 sieesevvsgf stprmllpim qkvhegqvtv ilnnsasqit ditssmwlsn qkynlpcqve
1921 iimmdaette nlnrsqlyra vynlildhid pqylkvvvlk vflsdiegil windylaplf
1981 gagylikpit ssarssewyl clsnlistnr rsahqthkac lgvirdalqa qvqrgvywls
2041 hiaqyatknl hceyiglgfp slekvlyhry nlvdtglgpl ssvirhltnl qaeirdlvld
2101 ynlmresrtq tyhfiktakg ritklvndfl kfslivqalk nnsswyteik klpevinvcn
2161 rfyhthncec qekffvqtly lqrlrdaeik lierltglmr fypegliysn ht   SEQ ID NO: 37

FIG. 2 CONTINUED

Sudan Ebola virus polymerase

```
   1 mmatqhtqyp darlsspivl dqcdlvtrac glyseyslnp klrtcrlpkh iyrlkydaiv
  61 lrfisdvpva tipidyiapm linvladskn apleppclsf ldeivnytvq daaflnyymn
 121 qiktqegvit dqlkqnirrv ihknrylsal ffwhdlsilt rrgrmnrgnv rstwfvtnev
 181 vdilgygdyi fwkipiallp mnsanvphas tdwyqpnifk eaiqghthii svstaevlim
 241 ckdlvtsrfn tlliaelarl edpvsadypl vddiqslyna gdyllsilgs egyqiikyle
 301 plclakiqlc sqyterkgrf ltqmhlaviq tlrelllnrg lkksqlskir efhqllrlr
 361 stpqqlcelf siqkhwghpv lhsekaiqkv knhatvlkal rpiiifetyc vfkysvakhf
 421 fdsqgtwysv isdrcltpgl nsyirrnqfp plpmikdllw efyhldhppl fstkiisdls
 481 ifikdratav eqtcwdavfe pnvlgysppy rfntkrvpeq fleqedfsie svlqyaqelr
 541 yllpqnrmfs fslkekelnv grtfgklpyl trnvqtlcea lladglakaf psnmmvvter
 601 eqkesllhqa swhhtsddfg ehatvrgssf vtdlekynla fryeftapfi kycnqcygvr
 661 nvfdwmhfli pqcymhvsdy ynpphnvtle nreyppegps ayrghlggie glqqklwtsi
 721 scaqislvei ktgfklrsav mgdnqcitvl svfplesspn eqercaedna arvaaslakv
 781 tsacgiflkp detfvhsgfi yfgpkqylng iqlpqslkta armaplsdai fddlqgtlas
 841 igtafersis etrhilpsrv aaafhtyfsv rilqhhhlgf hkgsdlgqla inkpldfgti
 901 aislavpqvl gglsflnpek clyrnlgdpv tsglfqlkhy lsmvgmsdif halvakspgn
 961 csaidfvlnp gglnvpgsqd ltsflrqivr rsitlsarnk lintlfhasa dledelvckw
1021 llsstpvmsr faadifsrtp sgkrlqilgy legtrtllas kmisnnaetp ilerlrkitl
1081 qrwnlwfsyl dhcdsalmea iqpirctvdi aqilreyswa hilggrqlig atlpcipeqf
1141 qttwlkpyeq cvecsstnns spyvsvalkr nvvsawpdas rlgwtigdgi pyigsrtedk
1201 igqpaikprc psaalreaie ltsrltwvtq gsansdqlir pflearvnls vqeilqmtps
1261 hysgnivhry ndqysphsfm anrmsntatr lmvstntlge fsgggqaard sniifqnvin
1321 favalydirf rntctssiqy hrahihltdc ctrevpaqyl tytttlnldl skyrnneliy
1381 dseplrggln cnlsidsplm kgprlniied dlirlphlsg welaktvlqs iisdssnsst
1441 dpissgetrs ftthfltypk igllysfgal isfylgntil ctkkigltef lyylqnqihn
1501 lshrslrifk ptfrhssvms rlmdidpnfs iyiggtagdr glsdaarlfl riaistflsf
1561 veewvifrka niplwvvypl egqrpdppge flnrvksliv gieddknkgs ilsrseekcs
1621 snlvynckst asnffhasla ywrgrhrpkk tigatkatta phiilplgns drppgldlnq
1681 sndtfiptri kqivqgdsrn drttttrlpp qsrstptsat epptkiyegs ttyrgkstdt
1741 hldeghnake fpfnphrlvv pffkltkdge ysiepspees rsnikgllqh lrtmvdttiy
1801 crftgivssm hykldevlwe ynkfesavtl aegegsgall liqkygvkkl flntlatehs
1861 iesevisgyt tprmllsvmp rthrgelevi lnnsasqitd ithrdwfsnq knripndvdi
1921 itmdaetten ldrsrlyeav ytiicnhinp ktlkvvilkv flsdldgmcw innylapmfg
1981 sgylikpits sarssewylc lsnllstlrt tqhqtqancl hvvqcalqqq vqrgsywlsh
2041 ltkyttsrlh nsyiafgfps lekvlyhryn lvdsmgplv sitrhlallq teirelvtdy
2101 nqlrqsrtqt yhfiktskgr itklvndylr felviralkn nstwhhelyl lpeligvchr
2161 fnhtrnctcs erflvqtlyl hrmsdaeikl mdrltslvnm fpegfrsssv
```

SEQ ID NO: 34

Cote d/Ivoire Ebola virus polymerase

```
  1 matqhtqypd arlsspivld qcdlvtracg lysayslnpq lkncrlpkhi yrlkydttvt
 61 eflsdvpvat lpadflvptf lrtlsgngsc pidpkcsqfl eeivnytlqd irflnyylnr
121 agvhndhvdr dfgqkirnli cdnevlhqmf hwydlailar rgrlnrgnnr stwfasdnlv
```

FIG. 2 CONTINUED

```
 181 dilgygdyif wkiplsllpv dtqglphaak dwyhesvfke aiqghthivs istadvlimc
 241 kdiitcrfnt lliaavanle dsvhsdyplp etvsdlykag dylisllgse gykvikflep
 301 lclakiqlcs nyterkgrfl tqmhlavnht leeltgsrel rpqqirkvre fhqmlinlka
 361 tpqqlcelfs vqkhwghpvl hsekaiqkvk khatvikalr piiifetycv fkysiakhyf
 421 dsqgtwysvt sdrcltpgls syikrnqfpp lpmikellwe fyhldhpplf stkvisdlsi
 481 fikdratave ktcwdavfep nvlgynppnk fatkrvpeqf leqenfsies vlhyaqrley
 541 llpeyrnfsf slkekelnig rafgklpypt rnvqtlceal ladglakafp snmmvvtere
 601 qkesllhqas whhtsddfge natvrgssfv tdlekynlaf ryeftapfie ycnrcygvrn
 661 lfnwmhytip qcyihvsdyy npphgvslen renppegpss yrghlggieg lqqklwtsis
 721 caqislveik tgfklrsavm gdnqcitvls vfpletesse qelssednaa rvaaslakvt
 781 sacgiflkpd etfvhsgfiy fgkkqylngv qlpqslktat riaplsdaif ddlqgtlasi
 841 gtafersise trhvvpcrva aafhtffsvr ilqyhhlgfn kgtdlgqlsl skpldfgtit
 901 lalavpqvlg glsflnpekc fyrnlgdpvt sglfqlktyl qmihmddlfl pliaknpgnc
 961 saidfvlnps glnvpgsqdl tsflrqivrr titlsaknkl intlfhssad ledemvckwl
1021 lsstpvmsrf aadifsrtps gkrlqilgyl egtrtllask iinhntetpi ldrlrkitlq
1081 rwslwfsyld hcdqvladal tqitctvdla qilreytwah ilegrqliga tlpcileqln
1141 viwlkpyehc pkcaksanpk gepfvsiaik khvvsawpdq srlswtigdg ipyigsrted
1201 kigqpaikpk cpsaalreai eltsrltwvt qggansdllv kpfiearvnl svqeilqmtp
1261 shysgnivhr yndqysphsf manrmsnsat rlvvstntlg efsgggqsar dsniifqnvi
1321 nfavalfdlr frnvatssiq hhrahlhlsk cctrevpaqy lvytstlpld ltryrdneli
1381 yddnplrggl ncnlsfdnpl fkgqrlniie edlirlpyls gwelaktviq siisdsnnss
1441 tdpissgetr sftthfltyp kigllysfga lisyylgnti irtkkltlnn fiyylatqih
1501 nlphrslril kptlkhasvi srlisidshf siyiggtagd rglsdaarlf lrtaitvflq
1561 fvrkwiverk taiplwviyp legqspspin sflhhviall qhesshdhvc aaeahsrvet
1621 fdnlvymcks tasnffhasl aywrsrsknq dkremtkils ltqtekknsf gytahpesta
1681 vlgslqtsla pppsadeaty drknkvlkas rpgkysqntt kappnqtscr dvspnitgtd
1741 gcpsanegsn snmnnlvshr ivlpfftlsh nynerpsirk segtteivrl trqlraipdt
1801 tiycrftgiv ssmhykldev lwefdnfksa itlaegegsg alllqkykv etlffntlat
1861 ehsieaeiis gittprmllp imsrfhggqi kvtlnnsasq itditnpswl adqksripkq
1921 veiitmdaet teninrskly eavqqlivsh idpnalkvvv lkvflsdidg ilwlndnltp
1981 lfglgylikp itsspkssew ylclsnllst srrlphqsht tcmhviqtal qlqiqrssyw
2041 lshlvqyanh nlhldyinlg fpslervlyh rynlvdsqkg pltsivqhla hlqteirelv
2101 ndynqqrqsr tqtyhfikti kgritklvnd ylkffliiqa lkhnctwqee lralpdlisv
2161 ctrfyhtrnc scenrflvqt lylsrmqdse iklidrltgl lslcpngffr
```

SEQ ID NO: 40

FIG. 2 CONTINUED

RECOMBINANT BIOLOGICALLY CONTAINED FILOVIRUS VACCINE

CROSS-REFERENCE TO RELATED APPLICATIONS

This application is a U.S. national stage filing under 35 U.S.C. 371 from International Application No. PCT/US2019/045476, filed on 7 Aug. 2019, and published as WO 2020/033527 A2 on 13 Feb. 2020, which claims the benefit of U.S. Provisional Application Ser. No. 62/715,673, filed Aug. 7, 2018, which applications are incorporated by reference herein in their entirety.

STATEMENT OF GOVERNMENT RIGHTS

This invention was made with government support under AI109762 awarded by the National Institutes of Health. The government has certain rights in the invention.

BACKGROUND

Ebolaviruses cause hemorrhagic fevers in humans and nonhuman primates, with case fatality rates of 90% in some outbreaks (Sanchez et al., 2007). Ebolaviruses and the closely related Marburgviruses belong to the Filoviridae family (Feldman et al., 2004). Currently, there are no approved vaccines or antivirals for use against filoviruses, making biosafety level-4 (BSL-4) containment a mandatory requirement for work with these viruses. The lack of sufficient BSL-4 space, trained personnel, and the rigors of working in BSL-4 laboratories have severely hampered basic research with Ebolaviruses as well as the development of vaccines and large-scale screening for effective antiviral compounds. These limitations have prompted examination of various steps in the Ebolavirus viral life cycle in the absence of infectious virus: (i) replication and transcription were studied by use of reporter gene assays that are based on the expression of necessary viral components from plasmids (Boehmann et al., 2005; Groseth et al., 2005; Muhlberger et al., 1999; Modrof et al., 2003; Modrof et al., 2002); (ii) entry and fusion processes were assessed with pseudotyping assays that rely on the use of recombinant vesicular stomatitis or retroviruses (Yonezawa et al., 2005; Wool-Lewis et al., 1998; Takada et al., 1997; Marzi et al., 2006); and (iii) budding was examined using virus-like particles that are generated from viral proteins provided by protein expression plasmids (Jasenosky et al., 2001; Licata et al., 2004; Noda et al., 2002; McCarthy et al., 2006; Johnson et al., 2006). However, several recent findings suggest that data obtained with these artificial systems may not always be reproducible with live, authentic Ebolavirus (Neumann et al., 2005). Thus, biologically contained Ebolaviruses that resemble wild-type virus but can be handled outside BSL-4 containment are clearly needed.

SUMMARY

The invention provides a vaccine comprising an effective amount of a recombinant negative-sense, single stranded RNA virus, the genome of which contains a deletion of viral sequences corresponding to those for a nonstructural or nonglycosylated viral protein that is essential in trans for viral replication, and in one embodiment, one or more adjuvants, or in one embodiment, one or more insertions of a nucleotide sequence encoding one or more heterologous gene products, or in one embodiment, one or more adjuvants and one or more insertions of a nucleotide sequence encoding one or more heterologous gene products, wherein the insertions may be in coding or non-coding sequences. In one embodiment, the heterologous gene product is from a Zaïre, Sudan, Côte d'lvoire, Bundibugyo, Reston, or Marburg filovirus, a glycoprotein of one or more of those filoviruses. In one embodiment, the insertions may replace coding sequences, e.g., glycoprotein coding sequences, or a portion thereof, or may replace non-coding sequences. In one embodiment, the deletion is effective to inhibit or prevent viral replication upon infection of a cell with the recombinant negative-sense, single stranded RNA virus. For example, the deletion of viral sequences corresponding to those for a nonstructural or nonglycosylated viral protein that is essential in trans for viral replication may be effective to prevent expression of a functional nonstructural or nonglycosylated protein upon infection of a cell with the recombinant negative-sense, single stranded RNA virus. In one embodiment, the deletion of viral sequences corresponding to those for a nonstructural or nonglycosylated viral protein that is essential in trans for viral replication may be in filovirus sequences for a viral protein corresponding to Ebola virus VP30 protein. In one embodiment, the genome of the recombinant, biologically contained filovirus comprises heterologous sequences, for instance, positioned within the deletion in VP30 related sequences. Any of the deletions in viral sequences of a negative-sense, single stranded RNA virus may include a deletion of 1 or more nucleotides, e.g., a deletion of at least 0.1%, 1%, 5%, 10%, 50%, 60%, 70%, 80%, 90%, or any integer in between, and up to 100% of the viral sequences corresponding to those for a nonstructural, glycosylated or nonglycosylated viral protein. The deletion of viral sequences corresponding to those for a nonstructural or nonglycosylated viral protein that is essential in trans for viral replication is one that is stable over multiple passages and is readily detectable, e.g., by RT-PCR. In one embodiment, the genome of the recombinant virus has a deletion in viral sequences for two or more nonstructural or nonglycosylated proteins, for example, a deletion in sequences for viral proteins that are not contiguous with each other, such as sequences for a viral protein corresponding to Ebola virus VP30 protein and for a viral protein corresponding to Ebola virus GP protein. In one embodiment, where the genome of the recombinant virus has a deletion in viral sequences for a nonstructural, glycosylated or nonglycosylated protein, at least a portion of the deleted viral sequences may be replaced with a nucleotide sequence encoding an antigen that is expressed in the recombinant filovirus which, when administered to a mammal, is prophylactic or therapeutic. In one embodiment, where the genome of the recombinant virus has a deletion in viral sequences for two or more proteins that are nonstructural, glycosylated or nonglycosylated proteins, at least a portion of one of the deleted viral sequences may be replaced with a nucleotide sequence encoding an antigen that is expressed in the recombinant filovirus which, when administered to a mammal, is prophylactic or therapeutic. The vaccine of the invention may provide for subtype cross protection, for filovirus cross protection and optionally as a bi- or multi-valent vaccine for pathogens other than filovirus.

As shown hereinbelow, incorporating an adjuvant into the vaccine provided unexpected results. Moreover, not all adjuvants were effective, e.g., alum did not enhance the efficacy of the vaccine virus of the invention relative to a control (no adjuvant). In one embodiment, a monovalent recombinant filovirus vaccine comprises one or more adjuvants and a recombinant filovirus, the expression of the genome results in a virus having a homologous glycoprotein, e.g., a Zaire genome expresses a Zaire glycoprotein. In one embodiment, a monovalent recombinant filovirus vaccine comprises one or more adjuvants and a recombinant filovirus, the expression of the genome results in a virus having a heterologous glycoprotein, e.g., a Zaire genome expresses a Marburg virus, Sudan ebolavirus, or Bundibugyo ebolavirus glycoprotein, e.g., inserted into ORF 4 (to replace the parent glycoprotein). In one embodiment, a monovalent recombinant filovirus vaccine comprises one or more adjuvants and a recombinant filovirus, the expression of the genome results in a virus having a heterologous glycoprotein, e.g., a Zaire genome expresses a Marburg virus, Sudan ebolavirus, or Bundibugyo ebolavirus glycoprotein, e.g., inserted into sequences corresponding to Ebola virus VP30 (ORF5) or the resulting deletion of ORF5 or a portion thereof, e.g., two different glycoproteins are expressed.

In one embodiment, a vaccine comprising an effective amount of a recombinant filovirus and one or more adjuvants is provided. The genome of the recombinant filovirus contains a deletion of one or more nucleotides in a polynucleotide sequence for a viral protein corresponding to Ebola virus VP30, and the deletion is effective to prevent expression of a functional viral protein corresponding to Ebola virus VP30 upon infection of a cell with the recombinant filovirus. In one embodiment, at least 90% of sequences corresponding to VP30 sequences in the viral genome of the virus are deleted. In one embodiment, the genome further comprises a nucleotide sequence encoding a prophylactic or therapeutic heterologous gene product. In one embodiment, the nucleotide sequence is inserted within 500 nucleotides of the deletion site or at the site of the deletion. In one embodiment, the nucleotide sequence is inserted into the filovirus genome at a site other than the site of the deletion in the polynucleotide. In one embodiment, the nucleotide sequence is inserted between NP coding sequences and VP35 coding sequences in the filovirus genome. In one embodiment, the nucleotide sequence replaces GP/sGP sequences or a portion thereof. In one embodiment, the nucleotide sequence is inserted into GP/sGP coding sequences. In one embodiment, the heterologous gene product comprises a heterologous filovirus glycoprotein. In one embodiment, the filovirus glycoprotein comprises a Marburg virus, Ebola virus, Sudan virus, Tai Forest virus, Reston virus, or Bundibugyo virus glycoprotein. In one embodiment, the recombinant filovirus genome is a recombinant Ebola virus genome. In one embodiment, the vaccine of further comprises a pharmaceutically acceptable carrier.

In one embodiment, the adjuvant comprises lipopolysaccharide. In one embodiment, the lipopolysaccharide comprises monophosphoryl lipid A. In one embodiment, the adjuvant comprises squalene. In one embodiment, the adjuvant comprises an extract of Quillaja *saponaria*. In one embodiment, the adjuvant comprises saponin. In one embodiment, the recombinant filovirus in the vaccine is inactivated. A method to immunize a mammal using a composition having the recombinant filovirus is also provided. In one embodiment, the mammal is a human. In one embodiment, two doses of the composition are administered. In one embodiment, a single dose is administered. In one embodiment, three doses of the composition are administered. In one embodiment, the recombinant filovirus is inactivated, e.g., using heat, one or more chemicals, e.g., formaldehyde, formalin, beta-propiolactone, diethylpyrocarbonate, an oxidizing agent such as hydrogen peroxide, 2,2'-dithiodipyridine, binary ethylene imine, glutaraldehyde or radiation, e.g., gamma or UV.

Since most areas in Africa experience several specific endemic or recurring diseases, and the combinations vary among regions, the disclosure provide for bi-/multi-valent vaccines to address combinations of diseases that impact particular areas. Monovalent vaccines may be particularly useful in response to any outbreaks that don't correspond well to other vaccines. Multivalent vaccines may be based on the addition of exogenous sequences into any of several positions in the filovirus genome including but not limited to: 1) an artificial transcriptional unit between open reading frame (ORF) 1 (e.g., NP) and ORF 2 (e.g., VP35), 2) ORF 4 (e.g., Zaire glycoprotein gene), and 3) ORF 5 (e.g., VP30 gene). In one embodiment, a bivalent vaccine virus may express a one or more nonglycosylated proteins, one or more glycosylated proteins, or at least one nonglycosylated protein and at least one glycosylated protein from, for example, Zaire ebolavirus and Marburg virus, Ebola and Marburg viruses, a filovirus and Lassa virus, or a filovirus and *Plasmodium* (malaria).

Thus, in one embodiment, a recombinant filovirus, wherein the genome of the recombinant filovirus contains a first deletion of one or more nucleotides in a polynucleotide sequence for a viral protein corresponding to Ebola virus VP30 which first deletion is effective to prevent expression of a functional viral protein corresponding to Ebola virus VP30 upon infection of a cell with the recombinant filovirus, and the genome encodes one or more filovirus glycoproteins. The genome may contain a mutation in a region that is flanked by NP coding sequences and VP35 coding sequences, a mutation in GP/sGP coding sequences, and/or an insertion within 500 nucleotides of the first deletion site or at the first deletion site, or a combination thereof, and the genome encodes one or more filovirus glycoproteins. The mutation in the region that is flanked by NP coding sequences and VP35 coding sequences comprises an insertion of a nucleotide sequence encoding a prophylactic or therapeutic heterologous gene product and optionally also a deletion of one or more nucleotides in the region that flanks the NP coding sequences and VP35 coding sequences. The mutation in the GP/sGP coding sequences comprises an insertion of a nucleotide sequence encoding a prophylactic or therapeutic heterologous gene product and optionally also a deletion of one or more nucleotides in the GP/sGP coding sequences. The insertion that is within 500 nucleotides of or at the first deletion site encodes a prophylactic or therapeutic heterologous gene product. In one embodiment, the recombinant filovirus is inactivated, e.g., using heat, one or more chemicals, e.g., formaldehyde, formalin, beta-propiolactone, diethylpyrocarbonate, an oxidizing agent such as hydrogen peroxide, 2,2'-dithiodipyridine, binary ethylene imine, glutaraldehyde or radiation, e.g., gamma or UV.

Further provided is a multivalent vaccine comprising an effective amount of a recombinant filovirus, wherein the genome of the recombinant filovirus contains a first deletion in one or more nucleotides for a polynucleotide sequence for a viral protein corresponding to Ebola virus VP30 which deletion is effective to prevent expression of a functional viral protein corresponding to Ebola virus VP30 upon infection of a cell with the recombinant filovirus, and wherein the genome encodes one or more filovirus glycoproteins. The genome may contain a mutation in a region that is flanked by NP coding sequences and VP35 coding sequences, a mutation in GP/sGP coding sequences, and/or an insertion within 500 nucleotides of the first deletion site or at the first deletion site, or a combination thereof. The mutation in the region that is flanked by NP coding sequences and VP35 coding sequences comprises an insertion of a nucleotide sequence encoding a prophylactic or therapeutic heterologous gene product and optionally also a deletion of one or more nucleotides in the region that flanks the NP coding sequences and VP35 coding sequences. The mutation in the GP/sGP coding sequences comprises an insertion of a nucleotide sequence encoding a prophylactic or therapeutic heterologous gene product and optionally also a deletion of one or more nucleotides in the GP/sGP coding sequences. The insertion that is within 500 nucleotides, e.g., within at least 1000 nucleotides, of or at the first deletion site encodes a prophylactic or therapeutic heterologous gene product. In one embodiment, one of the filovirus glycoproteins encoded by the genome comprises a homologous filovirus glycoprotein. In one embodiment, one of the filovirus glycoproteins encoded by the genome comprises a heterologous filovirus glycoprotein. In one embodiment, the prophylactic or therapeutic heterologous gene product is not a glycoprotein. In one embodiment, the prophylactic or therapeutic heterologous gene In one embodiment, product comprises a glycoprotein. In one embodiment, the vaccine further comprises an adjuvant. In one embodiment, the adjuvant comprises lipopolysaccharide. In one embodiment, the adjuvant comprises squalene. In one embodiment, the adjuvant comprises an extract of *Quillaja saponaria*. In one embodiment, the adjuvant comprises saponin. In one embodiment, the vaccine further comprises a pharmaceutically acceptable carrier. In one embodiment, the recombinant filovirus in the vaccine is inactivated. Further provided is a method to immunize a mammal, e.g., a human, by administering to the mammal an effective amount of the vaccine. For example, a human in contact with filovirus infected individuals or inadvertently exposed to filovirus, e.g., in a laboratory, may be administered the recombinant infectious, biologically contained virus of the invention in an amount effective to inhibit or substantially eliminate filovirus replication in the human.

To prepare such viruses, a reverse genetics systems for negative-sense RNA viruses was exploited to generate Eboleviruses that lack a substantial portion of the VP30 gene (which encodes an essential transcription factor), termed EbolaΔVP30 virus, lack a substantial portion of the L gene, or lack a substantial portion of both genes. EbolaΔVP30 viruses were maintained, genetically stable, and biologically confined to a cell line expressing VP30. Hence, the EbolaΔVP30 virus fulfills several criteria of a vaccine virus: it can be grown to reasonably high titers in helper cells, is genetically stable (as determined by sequence analysis after seven serial passages in VP30-expressing Vero cells), and is safe. Moreover, the resultant viruses resemble wild-type virus in their life cycle, their morphology, and their growth properties, but could be handled in a non-BSL-4 laboratory, opening new opportunities for study of the Ebolavirus life cycle and for the identification of effective antiviral compounds.

Other negative-sense, single stranded RNA viruses may likewise be manipulated, e.g., the genome of Nipah virus, Hendravirus, Henipavirus, and the like, may be manipulated to mutate or delete sequences corresponding to those for a nonstructural or nonglycoslyated viral protein that is required for viral replication. Thus, genomes of viruses in the following families may be manipulated to provide for an infectious, biologically contained virus that resembles wild-type virus in its life cycle, morphology, and growth properties, can be grown to reasonably high titers in helper cells, is genetically stable, and is safe: Bornaviridae, Rhabdoviridae, Filoviridae (genera Marburgvirus and Ebolavirus), Paramyxoviridae, Avulavirus, Henipavirus, Morbillivirus, Respirovirus, or Rubulavirus.

The disclosure also provides a method to prepare an infectious, biologically contained negative-sense, single stranded RNA virus, e.g., filovirus. In one embodiment, the method includes providing a host cell, e.g., a Vero cell, having a plurality of viral vectors which when expressed (stably or transiently) are effective to yield infectious, biologically contained negative-sense, single stranded RNA virus. In one embodiment, the plurality of vectors includes a vector for vRNA production comprising a promoter operably linked to a virus DNA which contains a deletion of sequences for a viral gene corresponding to Ebola virus VP30 which deletion is effective to prevent expression of a functional viral protein corresponding to Ebola virus VP30, linked to a transcription termination sequence, and an insertion of heterologous sequences as discussed above. The host cell also includes a vector for mRNA production comprising a promoter operably linked to a DNA segment encoding a viral polymerase, a vector for mRNA production comprising a promoter operably linked to a DNA segment encoding viral nucleoprotein, a vector for mRNA production comprising a promoter operably linked to a DNA segment encoding one or more other viral proteins which along with the viral polymerase and nucleoprotein, are viral proteins needed for viral replication, and a vector comprising a promoter operably linked to a DNA encoding a RNA polymerase that is heterologous to the host cell. The heterologous RNA polymerase is selected to promote transcription of the viral DNA which contains the deletion. In one embodiment, the vector for vRNA includes a T7 polymerase promoter and a ribozyme sequence capable of cleaving a transcript to yield a vRNA-like 3' end. Then infectious, biologically contained virus is isolated from the cell. In one embodiment, the host cell is transiently transfected with the plurality of vectors and virus collected within 1, 2, 3, and up to 7 days post-transfection. In one embodiment, the host cell is one that is approved for vaccine production. In one embodiment, additional heterologous sequences are included in the vRNA vector or in mRNA vectors subsequently introduced to the host cell, and/or are introduced to the host cell via a mRNA vector. In one embodiment, the additional heterologous sequences are for an immunogenic polypeptide or peptide of a pathogen, a tumor antigen, or a therapeutic protein.

In one embodiment, a method to prepare a multivalent infectious, biologically contained filovirus is provided. The method includes providing a host cell comprising a plurality of filovirus vectors which, when expressed in the host cell, are effective to yield infectious, biologically contained filovirus, wherein the plurality of vectors includes a vector for vRNA production comprising a promoter operably linked to a filovirus DNA which contains a deletion in sequences for a functional viral protein corresponding to Ebola virus VP30, which deletion is effective to prevent expression of the functional viral protein linked to a transcription termination sequence, and other sequences as disclosed herein above, a vector for mRNA production comprising a promoter operably linked to a DNA segment encoding a filovirus polymerase, a vector for mRNA production comprising a promoter operably linked to a DNA segment encoding a filovirus nucleoprotein, a vector for mRNA production comprising a promoter operably linked to a DNA segment encoding a filovirus protein corresponding to Ebola virus VP30, a vector for mRNA production comprising a promoter operably linked to a DNA segment encoding a filovirus protein corresponding to Ebola virus VP35, and a vector for mRNA production comprising a promoter operably linked to a DNA encoding a RNA polymerase that is heterologous to the host cell, wherein the heterologous RNA polymerase promotes transcription of vRNA from the filovirus DNA which contains the deletion; and isolating infectious, biologically contained filovirus from the host cell. In one embodiment, the cells are mammalian cells. In one embodiment, the cells are primate cells. In one embodiment, the cells are Vero cells. In one embodiment, the heterologous RNA polymerase is a T3, T7, or SP6 polymerase. In one embodiment, the gene product sequences for an immunogenic polypeptide or peptide of a pathogen, a tumor antigen, or a therapeutic protein. In one embodiment, each vector encoding a filovirus protein is on a separate plasmid.

Further provided is a method of manufacturing, e.g., large scale manufacturing, recombinant filovirus, e.g., for vaccine production. The method includes culturing mammalian cells expressing a recombinant filovirus genome in serum free medium in a cell culture system so as to result in progeny recombinant biologically contained filovirus. The genome of the recombinant filovirus contains a deletion of one or more nucleotides in a polynucleotide sequence for a viral protein corresponding to Ebola virus VP30, and wherein the deletion is effective to prevent expression of a functional viral protein corresponding to Ebola virus VP30 upon infection of a cell with the recombinant filovirus. The mammalian cells express a viral protein corresponding to Ebola virus VP30. In one embodiment, the serum free media comprises non-animal proteins or peptides, e.g., plant proteins or peptides, an iron chelator, e.g., EDTA, ferric nitrate, ferrous sulfate, or transferrin, or a combination thereof. The supernatant from the mammalian cells having the progeny is collected and contacted with a DNase and a virus inactivating agent, e.g., beta-propriolactone, heat, formaldehyde, gamma radiation, or hydroxylamine, thereby providing an inactivated viral preparation. The inactivated viral preparation is then purified, concentrated, desalted and/or fractionated from other molecules, e.g., via filtration, optionally under conditions that do not result in precipitation, e.g., precipitation visible to the naked eye, of the inactivated viral particles.

In one embodiment, the mammalian cells are Vero cells. In one embodiment, the collected supernatant is subject to separation, e.g., filtration, before contact with the DNase or the viral inactivating agent. In one embodiment, the collected supernatant is subjected to filtration with a 0.5 to 5 micron filter or a 1 to 5 micron filter. In one embodiment, the collected supernatant is subjected to filtration with 0.01 to 1 micron filter or a 0.05 to 0.25 micron filter. In one embodiment, the inactivated viral preparation is subjected to filtration through a 0.01 to 1 micron filter or a 0.05 to 0.25 micron filter. In one embodiment, the inactivated viral preparation is combined with one or more adjuvants.

BRIEF DESCRIPTION OF THE FIGURES

FIG. 1. Schematic diagram of EbolaΔVP30 constructs. (Top row) Schematic diagram of the Ebolavirus genome flanked by the leader sequence (l) and the trailer sequence (t) in positive-sense orientation. Two unique restriction sites for SalI and SacI (positions 6180 and 10942 of the viral antigenome, respectively) allowed the subcloning of a fragment that spans the VP30 gene. The subgenomic fragment was then used to replace the VP30 gene with genes encoding neomycin (neo) or enhanced green fluorescence protein (eGFP), respectively. Using the unique restriction sites, the altered subgenomic fragments were cloned back into the full-length Ebolavirus cDNA construct.

FIG. 2. Representative filovirus sequences (Accession numbers NC006432, NC004161, AY769362, AY142960, AF522874, AF499101, L11365, NC001608, DQ447652, DQ447649, AB050936, NC002549, NC001608, AF086833 and AF272001, the disclosures of which are incorporated by reference herein; SEQ ID Nos. 1-15 and 18-40).

DETAILED DESCRIPTION

Definitions

A "vector" or "construct" (sometimes referred to as gene delivery or gene transfer "vehicle") refers to a macromolecule or complex of molecules comprising a polynucleotide or virus to be delivered to a host cell, either in vitro or in vivo. The polynucleotide or virus to be delivered may comprise a coding sequence of interest for gene therapy. Vectors include, for example, viral vectors (such as filoviruses, adenoviruses, adeno-associated viruses (AAV), lentiviruses, herpesvirus and retroviruses), liposomes and other lipid-containing complexes, and other macromolecular complexes capable of mediating delivery of a polynucleotide to a host cell. Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more modifications, including deletions, insertions and/or heterologous genes or sequences. Since many viral vectors exhibit size constraints associated with packaging, the heterologous genes or sequences are typically introduced by replacing one or more portions of the viral genome. Such viruses may become replication-defective (biologically contained), requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described.

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include at least a portion of an open reading frame of a gene which is partly or entirely heterologous (i.e., foreign) to the transgenic organism, or may represent at least a portion of an open reading frame of a gene homologous to an endogenous gene of the organism, which portion optionally encodes a polypeptide with substantially the same activity as the corresponding full-length polypeptide or at least one activity of the corresponding full-length polypeptide.

By "transgenic cell" is meant a cell containing a transgene. For example, a cell stably or transiently transformed with a vector containing an expression cassette is a transgenic cell that can be used to produce a population of cells having altered phenotypic characteristics. A "recombinant cell" is one which has been genetically modified, e.g., by insertion, deletion or replacement of sequences in a nonrecombinant cell by genetic engineering.

The term "wild-type" or "native" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "transduction" denotes the delivery of a polynucleotide to a recipient cell either in vivo or in vitro, via a viral vector and preferably via a replication-defective viral vector.

The term "heterologous" as it relates to nucleic acid sequences such as gene sequences encoding a protein and control sequences, denotes sequences that are not normally joined together, and/or are not normally associated with a particular cell, e.g., are from different sources (for instance, sequences from a virus are heterologous to sequences in the genome of an uninfected cell). Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," "sequence," "segment," "fragment" or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

"Homology" refers to the percent of identity between two polynucleotides or two polypeptides. The correspondence between one sequence and to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single strand-specific nuclease(s), and size determination of the digested fragments. Two DNA, or two polypeptide, sequences are "substantially homologous" to each other when at least about 80%, preferably at least about 90%, and most preferably at least about 95% of the nucleotides, or amino acids, respectively match over a defined length of the molecules, as determined using the methods above.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide or virus refers to a nucleic acid sequence, peptide, polypeptide or virus that is identified and separated from at least one contaminant nucleic acid, polypeptide or other biological component with which it is ordinarily associated in its natural source, e.g., so that it is not associated with in vivo substances, or is substantially purified from in vitro substances. Isolated nucleic acid, peptide, polypeptide or virus is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded).

As used herein, the term "recombinant nucleic acid" or "recombinant DNA sequence, molecule or segment" refers to a nucleic acid, e.g., to DNA, that has been derived or isolated from a source, that may be subsequently chemically altered in vitro, and includes, but is not limited to, a sequence that is naturally occurring, is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more preferably homologous if their amino acids are greater than or equal to 50% identical when optimally aligned using the ALIGN program.

The term "corresponds to" is used herein to mean that a polynucleotide sequence is homologous (e.g., is identical, not strictly evolutionarily related) to all or a portion of a reference polynucleotide sequence that encodes a polypeptide or its complement, or that a polypeptide sequence is identical in sequence or function to a reference polypeptide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by using local homology algorithms or by a search for similarity method, by computerized implementations of these algorithms (GAP, BESTFIT, FASTA, and TFASTA Genetics Software Package or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

As applied to polypeptides, the term "substantial identity" means that two peptide sequences, when optimally aligned, such as by the programs GAP or BESTFIT using default gap weights, share at least about 80% sequence identity, preferably at least about 90% sequence identity, more preferably at least about 95% percent sequence identity, and most preferably at least about 99% sequence identity.

A "protective immune response" and "prophylactic immune response" are used interchangeably to refer to an immune response which targets an immunogen to which the individual has not yet been exposed or targets a protein associated with a disease in an individual who does not have the disease, such as a tumor associated protein in a patient who does not have a tumor.

A "therapeutic immune response" refers to an immune response which targets an immunogen to which the individual has been exposed or a protein associated with a disease in an individual who has the disease.

The term "prophylactically effective amount" is meant to refer to the amount necessary to, in the case of infectious agents, prevent an individual from developing an infection, and in the case of diseases, prevent an individual from developing a disease.

The term "therapeutically effective amount" is meant to refer to the amount necessary to, in the case of infectious agents, reduce the level of infection in an infected individual in order to reduce symptoms or eliminate the infection, and in the case of diseases, to reduce symptoms or cure the individual.

"Inducing an immune response against an immunogen" is meant to refer to induction of an immune response in a naïve individual and induction of an immune response in an individual previously exposed to an immunogen wherein the immune response against the immunogen is enhanced.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

"Transfected," "transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

Exemplary Viruses and Methods of the Invention

The invention provides isolated vectors, e.g., plasmids, which encode proteins of negative-sense, single stranded RNA viruses and/or express vRNA from recombinant nucleic acid corresponding to sequences for mutant negative-sense, single stranded RNA viruses. When introduced into a cell, a combination of these vectors is capable of yielding recombinant infectious, biologically contained virus. Thus, the invention includes host cells that produce recombinant infectious, biologically contained virus of the invention. In one embodiment, the invention provides isolated vectors, e.g., plasmids, which encode filovirus proteins and/or express mutant filovirus vRNA which, when introduced into a cell, are capable of yielding recombinant infectious, biologically contained filovirus. The invention includes host cells that transiently or stably produce recombinant infectious, biologically contained filovirus, including helper cells, and isolated recombinant filovirus prepared by the methods disclosed herein.

The vectors of the invention include those for mRNA production and vRNA production. In one embodiment, the vectors include filovirus DNA, for example, vectors for mRNA production with sequences corresponding to one or more open reading frames encoding filovirus proteins, or vectors for vRNA production that include a deletion of the full-length genomic sequence, which deletion includes internal filovirus sequences corresponding to at least a portion of one open reading frame. The RNA produced from the vRNA vector is capable of being packaged into virions in the presence of filovirus proteins but as part of the resulting virion, is not capable of being replicated and so does not result in virus production when that virion is introduced to a cell that otherwise supports filovirus replication and which cell does not express at least one filovirus protein in trans, e.g., a cell that is not a filovirus helper cell.

For example, Ebolaviruses possess a negative-sense, non-segmented RNA genome, approximately 19 kilobases in length that encodes seven structural proteins and at least one non-structural protein (Sanchez et al., 2007). NP, viral protein (VP) 35, VP30, and L, the RNA-dependent RNA polymerase, are components of the nucleocapsid involved in viral replication and transcription (Muhlberger et al., 1999). VP40 is the matrix protein and is involved in viral budding (Harty et al., 2000; Panchal et al., 2003). VP24 is involved in the formation of nucleocapsids composed of NP, VP35 and viral RNA (Huang et al., 2002). The only viral surface glycoprotein, GP, plays a role in viral attachment and entry (Chan et al., 2001; Manicassamy et al., 2005; Shimojima et al., 2006; Chandran et al., 2005). Candidate sequences for deletion/mutation/insertion and optional replacement with heterologous sequences include but are not limited to Ebola virus VP30 sequences or corresponding sequences in other negative-sense, single stranded RNA viruses, e.g., sequences for nonstructural, nonpolymerase and/or nonglycosylated viral proteins or non-coding regions. The vectors may include gene(s) or portions thereof other than those of a negative-sense, single stranded RNA virus such as a filovirus (heterologous sequences), which genes or portions thereof are intended to be expressed in a host cell, either as a protein or incorporated into vRNA. Thus, a vector of the invention may include in addition to viral sequences, for instance, filovirus sequences, a gene or open reading frame of interest, e.g., a heterologous gene for an immunogenic peptide or protein useful as a vaccine or a therapeutic protein.

If more than one vector is employed, the vectors may be physically linked or each vector may be present on an individual plasmid or other, e.g., linear, nucleic acid delivery vehicle. The vectors or plasmids may be introduced to any host cell, e.g., a eukaryotic cell such as a mammalian cell, that supports viral replication. Host cells useful to prepare virus of the invention include but are not limited to insect, avian or mammalian host cells such as canine, feline, equine, bovine, ovine, or primate cells including simian or human cells. In one embodiment, the host cell is one that is approved for vaccine production.

The viruses produced by methods described herein are useful in viral mutagenesis studies, drug screening and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). In particular, infectious, biologically contained filovirus of the invention which induces strong humoral and cellular immunity may be employed as a vaccine vector, as they are unlikely to give rise to infectious recombinant virus.

Thus, a virus for use in medical therapy (e.g., for a vaccine or gene therapy) is provided. For example, the invention provides a method to immunize an animal against a pathogen, e.g., a bacteria, virus such as Ebola virus, or parasite, or a malignant tumor. The method comprises administering to the animal an effective amount of at least one isolated virus of the invention which encodes and expresses, or comprises nucleic acid for an immunogenic peptide or protein of a pathogen or tumor, optionally in combination with an adjuvant, effective to immunize the animal.

To prepare expression cassettes for transformation herein, the recombinant DNA sequence or segment may be circular or linear, double-stranded or single-stranded. A DNA sequence which encodes an RNA sequence that is substantially complementary to a mRNA sequence encoding a gene product of interest is typically a "sense" DNA sequence cloned into a cassette in the opposite orientation (i.e., 3_ to 5_ rather than 5_ to 3_). Generally, the DNA sequence or segment is in the form of chimeric DNA, such as plasmid DNA, that can also contain coding regions flanked by control sequences which promote the expression of the DNA in a cell. As used herein, "chimeric" means that a vector comprises DNA from at least two different species, or comprises DNA from the same species, which is linked or associated in a manner which does not occur in the "native" or wild-type of the species.

Aside from DNA sequences that serve as transcription units, or portions thereof, a portion of the DNA may be untranscribed, serving a regulatory or a structural function. For example, the DNA may itself comprise a promoter that is active in eukaryotic cells, e.g., mammalian cells, or in certain cell types, or may utilize a promoter already present in the genome that is the transformation target of the lymphotropic virus. Such promoters include the CMV promoter, as well as the SV40 late promoter and retroviral LTRs (long terminal repeat elements), e.g., the MMTV, RSV, MLV or HIV LTR, although many other promoter elements well known to the art may be employed in the practice of the invention.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

The recombinant DNA to be introduced into the cells may contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, puro, hyg, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Exemplary reporter genes include the chloramphenicol acetyl transferase gene (cat) from Tn9 of *E. coli*, the beta-glucuronidase gene (gus) of the uidA locus of *E. coli*, the green, red, or blue fluorescent protein gene, and the luciferase gene. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, Sambrook et al., *Molecular Cloning: A Laboratory Manual* (2002) provides suitable methods of construction.

The recombinant DNA can be readily introduced into the host cells, e.g., mammalian, yeast or insect cells, by transfection with an expression vector comprising the recombinant DNA by any procedure useful for the introduction into a particular cell, e.g., physical or biological methods, to yield a transformed (transgenic) cell having the recombinant DNA so that the DNA sequence of interest is expressed by the host cell. In one embodiment, at least one of the recombinant DNA which is introduced to a cell is maintained extrachromosomally. In one embodiment, at least one recombinant DNA is stably integrated into the host cell genome.

Physical methods to introduce a recombinant DNA into a host cell include calcium-mediated methods, lipofection, particle bombardment, microinjection, electroporation, and the like. Biological methods to introduce the DNA of interest into a host cell include the use of DNA and RNA viral vectors. Viral vectors, e.g., retroviral or lentiviral vectors, have become a widely used method for inserting genes into eukaryotic, such as mammalian, e.g., human, cells. Other viral vectors useful to introduce genes into cells can be derived from poxviruses, e.g., vaccinia viruses, herpes viruses, adenoviruses, adeno-associated viruses, baculoviruses, and the like.

To confirm the presence of the recombinant DNA sequence in the host cell, a variety of assays may be performed. Such assays include, for example, molecular biological assays well known to those of skill in the art, such as Southern and Northern blotting, RT-PCR and PCR; biochemical assays, such as detecting the presence or absence of a particular gene product, e.g., by immunological means (ELISAs and Western blots) or by other molecular assays.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the recombinant DNA segment is being expressed. Expression may be evaluated by specifically identifying the peptide products of the introduced DNA sequences or evaluating the phenotypic changes brought about by the expression of the introduced DNA segment in the host cell.

The recombinant viruses described herein have modifications in genomic sequences relative to a corresponding wild-type viral genome, i.e., the genome of the recombinant virus has a modification which includes a deletion, and optionally an insertion, in a region corresponding to sequences for a viral protein that is associated with transcription, is nonstructural or nonglycosylated. The mutation in the viral genome is effective to inhibit or prevent production of at least one functional viral protein from that genome when those sequences are present in a nontransgenic cell which supports viral replication. In one embodiment, the deletion includes from 1 up to thousands of nucleotides, e.g., 1%, 10%, 50%, 90% or more of sequences corresponding to the coding region for the viral protein. In one embodiment, the deleted sequences correspond to sequences with a substantial identity, e.g., at least 80% or more, e.g., 85%, 90% or 95% and up to 100% or any integer in between, nucleic acid sequence identity, to VP30 sequences and/or GP/sGP sequences. In one embodiment, the deletion includes from 1 up to hundreds of nucleotides, e.g., 1%, 10%, 50%, 90% or more of sequences corresponding to at least non-coding sequences between NP coding sequences and VP35 coding sequences. In one embodiment, the deleted sequences correspond to sequences with a substantial identity, e.g., at least 80% or more, e.g., 85%, 90% or 95% and up to 100% or any integer in between, nucleic acid sequence identity, to non-coding sequences between NP coding sequences and VP35 coding sequences.

In one embodiment, the viral genome in an infectious, replication-incompetent negative-sense, single-stranded RNA virus of the invention includes a deletion in sequences corresponding to those in a wild-type viral genome for a protein that is associated with transcription or is nonstructural or nonglycoslyated, and includes heterologous sequences that are nontoxic to host cells including cells in an organism to be immunized. In one embodiment, the heterologous sequence is a marker sequence, a selectable sequence or other sequence which is detectable or capable of detection, e.g., GFP or luciferase, or a selectable gene such as an antibiotic resistance gene, e.g., a hygromycin B resistance gene or neomycin phosphotransferase gene, which marker gene or selectable gene is not present in the host cell prior to introduction of the vector.

Pharmaceutical Compositions

Pharmaceutical compositions of the present invention, suitable for inoculation, e.g., nasal, parenteral or oral administration, such as by intravenous, intramuscular, intranasal, topical or subcutaneous routes, comprise one or more virus isolates, e.g., one or more recombinant infectious, biologically contained negative-sense, single stranded RNA virus isolates, optionally further comprising sterile aqueous or non-aqueous solutions, suspensions, and emulsions. The compositions can further comprise auxiliary agents or excipients, as known in the art. The composition is generally presented in the form of individual doses (unit doses). Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

In one embodiment, the pharmaceutical composition is part of a controlled release system, e.g., one having a pump, or formed of polymeric materials (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger & Peppas, J. Macromol. Sci. Rev. Macromol. Chem., 23:61 (1983); see also Levy et al., Science, 228:190 (1985); During et al., Ann. Neurol., 25:351 (1989); Howard et al., J. Neurosurg. 71:105 (1989)). Other controlled release systems are discussed in the review by Langer (Science, 249:1527 (1990)).

The pharmaceutical compositions comprise a therapeutically effective amount of the virus, and a pharmaceutically acceptable carrier. In a specific embodiment, the term "pharmaceutically acceptable" means approved by a regulatory agency of the Federal or a state government or listed in the U.S. Pharmacopela or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. These compositions can be formulated as a suppository. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the virus, preferably in purified form, together with a suitable amount of carrier so as to provide the form for proper administration to the patient. The formulation should suit the mode of administration.

The compositions may be systemically administered, e.g., orally or intramuscularly, in combination with a pharmaceutically acceptable vehicle such as an inert diluent. For oral administration, the virus may be combined with one or more excipients and used in the form of ingestible capsules, elixirs, suspensions, syrups, wafers, and the like. Such compositions should contain at least 0.1% of active compound. The percentage of the compositions and preparations may, of course, be varied and may conveniently be between about 2 to about 60% of the weight of a given unit dosage form. The amount of active compound in such useful compositions is such that an effective dosage level will be obtained.

The compositions may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. Various other materials may be present. For instance, a syrup or elixir may contain the virus, sucrose or fructose as a sweetening agent, methyl and propylparabens as preservatives, a dye and flavoring such as cherry or orange flavor. Of course, any material used in preparing any unit dosage form, including sustained-release preparations or devices, should be pharmaceutically acceptable and substantially non-toxic in the amounts employed.

The composition also be administered intravenously or intraperitoneally by infusion or injection. Solutions of the virus can be prepared in water or a suitable buffer, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of undesirable microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of undesirable microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the virus in the required amount in the appropriate solvent with various of the other ingredients enumerated above, as required, followed by filter sterilization.

Useful liquid carriers include water, alcohols or glycols or water-alcohol/glycol blends, in which the present viruses can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the viruses of the invention can be determined by comparing their in vitro activity and in vivo activity in animal models.

Pharmaceutical Purposes

The administration of the composition may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of a virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the virus infection.

Pharmaceutical Administration

A composition of the present invention may confer resistance to one or more pathogens, e.g., one or more virus, bacterium or parasite strains, by either passive immunization or active immunization. In active immunization, a live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one virus strain.

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease.

At least one virus isolate of the present invention, may be administered by any means that achieve the intended purposes. For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating a viral related pathology, comprises administration of an effective amount of a vaccine composition as described herein, administered as a single treatment, or repeated as enhancing or booster dosages, for instance, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

Exemplary doses include but are not limited to from about $10^4$ to $10^8$ FFU or PFU, $10^6$ to $10^8$ FFU or PFU, $10^6$ to $10^{10}$ FFU or PFU, or $10^8$ to $10^{12}$ FFU or PFU, or more, or from about $10^6$ to $10^8$ particles, $10^8$ to $10^{10}$ particles, or $10^{10}$ to $10^{12}$ particles. In one embodiment a dose is from about $10^4$ to $10^8$ FFU or PFU, $10^6$ to $10^8$ FFU or PFU, $10^6$ to $10^{10}$ FFU or PFU, or $10^8$ to $10^{10}$ FFU or PFU.

Exemplary Adjuvants Adjuvants include but are not limited to aluminum, water in oil (W/O) emulsions, oil in water (O/W) emulsions, ISCOM, liposomes, nano- or microparticles, muramyl di- and/or tripeptides, saponin, non-ionic block co-polymers, lipid A, cytokines, bacterial toxins, carbohydrates, and derivatized polysaccharides and a combination of two or more these adjuvants in an Adjuvant System (AS).

Exemplary classes of adjuvants include but are not limited to agonists of TLR3, e.g., poly (I:C), agonists of TLR4, e.g., one or more components of bacterial lipopolysaccharide, e.g., monophosphoryl lipid A (MPLA), MPL®, and synthetic derivatives, e.g., E6020, agonists of TLR5, e.g., bacterial flagellin), agonists of TLR7, 8, e.g., single stranded RNA or imidazoquinolines (e.g., imiquimod, gardiquimod and R848), agonists of TLR9, e.g., CpG oligonucleotides and ISS immunostimulatory sequences, as well as Imidazoquinolines, agonists of the NLRP3 inflammasome, e.g., chitosan, and dual TLR1/2 agonists, e.g., Pam3CSK4, a lipopeptide.

In one embodiment, the adjuvant comprises saponin, a natural product derived from tree bark, which may be combined with cholesterol or a cholesterol like molecule, e.g., squalene.

In one embodiment, the adjuvant comprises an oil-in-water (O/W) emulsion comprising, for example, MF59 or AS03 and optionally 2% squalene. In one embodiment, the adjuvant comprises two different adjuvants, e.g., MPL and a saponin such as QS21, for example, in liposome.

In one embodiment, the adjuvant comprises Freund's Incomplete Adjuvant (IFA), MF59®, GLA-SE, IC31®, CAF01 AS03, AS04, or ISA51, and may include α-tocopherol, squalene and/or polysorbate 80 in an oil-in-water emulsion.

In one embodiment, the adjuvant comprises extracts and formulations prepared from Ayurvedic medicinal plants including but not limited to *Withania somnifera, Emblica officinalis, Panax notoginseng, Tinospora cordifolia* or *Asparagus racemosus.*

In one embodiment, the adjuvant comprises aluminum salts, saponin, muramyl di- and/or tripeptides, *Bordetella pertussis*, and/or cytokines.

In one embodiment, the adjuvant is not alum or an aluminum salt.

In one embodiment, the adjuvant is mixed with the recombinant filovirus just prior to administration.

Exemplary Antigens

Exemplary viral glycoproteins include but are not limited to those from ebolaviruses, e.g., Zaire, Sudan, Bundibugyo, Tai Forest (formerly known as Côte d'ivoire), or Reston, marburgviruses, arenaviruses such as Lassa virus; or bunyaviruses such a Crimean-Congo Hemorrhagic Fever virus or hantaviruses; or flaviruses such as Dengue virus, Zika virus, or Yellow Fever virus.

Exemplary parasite antigens include but are not limited to those from *Plasmodium, Leishmania, Giardia, Cryptosporidium* or *Cyclospora;*

Exemplary bacterial antigens include but are not limited to those from *Vibrio*, e.g. *V. cholera* or *Mycobacterium.*

Exemplary Methods to Prepare the Recombinant Filoviruses

Methods and Materials

Cells and cell lines. Vero cells (green monkey kidney cells) are grown in Eagle's minimal essential medium (MEM) supplemented with 10% fetal calf serum (FCS), L-glutamine, vitamins, nonessential amino acid solution and antibiotics. The VeroVP30 cell line is established by cotransfecting Vero cells with pCAG-VP30 (for the expression of VP30) and pPur, a protein expression plasmid for the puromycin resistance gene (Clontech, Mountain View, CA), using the transfection reagent TransIT LT-1 (Mirus, Madison, WI). Two days after transfection, puromycin-resistant cells are selected with 5 g/ml puromycin (Sigma, St. Louis, MO). Individual cell clones are screened for VP30 expression by flow cytometry with a polyclonal peptide antibody to VP30.

Human embryonic kidney 293T cells are grown in high-glucose Dulbecco's modified Eagle medium containing 10% FCS, L-glutamine, and antibiotics. All cells are maintained at 37° C. and 5% $CO_2$.

Flow cytometry. Cells are detached in phosphate-buffered saline (PBS) containing 0.02% EDTA and then washed once with cold PBS supplemented with 2% FCS and 0.1% sodium azide (wash buffer). Cells are incubated with a VP30 antibody on ice for 20 minutes. After washing in buffer, the cells are further incubated with a secondary antibody labeled with fluorescent isothiocyanate (Zymed Laboratories, Carlsbad, CA). They are then washed with buffer and analyzed by FACSCalibur with Cell Quest software (Becton Dickinson, Franklin Lakes, NJ).

Generation of EbolaΔVP30 viruses. The plasmid pTM-T7G-Ebo-Rib, containing the full-length Ebolavirus cDNA flanked by T7 RNA polymerase promoter and ribozyme sequences, is described in Newmann et al. (2002). First, a fragment encompassing nucleotides 6180 to 10942 (numbers refers to the positive-sense antigenome) is subcloned into a kanamycin-resistant cloning vector. Next, the VP30

Figure 1:
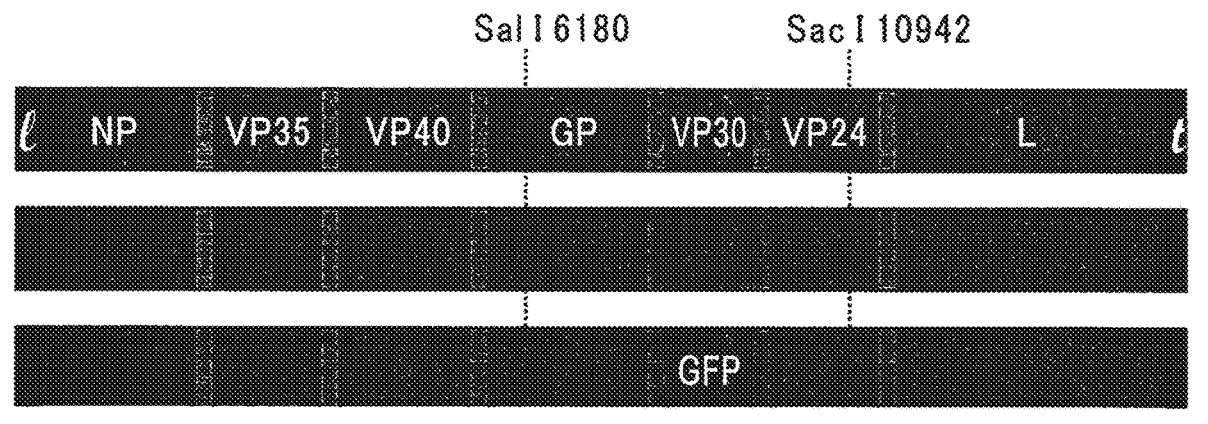

ORF is replaced with those encoding neo or eGFP, respectively, by a series of overlapping PCR amplification steps using Pfu Turbo (Stratagene, La Jolla, CA). The altered subgenomic fragments are transferred back into the full-length Ebolavirus cDNA plasmid using two unique restriction sites, SalI and SacI (FIG. 1). The resultant plasmids, designated pTM-EbolaΔVP30-neo or -eGFP, are sequenced to verify the replacement of the VP30 ORF and the lack of any unwanted mutations.

To artificially generate Ebolavirus, $5 \times 10^5$ 293T cells are transfected with 1.0 µg pTM-EbolaΔVP30, 2.0 µg pCAG-L, 1.0 µg pCAG-NP, 0.5 µg pCAG-VP35, 0.5 µg pCAG-VP30, and 1.0 µg pCAG-T7 pol, using TransIT LT1 (Mirus, Madison, WI) in BSL-4 containment (Neumann et al., 2002). Five days after transfection, the supernatant is harvested, cellular debris removed by low speed centrifugation, and the virus amplified in VeroVP30 cells at 37° C. and 5% $CO_2$ with propagation medium containing 2% FCS in MEM supplemented with L-glutamine, vitamins, nonessential amino acid solution and antibiotics without puromycin.

Plaque assay and immunostaining assay. To determine the titers of wild-type Ebolavirus or EbolaΔVP30 viruses, tenfold dilutions of the viruses are absorbed to confluent VeroVP30 or wild-type Vero cells for 1 hour at 37° C., after which any unbound virus was removed by washing cells with propagation medium. The cells are then overlaid with propagation medium containing 1.5% methyl cellulose (Sigma). Seven days after infection, cells are fixed with 10% buffered formaldehyde, taken out of BSL-4, permeabilized with 0.25% Triton X-100 in PBS for 10 minutes, and blocked with 4% goat serum and 1% bovine serum albumin (BSA) in PBS for 60 minutes. Cells are then incubated for 60 minutes with a 1:1000 dilution of a mouse anti-VP40 monoclonal antibody, washed with PBS, and incubated for 60 minutes with a 1:1000 dilution of an antimouse IgG-peroxidase-conjugated secondary antibody (Kirkegaard & Perry Laboratories Inc., Gaithersburg, MD). After washing with PBS, cells are incubated with 3,3'-diaminobenzidine tetrahydrochloride (DAB, Sigma) in PBS. The reaction is stopped by rinsing cells with water.

Western blotting. Partially purified virus is resuspended in lysis buffer (50 mM Tris-HCl [pH 7.5], 150 mM NaCl, 0.5% Triton X-100, and 0.1% SDS) containing protease inhibitors (complete protease inhibitor cocktails [Roche]) was incubated at 100° C. for 5 minutes, taken out of BSL-4, and separated on 4-20% polyacrylamide gels. Resolved proteins are transferred to Western polyvinylidine difluoride membranes (Schleicher & Schuell, Sanford, ME) and blocked overnight at 4° C. with 5% skim milk in PBST (0.05% Tween 20 [Sigma] in PBS). Blots are incubated with primary antibodies (a mouse anti-NP antibody, a rabbit anti-VP35 antibody, a rabbit anti-VP40 antibody, a mouse anti-GP antibody, a rabbit anti-VP30 antibody, or a mouse anti-VP24 antibody) for 60 minutes at room temperature, washed three times with PBST, incubated with the appropriate secondary antibody conjugated to horseradish peroxidase (Zymed) for 60 minutes, and finally washed three times with PBST. Blots were then incubated in Lumi-Light Western blotting substrate (Roche, Indianapolis, IN) and exposed to X-ray film (Kodak, Rochester, NY).

RNA isolation and RT-PCR. Cell culture supernatant from virus-infected VeroVP30 cells is inactivated with guanidinium isothiocyanate buffer and taken out of BSL-4. Viral RNA is isolated with the RNeasy Mini kit (Qiagen, Valencia, CA). RT-PCR is carried out with the RobusT One-Step RT-PCR kit (Finnzyme, Espoo, Finland), using 1 µg of isolated RNA and Ebolavirus-specific primers. The resultant PCR products are cloned into pT7Blue (Novagen, San Diego, CA) and sequenced.

Transmission electron microscopy. Ultrathin-section electronmicroscopy is performed as described in Noda et al. (2002). Briefly, at 36 hours postinfection, VeroVP30 cells infected with EbolaΔVP30-neo virus are fixed and inactivated with 2.5% glutaraldehyde in 0.1 M cacodylate buffer, taken out of BSL-4 and postfixed with 2% osmium tetroxide in the same buffer. Cells are then dehydrated with a series of ethanol gradients followed by propylene oxide, before being embedded in Epon 812 Resin mixture (TAAB Laboratories Equipment Ltd., Berkshire, UK). Thin sections are stained with 2% uranyl acetate and Raynold's lead, and examined under a HITACHI H-7500 electron microscope at 80 kV.

Selection of escape mutants. EbolaΔVP30-eGFP is diluted tenfold (10-1 to 10-6) and incubated with the indicated mAbs at a concentration of 250 to 500 µg of mAb/mL at 37° C. for 60 minutes. The virus/mAb mixtures are inoculated onto VeroVP30 cells for 60 minutes. Viruses are amplified for 5 days in the presence of antibodies. Then, viruses that grow in the presence of mAbs (as determined by GFP expression) are harvested at the highest virus-positive dilution and passaged for a total of 3-6 times in the presence of antibodies. Viral RNA is isolated, RT-PCR amplified, and the GP sequence determined by sequence analysis.

Generation and passage of EbolaΔVP30-neo virus. Previously a full-length cDNA clone of the Zaire ebolavirus-Mayinga was generated (Newmann et al., 2002). Using a subgenomic fragment that encompasses nucleotides 6180 to 10942 of the viral genome (numbers refers to the positive-sense antigenome), the ORF for VP30 was replaced with that of neomycin (neo), using a series of overlapping PCR amplification steps. After confirmation of the authenticity of the PCR fragments by sequence analysis, the altered subgenomic fragment was inserted into the full-length Ebolavirus cDNA construct via unique SalI and SacI restriction sites (FIG. 1), resulting in an Ebolavirus cDNA genome deficient in the VP30 ORF. The artificial generation of Ebolavirus from plasmids is afforded by flanking this viral cDNA with T7 RNA polymerase promoter and hepatitis delta virus ribozyme sequences (Neumann et al., 2002).

To amplify VP30-deficient Ebolaviruses, a stable Vero E6 cell line (designated VeroVP30) was established by cotransfecting Vero cells with two protein expression plasmids encoding VP30 (pCAG-VP30) and puromycin (pPur, Clontech), and selecting cell clones resistant to 5.0 µg/mL of puromycin. VP30 expression in individual clones was determined by flow cytometry with antibodies to VP30. The clone with the highest percentage of VP30-expressing cells (>90% as measured by flow cytometry) was used in further studies to amplify EbolaΔVP30 viruses.

Briefly, human embryonic kidney (293T) cells were transfected with a plasmid for the transcription of the VP30-deficient Ebolavirus RNA, with plasmids for the expression of the Ebolavirus NP, VP30, VP35, and L proteins, and with a plasmid for the expression of T7 RNA polymerase. Five days after transfection, VeroVP30 cells were incubated with undiluted supernatant derived from plasmid-transfected cells. Seven days later, the supernatant was harvested, diluted tenfold, and used to infect fresh VeroVP30 cells for the next passage. A total of seven passages were carried out, using the highest dilution of the inoculum that still produced replicating viruses for each passage. The presence of replicating virus was assessed by cytopathic effects (CPE) and immunostaining of infected VeroVP30 cells with an antibody to VP40. As a control, we also incubated the supernatants from each passage with wild-type Vero cells. As expected, CPE and viral antigens were undetectable in wild-type Vero cells, demonstrating that replicating EbolaΔVP30-neo virus was confined to VeroVP30 cells.

Although the manifestation of a CPE in infected VeroVP30 cells suggested the formation of infectious (but biologically contained) Ebolaviruses, further evidence was sought for the presence of virions in cell culture supernatant derived from infected VeroVP30 cells. Briefly, 5 days after VeroVP30 cells were infected with EbolaΔVP30-neo virus, supernatant was collected and partially purified over 20% sucrose. The pellet was suspended in PBS and separated on a 4-20% polyacrylamide gel. Western blot analyses were carried out with antibodies specific to the respective Ebolavirus protein. All viral proteins (with the exception of L, for which no antibody was available) were detected. Note that VP30 protein in virions originates from VeroVP30 cells while the remaining proteins are encoded by EbolaΔVP30-neo virus. By contrast, no viral proteins were detected in a control sample derived from wild-type Vero cells infected with EbolaΔVP30-neo virus.

Genetic stability of EbolaΔVP30-neo virus. A major concern with the use of VP30-deficient Ebolaviruses is the potential recombination with VP30 sequences integrated into the genome of the VeroVP30 helper cell line. Thus, to assess the genomic stability of EbolaΔVP30-neo virus, three independent passage experiments were performed (seven passages each). While EbolaΔVP30-neo virus replicated in VeroVP30 cells, viral replication was not observed in wild-type Vero cells. Total viral RNA was isolated from the cell culture supernatant of infected VeroVP30 cells after the seventh passage. A viral genomic fragment spanning the neo gene was amplified by RT-PCR, cloned and sequenced. A total of 20 clones were sequenced, and the sequences were identical to that of the EbolaΔVP30 cDNA construct used for virus generation. Hence, there was no evidence of recombination in any of three Independent passage experiments, attesting to the genomic stability of the EbolaΔVP30-neo viral genome.

To further demonstrate the biosafety of EbolaΔVP30-neo virus, EbolaΔVP30-neo virus was collected after seven consecutive passages in VeroVP30 cells and this virus used for three consecutive "blind" passages in wild-type Vero cells. Briefly, Vero cells were infected at a multiplicity of infection (m.o.i.) of 5 with EbolaΔVP30-neo virus (passage 7). Six days later, supernatant was used for the next "blind" passage as well as for Western blot analysis. No viral NP protein was detected after any of the "blind" passages (data not shown). After three consecutive "blind" passages, plaque assays and immunostaining were carried out in wild-type Vero cells to confirm the absence of replicating Ebolavirus. As expected, replicating virus was not detected. Collectively, these data further attest to the biosafety of the EbolaΔVP30 system.

Growth kinetics of EbolaΔVP30-neo virus. One of the major concerns raised by providing viral proteins in trans is that their amounts, expression kinetics or both may not match those found in cells infected with wild-type virus, leading to reduced virus titers and/or aberrant virion morphology. To address this potential pitfall, the growth kinetics of EbolaΔVP30-neo virus were compared with that of wild-type Ebolavirus. VeroVP30 cells or wild-type Vero cells were infected at a high m.o.i. of 1.0 or a low m.o.i. of 0.01 and supernatant was harvested every 24 hours. Virus titers of EbolaΔVP30-neo were determined in VeroVP30 cells, while virus titers of wild-type Ebolavirus were determined in wild-type Vero cells. To determine virus titers, cells were overlaid with 1.5% methylcellulose and 7 days later, assayed for VP40 expression using an immunostaining assay. EbolaΔVP30-neo virus replicated efficiently in Vero VP30 cells at both conditions tested, reaching $10^7$ focal-forming units (FFU)/ml on day 6 postinfection. No replication of EbolaΔVP30-neo was detected in wild-type Vero cells; the low titers that were detected for up to three days postinfection likely reflect input virus. Together, these findings attest to the biological confinement of the EbolaΔVP30 system. The replication kinetics of EbolaΔVP30-neo in VeroVP30 cells are similar to those of wild-type Ebolavirus in either VeroVP30 (FIG. 3, top panels, open circles) or wild-type Vero cells (FIG. 3, bottom panels, open circles), establishing the described approach as a highly efficient method for generating biologically contained Ebolaviruses.

Morphology of EbolaΔVP30-neo virus. Next, the morphology of EbolaΔVP30-neo virus was assessed by transmission electron microscopy (TEM). VeroVP30 cells were infected with EbolaΔVP30-neo virus and fixed 36 hours later. Samples were processed for TEM as described in Noda et al. (2002). As shown in FIG. 4 (right panels), the particles budding from VeroVP30 cells infected with EbolaΔVP30-neo virus were indistinguishable in their size and shape from wild-type Ebolaviruses. Thus, providing VP30 protein in trans does not have a discernable effect on virion morphology, suggesting that the described system would be suitable for studies of virion formation and budding, for example.

Taken together, the above results demonstrate that the EbolaΔVP30-neo virus is biologically contained, replicates to high titers in a helper cell line, is genetically stable, and is morphologically indistinguishable from wild-type virions. Having provided proof-of-concept for the generation of biologically contained Ebolaviruses, the utility of this strategy in basic research and drug screening applications was assessed.

Generation of an EbolaΔVP30-eGFP virus and its usefulness for basic research applications. An EbolaΔVP30 virus encoding enhanced green fluorescence protein (eGFP) instead of VP30 was generated (FIG. 1; designated EbolaΔVP30-eGFP), using the same procedures described above for EbolaΔVP30-neo virus. Analogous to EbolaΔVP30-neo virus, the eGFP variant replicated efficiently with virus titers reaching $8.0 \times 10^7$ FFU/mL. Expression of eGFP was observed as early as 10 hours postinfection (data not shown).

Takada et al. (2003) used replication-competent vesicular stomatitis virus (VSV) pseudotyped with Ebolavirus GP and two neutralizing monoclonal antibodies (mAb), 133/3.16 and 226/8.1, to map Ebolavirus GP epitopes and to generate escape mutants. To confirm with authentic Ebolavirus virions the findings of Takada et al. (2003) based on a VSV-pseudotyping system, escape mutants were generated by amplifying EbolaΔVP30-eGFP virus in the presence of mAb 133/3.16 or 226/8.1. Each of eight escape mutants to mAb 133/3.16 possessed a histidine-to-arginine substitution at position 549 (H549R) in GP, reported by Takada et al. (2003). Using mAb 226/8.1, 12 escape mutants were isolated that all contained an arginine-to-tryptophan substitution at position 134 (R134W), a mutation identical to one identified by Takada et al. (2003). However, the remaining two escape mutations described by Takada et al. (2003) were not detected. Whether this discrepancy in escape mutants reflects differences between the biological systems used or random mutations is presently unclear. Nonetheless, these experiments illustrated one of the ways that biologically contained Ebolaviruses could be used in basic research applications.

Biologically contained Ebolaviruses lacking the VP30 gene afford a safe, alternative way to study authentic Ebolavirus, to develop Ebolavirus vaccines, and to screen chemical libraries for compounds that interfere with the Ebolavirus life cycle. Indeed, each of the three different biologically contained viruses generated (encoding neomycin or eGFP instead of VP30) was biologically contained, as demonstrated by their ability to replicate in VeroVP30 (a Vero cell line that stably expresses VP30 in trans), but not in wild-type Vero cells. Moreover, virus titers were in the range of $10^7$ FFU/mL and hence comparable to those obtained for wild-type Ebolavirus (FIG. 3; Volchov et al., 2001; Neumann et al., 2002; Ebihara et al., 2006) while morphological, biochemical, and virological analyses indicated that the tested properties of EbolaΔVP30 viruses were indistinguishable from those of wild-type Ebolavirus.

Exemplary Efficacy Protocols

Ebola viruses (family Filoviridae), cause severe hemorrhagic fever in humans and nonhuman primates with mortality rates up to 90% (Johnson et al., 1977). Currently, there are no licensed vaccines or antivirals available against Ebola virus. A vaccine against Ebola virus is not only desirable for local populations in the epidemic areas of Africa, but also for health care workers during an outbreak and for post-exposure treatment of laboratory workers after accidental exposure to the virus. A few vaccine candidates have been shown to protect mice, guinea pigs, or nonhuman primates against a lethal challenge of Ebola virus; however, each of these candidates has disadvantages, such as lack of protection in nonhuman primates, preexisting immunity against the vector in humans, or potential central nervous system involvement (Reed et al., 2007). Moreover, the current vaccine candidates are based on virus-like particles (VLPs) or virus-vectored vaccines, none of which express the full components of the viral antigens. On the other hand, the use of live attenuated vaccines may not be feasible for Ebola virus from a biosafety perspective. To overcome these potential limitations, biologically contained viruses offer an attractive option since they are biologically safe but provide all the viral antigens.

Materials and Methods

Cells. VeroVP30 cells are established as described in Example 1 and grown in Eagle's minimal essential medium (MEM) supplemented with 10% fetal calf serum (FCS), L-glutamine, vitamins, non-essential amino acid solution, and 5 μg/mL puromycin (Sigma, St. Louis, MO).

Viruses. The EbolaΔVP30 virus is generated as described in Example 1. Briefly, using the plasmid containing the full-length Ebola cDNA genome of the Zaire Mayinga strain of Ebola virus (Neumann et al., 2002), the open reading frame (ORF) of VP30 is replaced with the ORF of the drug-resistant gene neomycin. Using Ebola virus reverse genetics (Neumann et al., 2002), the EbolaΔVP30 virus is generated and passaged in a Vero cell line stably expressing VP30. EbolaΔVP30 was propagated in VeroVP30 cells in MEM medium as described above, but supplemented with 2% FCS. The virus is harvested six days after infection of the cells at a multiplicity of infection (MOI) of 1 and directly stored at −80° C. Harvested virus is also partially purified by ultracentrifugation at 27,000 rpm for 2 hours over 20% sucrose. The viral pellet was resuspended in sterile PBS and stored at −80° C. Viral titers are determined by plaque assay in confluent VeroVP30 cells overlaid with 2% FCS-MEM containing 1.5% methyl cellulose (Sigma).

Since wild-type Ebola virus does not kill mice, challenge studies are carried out with a mouse-adapted Ebola virus (Bray et al., 1998). This virus is generated as described in Ebihara et al., 2006.

Antibody titers. The levels of Ebola glycoprotein (GP)-specific immunoglobulin G (IgG) antibodies in vaccinated mice are examined by using an enzyme-linked immunosorbent assay (ELISA). Briefly, wells of Immulon 2HB plates (Thermon Labsystems, Franklin, MA) are coated with purified Ebola GP (Takada et al., 2001) and blocked with PBS containing 10 mg/ml bovine serum albumin. After incubation of Ebola GP-coated wells with mouse serum from control and vaccinated mice, bound antibodies are detected with goat anti-mouse IgG conjugated to horseradish peroxidase (Kirkegaard & Perry Laboratories Inc., Gaithersburg, MD) by an ELISA plate reader at an absorbance of 405 nm.

Intracellular staining and flow cytometry. The number of cytokine-producing $CD8^+$ T cells is determined by intracellular staining as described Murali-Krishna et al. (1998). Briefly, splenocytes are stimulated with the Ebola peptide $NP_{279-288}$ (SFKAALSSLA, derived from the nucleoprotein NP; SEQ ID NO: 16) (Olinger et al., 2006; Simmons et al., 2004), $VP40_{171-180}$ (YFTFDLTALK, derived from the matrix protein VP40; SEQ ID NO:17), or $GP_{161-169}$ (LYDRLASTV, derived from GP) (Olinger et al., 2005; Warfield et al., 2005) for 5 hours in the presence of brefeldin A and IL-2. Following activation, cells are stained for cell surface $CD8^+$ and intracellular IFNγ by using the Cytofix/Cytoperm kit from BD Biosciences (San Jose, CA). The number of cytokine-producing $CD8^+$ T cells is determined by using a FACSCalibur flow cytometer (BD Biosciences).

Vaccination and challenge. Four-week-old female BALB/c mice (The Jackson Laboratory, Bar Harbor, ME) are anesthetized with isoflurane and intraperitoneally (IP) inoculated twice at three-week intervals with $10^6$ focus forming units (FFU) of sucrose-purified EbolaΔVP30 virus; control mice were simultaneously inoculated with PBS. A second group of mice receives three immunizations (at three-week intervals) with $10^7$ FFU of virus harvested from cell culture supernatant, or, as a control, 2% FCS-MEM. Vaccinations are conducted at the University of Wisconsin-Madison. Mice are then transported to the BSL-4 laboratory at the National Microbiology Laboratory of the Public Health Agency of Canada, where they were challenged with 1000 mouse lethal doses 50 ($MLD_{50}$; i.e., the dose required to kill 50% of infected animals) of mouse-adapted Ebola virus. Four days after challenge, viral titers are determined in the serum of three control and three vaccinated mice from each group. The remaining mice were monitored for survival for 28 days.

Antibody response of mice immunized with EbolaΔVP30 virus. To assess the EbolaΔVP30 virus as a potential vaccine, its immunogenicity in mice was determined. Mice vaccinated with the EbolaΔVP30 virus did not show any signs of disease, demonstrating the lack of pathogenicity of the EbolaΔVP30 virus. When serum samples, collected two weeks after each vaccination to determine the levels of antibodies to the Ebola glycoprotein (GP), were tested for IgG antibody by ELISA with purified GP, vaccinated animals showed elevated levels of antibody titers against GP after the first vaccination compared to control mice; these antibody titers further increased after the second and third vaccinations. This finding demonstrates the ability of the biologically contained EbolaΔVP30 virus to elicit antibodies to GP.

$CD8^+$ T-cell responses in vaccinated mice. The cellular response to vaccination in mice was examined. Mice were vaccinated as described above. Eight days after the second immunization, four vaccinated and two control mice were euthanized and their spleens removed. Splenocytes were isolated and stimulated with the Ebola peptide $NP_{279\text{-}288}$ (SFKAALSSLA), $VP40_{171\text{-}180}$ (YFTFDLTALK) or $GP_{161\text{-}169}$ (LYDRLASTV) for 5 hours in the presence of brefeldin A and IL-2. Vaccinated mice had IFNγ-positive CD8+ cells in the range of 0.017% to 0.22% for cells stimulated with Ebola peptide $NP_{279\text{-}288}$ (FIG. 6). For control mice, the number of IFNγ-positive CD8+ cells was significantly lower, ranging from 0.00513% to 0.00794%. No IFNγ-positive CD8+ cells were detected for cells stimulated with Ebola peptide $VP40_{171\text{-}180}$ or GP 161-169 (data not shown).

Protective efficacy of EbolaΔVP30 virus in mice. To assess the protective efficacy of the EbolaΔVP30 virus, two groups of 4-week-old mice were intraperitoneally immunized, then subjected to lethal challenge with mouse-adapted Ebola virus. 'Group 1' mice were immunized three times at three-week intervals with $10^7$ FFU of non-purified EbolaΔVP30 virus (i.e., virus harvested from cell culture supernatant); eight control mice were inoculated in the same manner with 2% FCS-MEM. Mice from this group were challenged seven weeks after the last immunization with 1000 $MLD_{50}$ of mouse-adapted Ebola virus, which consistently kills mice (Bray et al., 1998; Ebihara et al., 2006). 'Group 2' mice were immunized twice (with a three-week interval) with $10^6$ FFU of purified EbolaΔVP30 virus; ten control mice were similarly inoculated with PBS. Mice from 'Group 2' were challenged eight weeks after the last Immunization with 1000 MLDs % of mouse-adapted Ebola virus. No signs of disease or illness were seen in mice vaccinated with purified or non-purified EbolaΔVP30 virus, whereas control mice from both groups began showing signs of sickness (e.g., ruffled fur) along with weight loss on day 3 post-challenge. By day 7 post-challenge, all control mice had succumbed to infection. By contrast, vaccinated mice from both groups showed no signs of disease, as characterized by ruffled fur and weight loss, and were fully protected against lethal challenge up to day 28, when all surviving mice were euthanized. On day 4 post-challenge, mice were sacrificed to determine viral titers in the sera. Vaccinated mice from both groups showed a 3 to 4 $\log_{10}$ reduction in viral titers compared to their respective control mice. Taken together, these data demonstrate that the EbolaΔVP30 virus efficiently protects mice against challenge with a lethal dose of mouse-adapted Ebola virus. Similar results were obtained in guinea pigs.

EbolaΔVP30-immunized mice were completely protected from a lethal challenge with mouse-adapted Ebola virus and that the virus titers in sera from these mice were more than 1000-fold lower than those in control mice.

The humoral response to Ebola virus infection is important, as demonstrated by protection from a lethal challenge by passive transfer of antibodies to the viral glycoprotein GP (Gupta et al., 2001; Warfield et al., 2003). However, the ability of a vaccine to elicit an antibody response does not in itself correlate with protection from Ebola virus infection. For example, classical vaccine approaches, such as γ-irradiated Ebola and Marburg viruses, along with GP expressed in baculovirus generate a moderate antibody response; however, they fail to protect mice against a lethal challenge (Ignatyeve et al., 1996; Lupton et al., 1980; Mellquist-Riemenschneider et al., 2003). By contrast, Ebola and Marburg VLPs protect mice from a lethal challenge of Ebola or Marburg virus (Warfield et al., 2003; Warfield et al., 2004; Warfield et al., 2005), and not only elicit a humoral response, but also induce a CD8+ T-cell response, highlighting the importance of the latter response for protection against a lethal challenge of Ebola virus (Warfield et al., 2005). Similarly, in non-human primates (NHPs), full protection from a lethal challenge appears to depend on both the humoral response and a CD8+ cellular response (Sullivan et al., 2000). Vaccine candidates that protect NHPs from a lethal Ebola virus challenge, such as recombinant vesicular stomatitis virus (VSV) (Jones et al., 2005) and adenovirus (Sullivan et al., 2000), induce a CD8+ T-cell response in NHPs, albeit to varying degrees (Jones et al., 2005; Sullivan et al., 2000). The EbolaΔVP30 virus induced both humoral and CD8+ T-cell (specific for an Ebola NP epitope) responses, although the extent of the latter responses varied among animals. Whether this CD8+ T-cell response is sufficient to provide protection to NHPs from a lethal Ebola virus infection remains to be tested.

Although vaccine candidates such as recombinant VSV or parainfluenza virus offer protection in various animal models (Bukreyev et al., 2006; Jones et al., 2005), there are safety concerns with the use of these vaccines in humans (Bukreyev et al., 2006; Jones et al., 2005; Reed et al., 2007). Preexisting immunity to a vaccine based on recombinant adenovirus is also a concern, as is the large amount of virus ($10^{10}$ particles) needed to confer protection in NHPs (Jones et al., 2005; Sullivan et al., 2000). Ebola and Marburg VLPs have been shown to protect mice and guinea pigs from a lethal challenge of these viruses (Warfield et al., 2004; Warfield et al., 2005). While VLPs are safe and, due to the rarity of Ebola virus infection, preexisting immunity to Ebola or Marburg viruses is not a concern for VLP vaccines, it is difficult to produce large quantities of VLPs from cell culture.

The biologically contained EbolaΔVP30 virus is thus an ideal vaccine candidate since it combines the advantages of VLPs and vectored vaccines (i.e., safety and efficacy), yet it can be propagated to high titers in VeroVP30 cells like standard viruses (Example 1). Further studies will include testing the EbolaΔVP30 virus for its protective efficacy in NHPs. In addition, shorter, single vaccination protocols will be evaluated to determine if the EbolaΔVP30 virus vaccine could elicit fast and effective immunity in the event of an outbreak or bioterrorism attack. This includes evaluating the EbolaΔVP30 virus as a vaccine for post-exposure treatment.

The invention will be further described in the following nonlimiting examples.

Example 1

Nonhuman primates were vaccinated with one or two (prime and boost) doses of vaccine virus (IM or aerosol) and then challenged (heterologous challenge or homologous challenge) 4 weeks after the last dose. Some vaccinations included one of three different adjuvants. As shown by the data from Study #2, which employed 10-fold more vaccine virus than Study #1, only those animals vaccinated with virus and an adjuvant survived heterologous challenge. In Study #3, in addition to protocols that used a vaccine of the invention (3A and 3D), two other anti-ebola virus vaccines currently undergoing testing (Vaccine A, intranasal administration of a vaccine having a replication competent virus; Vaccine B, intramuscular administration of a vaccine having a replication incompetent virus) were also tested. In one protocol, immunization only included Vaccine A (3G). In other immunization protocols, a combination of a vaccine of the invention and Vaccine A (3B and 3C) and a combination of Vaccine A and Vaccine B (3E and 3F) were tested. Some protocols included an adjuvant (3A-3D).

|  | Number of NHPs | Prime dose (route) | Boost dose (route) | Time between doses (weeks) | Challenge virus and dose (route) | Time between immunization and challenge (weeks) | Adjuvant | Survival | Notes |
|---|---|---|---|---|---|---|---|---|---|
| Study #1 | | | | | | | | | |
| | 4 | $10^7$ FFU (IM) | — | 4 | Kikwit $10^4$ FFU (IM) | 4 | — | 100% | Viremia in 1 animal |
| | 4 | $10^7$ FFU (IM) | $10^7$ FFU (IM) | 4 | Kikwit $10^4$ FFU (IM) | 4 | — | 100% | — |
| | 2 | $10^7$ FFU (IM) | $10^7$ FFU (IM) | 4 | Kikwit $10^4$ FFU (IM) | 4 | — | 100% | — |
| Study #2 | | | | | | | | | |
| | 4 | $10^8$ FFU (IM) | $10^8$ FFU (IM) | 4 | Makona $10^4$ FFU (IM) | 4 | MF-59 | 100% | Viremia in 4 animals |
| | 4 | $10^8$ FFU (IM) | $10^8$ FFU (IM) | 4 | Makona $10^4$ FFU (IM) | 4 | MPLA | 50% | Viremia in 4 animals |
| | 4 | $10^8$ FFU (IM) | $10^8$ FFU (IM) | 4 | Makona $10^4$ FFU (IM) | 4 | — | 0% | Viremia in 4 animals |

Vaccine virus is Zaire Ebola, strain Mayinga. Studies 1 and 2 are heterologous Zaire challenge viruses; study 3 is a homologous Zaire challenge virus. Study 1 is with non-inactivated vaccine virus. Studies 2 and 3 are with inactivated vaccine virus of the invention; Vaccine A is also inactivated.
FFU = focus-forming units;
IM = intramuscular

|  | Number of NHPs | Prime dose (route) | Boost dose (route) | Time between doses (weeks) | Challenge virus and dose (route) | Time between immunization and challenge (weeks) | Adjuvant (used with deltaVP30 only) | Survival | Notes |
|---|---|---|---|---|---|---|---|---|---|
| Study #3 | | | | | | | | | |
| A | 2 | $10^8$ FFU (IM) | $10^8$ FFU (IM) | 8 | Mayinga $10^2$ FFU (aerosol) | 7 | QS-21 | 50% | — |
| B | 2 | Vaccine A $4 \times 10^8$ FFU | $10^8$ FFU (IM) | 8 | Mayinga $10^2$ FFU (aerosol) | 7 | QS-21 | 100% | — |
| C | 2 | $10^8$ FFU (IM) | Vaccine A $4 \times 10^8$ FFU | 8 | Mayinga $10^2$ FFU (aerosol) | 7 | QS-21 | 50% | — |
| D | 2 | $10^8$ FFU (IM) | $10^8$ FFU (IM) | 8 | Mayinga $10^4$ FFU (IM) | 7 | QS-21 | 100% | — |
| E | 2 | Vaccine B $5 \times 10^{10}$ particles | Vaccine A $2 \times 10^8$ particles | 8 | Mayinga $10^2$ FFU (aerosol) | 7 | — | 0% | — |
| F | 2 | Vaccine A $2 \times 10^8$ particles | Vaccine B $5 \times 10^{10}$ particles | 8 | Mayinga $10^2$ FFU (aerosol) | 7 | — | 50% | — |
| G | 2 | Vaccine A $4 \times 10^8$ particles | Vaccine A $4 \times 10^8$ particles | 8 | Mayinga $10^2$ FFU (aerosol) | 7 | — | 50% | — |

Vaccine A - completed phase I clinical trial.
Vaccine B - completed phase I, II, and III clinical trials.
0.1 mg of QS-21 (quil-A) was employed in 3A-3D.

Example 2

Exemplary Manufacturing Process
Generation of a Master Virus Seed (MVS)

Chemical transfection reagents to introduce the plasmids for the generation of the vaccine virus by the technique of reverse genetics is inefficient for VeroVP30 cells. Therefore, electroporation was performed using the Neon Transfection system. Prior to use, the Neon Transfection system was sterilized by ethylene oxide. Six microfuge tubes each containing 1×10e6 VeroVP30 cells were mixed with 10 ug total plasmid (2:1:1:2 mass ratio of pCAGGS EBOV L, pCAGGS EBOV NP-VP35, T7, and pTM EbolaΔVP30 plasmids, respectively) and electroporated in the Neon Transfection system at 1200 V with three 20 millisecond pulses. Transfected cells were seeded in each well of a 6-well plate and incubated at 37±2° C., 5±2% CO2 for 4 days before expansion in TC75 flasks.

Cell Culture and Vaccine Virus Harvest

Cell culture is initiated with Complete Medium (virus production-serum free medium [VP-SFM, Thermo Fisher Scientific]) supplemented with 1% Glutamax and expanded into 18×10-layer Cell Factories (Nunc). The VP-SFM performed better than OptiVERO medium (InVitria) and the 10-layer Cell Factories performed better than hyperstacks (Corning) in terms of virus production, resulting in an increase in virus titers (1-1.5 log increase in titer expressed in focus-forming units).

When cells reached 80-90% confluency, each 10-layer Cell Factory is washed three times with DPBS and then infected with the MVS at a MOI of 0.1 in VP-SFM plus 1% Glutamax. Each infected 10-layer Cell Factory was incubated for 7 days at 37±2° C., 5±2% $CO_2$. Following the seven day infection period, each 10-layer Cell Factory was inspected for contamination and the contents were harvested into a sterile 20 L bioprocess bag. Samples of pooled and the bulk harvest were pumped through a depth filter (1.2 µM filtration by Sartorius 2 XLG MidiCap) into a new sterile bioprocess bag.

Host genomic DNA was removed by benzonase treatment. $MgCl_2$ was added to the filtered viral harvest up to a final concentration of 2 mM $MgCl_2$. Benzonase (Millipore Sigma) was then added to a final concentration of 10 U/mL of filtered harvest and incubated at 37±2° C. for 4-6 hours. After benzonase treatment, β-Propiolactone (BPL) was added to a final concentration of 0.1% v/v and incubated at 2-8° C. for 16-18 hours.

Degraded host DNA, benzonase, BPL and other host impurities were subsequently removed by tangential flow filtration (TFF). The benzonase/BPL treated viral harvest was concentrated approximately 10× (e.g., concentrated so as not to result in precipitation), diafiltered, e.g., using 0.1 um pore size, into Dulbecco's Phosphate-Buffered Saline (DPBS) with $Ca^{2+}/Mg^{2+}$, then further concentrated using a sterile/closed TFF system (the TFF filter has a 0.1 um pore size, 30 cm path length, e.g., GE RTPCFP-1E-8S hollow fiber cartridge from GE Health) to ~2× the desired product concentration (e.g., $6×10^7$ FFU/ml). Following diafiltration, samples of the TFF retentate and wash pools were analyzed to determine titer by ELISA and host protein. Retentate and wash samples meeting host protein specifications (e.g., ≤500 ng/ml) were pooled, centrifuged to remove any residual particulate matter, transferred to a sterile 2 L Erlenmeyer flask, and stored at 2-8° C. until product manufacturing (e.g., in DPBS).

Testing of Media and Conditions

When TC175 flasks were used to culture and infect cells, OPTIVero medium resulted in virus titers that were about 1 log unit greater than VP-SFM (e.g., 6.84 log 10 FFU/ml [OPTIVero] vs. 5.75 log 10 FFU/ml [VP-SFM]). When a 10-tray system was used to culture and infect cells (large culture vessels for vaccine production), VP-SFM medium resulted in virus titers that were about 1 log unit greater than OPTIVero medium (e.g., 6.52 log 10 FFU/ml [VP-SFM] vs. 5.52 log 10 FFU/ml [OPTIVero]). When VP-SFM medium was used to culture and infect cell in a 10-tray system, that system produce about 1 log unit greater titers than VP-SFM medium was used to culture and infect cells in a hyperstack (e.g., 6.69 log 10 FFU/ml [10-tray system] vs. 5.58 log 10 FFU/ml [hyperstack]). VP-SFM medium includes a plant hydrosylate (e.g., comprising di- and tri-plant peptides) and an iron chelator while OPTIVero medium includes recombinant human albumin, recombinant human transferrin (i.e., no plant hydrosylate or iron chelator).

REFERENCES

Boehmann et al., *Virology*, 332:406 (2005).w
Bray et al., *J. Infect. Dis.*, 178:651 (1998).
Bukreyev et al., *J. Virol.*, 80:2267 (2006).
Chan et al., *Cell*, 106:117 (2001).
Chandran et al., *Science*, 308:1643 (2005).
Ebihara et al., *PloS Pathogens*, 2:0705 (2006).
Ebihara et al., *PLOS. Pathog.*, 2: e73 (2006).
Feldmann et al., in Virus Taxonomy: Eighth Report of the International Committee of Taxonomy of Viruses, eds. Fauquet, C., Mayo, M. A., Desselberger, U., & Ball, L. A. (Elsevier, London), pp. 645 (2004).
Groseth et al., *J. Virol.*, 79:4425 (2005).
Gupta et al., *J. Virol . . .* 75:4649 (2001).
Halfmann et al., *In submission* (2007).
Hartman et al., *J. Virol.* 80:6430 (2006).
Harty et al., *Proc. Natl. Acad. Sci. USA*, 97:13871 (2000).
Huang et al., *Mol. Cell*, 10:307 (2002).
Ignatyeve et al., *J. Biotechnol.*, 44:111 (1996).
Jasenosky et al., *J. Virol.*, 75:5205 (2001).
Johnson et al., *Lancet*, 1:569 (1977).
Johnson et al., *Virol. J.* 3:31 (2006).
Jones et al., *Nat. Med.*, 11:786 (2005).
Licata et al., *J. Virol.*, 78:7344 (2004).
Lupton et al., *Lancet*, 2:1294 (1980).
Manicassamy et al., *J. Virol.*, 79:4793 (2005).
Marzi et al., *Virology*, 352:345 (2006).
McCarthy et al., *J. Virol. Methods*, 137:115 (2006).
Mellquist-Riemenschneider et al., *Virus Res.*, 92:187 (2003).
Modrof et al., *J. Biol. Chem.*, 277:33099 (2002).
Modrof et al., *J. Virol.*, 77:3334 (2003).
Muhlberger et al., *J. Virol.*, 73:2333 (1999).
Murali-Krishna et al., *Immunity*, 8:177 (1998).
Neumann et al., *J. Virol.*, 76:406 (2002).
Neumann et al., *J. Virol.*, 79:10300 (2005).
Noda et al., *J. Virol.*, 76:4855 (2002).
Olinger et al., *J. Virol.*, 79:14189 (2005).
Panchal et al., *Proc. Natl. Acad. Sci. USA*, 100:15936 (2003).
Reed et al., *Vaccine*, 25:1923 (2007).
Sanchez et al., in Fields Virology, eds. Knipe, D. M., Howley, P. M., Griffin, D. E., Martin, M. A., Lamb, R. A., Roizman, B., & Straus, S. E. (Lippincott, Williams & Wilkins, Philadelphia), pp. 1409 (2007).
Sanchez et al., *Virus Res.* 29:215 (1993).
Shimojima et al., *J. Virol.*, 80:10109 (2006).

Simmons et al., *Virology*, 318:224 (2004).
Sullivan et al., *Nature*, 408:681 (2000).
Takada et al., *J. Virol.*, 75:2324 (2001).
Takada et al., *Proc. Natl. Acad. Sci. U.S.A.*, 94:14764 (1997).
Takada et al., *Vaccine*, 25:993 (2007).
Takada, *J. Virol.*, 77:1069 (2003).
Theriault et al., *Arch. Virol.* Suppl., 19:157 (2005).
Volchkov et al., *Science*, 291:1965 (2001).
Warfield et al., *J. Immunol.* 175:1184 (2005).
Warfield et al., *Pro. Natl. Acad. Sci. USA*, 100:15889 (2003).
Warfield et al., *Vaccine*, 22:3495 (2004).
Wool-Lewis et al., *J. Virol.*, 72:155 1998).
Yonezawa et al., *J. Virol.*, 79:918 (2005).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A vaccine comprising an effective amount of a recombinant filovirus and one or more adjuvants comprising a saponin, wherein the genome of the recombinant filovirus contains a deletion of one or more nucleotides in a polynucleotide sequence for a viral protein corresponding to Ebola virus VP30, and wherein the deletion is effective to prevent expression of a functional viral protein corresponding to Ebola virus VP30 upon infection of a cell with the recombinant filovirus, wherein the genome further comprises a nucleotide sequence encoding a prophylactic or therapeutic heterologous gene product and wherein the nucleotide sequence is inserted into the filovirus genome at a site other than the site of the deletion in the polynucleotide or wherein the genome further comprises a nucleotide sequence encoding a prophylactic or therapeutic heterologous gene product and the nucleotide sequence replaces or is inserted into GP/sGP sequences or a portion thereof.

2. The vaccine of claim 1 wherein the nucleotide sequence that is inserted into the filovirus genome at a site other than the site of the deletion is inserted between NP coding sequences and VP35 coding sequences in the filovirus genome.

3. The vaccine of claim 1, wherein the heterologous gene product comprises a heterologous filovirus glycoprotein.

4. The vaccine of claim 3 wherein the filovirus glycoprotein comprises a Marburg virus, Ebola virus, Sudan virus, Tai Forest virus, Reston virus, or Bundibugyo virus glycoprotein.

5. The vaccine of claim 1 wherein the adjuvant comprises an extract of *Quillaja saponaria*.

6. A method to immunize a mammal, comprising administering to the mammal an effective amount of the vaccine of claim 1.

7. A multivalent vaccine comprising an effective amount of a recombinant filovirus and comprising a saponin, wherein the genome of the recombinant filovirus contains a first deletion in one or more nucleotides for a polynucleotide sequence for a viral protein corresponding to Ebola virus VP30 which deletion is effective to prevent expression of a functional viral protein corresponding to Ebola virus VP30 upon infection of a cell with the recombinant filovirus, wherein the genome further comprises a nucleotide sequence encoding a prophylactic or therapeutic heterologous gene product and wherein the nucleotide sequence is inserted into the filovirus genome at a site other than the site of the deletion in the polynucleotide or wherein the genome further comprises a nucleotide sequence encoding a prophylactic or therapeutic heterologous gene product and the nucleotide sequence replaces or is inserted into GP/sGP sequences or a portion thereof, and wherein the genome encodes one or more filovirus glycoproteins.

8. The vaccine of claim 7 wherein one of the gene products comprises Ebola NP, Ebola VP40, Ebola VP35, Marburg NP, Marburg NP VP40, Marburg NP VP35, *Plasmodium* circumsporozoite protein (CSP), *Plasmodium* apical membrane antigen (AMA), *Plasmodium* rhoptry neck protein 2 (RON2), *Plasmodium* RH5, Marburg GP, flavivirus membrane protein, flavivirus envelope protein, or a bunyavirus glycoprotein precursor (GPC) protein.

9. A method to immunize a mammal, comprising administering to the mammal an effective amount of the vaccine of claim 7.

10. A method of manufacturing a composition comprising recombinant filovirus and an adjuvant, comprising: providing supernatant from mammalian cells expressing a recombinant filovirus genome that are cultured in serum free medium so as to result in progeny filovirus, wherein the genome of the recombinant filovirus contains a deletion of one or more nucleotides in a polynucleotide sequence for a viral protein corresponding to Ebola virus VP30 which deletion is effective to prevent expression of a functional viral protein corresponding to Ebola virus VP30 upon infection of a cell with the recombinant filovirus, wherein the genome further comprises a nucleotide sequence encoding a prophylactic or therapeutic heterologous gene product, and wherein the nucleotide sequence is inserted into the filovirus genome at a site other than the site of the deletion in the polynucleotide or wherein the nucleotide sequence replaces or is inserted into GP/sGP sequences or a portion thereof, and wherein the mammalian cells express a viral protein corresponding to Ebola virus VP30;
contacting the supernatant with a DNase and a virus inactivating agent, thereby providing an inactivated viral preparation;
concentrating the inactivated viral preparation; and
combining the inactivated viral preparation and one or more saponin adjuvants.

11. The method of claim 10 wherein the cells are Vero cells.

12. The method of claim 10 wherein the collected supernatant is filtered before contact with the DNase or the viral inactivating agent.

13. The method of claim 12 wherein the collected supernatant is subjected to filtration with a 0.5 to 5 micron filter or a 1 to 5 micron filter.

14. The method of claim 10 wherein the inactivated viral preparation is subjected to filtration.

15. The method of claim 14 wherein the filtration of the inactivated viral preparation is through a 0.01 to 1 micron filter or a 0.05 to 0.25 micron filter.

16. A composition comprising the inactivated virus produced by the method of claim 10.

17. A vaccine comprising an effective amount of a recombinant filovirus and one or more adjuvants comprising a squalene or a saponin, wherein the genome of the recombinant filovirus contains a deletion of one or more nucleotides in a polynucleotide sequence for a viral protein corresponding to Ebola virus VP30, and wherein the deletion is effective to prevent expression of a functional viral protein corresponding to Ebola virus VP30 upon infection of a cell with the recombinant filovirus, wherein the genome further comprises a nucleotide sequence encoding a prophylactic or therapeutic heterologous gene product, and wherein the nucleotide sequence is inserted into the filovirus genome at a site other than the site of the deletion in the polynucleotide or wherein the nucleotide sequence replaces or is inserted into GP/sGP sequences or a portion thereof.

18. The vaccine of claim 17 wherein the nucleotide sequence is inserted between NP coding sequences and VP35 coding sequences in the filovirus genome.

* * * * *